(12) United States Patent
Barthe et al.

(10) Patent No.: US 10,046,182 B2
(45) Date of Patent: *Aug. 14, 2018

(54) METHODS FOR FACE AND NECK LIFTS

(71) Applicant: Guided Therapy Systems, LLC, Mesa, AZ (US)

(72) Inventors: Peter G. Barthe, Phoenix, AZ (US); Michael H. Slayton, Tempe, AZ (US); Inder Raj S. Makin, Mesa, AZ (US)

(73) Assignee: Guided Therapy Systems, LLC, Mesa, AZ (US)

( * ) Notice: Subject to any disclaimer, the term of this patent is extended or adjusted under 35 U.S.C. 154(b) by 127 days.

This patent is subject to a terminal disclaimer.

(21) Appl. No.: 15/248,454

(22) Filed: Aug. 26, 2016

(65) Prior Publication Data
US 2016/0361574 A1    Dec. 15, 2016

Related U.S. Application Data

(63) Continuation of application No. 14/554,571, filed on Nov. 26, 2014, now Pat. No. 9,427,601, which is a
(Continued)

(51) Int. Cl.
*A61N 7/02* (2006.01)
*A61B 5/00* (2006.01)
(Continued)

(52) U.S. Cl.
CPC .............. *A61N 7/02* (2013.01); *A61B 5/7405* (2013.01); *A61B 8/08* (2013.01); *A61B 8/0858* (2013.01);
(Continued)

(58) Field of Classification Search
CPC .... A61N 7/00; A61N 7/02; A61N 2007/0007; A61N 2007/0034; A61N 2007/0052;
(Continued)

(56) References Cited

U.S. PATENT DOCUMENTS

| 2,427,348 A | 9/1947 | Bond et al. |
| 2,792,829 A | 2/1952 | Calosi |

(Continued)

FOREIGN PATENT DOCUMENTS

| CN | 104027893 | 9/2014 |
| DE | 4029175 | 3/1992 |

(Continued)

OTHER PUBLICATIONS

Agren, Magnus S. et al., Collagenase in Wound Healing: Effect of Wound Age and Type. The Journal of Investigative Dermatology, vol. 99/No. 6, (Dec. 1992).

(Continued)

*Primary Examiner* — Ronald Hupczey, Jr.
(74) *Attorney, Agent, or Firm* — Knobbe Martens Olson & Bear LLP

(57) ABSTRACT

Methods for treating skin and subcutaneous tissue with energy such as ultrasound energy are disclosed. In various embodiments, ultrasound energy is applied at a region of interest to affect tissue by cutting, ablating, micro-ablating, coagulating, or otherwise affecting the subcutaneous tissue to conduct numerous procedures that are traditionally done invasively in a non-invasive manner. Methods of lifting sagging tissue on a face and/or neck are described.

20 Claims, 71 Drawing Sheets

Related U.S. Application Data continuation of application No. 13/835,635, filed on Mar. 15, 2013, now Pat. No. 8,915,853, which is a continuation of application No. 13/494,856, filed on Jun. 12, 2012, now Pat. No. 8,444,562, which is a continuation of application No. 11/847,989, filed on Sep. 19, 2007, now abandoned, and a continuation-in-part of application No. 12/028,636, filed on Feb. 8, 2008, now Pat. No. 8,535,228, which is a continuation of application No. 11/163,151, filed on Oct. 6, 2005, now abandoned, and a continuation-in-part of application No. 11/163,148, filed on Oct. 6, 2005, now abandoned.

(60) Provisional application No. 60/826,199, filed on Sep. 19, 2006, provisional application No. 60/616,754, filed on Oct. 6, 2004, provisional application No. 60/616,755, filed on Oct. 6, 2004.

(51) Int. Cl.
*A61B 8/08* (2006.01)
*A61B 8/00* (2006.01)
*A61B 8/13* (2006.01)
*A61B 8/14* (2006.01)
*A61N 7/00* (2006.01)
*A61B 90/00* (2016.01)

(52) U.S. Cl.
CPC .............. *A61B 8/13* (2013.01); *A61B 8/14* (2013.01); *A61B 8/4281* (2013.01); *A61B 8/4444* (2013.01); *A61B 8/4461* (2013.01); *A61B 8/4483* (2013.01); *A61B 8/461* (2013.01); *A61B 8/469* (2013.01); *A61B 2090/378* (2016.02); *A61B 2562/046* (2013.01); *A61N 2007/0008* (2013.01); *A61N 2007/0034* (2013.01); *A61N 2007/0052* (2013.01); *A61N 2007/0078* (2013.01); *A61N 2007/0082* (2013.01); *A61N 2007/027* (2013.01)

(58) Field of Classification Search
CPC .... A61N 2007/0056; A61N 2007/0065; A61N 2007/0082
See application file for complete search history.

(56) References Cited

U.S. PATENT DOCUMENTS

| | | |
|---|---|---|
| 3,913,386 A | 10/1975 | Saglio |
| 3,965,455 A | 6/1976 | Hurwitz |
| 3,992,925 A | 11/1976 | Perilhou |
| 4,039,312 A | 8/1977 | Patru |
| 4,059,098 A | 11/1977 | Murdock |
| 4,101,795 A | 7/1978 | Fukumoto |
| 4,151,834 A | 5/1979 | Sato et al. |
| 4,166,967 A | 9/1979 | Benes et al. |
| 4,211,948 A | 7/1980 | Smith et al. |
| 4,211,949 A | 7/1980 | Brisken et al. |
| 4,213,344 A | 7/1980 | Rose |
| 4,276,491 A | 6/1981 | Daniel |
| 4,315,514 A | 2/1982 | Drewes et al. |
| 4,325,381 A | 4/1982 | Glenn |
| 4,343,301 A | 8/1982 | Indech |
| 4,372,296 A | 2/1983 | Fahim |
| 4,379,145 A | 4/1983 | Masuho et al. |
| 4,381,007 A | 4/1983 | Doss |
| 4,381,787 A | 5/1983 | Hottinger |
| 4,397,314 A | 8/1983 | Vaguine |
| 4,409,839 A | 10/1983 | Taenzer |
| 4,431,008 A | 2/1984 | Wanner et al. |
| 4,441,486 A | 4/1984 | Pounds |
| 4,452,084 A | 6/1984 | Taenzer |
| 4,484,569 A | 11/1984 | Driller |
| 4,507,582 A | 3/1985 | Glenn |
| 4,513,749 A | 4/1985 | Kino |
| 4,513,750 A | 4/1985 | Heyman et al. |
| 4,527,550 A | 7/1985 | Ruggera et al. |
| 4,528,979 A | 7/1985 | Marchenko |
| 4,534,221 A | 8/1985 | Fife et al. |
| 4,566,459 A | 1/1986 | Umemura et al. |
| 4,567,895 A | 2/1986 | Putzke |
| 4,586,512 A | 5/1986 | Do-Huu |
| 4,601,296 A | 7/1986 | Yerushalmi |
| 4,620,546 A | 11/1986 | Aida et al. |
| 4,637,256 A | 1/1987 | Sugiyama et al. |
| 4,646,756 A | 3/1987 | Watmough |
| 4,663,358 A | 5/1987 | Hyon |
| 4,668,516 A | 5/1987 | Duraffourd et al. |
| 4,672,591 A | 6/1987 | Breimesser et al. |
| 4,680,499 A | 7/1987 | Umemura et al. |
| 4,697,588 A | 10/1987 | Reichenberger |
| 4,754,760 A | 7/1988 | Fukukita et al. |
| 4,757,820 A | 7/1988 | Itoh |
| 4,771,205 A | 9/1988 | Mequio |
| 4,801,459 A | 1/1989 | Liburdy |
| 4,803,625 A | 2/1989 | Fu et al. |
| 4,807,633 A | 2/1989 | Fry |
| 4,817,615 A | 4/1989 | Fukukita et al. |
| 4,858,613 A | 8/1989 | Fry |
| 4,860,732 A | 8/1989 | Hasegawa et al. |
| 4,865,041 A | 9/1989 | Hassler |
| 4,865,042 A | 9/1989 | Umemura |
| 4,867,169 A | 9/1989 | Machida |
| 4,874,562 A | 10/1989 | Hyon |
| 4,875,487 A | 10/1989 | Seppi |
| 4,881,212 A | 11/1989 | Takeuchi |
| 4,891,043 A | 1/1990 | Zeimer et al. |
| 4,893,624 A | 1/1990 | Lele |
| 4,896,673 A | 1/1990 | Rose |
| 4,900,540 A | 2/1990 | Ryan et al. |
| 4,901,729 A | 2/1990 | Saitoh |
| 4,917,096 A | 4/1990 | Englehart |
| 4,932,414 A | 6/1990 | Coleman et al. |
| 4,938,216 A | 7/1990 | Lele |
| 4,938,217 A | 7/1990 | Lele |
| 4,947,046 A | 8/1990 | Kawabata et al. |
| 4,951,653 A | 8/1990 | Fry |
| 4,955,365 A | 9/1990 | Fry |
| 4,958,626 A | 9/1990 | Nambu |
| 4,976,709 A | 12/1990 | Sand |
| 4,979,501 A | 12/1990 | Valchanov |
| 4,992,989 A | 2/1991 | Watanabe et al. |
| 5,012,797 A | 5/1991 | Liang |
| 5,018,508 A | 5/1991 | Fry et al. |
| 5,030,874 A | 7/1991 | Saito et al. |
| 5,036,855 A | 8/1991 | Fry |
| 5,040,537 A | 8/1991 | Katakura |
| 5,054,310 A | 10/1991 | Flynn |
| 5,054,470 A | 10/1991 | Fry |
| 5,054,491 A | 10/1991 | Saito et al. |
| 5,070,879 A | 12/1991 | Herres |
| 5,088,495 A | 2/1992 | Miyagawa |
| 5,115,814 A | 5/1992 | Griffith |
| 5,117,832 A | 6/1992 | Sanghvi |
| 5,123,418 A | 6/1992 | Saurel |
| 5,142,511 A | 8/1992 | Kanai et al. |
| 5,143,063 A | 9/1992 | Fellner |
| 5,143,074 A | 9/1992 | Dory |
| 5,149,319 A | 9/1992 | Unger |
| 5,150,711 A | 9/1992 | Dory |
| 5,150,714 A | 9/1992 | Green |
| 5,152,294 A | 10/1992 | Mochizuki et al. |
| 5,156,144 A | 10/1992 | Iwasaki |
| 5,158,536 A | 10/1992 | Sekins |
| 5,159,931 A | 11/1992 | Pini |
| 5,163,421 A | 11/1992 | Bernstein |
| 5,163,436 A | 11/1992 | Saitoh et al. |
| 5,178,135 A | 1/1993 | Uchiyama et al. |
| 5,190,518 A | 3/1993 | Takasu |
| 5,190,766 A | 3/1993 | Ishihara |

(56) References Cited

U.S. PATENT DOCUMENTS

| | | |
|---|---|---|
| 5,191,880 A | 3/1993 | McLeod |
| 5,205,287 A | 4/1993 | Erbel et al. |
| 5,209,720 A | 5/1993 | Unger |
| 5,212,671 A | 5/1993 | Fujii et al. |
| 5,215,680 A | 6/1993 | D'Arrigo |
| 5,224,467 A | 7/1993 | Oku |
| 5,230,334 A | 7/1993 | Klopotek |
| 5,230,338 A | 7/1993 | Allen et al. |
| 5,247,924 A | 9/1993 | Suzuki et al. |
| 5,255,681 A | 10/1993 | Ishimura et al. |
| 5,257,970 A | 11/1993 | Dougherty |
| 5,265,614 A | 11/1993 | Hayakawa |
| 5,267,985 A | 12/1993 | Shimada |
| 5,269,297 A | 12/1993 | Weng |
| 5,282,797 A | 2/1994 | Chess |
| 5,295,484 A | 3/1994 | Marcus |
| 5,295,486 A | 3/1994 | Wollschlager et al. |
| 5,304,169 A | 4/1994 | Sand |
| 5,305,756 A | 4/1994 | Entrekin et al. |
| 5,321,520 A | 6/1994 | Inga et al. |
| 5,323,779 A | 6/1994 | Hardy et al. |
| 5,327,895 A | 7/1994 | Hashimoto et al. |
| 5,329,202 A | 7/1994 | Garlick et al. |
| 5,348,016 A | 9/1994 | Unger et al. |
| 5,358,466 A | 10/1994 | Aida et al. |
| 5,360,268 A | 11/1994 | Hayashi |
| 5,370,121 A | 12/1994 | Reichenberger |
| 5,370,122 A | 12/1994 | Kunig et al. |
| 5,371,483 A | 12/1994 | Bhardwaj |
| 5,375,602 A | 12/1994 | Lancee et al. |
| 5,379,773 A | 1/1995 | Hornsby |
| 5,380,280 A | 1/1995 | Peterson |
| 5,380,519 A | 1/1995 | Schneider et al. |
| 5,383,917 A | 1/1995 | Desai et al. |
| 5,391,140 A | 2/1995 | Schaetzle et al. |
| 5,391,197 A | 2/1995 | Burdette et al. |
| 5,392,259 A | 2/1995 | Bolorforosh |
| 5,396,143 A | 3/1995 | Seyed-Bolorforosh et al. |
| 5,398,689 A | 3/1995 | Connor et al. |
| 5,406,503 A | 4/1995 | Williams |
| 5,413,550 A | 5/1995 | Castel |
| 5,417,216 A | 5/1995 | Tanaka |
| 5,419,327 A | 5/1995 | Rohwedder |
| 5,423,220 A | 6/1995 | Finsterwald et al. |
| 5,435,311 A | 7/1995 | Umemura |
| 5,438,998 A | 8/1995 | Hanafy |
| 5,443,068 A | 8/1995 | Cline et al. |
| 5,445,611 A | 8/1995 | Eppstein et al. |
| 5,458,596 A | 10/1995 | Lax |
| 5,460,179 A | 10/1995 | Okunuki et al. |
| 5,460,595 A | 10/1995 | Hall et al. |
| 5,469,854 A | 11/1995 | Unger et al. |
| 5,471,488 A | 12/1995 | Fujio |
| 5,472,405 A | 12/1995 | Buchholtz et al. |
| 5,487,388 A | 1/1996 | Rello et al. |
| 5,492,126 A | 2/1996 | Hennige |
| 5,496,256 A | 3/1996 | Bock |
| 5,501,655 A | 3/1996 | Rolt |
| 5,503,152 A | 4/1996 | Oakley et al. |
| 5,503,320 A | 4/1996 | Webster et al. |
| 5,507,790 A | 4/1996 | Weiss |
| 5,511,296 A | 4/1996 | Dias et al. |
| 5,520,188 A | 5/1996 | Hennige |
| 5,522,869 A | 6/1996 | Burdette |
| 5,523,058 A | 6/1996 | Umemura et al. |
| 5,524,620 A | 6/1996 | Rosenchein |
| 5,524,624 A | 6/1996 | Tepper |
| 5,524,625 A | 6/1996 | Okazaki |
| 5,526,624 A | 6/1996 | Berg |
| 5,526,812 A | 6/1996 | Dumoulin et al. |
| 5,526,814 A | 6/1996 | Cline et al. |
| 5,526,815 A | 6/1996 | Granz |
| 5,529,070 A | 6/1996 | Augustine et al. |
| 5,540,235 A | 7/1996 | Wilson |
| 5,558,092 A | 9/1996 | Unger |
| 5,560,362 A | 10/1996 | Sliwa et al. |
| 5,573,497 A | 11/1996 | Chapelon |
| 5,575,291 A | 11/1996 | Hayakawa |
| 5,575,807 A | 11/1996 | Faller |
| 5,577,502 A | 11/1996 | Darrow et al. |
| 5,577,507 A | 11/1996 | Snyder et al. |
| 5,577,991 A | 11/1996 | Akui et al. |
| 5,580,575 A | 12/1996 | Unger et al. |
| 5,643,179 A | 1/1997 | Fujimoto |
| 5,601,526 A | 2/1997 | Chapelon |
| 5,603,323 A | 2/1997 | Pflugrath et al. |
| 5,605,154 A | 2/1997 | Ries et al. |
| 5,609,562 A | 3/1997 | Kaali |
| 5,615,091 A | 3/1997 | Palatnik |
| 5,618,275 A | 4/1997 | Bock |
| 5,620,479 A | 4/1997 | Diederich |
| 5,622,175 A | 4/1997 | Sudol et al. |
| 5,617,858 A | 5/1997 | Taverna et al. |
| 5,638,819 A | 6/1997 | Manwaring et al. |
| 5,644,085 A | 7/1997 | Lorraine et al. |
| 5,647,373 A | 7/1997 | Paltieli |
| 5,655,535 A | 8/1997 | FrIemel et al. |
| 5,655,538 A | 8/1997 | Lorraine |
| 5,657,760 A | 8/1997 | Ying |
| 5,658,328 A | 8/1997 | Johnson |
| 5,660,836 A | 8/1997 | Knowlton |
| 5,662,116 A | 9/1997 | Kondo |
| 5,665,053 A | 9/1997 | Jacobs |
| 5,665,141 A | 9/1997 | Vago |
| 5,671,746 A | 9/1997 | Dreschel et al. |
| 5,673,699 A | 10/1997 | Trahey et al. |
| 5,676,692 A | 10/1997 | Sanghvi |
| 5,685,820 A | 11/1997 | Riek et al. |
| 5,690,608 A | 11/1997 | Watanabe |
| 5,694,936 A | 12/1997 | Fujimoto |
| 5,697,897 A | 12/1997 | Buchholtz |
| 5,701,900 A | 12/1997 | Shehada et al. |
| 5,704,361 A | 1/1998 | Seward et al. |
| 5,706,252 A | 1/1998 | Le Verrier et al. |
| 5,706,564 A | 1/1998 | Rhyne |
| 5,715,823 A | 2/1998 | Wood et al. |
| 5,720,287 A | 2/1998 | Chapelon et al. |
| 5,722,411 A | 3/1998 | Suzuki |
| 5,727,554 A | 3/1998 | Kalend et al. |
| 5,735,280 A | 4/1998 | Sherman et al. |
| 5,743,863 A | 4/1998 | Chapelon |
| 5,746,005 A | 5/1998 | Steinberg |
| 5,746,762 A | 5/1998 | Bass |
| 5,748,767 A | 5/1998 | Raab |
| 5,749,364 A | 5/1998 | Sliwa et al. |
| 5,755,228 A | 5/1998 | Wilson et al. |
| 5,755,753 A | 5/1998 | Knowlton |
| 5,762,066 A | 6/1998 | Law |
| 5,763,886 A | 6/1998 | Schulte |
| 5,769,790 A | 6/1998 | Watkins |
| 5,779,644 A | 7/1998 | Eberle et al. |
| 5,792,058 A | 8/1998 | Lee |
| 5,795,297 A | 8/1998 | Daigle |
| 5,795,311 A | 8/1998 | Wess |
| 5,810,009 A | 9/1998 | Mine et al. |
| 5,810,888 A | 9/1998 | Fenn |
| 5,814,599 A | 9/1998 | Mitragotri et al. |
| 5,817,013 A | 10/1998 | Ginn et al. |
| 5,817,021 A | 10/1998 | Reichenberger |
| 5,820,564 A | 10/1998 | Slayton |
| 5,823,962 A | 10/1998 | Schaetzle |
| 5,827,204 A | 10/1998 | Grandia et al. |
| 5,840,032 A | 11/1998 | Hatfield et al. |
| 5,844,140 A | 12/1998 | Seale |
| 5,853,367 A | 12/1998 | Chalek et al. |
| 5,869,751 A | 2/1999 | Bonin |
| 5,871,524 A | 2/1999 | Knowlton |
| 5,873,902 A | 2/1999 | Sanghvi |
| 5,876,341 A | 3/1999 | Wang et al. |
| 5,879,303 A | 3/1999 | Averkiou et al. |
| 5,882,557 A | 3/1999 | Hayakawa |
| 5,891,034 A | 4/1999 | Bucholz |
| 5,895,356 A | 4/1999 | Andrus et al. |
| 5,899,861 A | 5/1999 | Friemel et al. |

(56) References Cited

U.S. PATENT DOCUMENTS

| | | |
|---|---|---|
| 5,904,659 A | 5/1999 | Duarte |
| 5,919,219 A | 7/1999 | Knowlton |
| 5,923,099 A | 7/1999 | Bilir |
| 5,924,989 A | 7/1999 | Polz |
| 5,928,169 A | 7/1999 | Schatzle et al. |
| 5,931,805 A | 8/1999 | Brisken |
| 5,938,606 A | 8/1999 | Bonnefous |
| 5,938,612 A | 8/1999 | Kline-Schoder |
| 5,948,011 A | 9/1999 | Knowlton |
| 5,957,844 A | 9/1999 | Dekel |
| 5,957,882 A | 9/1999 | Nita et al. |
| 5,957,941 A | 9/1999 | Ream |
| 5,964,707 A | 10/1999 | Fenster et al. |
| 5,967,980 A | 10/1999 | Ferre et al. |
| 5,968,034 A | 10/1999 | Fullmer |
| 5,971,949 A | 10/1999 | Levin |
| 5,977,538 A | 11/1999 | Unger et al. |
| 5,984,881 A | 11/1999 | Ishibashi et al. |
| 5,984,882 A | 11/1999 | Rosenchein |
| 5,990,598 A | 11/1999 | Sudol et al. |
| 5,997,471 A | 12/1999 | Gumb et al. |
| 5,997,497 A | 12/1999 | Nita et al. |
| 5,999,843 A | 12/1999 | Anbar |
| 6,004,262 A | 12/1999 | Putz et al. |
| 6,007,499 A | 12/1999 | Martin et al. |
| 6,013,032 A | 1/2000 | Savord |
| 6,014,473 A | 1/2000 | Hossack et al. |
| 6,016,255 A | 1/2000 | Bolan et al. |
| 6,019,724 A | 2/2000 | Gronningsaeter et al. |
| 6,022,308 A | 2/2000 | Williams |
| 6,022,317 A | 2/2000 | Cruanas et al. |
| 6,022,327 A | 2/2000 | Chang |
| 6,030,374 A | 2/2000 | McDaniel |
| 6,036,646 A | 3/2000 | Barthe |
| 6,039,048 A | 3/2000 | Silberg |
| 6,039,689 A | 3/2000 | Lizzi |
| 6,042,556 A | 3/2000 | Beach |
| 6,049,159 A | 4/2000 | Barthe |
| 6,050,943 A | 4/2000 | Slayton |
| 6,059,727 A | 5/2000 | Fowlkes |
| 6,071,239 A | 6/2000 | Cribbs |
| 6,080,108 A | 6/2000 | Dunham |
| 6,083,148 A | 7/2000 | Williams |
| 6,086,535 A | 7/2000 | Ishibashi |
| 6,086,580 A | 7/2000 | Mordon et al. |
| 6,090,054 A | 7/2000 | Tagishi |
| 6,093,148 A | 7/2000 | Fujimoto |
| 6,093,883 A | 7/2000 | Sanghvi |
| 6,101,407 A | 8/2000 | Groezinger |
| 6,106,469 A | 8/2000 | Suzuki et al. |
| 6,113,558 A | 9/2000 | Rosenchein |
| 6,113,559 A | 9/2000 | Klopotek |
| 6,120,452 A | 9/2000 | Barthe |
| 6,123,081 A | 9/2000 | Durette |
| 6,126,619 A | 10/2000 | Peterson et al. |
| 6,135,971 A | 10/2000 | Hutchinson |
| 6,139,499 A | 10/2000 | Wilk |
| 6,159,150 A | 12/2000 | Yale et al. |
| 6,171,244 B1 | 1/2001 | Finger et al. |
| 6,176,840 B1 | 1/2001 | Nishimura |
| 6,183,426 B1 | 2/2001 | Akisada |
| 6,183,502 B1 | 2/2001 | Takeuchi |
| 6,183,773 B1 | 2/2001 | Anderson |
| 6,190,323 B1 | 2/2001 | Dias |
| 6,190,336 B1 | 2/2001 | Duarte |
| 6,193,658 B1 | 2/2001 | Wendelken |
| 6,198,956 B1 | 3/2001 | Dunne |
| 6,210,327 B1 | 4/2001 | Brackett et al. |
| 6,213,948 B1 | 4/2001 | Barthe |
| 6,216,029 B1 | 4/2001 | Paltieli |
| 6,233,476 B1 | 5/2001 | Strommer et al. |
| 6,234,990 B1 | 5/2001 | Rowe et al. |
| 6,241,753 B1 | 6/2001 | Knowlton |
| 6,246,898 B1 | 6/2001 | Vesely et al. |
| 6,251,074 B1 | 6/2001 | Averkiou et al. |
| 6,251,088 B1 | 6/2001 | Kaufman et al. |
| 6,268,405 B1 | 7/2001 | Yao |
| 6,273,864 B1 | 8/2001 | Duarte |
| 6,280,402 B1 | 8/2001 | Ishibashi et al. |
| 6,287,257 B1 | 9/2001 | Matichuk |
| 6,287,304 B1 | 9/2001 | Eggers et al. |
| 6,296,619 B1 | 10/2001 | Brisken |
| 6,301,989 B1 | 10/2001 | Brown et al. |
| 6,307,302 B1 | 10/2001 | Toda |
| 6,309,355 B1 | 10/2001 | Cain et al. |
| 6,311,090 B1 | 10/2001 | Knowlton |
| 6,315,741 B1 | 11/2001 | Martin |
| 6,322,509 B1 | 11/2001 | Pan et al. |
| 6,322,532 B1 | 11/2001 | D'Sa |
| 6,325,540 B1 | 12/2001 | Lounsberry et al. |
| 6,325,758 B1 | 12/2001 | Carol et al. |
| 6,325,769 B1 | 12/2001 | Klopotek |
| 6,325,798 B1 | 12/2001 | Edwards et al. |
| 6,338,716 B1 | 1/2002 | Hossack et al. |
| 6,350,276 B1 | 2/2002 | Knowlton |
| 6,356,780 B1 | 3/2002 | Licato et al. |
| 6,361,531 B1 | 3/2002 | Hissong |
| 6,370,411 B1 | 4/2002 | Osadchy et al. |
| 6,375,672 B1 | 4/2002 | Aksan |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,390,982 B1 | 5/2002 | Bova et al. |
| 6,405,090 B1 | 6/2002 | Knowlton |
| 6,409,720 B1 | 6/2002 | Hissong |
| 6,413,216 B1 | 7/2002 | Cain et al. |
| 6,413,253 B1 | 7/2002 | Koop |
| 6,413,254 B1 | 7/2002 | Hissong |
| 6,419,648 B1 | 7/2002 | Vitek |
| 6,423,007 B2 | 7/2002 | Lizzi et al. |
| 6,425,865 B1 | 7/2002 | Salcudean |
| 6,425,867 B1 | 7/2002 | Vaezy |
| 6,425,912 B1 | 7/2002 | Knowlton |
| 6,428,477 B1 | 8/2002 | Mason |
| 6,428,532 B1 | 8/2002 | Doukas |
| 6,430,446 B1 | 8/2002 | Knowlton |
| 6,432,057 B1 | 8/2002 | Mazess et al. |
| 6,432,067 B1 | 8/2002 | Martin |
| 6,432,101 B1 | 8/2002 | Weber |
| 6,436,061 B1 | 8/2002 | Costantino |
| 6,438,424 B1 | 8/2002 | Knowlton |
| 6,440,071 B1 | 8/2002 | Slayton |
| 6,440,121 B1 | 8/2002 | Weber |
| 6,443,914 B1 | 9/2002 | Costantino |
| 6,447,443 B1 | 9/2002 | Keogh et al. |
| 6,451,013 B1 | 9/2002 | Bays et al. |
| 6,453,202 B1 | 9/2002 | Knowlton |
| 6,461,304 B1 | 10/2002 | Tanaka et al. |
| 6,461,378 B1 | 10/2002 | Knowlton |
| 6,470,216 B1 | 10/2002 | Knowlton |
| 6,488,626 B1 | 12/2002 | Lizzi |
| 6,491,657 B2 | 12/2002 | Rowe |
| 6,500,121 B1 | 12/2002 | Slayton |
| 6,500,141 B1 | 12/2002 | Irion |
| 6,506,171 B1 | 1/2003 | Vitek et al. |
| 6,508,774 B1 | 1/2003 | Acker |
| 6,511,427 B1 | 1/2003 | Sliwa, Jr. et al. |
| 6,511,428 B1 | 1/2003 | Azuma |
| 6,514,244 B2 | 2/2003 | Pope |
| 6,517,484 B1 | 2/2003 | Wilk |
| 6,524,250 B1 | 2/2003 | Weber |
| 6,666,835 B2 | 3/2003 | Martin |
| 6,540,679 B2 | 4/2003 | Slayton |
| 6,540,685 B1 | 4/2003 | Rhoads et al. |
| 6,540,700 B1 | 4/2003 | Fujimoto et al. |
| 6,547,788 B1 | 4/2003 | Maguire et al. |
| 6,554,771 B1 | 4/2003 | Buil et al. |
| 6,569,099 B1 | 5/2003 | Babaev |
| 6,569,108 B2 | 5/2003 | Sarvazyan et al. |
| 6,572,552 B2 | 6/2003 | Fukukita |
| 6,575,956 B1 | 6/2003 | Brisken et al. |
| 6,595,934 B1 | 7/2003 | Hissong |

(56) References Cited

U.S. PATENT DOCUMENTS

| | | |
|---|---|---|
| 6,599,256 B1 | 7/2003 | Acker |
| 6,605,043 B1 | 8/2003 | Dreschel |
| 6,605,080 B1 | 8/2003 | Altshuler et al. |
| 6,607,498 B2 | 8/2003 | Eshel |
| 6,618,620 B1 | 9/2003 | Freundlich et al. |
| 6,623,430 B1 | 9/2003 | Slayton |
| 6,626,854 B2 | 9/2003 | Friedman |
| 6,626,855 B1 | 9/2003 | Weng |
| 6,638,226 B2 | 10/2003 | He et al. |
| 6,645,150 B2 | 11/2003 | Angelsen et al. |
| 6,645,162 B2 | 11/2003 | Friedman |
| 6,662,054 B2 | 12/2003 | Kreindel |
| 6,663,627 B2 | 12/2003 | Francischelli |
| 6,665,806 B1 | 12/2003 | Shimizu |
| 6,669,638 B1 | 12/2003 | Miller |
| 6,685,639 B1 | 2/2004 | Wang et al. |
| 6,685,640 B1 | 2/2004 | Fry |
| 6,692,450 B1 | 2/2004 | Coleman |
| 6,699,237 B2 | 3/2004 | Weber |
| 6,716,184 B2 | 4/2004 | Vaezy et al. |
| 6,719,449 B1 | 4/2004 | Laughlin |
| 6,719,694 B2 | 4/2004 | Weng |
| 6,726,627 B1 | 4/2004 | Lizzi et al. |
| 6,733,449 B1 | 5/2004 | Krishnamurthy et al. |
| 6,749,624 B2 | 6/2004 | Knowlton |
| 6,772,490 B2 | 8/2004 | Toda |
| 6,773,409 B2 | 8/2004 | Truckai et al. |
| 6,775,404 B1 | 8/2004 | Pagoulatos et al. |
| 6,790,187 B2 | 9/2004 | Thompson et al. |
| 6,824,516 B2 | 11/2004 | Batten et al. |
| 6,825,176 B2 | 11/2004 | White et al. |
| 6,835,940 B2 | 12/2004 | Morikawa et al. |
| 6,846,290 B2 | 1/2005 | Lizzi et al. |
| 6,875,176 B2 | 4/2005 | Mourad et al. |
| 6,882,884 B1 | 4/2005 | Mosk et al. |
| 6,887,239 B2 | 5/2005 | Elstrom |
| 6,889,089 B2 | 5/2005 | Behl |
| 6,896,657 B2 | 5/2005 | Willis |
| 6,902,536 B2 | 6/2005 | Manna |
| 6,905,466 B2 | 6/2005 | Salgo |
| 6,918,907 B2 | 7/2005 | Kelly |
| 6,920,883 B2 | 7/2005 | Bessette |
| 6,921,371 B2 | 7/2005 | Wilson |
| 6,932,771 B2 | 8/2005 | Whitmore |
| 6,932,814 B2 | 8/2005 | Wood |
| 6,936,044 B2 | 8/2005 | McDaniel |
| 6,936,046 B2 | 8/2005 | Hissong |
| 6,945,937 B2 | 9/2005 | Culp et al. |
| 6,948,843 B2 | 9/2005 | Laugharn et al. |
| 6,953,941 B2 | 10/2005 | Nakano et al. |
| 6,958,043 B2 | 10/2005 | Hissong |
| 6,971,994 B1 | 12/2005 | Young et al. |
| 6,974,417 B2 | 12/2005 | Lockwood |
| 6,976,492 B2 | 12/2005 | Ingle |
| 6,992,305 B2 | 1/2006 | Maezawa et al. |
| 6,997,923 B2 | 2/2006 | Anderson |
| 7,006,874 B2 | 2/2006 | Knowlton |
| 7,020,528 B2 | 3/2006 | Neev |
| 7,022,089 B2 | 4/2006 | Ooba |
| 7,058,440 B2 | 6/2006 | Heuscher et al. |
| 7,063,666 B2 | 6/2006 | Weng |
| 7,070,565 B2 | 7/2006 | Vaezy et al. |
| 7,074,218 B2 | 7/2006 | Washington et al. |
| 7,094,252 B2 | 8/2006 | Koop |
| 7,108,663 B2 | 9/2006 | Talish et al. |
| 7,115,123 B2 | 10/2006 | Knowlton |
| 7,122,029 B2 | 10/2006 | Koop et al. |
| 7,142,905 B2 | 11/2006 | Slayton |
| 7,165,451 B1 | 1/2007 | Brooks et al. |
| 7,179,238 B2 | 2/2007 | Hissong |
| 7,189,230 B2 | 3/2007 | Knowlton |
| 7,229,411 B2 | 6/2007 | Slayton |
| 7,235,592 B2 | 6/2007 | Muratoglu |
| 7,258,674 B2 | 8/2007 | Cribbs |
| 7,273,459 B2 | 9/2007 | Desilets |
| 7,294,125 B2 | 11/2007 | Phalen et al. |
| 7,297,117 B2 | 11/2007 | Trucco |
| 7,303,555 B2 | 12/2007 | Makin et al. |
| 7,311,679 B2 | 12/2007 | Desilets et al. |
| 7,327,071 B2 | 2/2008 | Nishiyama et al. |
| 7,331,951 B2 | 2/2008 | Eshel et al. |
| 7,332,985 B2 | 2/2008 | Larson et al. |
| 7,338,434 B1 | 3/2008 | Haarstad et al. |
| 7,347,855 B2 | 3/2008 | Eshel |
| RE40,403 E | 6/2008 | Cho et al. |
| 7,393,325 B2 | 7/2008 | Barthe |
| 7,398,116 B2 | 7/2008 | Edwards |
| 7,399,279 B2 | 7/2008 | Abend et al. |
| 7,491,171 B2 | 2/2009 | Barthe et al. |
| 7,507,235 B2 | 3/2009 | Keogh et al. |
| 7,510,536 B2 | 3/2009 | Foley et al. |
| 7,517,315 B2 | 4/2009 | Willis |
| 7,530,356 B2 | 5/2009 | Slayton |
| 7,530,958 B2 | 5/2009 | Slayton |
| 7,532,201 B2 | 5/2009 | Quistgaard et al. |
| 7,571,336 B2 | 8/2009 | Barthe |
| 7,601,120 B2 | 10/2009 | Moilanen et al. |
| 7,615,015 B2 | 11/2009 | Coleman |
| 7,615,016 B2 | 11/2009 | Barthe |
| 7,631,611 B1 | 12/2009 | Dick et al. |
| 7,652,411 B2 | 1/2010 | Crunkilton et al. |
| 7,662,114 B2 | 2/2010 | Seip et al. |
| 7,674,257 B2 | 3/2010 | Pless et al. |
| 7,686,763 B2 | 3/2010 | Vaezy et al. |
| 7,713,203 B2 | 3/2010 | Lacoste et al. |
| 7,694,406 B2 | 4/2010 | Wildes et al. |
| 7,695,437 B2 | 4/2010 | Quistgaard et al. |
| 7,727,156 B2 | 6/2010 | Angelsen et al. |
| 7,758,524 B2 | 7/2010 | Barthe |
| 7,766,848 B2 | 8/2010 | Desilets et al. |
| 7,789,841 B2 | 9/2010 | Huckle et al. |
| 7,806,839 B2 | 10/2010 | Mast et al. |
| 7,815,570 B2 | 10/2010 | Eshel et al. |
| 7,819,826 B2 | 10/2010 | Diederich et al. |
| 7,828,734 B2 | 10/2010 | Azhari et al. |
| 7,824,348 B2 | 11/2010 | Barthe |
| 7,833,162 B2 | 11/2010 | Hasegawa et al. |
| 7,841,984 B2 | 11/2010 | Cribbs et al. |
| 7,846,096 B2 | 12/2010 | Mast et al. |
| 7,857,773 B2 | 12/2010 | Desilets et al. |
| 7,875,023 B2 | 1/2011 | Eshel et al. |
| 7,901,359 B2 | 3/2011 | Mandrusov et al. |
| 7,905,007 B2 | 3/2011 | Calisti et al. |
| 7,905,844 B2 | 3/2011 | Desilets et al. |
| 7,914,453 B2 | 3/2011 | Slayton et al. |
| 7,914,469 B2 | 3/2011 | Torbati |
| 7,955,281 B2 | 6/2011 | Pedersen et al. |
| 7,967,764 B2 | 6/2011 | Lidgren et al. |
| 7,967,839 B2 | 6/2011 | Flock et al. |
| 7,955,262 B2 | 7/2011 | Rosenberg |
| 7,993,289 B2 | 8/2011 | Quistgaard et al. |
| 8,057,465 B2 | 9/2011 | Sliwa, Jr. et al. |
| 8,057,389 B2 | 11/2011 | Barthe et al. |
| 8,066,641 B2 | 11/2011 | Barthe et al. |
| 8,123,707 B2 | 2/2012 | Huckle et al. |
| 8,128,618 B2 | 3/2012 | Gliklich et al. |
| 8,133,180 B2 | 3/2012 | Slayton et al. |
| 8,133,191 B2 | 3/2012 | Rosenberg et al. |
| 8,142,200 B2 | 3/2012 | Crunkilton et al. |
| 8,152,904 B2 | 4/2012 | Slobodzian et al. |
| 8,162,858 B2 | 4/2012 | Manna et al. |
| 8,166,332 B2 | 4/2012 | Barthe et al. |
| 8,182,428 B2 | 5/2012 | Angelsen et al. |
| 8,197,409 B2 | 6/2012 | Foley et al. |
| 8,206,299 B2 | 6/2012 | Foley et al. |
| 8,208,346 B2 | 6/2012 | Crunkilton |
| 8,211,017 B2 | 7/2012 | Foley et al. |
| 8,262,591 B2 | 9/2012 | Pedersen et al. |
| 8,262,650 B2 | 9/2012 | Zanelli et al. |
| 8,264,126 B2 | 9/2012 | Toda et al. |
| 8,273,037 B2 | 9/2012 | Kreindel et al. |
| 8,282,554 B2 | 10/2012 | Makin et al. |
| 8,292,835 B1 | 10/2012 | Cimino |
| 8,298,163 B1 | 10/2012 | Cimino |

(56) References Cited

U.S. PATENT DOCUMENTS

| | | |
|---|---|---|
| 8,333,700 B1 | 12/2012 | Barthe et al. |
| 8,334,637 B2 | 12/2012 | Crunkilton et al. |
| 8,337,407 B2 | 12/2012 | Quistgaard et al. |
| 8,343,051 B2 | 1/2013 | Desilets et al. |
| 8,454,540 B2 | 1/2013 | Eshel et al. |
| 8,366,622 B2 * | 2/2013 | Slayton .................. A61B 5/682 600/439 |
| 8,398,549 B2 | 3/2013 | Palmeri et al. |
| 8,409,097 B2 | 4/2013 | Slayton et al. |
| 8,425,435 B2 | 4/2013 | Wing et al. |
| 8,388,535 B2 | 5/2013 | Weng et al. |
| 8,444,562 B2 * | 5/2013 | Barthe .................. A61B 5/7405 600/437 |
| 8,460,193 B2 | 6/2013 | Barthe et al. |
| 8,480,585 B2 | 7/2013 | Slayton et al. |
| 8,486,001 B2 | 7/2013 | Weyant |
| 8,506,486 B2 * | 8/2013 | Slayton .................. A61B 5/682 600/439 |
| 8,512,250 B2 | 8/2013 | Quistgaard et al. |
| 8,523,775 B2 | 9/2013 | Barthe et al. |
| 8,535,228 B2 | 9/2013 | Slayton et al. |
| 8,570,837 B2 | 10/2013 | Toda et al. |
| 8,573,392 B2 | 11/2013 | Bennett et al. |
| 8,583,211 B2 | 11/2013 | Salomir et al. |
| 8,585,618 B2 | 11/2013 | Hunziker et al. |
| 8,604,672 B2 | 12/2013 | Toda et al. |
| 8,622,937 B2 | 1/2014 | Weng et al. |
| 8,636,665 B2 | 1/2014 | Slayton et al. |
| 8,640,193 B2 | 1/2014 | Shigeeda |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,708,935 B2 | 4/2014 | Barthe et al. |
| 8,715,186 B2 | 5/2014 | Slayton et al. |
| 8,726,781 B2 | 5/2014 | Eckhoff et al. |
| 8,728,071 B2 | 5/2014 | Lischinsky et al. |
| 8,753,295 B2 | 6/2014 | Thierman |
| 8,758,253 B2 | 6/2014 | Sano et al. |
| 8,836,203 B2 | 9/2014 | Nobles et al. |
| 8,857,438 B2 | 10/2014 | Barthe et al. |
| 8,858,471 B2 | 10/2014 | Barthe et al. |
| 8,915,853 B2 * | 12/2014 | Barthe .................. A61B 5/7405 600/437 |
| 8,915,854 B2 | 12/2014 | Slayton et al. |
| 8,915,870 B2 | 12/2014 | Barthe et al. |
| 8,920,320 B2 | 12/2014 | Stecco et al. |
| 8,920,324 B2 | 12/2014 | Slayton et al. |
| 8,926,533 B2 | 1/2015 | Bockenstedt et al. |
| 8,932,224 B2 | 1/2015 | Barthe et al. |
| 8,932,238 B2 | 1/2015 | Wing et al. |
| 8,968,205 B2 | 3/2015 | Zeng et al. |
| 9,011,336 B2 | 4/2015 | Slayton et al. |
| 9,039,617 B2 | 5/2015 | Slayton et al. |
| 9,039,619 B2 | 5/2015 | Barthe et al. |
| 9,095,697 B2 | 8/2015 | Barthe et al. |
| 9,114,247 B2 | 8/2015 | Barthe et al. |
| 9,216,276 B2 | 12/2015 | Slayton et al. |
| 9,272,162 B2 | 3/2016 | Slayton et al. |
| 9,283,409 B2 | 3/2016 | Slayton et al. |
| 9,283,410 B2 | 3/2016 | Slayton et al. |
| 9,320,537 B2 | 4/2016 | Slayton et al. |
| 9,421,029 B2 | 8/2016 | Barthe et al. |
| 9,427,600 B2 | 8/2016 | Barthe et al. |
| 9,427,601 B2 * | 8/2016 | Barthe .................. A61B 5/7405 |
| 9,440,096 B2 | 9/2016 | Barthe et al. |
| 9,510,802 B2 | 12/2016 | Barthe et al. |
| 9,522,290 B2 | 12/2016 | Slayton et al. |
| 9,533,175 B2 | 1/2017 | Slayton et al. |
| 9,694,211 B2 | 7/2017 | Barthe et al. |
| 9,694,212 B2 | 7/2017 | Barthe et al. |
| 9,707,412 B2 | 7/2017 | Slayton et al. |
| 9,713,731 B2 | 7/2017 | Slayton et al. |
| 9,802,063 B2 | 10/2017 | Barthe et al. |
| 9,827,449 B2 | 11/2017 | Barthe et al. |
| 9,827,450 B2 | 11/2017 | Slayton et al. |
| 9,833,639 B2 | 12/2017 | Slayton et al. |
| 9,833,640 B2 | 12/2017 | Barthe et al. |
| 9,907,535 B2 | 3/2018 | Barthe et al. |
| 2001/0009997 A1 | 7/2001 | Pope |
| 2001/0009999 A1 | 7/2001 | Kaufman et al. |
| 2001/0014780 A1 | 8/2001 | Martin |
| 2001/0014819 A1 | 8/2001 | Ingle |
| 2001/0031922 A1 | 10/2001 | Weng |
| 2001/0039380 A1 | 11/2001 | Larson et al. |
| 2001/0041880 A1 | 11/2001 | Brisken |
| 2002/0000763 A1 | 1/2002 | Jones |
| 2002/0002345 A1 | 1/2002 | Marlinghaus |
| 2002/0040199 A1 | 4/2002 | Klopotek |
| 2002/0040442 A1 | 4/2002 | Ishidera |
| 2002/0055702 A1 | 5/2002 | Atala |
| 2002/0062077 A1 | 5/2002 | Emmenegger |
| 2002/0062142 A1 | 5/2002 | Knowlton |
| 2002/0072691 A1 | 6/2002 | Thompson et al. |
| 2002/0082528 A1 | 6/2002 | Friedman |
| 2002/0082529 A1 | 6/2002 | Suorsa et al. |
| 2002/0082589 A1 | 6/2002 | Friedman |
| 2002/0087080 A1 | 7/2002 | Slayton |
| 2002/0095143 A1 | 7/2002 | Key |
| 2002/0099094 A1 | 7/2002 | Anderson |
| 2002/0115917 A1 | 8/2002 | Honda et al. |
| 2002/0128639 A1 | 8/2002 | Pless et al. |
| 2002/0128648 A1 | 9/2002 | Weber |
| 2002/0143252 A1 | 10/2002 | Dunne et al. |
| 2002/0156400 A1 | 10/2002 | Babaev |
| 2002/0161357 A1 | 10/2002 | Anderson |
| 2002/0165529 A1 | 11/2002 | Danek |
| 2002/0168049 A1 | 11/2002 | Schriever |
| 2002/0169394 A1 | 11/2002 | Eppstein et al. |
| 2002/0169442 A1 | 11/2002 | Neev |
| 2002/0173721 A1 | 11/2002 | Grunwald et al. |
| 2002/0193784 A1 | 12/2002 | McHale et al. |
| 2002/0193831 A1 | 12/2002 | Smith |
| 2003/0009153 A1 | 1/2003 | Brisken et al. |
| 2003/0014039 A1 | 1/2003 | Barzell et al. |
| 2003/0018255 A1 | 1/2003 | Martin |
| 2003/0018270 A1 | 1/2003 | Makin et al. |
| 2003/0023283 A1 | 1/2003 | McDaniel |
| 2003/0028111 A1 | 2/2003 | Vaezy et al. |
| 2003/0028113 A1 | 2/2003 | Gilbert et al. |
| 2003/0032900 A1 | 2/2003 | Ella |
| 2003/0036706 A1 | 2/2003 | Slayton et al. |
| 2003/0040739 A1 | 2/2003 | Koop |
| 2003/0050678 A1 | 3/2003 | Sierra |
| 2003/0055308 A1 | 3/2003 | Friemel et al. |
| 2003/0055417 A1 | 3/2003 | Truckai et al. |
| 2003/0060736 A1 | 3/2003 | Martin et al. |
| 2003/0065313 A1 | 4/2003 | Koop |
| 2003/0066708 A1 | 4/2003 | Allison et al. |
| 2003/0073907 A1 | 4/2003 | Taylor |
| 2003/0074023 A1 | 4/2003 | Kaplan |
| 2003/0083536 A1 | 5/2003 | Eshel |
| 2003/0092988 A1 | 5/2003 | Makin |
| 2003/0097071 A1 | 5/2003 | Halmann et al. |
| 2003/0099383 A1 | 5/2003 | Lefebvre |
| 2003/0125629 A1 | 7/2003 | Ustuner |
| 2003/0135135 A1 | 7/2003 | Miwa et al. |
| 2003/0139790 A1 | 7/2003 | Ingle et al. |
| 2003/0149366 A1 | 8/2003 | Stringer et al. |
| 2003/0153961 A1 | 8/2003 | Babaev |
| 2003/0171678 A1 | 9/2003 | Batten et al. |
| 2003/0171701 A1 | 9/2003 | Babaev |
| 2003/0176790 A1 | 9/2003 | Slayton |
| 2003/0191396 A1 | 10/2003 | Sanghvi |
| 2003/0199794 A1 | 10/2003 | Sakurai et al. |
| 2003/0200481 A1 | 10/2003 | Stanley |
| 2003/0212129 A1 | 11/2003 | Liu et al. |
| 2003/0212351 A1 | 11/2003 | Hissong |
| 2003/0212393 A1 | 11/2003 | Knowlton |
| 2003/0216648 A1 | 11/2003 | Lizzi et al. |
| 2003/0216795 A1 | 11/2003 | Harth |
| 2003/0220536 A1 | 11/2003 | Hissong |

(56) References Cited

U.S. PATENT DOCUMENTS

| | | |
|---|---|---|
| 2003/0220585 A1 | 11/2003 | Hissong |
| 2003/0229331 A1 | 12/2003 | Brisken et al. |
| 2003/0233085 A1 | 12/2003 | Giammarusti |
| 2003/0236487 A1 | 12/2003 | Knowlton |
| 2004/0000316 A1 | 1/2004 | Knowlton |
| 2004/0001809 A1 | 1/2004 | Brisken |
| 2004/0002658 A1 | 1/2004 | Marian, Jr. |
| 2004/0002705 A1 | 1/2004 | Knowlton |
| 2004/0010222 A1 | 1/2004 | Nunomura et al. |
| 2004/0015079 A1 | 1/2004 | Berger et al. |
| 2004/0015106 A1 | 1/2004 | Coleman |
| 2004/0030227 A1 | 2/2004 | Littrup |
| 2004/0030268 A1 | 2/2004 | Weng et al. |
| 2004/0039312 A1 | 2/2004 | Hillstead |
| 2004/0039418 A1 | 2/2004 | Elstrom |
| 2004/0041563 A1 | 3/2004 | Lewin et al. |
| 2004/0041880 A1 | 3/2004 | Ikeda et al. |
| 2004/0042168 A1 | 3/2004 | Yang et al. |
| 2004/0044375 A1 | 3/2004 | Diederich et al. |
| 2004/0049134 A1 | 3/2004 | Tosaya et al. |
| 2004/0049734 A1 | 3/2004 | Tosaya et al. |
| 2004/0059266 A1 | 3/2004 | Fry |
| 2004/0068186 A1 | 4/2004 | Ishida et al. |
| 2004/0073079 A1 | 4/2004 | Altshuler et al. |
| 2004/0073113 A1 | 4/2004 | Salgo |
| 2004/0073115 A1 | 4/2004 | Horzewski et al. |
| 2004/0073116 A1 | 4/2004 | Smith |
| 2004/0073204 A1 | 4/2004 | Ryan et al. |
| 2004/0077977 A1 | 4/2004 | Ella et al. |
| 2004/0082857 A1 | 4/2004 | Schonenberger |
| 2004/0082859 A1 | 4/2004 | Schaer |
| 2004/0102697 A1 | 5/2004 | Evron |
| 2004/0105559 A1 | 6/2004 | Aylward et al. |
| 2004/0106867 A1 | 6/2004 | Eshel et al. |
| 2004/0122323 A1 | 6/2004 | Vortman et al. |
| 2004/0122493 A1 | 6/2004 | Ishibashi et al. |
| 2004/0143297 A1 | 7/2004 | Ramsey |
| 2004/0152982 A1 | 8/2004 | Hwang et al. |
| 2004/0158150 A1 | 8/2004 | Rabiner et al. |
| 2004/0186535 A1 | 9/2004 | Knowlton |
| 2004/0189155 A1 | 9/2004 | Funakubo |
| 2004/0206365 A1 | 10/2004 | Knowlton |
| 2004/0210214 A1 | 10/2004 | Knowlton |
| 2004/0217675 A1 | 11/2004 | Desilets |
| 2004/0249318 A1 | 12/2004 | Tanaka |
| 2004/0254620 A1 | 12/2004 | Lacoste |
| 2004/0267252 A1 | 12/2004 | Washington et al. |
| 2005/0033201 A1 | 2/2005 | Takahashi |
| 2005/0033316 A1 | 2/2005 | Kertz |
| 2005/0038340 A1 | 2/2005 | Vaezy et al. |
| 2005/0055018 A1 | 3/2005 | Kreindel |
| 2005/0055073 A1 | 3/2005 | Weber |
| 2005/0061834 A1 | 3/2005 | Garcia et al. |
| 2005/0070961 A1 | 3/2005 | Maki |
| 2005/0074407 A1 | 4/2005 | Smith |
| 2005/0080469 A1 | 4/2005 | Larson |
| 2005/0085731 A1 | 4/2005 | Miller et al. |
| 2005/0091770 A1 | 5/2005 | Mourad et al. |
| 2005/0096542 A1 | 5/2005 | Weng |
| 2005/0104690 A1 | 5/2005 | Larson et al. |
| 2005/0113689 A1 | 5/2005 | Gritzky |
| 2005/0131302 A1 | 6/2005 | Poland |
| 2005/0137656 A1 | 6/2005 | Malak |
| 2005/0143677 A1 | 6/2005 | Young et al. |
| 2005/0154313 A1 | 7/2005 | Desilets |
| 2005/0154314 A1 | 7/2005 | Quistgaard |
| 2005/0154332 A1 | 7/2005 | Zanelli |
| 2005/0154431 A1 | 7/2005 | Quistgaard |
| 2005/0187495 A1 | 8/2005 | Quistgaard |
| 2005/0191252 A1 | 9/2005 | Mitsui |
| 2005/0193451 A1 | 9/2005 | Quistgaard |
| 2005/0193820 A1 | 9/2005 | Sheljaskow et al. |
| 2005/0197681 A1 | 9/2005 | Barolet et al. |
| 2005/0228281 A1 | 10/2005 | Nefos |
| 2005/0240127 A1 | 10/2005 | Seip et al. |
| 2005/0240170 A1 | 10/2005 | Zhang et al. |
| 2005/0251120 A1 | 11/2005 | Anderson et al. |
| 2005/0251125 A1 | 11/2005 | Pless et al. |
| 2005/0256406 A1 | 11/2005 | Barthe |
| 2005/0261584 A1 | 11/2005 | Eshel |
| 2005/0261585 A1 | 11/2005 | Makin et al. |
| 2005/0267454 A1 | 12/2005 | Hissong |
| 2005/0288748 A1 | 12/2005 | Li et al. |
| 2006/0004306 A1 | 1/2006 | Altshuler |
| 2006/0020260 A1 | 1/2006 | Dover et al. |
| 2006/0025756 A1 | 2/2006 | Francischelli |
| 2006/0042201 A1 | 3/2006 | Curry |
| 2006/0058664 A1 | 3/2006 | Barthe |
| 2006/0058671 A1 | 3/2006 | Vitek et al. |
| 2006/0058707 A1 | 3/2006 | Barthe |
| 2006/0058712 A1 | 3/2006 | Altshuler et al. |
| 2006/0074309 A1 | 4/2006 | Bonnefous |
| 2006/0074313 A1 | 4/2006 | Slayton et al. |
| 2006/0074314 A1 | 4/2006 | Slayton |
| 2006/0074355 A1 | 4/2006 | Slayton |
| 2006/0079816 A1 | 4/2006 | Barthe |
| 2006/0079868 A1 | 4/2006 | Makin |
| 2006/0084891 A1 | 4/2006 | Barthe |
| 2006/0089632 A1 | 4/2006 | Barthe |
| 2006/0089688 A1 | 4/2006 | Panescu |
| 2006/0094988 A1 | 5/2006 | Tosaya |
| 2006/0111744 A1 | 5/2006 | Makin |
| 2006/0116583 A1 | 6/2006 | Ogasawara et al. |
| 2006/0116671 A1 | 6/2006 | Slayton |
| 2006/0122508 A1 | 6/2006 | Slayton |
| 2006/0122509 A1 | 6/2006 | Desilets |
| 2006/0161062 A1 | 7/2006 | Arditi et al. |
| 2006/0184069 A1 | 8/2006 | Vaitekunas |
| 2006/0184071 A1 | 8/2006 | Klopotek |
| 2006/0189972 A1 | 8/2006 | Grossman |
| 2006/0206105 A1 | 9/2006 | Chopra |
| 2006/0224090 A1 | 10/2006 | Ostrovsky et al. |
| 2006/0229514 A1 | 10/2006 | Wiener |
| 2006/0241440 A1 | 10/2006 | Eshel |
| 2006/0241442 A1 | 10/2006 | Barthe |
| 2006/0241470 A1 | 10/2006 | Novak et al. |
| 2006/0241576 A1 | 10/2006 | Diederich et al. |
| 2006/0250046 A1 | 11/2006 | Koizumi et al. |
| 2006/0282691 A1 | 12/2006 | Barthe |
| 2006/0291710 A1 | 12/2006 | Wang et al. |
| 2007/0016039 A1 | 1/2007 | Vortman et al. |
| 2007/0032784 A1 | 2/2007 | Gliklich et al. |
| 2007/0035201 A1 | 2/2007 | Desilets |
| 2007/0055154 A1 | 3/2007 | Torbati |
| 2007/0055155 A1 | 3/2007 | Owen et al. |
| 2007/0055156 A1 | 3/2007 | Desilets et al. |
| 2007/0065420 A1 | 3/2007 | Johnson |
| 2007/0083120 A1 | 4/2007 | Cain et al. |
| 2007/0087060 A1 | 4/2007 | Dietrich |
| 2007/0088245 A1 | 4/2007 | Babaev et al. |
| 2007/0088346 A1 | 4/2007 | Mirizzi et al. |
| 2007/0161902 A1 | 7/2007 | Dan |
| 2007/0166357 A1 | 7/2007 | Shaffer et al. |
| 2007/0167709 A1 | 7/2007 | Slayton |
| 2007/0208253 A1 | 9/2007 | Slayton |
| 2007/0219604 A1 | 9/2007 | Yaroslaysky et al. |
| 2007/0219605 A1 | 9/2007 | Yaroslaysky et al. |
| 2007/0238994 A1 | 10/2007 | Stecco et al. |
| 2007/0239075 A1 | 10/2007 | Rosenberg |
| 2007/0239077 A1 | 10/2007 | Azhari et al. |
| 2007/0239079 A1 | 10/2007 | Manstein et al. |
| 2007/0239142 A1 | 10/2007 | Altshuler |
| 2008/0015435 A1 | 1/2008 | Cribbs et al. |
| 2008/0027328 A1 | 1/2008 | Klopotek |
| 2008/0039724 A1 | 2/2008 | Seip et al. |
| 2008/0071255 A1 | 3/2008 | Barthe |
| 2008/0086054 A1 | 4/2008 | Slayton |
| 2008/0086056 A1 | 4/2008 | Chang et al. |
| 2008/0097214 A1 | 4/2008 | Meyers et al. |
| 2008/0097253 A1 | 4/2008 | Pedersen et al. |
| 2008/0114251 A1 | 5/2008 | Weymer |
| 2008/0139974 A1 | 6/2008 | Da Silva |
| 2008/0146970 A1 | 6/2008 | Litman et al. |
| 2008/0167556 A1 | 7/2008 | Thompson |

(56) References Cited

U.S. PATENT DOCUMENTS

| | | |
|---|---|---|
| 2008/0183077 A1 | 7/2008 | Moreau-Gobard et al. |
| 2008/0183110 A1 | 7/2008 | Davenport et al. |
| 2008/0188745 A1 | 8/2008 | Chen et al. |
| 2008/0194964 A1 | 8/2008 | Randall et al. |
| 2008/0195000 A1 | 8/2008 | Spooner et al. |
| 2008/0200810 A1 | 8/2008 | Buchalter |
| 2008/0200813 A1 | 8/2008 | Quistgaard |
| 2008/0214966 A1 | 9/2008 | Slayton |
| 2008/0214988 A1 | 9/2008 | Altshuler et al. |
| 2008/0221491 A1 | 9/2008 | Slayton |
| 2008/0223379 A1 | 9/2008 | Stuker et al. |
| 2008/0242991 A1 | 10/2008 | Moon et al. |
| 2008/0243035 A1 | 10/2008 | Crunkilton |
| 2008/0269608 A1 | 10/2008 | Anderson et al. |
| 2008/0275342 A1 | 11/2008 | Barthe |
| 2008/0281206 A1 | 11/2008 | Bartlett et al. |
| 2008/0281236 A1 | 11/2008 | Eshel et al. |
| 2008/0281237 A1 | 11/2008 | Slayton |
| 2008/0281255 A1 | 11/2008 | Slayton |
| 2008/0294073 A1 | 11/2008 | Barthe |
| 2008/0319356 A1 | 12/2008 | Cain |
| 2009/0005680 A1 | 1/2009 | Jones et al. |
| 2009/0012394 A1 | 1/2009 | Hobelsberger et al. |
| 2009/0043198 A1 | 2/2009 | Milner et al. |
| 2009/0043293 A1 | 2/2009 | Pankratov et al. |
| 2009/0048514 A1 | 2/2009 | Azhari et al. |
| 2009/0069677 A1 | 3/2009 | Chen et al. |
| 2009/0093737 A1 | 4/2009 | Chomas et al. |
| 2009/0156969 A1 | 6/2009 | Santangelo |
| 2009/0163807 A1 | 6/2009 | Sliwa |
| 2009/0171252 A1 | 7/2009 | Bockenstedt et al. |
| 2009/0177122 A1 | 7/2009 | Peterson |
| 2009/0177123 A1 | 7/2009 | Peterson |
| 2009/0182231 A1 | 7/2009 | Barthe et al. |
| 2009/0198157 A1 | 8/2009 | Babaev et al. |
| 2009/0216159 A1 | 8/2009 | Slayton et al. |
| 2009/0226424 A1 | 9/2009 | Hsu |
| 2009/0227910 A1 | 9/2009 | Pedersen et al. |
| 2009/0230823 A1 | 9/2009 | Kushculey et al. |
| 2009/0253988 A1 | 10/2009 | Slayton et al. |
| 2009/0281463 A1 | 11/2009 | Chapelon et al. |
| 2009/0312693 A1 | 12/2009 | Thapliyal et al. |
| 2009/0318909 A1 | 12/2009 | Debenedictis et al. |
| 2009/0326420 A1 | 12/2009 | Moonen et al. |
| 2010/0011236 A1 | 1/2010 | Barthe et al. |
| 2010/0022919 A1 | 1/2010 | Peterson |
| 2010/0022921 A1 | 1/2010 | Seip et al. |
| 2010/0022922 A1 | 1/2010 | Barthe et al. |
| 2010/0030076 A1 | 2/2010 | Vortman et al. |
| 2010/0042020 A1 | 2/2010 | Ben-Ezra |
| 2010/0049178 A1 | 2/2010 | Deem et al. |
| 2010/0056925 A1 | 3/2010 | Zhang et al. |
| 2010/0100014 A1 | 4/2010 | Eshel et al. |
| 2010/0113983 A1 | 5/2010 | Heckerman et al. |
| 2010/0130891 A1 | 5/2010 | Taggart et al. |
| 2010/0160782 A1 | 6/2010 | Slayton et al. |
| 2010/0160837 A1 | 6/2010 | Hunziker et al. |
| 2010/0168576 A1 | 7/2010 | Poland et al. |
| 2010/0191120 A1 | 7/2010 | Kraus et al. |
| 2010/0241035 A1 | 9/2010 | Barthe et al. |
| 2010/0249602 A1 | 9/2010 | Buckley et al. |
| 2010/0249669 A1 | 9/2010 | Ulric et al. |
| 2010/0256489 A1 | 10/2010 | Pedersen et al. |
| 2010/0274161 A1 | 10/2010 | Azhari et al. |
| 2010/0280420 A1 | 11/2010 | Barthe et al. |
| 2010/0286518 A1 | 11/2010 | Lee et al. |
| 2010/0312150 A1 | 12/2010 | Douglas et al. |
| 2011/0040171 A1 | 2/2011 | Foley et al. |
| 2011/0040190 A1 | 2/2011 | Jahnke et al. |
| 2011/0040213 A1 | 2/2011 | Dietz et al. |
| 2011/0040214 A1 | 2/2011 | Foley et al. |
| 2011/0066084 A1 | 3/2011 | Desilets et al. |
| 2011/0087099 A1 | 4/2011 | Eshel et al. |
| 2011/0087255 A1 | 4/2011 | McCormack et al. |
| 2011/0112405 A1 | 5/2011 | Barthe et al. |
| 2011/0144490 A1 | 6/2011 | Davis et al. |
| 2011/0178444 A1 | 7/2011 | Slayton et al. |
| 2011/0178541 A1 | 7/2011 | Azhari |
| 2011/0190745 A1 | 8/2011 | Uebelhoer et al. |
| 2011/0201976 A1 | 8/2011 | Sanghvi et al. |
| 2011/0251524 A1 | 10/2011 | Azhari et al. |
| 2011/0251527 A1 | 10/2011 | Kushculey et al. |
| 2011/0270137 A1 | 11/2011 | Goren et al. |
| 2011/0319793 A1 | 12/2011 | Henrik et al. |
| 2011/0319794 A1 | 12/2011 | Gertner |
| 2012/0004549 A1 | 1/2012 | Barthe et al. |
| 2012/0016239 A1 | 1/2012 | Barthe et al. |
| 2012/0029353 A1 | 2/2012 | Slayton et al. |
| 2012/0035473 A1 | 2/2012 | Sanghvi et al. |
| 2012/0035475 A1 | 2/2012 | Barthe et al. |
| 2012/0035476 A1 | 2/2012 | Barthe et al. |
| 2012/0046547 A1 | 2/2012 | Barthe et al. |
| 2012/0053458 A1 | 3/2012 | Barthe et al. |
| 2012/0059288 A1 | 3/2012 | Barthe et al. |
| 2012/0111339 A1 | 5/2012 | Barthe et al. |
| 2012/0123304 A1 | 5/2012 | Rybyanets et al. |
| 2012/0136280 A1 | 5/2012 | Rosenberg et al. |
| 2012/0136282 A1 | 5/2012 | Rosenberg et al. |
| 2012/0143056 A1 | 6/2012 | Slayton et al. |
| 2012/0143100 A1 | 6/2012 | Jeong et al. |
| 2012/0165668 A1 | 6/2012 | Slayton et al. |
| 2012/0165848 A1 | 6/2012 | Slayton et al. |
| 2012/0191019 A1 | 7/2012 | Desilets et al. |
| 2012/0191020 A1 | 7/2012 | Vitek et al. |
| 2012/0197120 A1 | 8/2012 | Makin et al. |
| 2012/0197121 A1 | 8/2012 | Slayton et al. |
| 2012/0209150 A1 | 8/2012 | Zeng et al. |
| 2012/0215105 A1 | 8/2012 | Slayton et al. |
| 2012/0271202 A1 | 10/2012 | Wisdom |
| 2012/0271294 A1 | 10/2012 | Barthe et al. |
| 2012/0296240 A1 | 11/2012 | Azhari et al. |
| 2012/0302883 A1 | 11/2012 | Kong et al. |
| 2012/0316426 A1 | 12/2012 | Foley et al. |
| 2012/0330197 A1 | 12/2012 | Makin et al. |
| 2012/0330222 A1 | 12/2012 | Makin et al. |
| 2012/0330223 A1 | 12/2012 | Makin et al. |
| 2012/0330283 A1 | 12/2012 | Hyde et al. |
| 2012/0330284 A1 | 12/2012 | Hyde et al. |
| 2013/0012755 A1 | 1/2013 | Slayton |
| 2013/0012816 A1 | 1/2013 | Slayton et al. |
| 2013/0012838 A1 | 1/2013 | Jaeger et al. |
| 2013/0012842 A1 | 1/2013 | Barthe |
| 2013/0018285 A1 | 1/2013 | Park et al. |
| 2013/0018286 A1 | 1/2013 | Slayton et al. |
| 2013/0046209 A1 | 2/2013 | Slayton et al. |
| 2013/0051178 A1 | 2/2013 | Rybyanets |
| 2013/0060170 A1 | 3/2013 | Lee et al. |
| 2013/0066208 A1 | 3/2013 | Barthe et al. |
| 2013/0066237 A1 | 3/2013 | Smotrich et al. |
| 2013/0072826 A1 | 3/2013 | Slayton et al. |
| 2013/0073001 A1 | 3/2013 | Campbell |
| 2013/0096471 A1 | 4/2013 | Slayton et al. |
| 2013/0190659 A1 | 7/2013 | Slayton et al. |
| 2013/0211293 A1 | 8/2013 | Auboiroux et al. |
| 2013/0225994 A1 | 8/2013 | Hsu et al. |
| 2013/0268032 A1 | 10/2013 | Neev |
| 2013/0274603 A1 | 10/2013 | Barthe et al. |
| 2013/0281853 A1 | 10/2013 | Slayton et al. |
| 2013/0281891 A1 | 10/2013 | Slayton et al. |
| 2013/0296697 A1 | 11/2013 | Slayton et al. |
| 2013/0296700 A1 | 11/2013 | Slayton et al. |
| 2013/0296743 A1 | 11/2013 | Lee et al. |
| 2013/0303904 A1 | 11/2013 | Barthe et al. |
| 2013/0303905 A1 | 11/2013 | Barthe et al. |
| 2013/0310714 A1 | 11/2013 | Eshel et al. |
| 2013/0310863 A1 | 11/2013 | Makin et al. |
| 2013/0345562 A1 | 12/2013 | Barthe et al. |
| 2014/0024974 A1 | 1/2014 | Slayton et al. |
| 2014/0050054 A1 | 2/2014 | Toda et al. |
| 2014/0081300 A1 | 3/2014 | Melodelima et al. |
| 2014/0082907 A1 | 3/2014 | Barthe et al. |
| 2014/0117814 A1 | 5/2014 | Toda et al. |
| 2014/0142430 A1 | 5/2014 | Slayton et al. |
| 2014/0148834 A1 | 5/2014 | Barthe et al. |

(56) References Cited

U.S. PATENT DOCUMENTS

| | | |
|---|---|---|
| 2014/0180174 A1 | 6/2014 | Slayton et al. |
| 2014/0187944 A1 | 7/2014 | Slayton et al. |
| 2014/0188015 A1 | 7/2014 | Slayton et al. |
| 2014/0188145 A1 | 7/2014 | Slayton et al. |
| 2014/0194723 A1 | 7/2014 | Herzog et al. |
| 2014/0208856 A1 | 7/2014 | Schmid |
| 2014/0221823 A1 | 8/2014 | Keogh et al. |
| 2014/0236049 A1 | 8/2014 | Barthe et al. |
| 2014/0236061 A1 | 8/2014 | Lee et al. |
| 2014/0243713 A1 | 8/2014 | Slayton et al. |
| 2014/0257145 A1 | 9/2014 | Emery |
| 2014/0276055 A1 | 9/2014 | Barthe et al. |
| 2015/0000674 A1 | 1/2015 | Barthe et al. |
| 2015/0080723 A1 | 3/2015 | Barthe et al. |
| 2015/0080771 A1 | 3/2015 | Barthe et al. |
| 2015/0080874 A1 | 3/2015 | Slayton et al. |
| 2015/0088182 A1 | 3/2015 | Slayton et al. |
| 2015/0164734 A1 | 6/2015 | Slayton et al. |
| 2015/0165238 A1 | 6/2015 | Slayton et al. |
| 2015/0165243 A1 | 6/2015 | Slayton et al. |
| 2015/0174388 A1 | 6/2015 | Slayton |
| 2015/0202468 A1 | 7/2015 | Slayton et al. |
| 2015/0217141 A1 | 8/2015 | Barthe et al. |
| 2015/0360058 A1 | 12/2015 | Barthe et al. |
| 2015/0374333 A1 | 12/2015 | Barthe et al. |
| 2015/0375014 A1 | 12/2015 | Slayton et al. |
| 2016/0027994 A1 | 1/2016 | Toda et al. |
| 2016/0151618 A1 | 6/2016 | Powers et al. |
| 2016/0175619 A1 | 6/2016 | Lee et al. |
| 2016/0206335 A1 | 7/2016 | Slayton |
| 2016/0206341 A1 | 7/2016 | Slayton |
| 2016/0256675 A1 | 9/2016 | Slayton |
| 2016/0296769 A1 | 10/2016 | Barthe et al. |
| 2016/0361572 A1 | 12/2016 | Slayton |
| 2017/0028227 A1 | 2/2017 | Emery et al. |

FOREIGN PATENT DOCUMENTS

| | | |
|---|---|---|
| DE | 10140064 | 3/2003 |
| DE | 10219297 | 11/2003 |
| DE | 10219217 | 12/2004 |
| DE | 20314479 | 12/2004 |
| EP | 0142215 | 5/1984 |
| EP | 0344773 | 12/1989 |
| EP | 1479412 | 11/1991 |
| EP | 0473553 | 4/1992 |
| EP | 670147 | 2/1995 |
| EP | 0661029 | 7/1995 |
| EP | 724894 | 2/1996 |
| EP | 763371 | 11/1996 |
| EP | 1044038 | 10/2000 |
| EP | 1050322 | 11/2000 |
| EP | 1234566 | 8/2002 |
| EP | 1262160 | 12/2002 |
| EP | 0659387 | 4/2003 |
| EP | 1374944 | 1/2004 |
| EP | 1028660 | 1/2008 |
| EP | 1874241 | 1/2008 |
| EP | 1362223 | 5/2008 |
| EP | 1750804 | 7/2008 |
| EP | 1283690 | 11/2008 |
| EP | 1811901 | 4/2009 |
| EP | 1785164 | 8/2009 |
| EP | 2230904 | 9/2010 |
| EP | 1501331 | 6/2011 |
| EP | 2066405 | 11/2011 |
| EP | 2474050 | 7/2012 |
| FR | 2532851 | 9/1983 |
| FR | 2685872 | 1/1992 |
| FR | 2672486 | 8/1992 |
| FR | 2703254 | 3/1994 |
| GB | 2113099 | 8/1983 |
| IL | 102516 | 1/1996 |
| IL | 112369 | 8/1999 |
| IL | 120079 | 3/2001 |
| JP | 63036171 | 2/1988 |
| JP | 03048299 | 3/1991 |
| JP | 3123559 | 5/1991 |
| JP | 03136642 | 6/1991 |
| JP | 4089058 | 3/1992 |
| JP | 04150847 | 5/1992 |
| JP | 7080087 | 3/1995 |
| JP | 07505793 | 6/1995 |
| JP | 7184907 | 7/1995 |
| JP | 7222782 | 8/1995 |
| JP | 09047458 | 2/1997 |
| JP | 9108288 | 4/1997 |
| JP | 9503926 | 4/1997 |
| JP | 11123226 | 5/1999 |
| JP | 11505440 | 5/1999 |
| JP | 11506636 | 6/1999 |
| JP | 10248850 | 9/1999 |
| JP | 2000126310 | 5/2000 |
| JP | 2000166940 | 6/2000 |
| JP | 2000233009 | 8/2000 |
| JP | 2001170068 | 6/2001 |
| JP | 2002505596 | 2/2002 |
| JP | 2002078764 | 3/2002 |
| JP | 2002515786 | 5/2002 |
| JP | 2002521118 | 7/2002 |
| JP | 2002537939 | 11/2002 |
| JP | 2003050298 | 7/2003 |
| JP | 2003204982 | 7/2003 |
| JP | 2004-504898 | 2/2004 |
| JP | 2004-507280 | 3/2004 |
| JP | 2004-509671 | 4/2004 |
| JP | 2004-512856 | 4/2004 |
| JP | 2004147719 | 5/2004 |
| JP | 2005503388 | 2/2005 |
| JP | 2005527336 | 9/2005 |
| JP | 2005323213 | 11/2005 |
| JP | 2006520247 | 9/2006 |
| JP | 2008515559 | 5/2008 |
| JP | 2009518126 | 5/2009 |
| JP | 2010517695 | 5/2010 |
| KR | 1020010024871 | 3/2001 |
| KR | 100400870 | 10/2003 |
| KR | 20060121267 | 11/2006 |
| KR | 1020060113930 | 11/2006 |
| KR | 1020070065332 | 6/2007 |
| KR | 1020070070161 | 7/2007 |
| KR | 1020070098856 | 10/2007 |
| KR | 1020070104878 | 10/2007 |
| KR | 1020070114105 | 11/2007 |
| KR | 1020000059516 | 4/2012 |
| KR | 10-2013-0124598 | 11/2013 |
| KR | 10-1365946 | 2/2014 |
| TW | 386883 | 9/2000 |
| TW | 201208734 A | 3/2012 |
| WO | WO9312742 | 7/1993 |
| WO | WO9524159 | 9/1995 |
| WO | WO9625888 | 8/1996 |
| WO | WO9634568 | 11/1996 |
| WO | WO9639079 | 12/1996 |
| WO | WO9735518 | 10/1997 |
| WO | WO9832379 | 7/1998 |
| WO | WO9852465 | 11/1998 |
| WO | WO9933520 | 7/1999 |
| WO | WO9949788 | 10/1999 |
| WO | WO200006032 | 2/2000 |
| WO | WO0015300 | 3/2000 |
| WO | WO0021612 | 4/2000 |
| WO | WO0053113 | 9/2000 |
| WO | WO0128623 | 4/2001 |
| WO | WO01045550 | 6/2001 |
| WO | WO0182777 | 11/2001 |
| WO | WO0182778 | 11/2001 |
| WO | WO0187161 | 11/2001 |
| WO | WO01080709 | 11/2001 |
| WO | WO2001087161 | 11/2001 |
| WO | WO0209812 | 2/2002 |
| WO | WO0209813 | 2/2002 |
| WO | WO02015768 | 2/2002 |
| WO | WO0224050 | 3/2002 |

(56) References Cited

FOREIGN PATENT DOCUMENTS

| | | |
|---|---|---|
| WO | WO2002054018 | 7/2002 |
| WO | WO02092168 | 11/2002 |
| WO | WO03053266 | 7/2003 |
| WO | WO03065347 | 8/2003 |
| WO | WO03070105 | 8/2003 |
| WO | WO03077833 | 9/2003 |
| WO | WO03086215 | 10/2003 |
| WO | WO03096883 | 11/2003 |
| WO | WO03099177 | 12/2003 |
| WO | WO03099382 | 12/2003 |
| WO | WO03101530 | 12/2003 |
| WO | WO2004000116 | 12/2003 |
| WO | WO2004080147 | 9/2004 |
| WO | WO2004110558 | 12/2004 |
| WO | WO2005/011804 | 2/2005 |
| WO | WO2005065408 | 7/2005 |
| WO | WO2005065409 | 7/2005 |
| WO | WO2005090978 | 9/2005 |
| WO | WO2005113068 | 12/2005 |
| WO | WO2006/042163 | 4/2006 |
| WO | WO2006036870 | 4/2006 |
| WO | WO2006042168 | 4/2006 |
| WO | WO2006042201 | 4/2006 |
| WO | WO2006065671 | 6/2006 |
| WO | WO2006082573 | 8/2006 |
| WO | WO2006104568 | 10/2006 |
| WO | WO2007067563 | 6/2007 |
| WO | WO2008036479 | 3/2008 |
| WO | WO2008036622 | 3/2008 |
| WO | WO2008144274 | 11/2008 |
| WO | WO2009013729 | 1/2009 |
| WO | WO2009149390 | 10/2009 |
| WO | WO2012134645 | 10/2012 |
| WO | WO2013048912 | 4/2013 |
| WO | WO2013178830 | 12/2013 |
| WO | WO2014045216 | 3/2014 |
| WO | WO2014055708 | 4/2014 |
| WO | WO2014057388 | 4/2014 |
| WO | WO2014127091 | 8/2014 |
| WO | WO2015160708 | 10/2015 |
| WO | WO 2016054155 | 4/2016 |
| WO | WO 2018/035012 | 2/2018 |

OTHER PUBLICATIONS

Alam, M., "The future of noninvasive procedural dermatology". Semin Cutan Med Surg. Mar. 2013; 32(1):59-61.

Alam, M., et al., "Ultrasound tightening of facial and neck skin: a rater-blinded prospective cohort study". J Am Acad Dermatol, 2010. 62(2): p. 262-69.

Alexiades-Armenakas, M., "Ultrasound Technologies for Dermatologic Techniques". J Drugs Derm. 2014. 12 (11): p. 1305.

Alster, T.S., et. al., "Noninvasive lifting of arm, thigh, and knee skin with transcutaneousintense focused ultrasound". Dermatol Surg, 2012. 38(5): p. 754-9.

Arosarena, O., "Options and Challenges for Facial Rejuvenation in Patients With Higher Fitzpatrick Skin Phototypes". JAMA Facial Plastic Surgery, 2015.

Bozec, Laurent et al., Thermal Denaturation Studies of Collagen by Microthermal Analysis and Atomic Force Microscopy, Biophysical Journal, vol. 101, pp. 228-236. (Jul. 2001).

Brobst, R.W., et. al., "Noninvasive Treatment of the Neck". Facial Plast Surg Clin North Am, 2014. 22(2): p. 191-202.

Brobst, R.W., et., al., "Ulthera: initial and six month results". Facial Plast Surg Clin North Am, 2012. 20(2): p. 163-76.

Casabona, G., et. al., "Microfocused Ultrasound With Visualization and Fillers for Increased Neocollagenesis: Clinical and Histological Evaluation". Dermatol Surg 2014;40:S194-S198.

Chan N.P., et al.,"Safety study of transcutaneous focused ultrasound for non-invasive skin tightening in Asians". Lasers Surg Med, 2011. 43(5): p. 366-75.

Chapelon et al., "Effects of Cavitation in the High Intensity Therapeutic Ultrasound", Ultrasonics Symposium—1357 (1991).

Chapelon, et al., "Thresholds for Tissue Ablation by Focused Ultrasound" (1990).

Dayan, S.H., et al., "Prospective, Multi-Center, Pivotal Trial Evaluating the Safety and Effectiveness of Micro-Focused Ultrasound with Visualization (MFU-V) for Improvement in Lines and Wrinkles of the Décolletage". Plast Reconstr Surg. Oct. 2014; 134(4 Suppl 1):1234.

Dierickx, Christine C., "The Role of Deep Heating for Noninvasive Skin Rejuvenation" Lasers in Surgery and Medicine 38:799-807 (2006).

Dobke, M.K., et al., "Tissue restructuring by energy-based surgical tools". Clin Plast Surg, 2012. 39(4): p. 399-408.

Dong, Yuan-Lin et al., "Effect of Ibuprofen on the Inflammatory Response to Surgical Wounds" The Journal of Trauma, vol. 35, No. 3. (1993).

Dvivedi, Sanjay, et al."Effect of Ibuprofen and diclofenac sodium on experimental wound healing"Indian Journal of Experimental Biology, vol. 35, pp. 1243-1245. (Nov. 1997).

Fabi, S.G., "Microfocused Ultrasound With Visualization for Skin Tightening and Lifting: My Experience and a Review of the Literature". Dermatol Surg. Dec. 2014; 40 Suppl 12:S164-7.

Fabi, S.G., "Noninvasive skin tightening: focus on new ultrasound techniques". Clin Cosmet Investig Dermatol. Feb. 5, 2015; 8:47-52.

Fabi, S.G., et. al., "A prospective multicenter pilot study of the safety and efficacy of microfocused ultrasound with visualization for improving lines and wrinkles of the décolleté". Dermatol Surg. Mar. 2015; 41(3):327-35.

Fabi, S.G., et. al., "Evaluation of microfocused ultrasound with visualization for lifting, tightening, and wrinkle reduction of the decolletage". J Am Acad Dermatol, 2013. 69(6): p. 965-71.

Fabi, S.G., et. al., "Future directions in cutaneous laser surgery". Dermatol Clin, 2014. 32(1): p. 61-9.

Fabi, S.G., et. al., "Retrospective Evaluation of Micro-focused Ultrasound for Lifting and Tightening the Face and Neck". Dermatol Surg, 2014.

Friedmann D.P., "Comments on evaluation of microfocused ultrasound system for improving skin laxity and tightening in the lower face". Aesthet Surg J. Mar. 2015;35(3):NP81-2.

Friedmann, D.P., et. al., "Combination of intense pulsed light, Sculptra, and Ultherapy for treatment of the aging face". J Cosmet Dermatol, 2014. 13(2): p. 109-18.

Fujimoto, et al., "A New Cavitation Suppression Technique for Local Ablation Using High-Intensity Focused Ultrasound" Ultrasonics Symposium—1629 (1995).

Gold, M.H., et. al., "Use of Micro-Focused Ultrasound with Visualization to Lift and Tighten Lax Knee Skin". J Cosmet Laser Ther, 2014: p. 1-15.

Goldberg, D.J., et. al., "Safety and Efficacy of Microfocused Ultrasound to Lift, Tighten, and Smooth the Buttocks". Dermatol Surg 2014; 40:1113-1117.

Greene, R.M., et al., "Skin tightening technologies". Facial Plast Surg. Feb. 2014; 30(1):62-7.

Greenhalgh, David G., "Wound healing and diabetes mellitus" Clinics in Plastic Surgery 30; 37-45. (2003).

Guo, S. et al.,"Factors Affecting Wound Healing" Critical Reviews in Oral Biology & Medicine, J Dent Res 89(3), pp. 219-229. (2010).

Hantash, Basil M. et al., "Bipolar Fractional Radiofrequency Treatment Induces Neoelastogenesis and Neocollagenesis" Lasers in Surgery and Medicine 41:1-9 (2009).

Hantash, Basil M. et al., "In Vivo Histological Evaluation of a Novel Ablative Fractional Resurfacing Device" Lasers in Surgery and Medicine 39:96-107 (2007).

Harris, M.O., "Safety of Microfocused Ultrasound With Visualization in Patients With Fitzpatrick Skin Phototypes III to VI". JAMA Facial Plast. Surg, 2015.

Hart, et. al., "Current Concepts in the Use of PLLA:Clinical Synergy Noted with Combined Use of Microfocused Ultrasound and Poly-I-Lactic Acid on the Face, Neck, and Décolletage". Amer. Soc. Plast. Surg. 2015. 136; 180-187S.

(56) References Cited

OTHER PUBLICATIONS

Hitchcock, T.M. et. al., "Review of the safety profile for microfocused ultrasound with Visualization". Journal of Cosmetic Dermatology, 13, 329-335. (2014).
Hynynen et al., Temperature Distributions During Local Ultrasound Induced Hyperthermia In Vivo, Ultrasonics Symposium—745 (1982).
Jeong, K.H., et al., "Neurologic complication associated with intense focused ultrasound". J Cosmet Laser Ther, 2013.
Kim, H.J., et al., "Coagulation and ablation patterns of high-intensity focused ultrasound on a tissue mimicking phantom and cadaveric skin". Laser Med Sci. Sep. 4, 2015.
Kornstein, A.N., "Ulthera for silicone lip correction". Plast Reconstr Surg, 2012. 129(6): p. 1014e-1015e.
Kornstein, A.N., "Ultherapy shrinks nasal skin after rhinoplasty following failure of conservative measures". Plast Reconstr Surg, 2013. 131(4): p. 664e-6e.
Krischak, G.D., et al., "The effects of non-steroidal anti-inflammatory drug application on incisional wound healing in rats" Journal of Wound Care, vol. 6, No. 2, (Feb. 2007).
Laubach, H.J., et. al., "Confined Thermal Damage with Intense Ultrasound (IUS)" [abstr.] American Society for Laser Medicine and Surgery Abstracts, p. 15 #43 (Apr. 2006).
Laubach, H.J., et. al., "Intense focused ultrasound: evaluation of a new treatment modality for precise microcoagulation within the skin". Dermatol Surg, 2008. 34(5): p. 727-34.
Lee, H.J., et. al.,"The efficacy and safety of intense focused ultrasound in the treatment of enlarged facial pores in Asian skin". J Dermatolog Treat, 2014.
Lee, H.S., et. al., "Multiple Pass Ultrasound Tightening of Skin Laxity of the Lower Face and Neck". Dermatol Surg, 2011.
Lin, Sung-Jan, et al., "Monitoring the thermally induced structural transitions of collagen by use of second-harmonic generation microscopy" Optics Letters, vol. 30, No. 6, (Mar. 15, 2005).
MacGregor J.L., et. al., "Microfocused Ultrasound for Skin Tightening". Semin Cutan Med Surg 32:18-25. (2013).
Meshkinpour, Azin, et al., "Treatment of Hypertrophic Scars and Keloids With a Radiofrequency Device: A Study of Collagen Effects" Lasers in Surgery and Medicine 37:343-349 (2005).
Minkis, K., et. al., "Ultrasound skin tightening". Dermatol Clin, 2014. 32(1): p. 71-7.
Mosser, David M. et al., "Exploring the full spectrum of macrophage activation" Nat Rev Immunol; 8(12): 958-969. (Dec. 2008).
Murota, Sei-Itsu, et al., "Stimulatory Effect of Prostaglandins on the Production of Hexosamine-Containing Substances by Cultured Fibroblasts (3) Induction of Hyaluronic Acid Synthetase by Prostaglandin" Department of Pharmacology, Tokyo Metropolitan Institute of Gerontology, Itabashiku, Tokyo-173, Japan. (Nov. 1977, vol. 14, No. 5).
Murota, Sei-Itsu, et al., "The Stimulatory Effect of Prostaglandins on Production of Hexosamine-Containing Substances by Cultured Fibroblasts" Department of Pharmacology, Tokyo Metropolitan Institute of Gerontology, Itabashiku, Tokyo-173, Japan. (Aug. 1976, vol. 12, No. 2).
Nestor, M.S. et. al., "Safety and Efficacy of Micro-focused Ultrasound Plus Visualization for the Treatment of Axillary Hyperhidrosis". J Clin Aesthet Dermatol, 2014. 7(4): p. 14-21.
Oni, G., et. al. "Response to 'comments on evaluation of microfocused ultrasound system for improving skin laxity and tightening in the lower face'". Aesthet Surg J. Mar. 2015;35(3):NP83-4.
Oni, G., et. al., "Evaluation of a Microfocused Ultrasound System for Improving Skin Laxity and Tightening in the Lower Face". Aesthet Surg J, 2014. 38:861-868.
Pak, C.S. et. al.,"Safety and Efficacy of Ulthera in the Rejuvenation of Aging Lower Eyelids: A Pivotal Clinical Trial". Aesthetic Plast Surg, 2014.
Pritzker, R.N. et. al, "Updates in noninvasive and minimally invasive skin tightening". Semin Cutan Med Surg. Dec. 2014;33(4):182-7.

Pritzker, R.N., et. al., "Comparison of different technologies for noninvasive skin tightening". Journal of Cosmetic Dermatology, 13, 315-323. (2014).
Rappolee, Daniel A., et al., "Wound Macrophages Express TGF and Other Growth Factors in Vivo: Analysis by mRNA Phenotyping" Science, vol. 241, No. 4866 (Aug. 1988).
Rokhsar, C., et. al., "Safety and efficacy of microfocused ultrasound in tightening of lax elbow skin". Dermatol Surg. 2015; 41(7):821-6.
Rosenberg, Carol S. "Wound Healing in the Patient with Diabetes Mellitus" Nursing Clinics of North America, vol. 25, No. 1, (Mar. 1990).
Sabet-Peyman, E.J. et. al., "Complications Using Intense Ultrasound Therapy to TreatDeep Dermal Facial Skin and Subcutaneous Tissues". Dermatol Surg 2014; 40:1108-1112.
Sandulache, Vlad C. et al., "Prostaglandin E2 inhibition of keloid fibroblast migration, contraction, and transforming growth factor (TGF)—B1—induced collagen synthesis" Wound Rep Reg 15 122-133, 2007. (2007).
Sasaki, G.H. et. al., "Clinical Efficacy and Safety of Focused-Image Ultrasonography: A 2-Year Experience". Aesthet Surg J, 2012.
Sasaki, G.H. et. al., "Microfocused Ultrasound for Nonablative Skin and Subdermal Tightening to the Periorbitum and Body Sites: Preliminary Report on Eighty-Two Patients". Journal of Cosmetics, Dermatological Sciences and Applications, 2012, 2, 108-116.
Sklar, L.R., et. al., "Use of transcutaneous ultrasound for lipolysis and skin tightening: a review". Aesthetic Plast Surg, 2014. 38(2): p. 429-41.
Suh, D.H., et. al., "A intense-focused ultrasound tightening for the treatment of infraorbital laxity". J Cosmet Laser Ther, 2012. 14(6): p. 290-5.
Suh, D.H., et. al., "Comparative histometric analysis of the effects of high-intensity focused ultrasound and radiofrequency on skin". J Cosmet Laser Ther. Mar. 2015 24:1-7.
Suh, D.H., et. al., "Intense Focused Ultrasound Tightening in Asian Skin: Clinical and Pathologic Results" American Society for Dermatologic Surgery, Inc.; 37:1595-1602. (2011).
Suh, D.H., et. al.,"Intense focused ultrasound tightening in asian skin: clinical and pathologic results". Dermatol Surg, 2011. 37(11): p. 1595-602.
Verhofstad, Michiel H.J. et al., "Collagen Synthesis in rat skin and ileum fibroblasts is affected differently by diabetes-related factors" Int. J. Exp. Path. (1998), 79, 321-328.
Weiss, M., "Commentary: noninvasive skin tightening: ultrasound and other technologies: where are we in 2011?" Dermatol Surg, 2012. 38(1): p. 28-30.
White, W. M., et al., "Selective Transcutaneous Delivery of Energy to Facial Subdermal Tissues Using the Ultrasound Therapy System" [abstr]. American Society for Laser Medicine and Surgery Abstracts, p. 37 #113 (Apr. 2006).
White, W. Matthew, et al., "Selective Transcutaneous Delivery of Energy to Porcine Soft Tissues Using Intense Ultrasound (IUS)" Lasers in Surgery and Medicine 40:67-75 (2008).
Woodward, J.A., et. al. "Safety and Efficacy of Combining Microfocused Ultrasound With Fractional CO2 Laser Resurfacing for Lifting and Tightening the Face and Neck". Dermatol Surg, Dec. 2014 40:S190-S193.
Zelickson, Brian D. et al., "Histological and Ultrastructural Evaluation of the Effects of a Radiofrequency-Based Nonablative Dermal Remodeling Device, A Pilot Study" Arch Dermatol, vol. 140, (Feb. 2004).
Ulthera, Inc., Petition for Inter Partes Review filed Jul. 19, 2016 in Re U.S. Pat. No. 6,113,559; IPR2016-01459; 63 pages.
Ulthera Exhibit 1001, U.S. Pat. No. 6,113,559 to Klopotek, filed Jul. 19, 2016 in re IPR2016-01459.
Ulthera Exhibit 1002, Patent file history of U.S. Pat. No. 6,113,559 Klopotek.
Ulthera Exhibit 1003, Declaration of Expert Witness Mark E. Schafer, Ph.D.
Ulthera Exhibit 1004, Curriculum Vitae of Mark E. Schafer, Ph.D.
Ulthera Exhibit 1005, International PCT Publication WO96/34568 Knowlton.
Ulthera Exhibit 1006, French Patent No. 2,672,486, Technomed patent.

(56) References Cited

OTHER PUBLICATIONS

Ulthera Exhibit 1007, English translation of French Patent No. 2,672,486, Technomed.
Ulthera Exhibit 1008, International PCT Publication WO93/12742, Technomed PCT.
Ulthera Exhibit 1009, English translation of International PCT Publication WO93/12742, Technomed PCT.
Ulthera Exhibit 1010, U.S. Pat. No. 5,601,526, which claims priority to Technomed PCT.
Ulthera Exhibit 1011, Patent file history for European Patent Application No. 98964890.2, Klopotek.
Ulthera Exhibit 1012, Translator Declaration.
Ulthera Exhibit 1013, U.S. Pat. No. 5,230,334 to Klopotek.
Ulthera Exhibit 1014, U.S. Pat. No. 5,755,753 to Knowlton.
Ulthera Exhibit 1015, Excerpts from The American Medical Association Encyclopedia of Medicine (1989).
Ulthera Exhibit 1016, The Simultaneous Study of Light Emissions and Shock Waves Produced by Cavitation Bubbles, G. Gimenez, J. Acoust. Soc. Am. 71(4), Apr. 1982, pp. 839-847.
Ulthera Exhibit 1017, Excerpts from Gray's Anatomy (1995).
Ulthera Exhibit 1018, Anatomy of the Superficial Venous System, Comjen G.M., Dermatol. Surg., 1995; 21:35-45.
Ulthera Exhibit 1019, Section 2.6 from Ultrasonics Theory and Application, by G.L. Gooberman (Hart Publishing Co., 1969).
Ulthera Exhibit 1020, Deep Local Hyperthermia for Cancer Therapy: External Electromagnetic and Ultrasound Techniques, A.Y. Cheung and A. Neyzari, Cancer Research (Suppl.), vol. 44, pp. 4736-4744 (1984).
Alster, Tinas S., Tanzi, Elizabeth L., "Cellulite Treatment using a Novel Combination Radiofrequency, Infrared Light, and Mechanical Tissue Manipulation Device," Journal of Cosmetic & Laser Therapy, Jun. 2005, vol. 7, Issue 2, pp. 81-85.
Arthur et al., "Non-invasive estimation of hyperthermia temperatures with ultrasound," Int. J. Hyperthermia, Sep. 2005, 21(6), pp. 589-600.
Barthe et al., "Ultrasound therapy system and ablation results utilizing miniature imaging/therapy arrays," Ultrasonics Symposium, 2004 IEEE, Aug. 23, 2004, pp. 1792-1795, vol. 3.
Calderhead et al., "One Mechanism Behind LED Photo-Therapy for Wound Healing and Skin Rejuvenation: Key Role of the Mast Cell" Laser Therapy 17.3: 141-148 (2008).
Chen, L. et al., "Effect of Blood Perfusion on the ablation of liver parenchyma with high intensity focused ultrasound," Phys. Med. Biol; 38:1661-1673; 1993b.
Coon, Joshua et al., "Protein identification using sequential ion/ion reactions and tandem mass spectrometry" Proceedings of the National Academy of Sciences of the USA, vol. 102, No. 27, Jul. 27, 2005, pp. 9463-9468.
Corry, Peter M., et al., "Human Cancer Treatment with Ultrasound", IEEE Transactions on Sonics and Ultrasonics, vol. SU-31, No. 5, Sep. 1984, pp. 444, 456.
Damianou et al., "Application of the Thermal Dose Concept for Predicting the Necrosed Tissue Volume During Ultrasound Surgery," 1993 IEEE Ultrasound Symposium, pp. 1199-1202.
Daum et al., "Design and Evaluation of a Feedback Based Phased Array System for Ultrasound Surgery, IEEE Transactions on Ultrasonics, Ferroelectrics, and Frequency Control, vol. 45, No. 2, Mar. 1998, pp. 431-438.
Davis, Brian J., et al., "An Acoustic Phase Shift Technique for the Non-Invasive Measurement of Temperature Changes in Tissues", 1985 Ultrasonics Symposium, pp. 921-924.
Fry, W.J. et al., "Production of Focal Destructive Lesions in the Central Nervous System with Ultrasound," J. Neurosurg., 11:471-478; 1954.
Decision of the Korean Intellectual Property Tribunal dated Jun. 28, 2013 regarding Korean Patent No. 10-1142108, which is related to the pending application and/or an application identified in the Table on pp. 1-4 of the Information Disclosure Statement herein (English translation, English translation certification, and Korean decision included).
Gliklich et al., Clinical Pilot Study of Intense Ultrasound therapy to Deep Dermal Facial Skin and Subcutaneous Tissues, Arch Facial Plastic Surgery, Mar. 1, 2007, vol. 9, No. 1.
Haar, G.R. et al., "Tissue Destruction with Focused Ultrasound in Vivo," Eur. Urol. 23 (suppl. 1):8-11; 1993.
Hassan et al., "Structure and Applications of Poly(vinyl alcohol) Hydrogels Produced by Conventional Crosslinking or by Freezing/Thawing Methods," advanced in Polymer Science, 2000, pp. 37-65, vol. 153.
Hassan et al., "Structure and Morphology of Freeze/Thawed PVA Hydrogels," Macromolecules, Mar. 11, 2000, pp. 2472-2479, vol. 33, No. 7.
Husseini et al, "The Role of Cavitation in Acoustically Activated Drug Delivery," J. Control Release, Oct. 3, 2005, pp. 253-261, vol. 107(2).
Husseini et al. "Investigating the mechanism of acoustically activated uptake of drugs from Pluronic micelles," BMD Cancer 2002, 2:20k, Aug. 30, 2002, pp. 1-6.
Jeffers et al., "Evaluation of the Effect of Cavitation Activity on Drug-Ultrasound Synergisms," 1993 IEEE Ultrasonics Symposium, pp. 925-928.
Jenne, J., et al., "Temperature Mapping for High Energy US-Therapy", 1994 Ultrasonics Symposium, pp. 1879-1882.
Johnson, S.A., et al., "Non-Intrusive Measurement of Microwave and Ultrasound-Induced Hyperthermia by Acoustic Temperature Tomography", Ultrasonics Symposium Proceedings, pp. 977-982. (1977).
Madersbacher, S. et al., "Tissue Ablation in Benign Prostatic Hyperplasia with High Intensity Focused Ultrasound," Dur. Urol., 23 (suppl. 1):39-43; 1993.
Makin et al, "B-Scan Imaging and Thermal Lesion Monitoring Using Miniaturized Dual-Functionality Ultrasound Arrays," Ultrasonics Symposium, 2004 IEEE, Aug. 23, 2004, pp. 1788-1791, vol. 3.
Makin et al, "Confirmed Bulk Ablation and Therapy Monitoring Using Intracorporeal Image-Treat Ultrasound Arrays," 4th International Symposium on Therapeutic Ultrasound, Sep. 19, 2004.
Makin et al., "Miniaturized Ultrasound Arrays for Interstitial Ablation and Imaging," UltraSound Med. Biol. 2005, Nov. 1, 2005, pp. 1539-1550, vol. 31(11).
Manohar et al, "Photoacoustic mammography laboratory prototype: imaging of breast tissue phantoms," Journal of Biomedical Optics, Nov./Dec. 2004, pp. 1172-1181, vol. 9, No. 6.
Mast et al, "Bulk Ablation of Soft Tissue with Intense Ultrasound; Modeling and Experiments," J. Acoust. Soc. Am., Oct. 1, 2005, pp. 2715-2724, vol. 118(4).
Mitragotri, S., "Healing sound: the use of ultrasound in drug delivery and other therapeutic applications," Nature Reviews; Drug Delivery, pp. 255-260, vol. 4 (Mar. 2005).
Paradossi et al., "Poly(vinyl alcohol) as versatile biomaterial for potential biomedical applications," Journal of Materials Science: Materials in Medicine, 2003, pp. 687-691, vol. 14.
Reid, Gavin, et al., "Tandem Mass spectrometry of ribonuclease A and B: N-linked glycosylation site analysis of whole protein ions," Analytical Chemistry. Feb. 1, 2002, vol. 74, No. 3, pp. 577-583.
Righetti et al, "Elastographic Characterization of HIFU-Induced Lesions in Canine Livers," 1999, Ultrasound in Med & Bio, vol. 25, No. 7, pp. 1099-1113.
Saad et al., "Ultrasound-Enhanced Effects of Adriamycin Against Murine Tumors," Ultrasouns in Med. & Bio. vol. 18, No. 8, pp. 715-723 (1992).
Sanghvi, N.T., et al., "Transrectal Ablation of Prostate Tissue Using Focused Ultrasound," 1993 Ultrasonics Symposium, IEEE, pp. 1207-1210.
Sassen, Sander, "ATI's R520 architecture, the new king of the hill?" http://www.hardwareanalysis.com/content/article/1813, Sep. 16, 2005, 2 pages.
Seip, Ralf, et al., "Noninvasive Detection of Thermal Effects Due to Highly Focused Ultrasonic Fields," IEEE Symposium, pp. 1229-1232, vol. 2, Oct. 3-Nov. 1993.

(56) References Cited

OTHER PUBLICATIONS

Seip, Ralf, et al., "Noninvasive Estimation of Tissue Temperature Response to Heating Fields Using Diagnostic Ultrasound," IEEE Transactions on Biomedical Engineering, vol. 42, No. 8, Aug. 1995, pp. 828-839.
Simon et al., "Applications of Lipid-Coated Microbubble Ultrasonic Contrast to Tumor Therapy," Ultrasound in Med. & Biol. vol. 19, No. 2, pp. 123-125 (1993).
Smith, Nadine Barrie, et al., "Non-invasive in Vivo Temperature Mapping of Ultrasound Heating Using Magnetic Resonance Techniques", 1994 Ultrasonics Symposium, pp. 1829-1832, vol. 3.
Surry et al., "Poly(vinyl alcohol) cryogel phantoms for use in ultrasound and MR imaging," Phys. Med. Biol., Dec. 6, 2004, pp. 5529-5546, vol. 49.
Syka J. E. P. et al., "Peptide and Protein Sequence Analysis by Electron Transfer Dissociation Mass Spectrometry," Proceedings of the National Academy of Sciences of USA, National Academy of Science, Washington, DC, vol. 101, No. 26, Jun. 29, 2004, pp. 9528-9533.
Talbert, D. G., "An Add-On Modification for Linear Array Real-Time Ultrasound Scanners to Produce 3D Displays," UTS Int'l 1977 Brighton, England (Jun. 28-30, 1977) pp. 57-67.
Tata et al., "Interaction of Ultrasound and Model Membrane Systems: Analyses and Predictions," American Chemical Society, Phys. Chem. 1992, 96, pp. 3548-3555.
Ueno, S., et al., "Ultrasound Thermometry in Hyperthermia", 1990 Ultrasonic Symposium, pp. 1645-1652.
Wang, H., et al., "Limits on Focused Ultrasound for Deep Hyperthermia", 1994 Ultrasonic Symposium, Nov. 1-4, 1994, pp. 1869-1872, vol. 3.
Wasson, Scott, "NVIDIA's GeForce 7800 GTX graphics processor Power MADD," http://techreport.com/reviews/2005q2/geforce-7800gtx/index.x?pg=1, Jun. 22, 2005, 4 pages.
White et al "Selective Creating of Thermal Injury Zones in the Superficial Musculoaponeurotic System Using Intense Ultrasound Therapy," Arch Facial Plastic Surgery, Jan./Feb. 2007, vol. 9, No. 1 (pp. 22-29).
Carruthers et al., "Consensus Recommendations for Combined Aesthetic Interventions in the Face Using Botulinum Toxin, Fillers,and Energy-Based Devices" Dermatol Surg 2016 (pp. 1-12).
Casabona, G., et. al., "Microfocused Ultrasound with Visualization and Calcium Hydroxylapatite for Improving Skin Laxity and Cellulite Appearance"; Plast Reconstr Surg Glob Open. Jul. 25, 2017;5(7):e1388, 8 pages.
Delon Martin, C., et al, "Venous Thrombosis Generation by Means of High-Intensity Focused Ultrasound" Ultrasound in Med. & Biol., vol. 21, No. 1, pp. 113-119 (1995).
Hexsel et al., "A Validated Photonumeric Cellulite Severity Scale"; J Eur Acad Dermatol Venereol. May 2009; 23(5):523-8, 6 pages.
Decision on Institution of Inter Partes Review in Re U.S. Pat. No. 6,113,559; IPR2016-01459; 20 pages [011] (Dated Jan. 23, 2017).
Dermafocus Response to Institution of Inter Partes Review in Re U.S. Pat. No. 6,113,559; IPR2016-01459; 73 pages [018] (Dated Apr. 26, 2017).
Dermafocus Exhibit List in Re U.S. Pat. No. 6,113,559; IPR2016-01459; 5 pages [019] (Dated Apr. 26, 2017).
Dermafocus Exhibit 2002, Declaration of Mark Palmeri, in Re U.S. Pat. No. 6,113,559; IPR2016-01459; 136 pages (Filed Apr. 26, 2017).
Dermafocus Exhibit 2003, Deposition of Dr. Mark Schafer, in Re U.S. Pat. No. 6,113,559; IPR2016-01459; 327 pages (Filed Apr. 26, 2017).
Dermafocus Exhibit 2004, Amendment No. 4 to Ulthera Form S-1, in Re U.S. Pat. No. 6,113,559; IPR2016-01459; 308 pages (Filed Apr. 26, 2017).
Dermafocus Exhibit 2005, Excerpt from Churchill Livingstone, Gray's Anatomy (38th ed. 1995), in Re U.S. Pat. No. 6,113,559; IPR2016-01459; 7 pages (Filed Apr. 26, 2017).
Dermafocus Exhibit 2006, Bo Eklof et al., "Revision of the CEAP Classification for Chronic Venous Disorders: Consensus Statement," ACTA FAC MED NAISS, vol. 25, No. 1 (2008), 3-10 in Re U.S. Pat. No. 6,113,559; IPR2016-01459; 7 pages (Filed Apr. 26, 2017).
Dermafocus Exhibit 2007, WebMD, "Varicose Veins and Spider Veins" downloaded from http://www.webmd.com/skin-problems-andtreatments/guide/varicose-spider-veins#1 in Re U.S. Pat. No. 6,113,559; IPR2016-01459; 3 pages (Filed Apr. 26, 2017).
Dermafocus Exhibit 2008, John M. Porter et al, "Reporting Standards in Venous Disease: An Update," Journal of Vascular Surgery, vol. 21, No. 4 (1995), 635-645 in Re U.S. Pat. No. 6,113,559; IPR2016-01459; 11 pages (Filed Apr. 26, 2017).
Dermafocus Exhibit 2009, Kullervo Hynynen, "Review of Ultrasound Therapy," 1997 Ultrasonics Symposium (1997), 1305-1313, in Re U.S. Pat. No. 6,113,559; IPR2016-01459; 9 pages (Filed Apr. 26, 2017).
Dermafocus Exhibit 2010, A.G. Visioli et al, "Preliminary Results of a Phase I Dose Escalation Clinical Trial Using Focused Ultrasound in the Treatment of Localised Tumours," European Journal of Ultrasound, vol. 9 (1999), 11-18, in Re U.S. Pat. No. 6,113,559; IPR2016-01459; 8 pages (Filed Apr. 26, 2017).
Dermafocus Exhibit 2011, U.S. Pat. No. 5,143,063, issued on Sep. 1,1992, Fellner, in Re U.S. Pat. No. 6,113,559; IPR2016-01459; 6 pages (Filed Apr. 26, 2017).
Dermafocus Exhibit 2012, Hugh G. Beebe et al, "Consensus Statement: Classification and Grading of Chronic Venous Disease in the Lower Limbs," European Journal of Vascular and Endovascular Surgery, vol. 12 (1996), 487-492, in Re U.S. Pat. No. 6,113,559; IPR2016-01459; 6 pages (Filed Apr. 26, 2017).
Dermafocus Exhibit 2013, Excerpt from Mosby's Medical Dictionary (3rd ed. 1990), in Re U.S. Pat. No. 6,113,559; IPR2016-01459; 4 pages (Filed Apr. 26, 2017).
Dermafocus Exhibit 2014, Excerpt from Miller-Keane Encyclopedia & Dictionary of Medicine, Nursing, & Allied Health (5th ed. 1992), in Re U.S. Pat. No. 6,113,559; IPR2016-01459; 6 pages (Filed Apr. 26, 2017).
Dermafocus Exhibit 2015, David J. Tibbs et al, Varicose Veins, Venous Disorders, and Lymphatic Problems in the Lower Limbs (1997), Chapter 4: Clinical Patterns of Venous Disorder I, 47-67, in Re U.S. Pat. No. 6,113,559; IPR2016-01459; 24 pages (Filed Apr. 26, 2017).
Dermafocus Exhibit 2016, Mitchel P. Goldman et al, Varicose Veins and Telangiectasias (2nd ed. 1999), Chapter 22: Treatment of Leg Telangiectasias with Laser and High-Intensity Pulsed Light, 470-497, in Re U.S. Pat. No. 6,113,559; IPR2016-01459; 31 pages (Filed Apr. 26, 2017).
Dermafocus Exhibit 2017, Email from Anderson to Klopotek dated May 25, 2004, in Re U.S. Pat. No. 6,113,559; IPR2016-01459; 1 page (Filed Apr. 26, 2017).
Dermafocus Exhibit 2018, List of Klopotek Patents, in Re U.S. Pat. No. 6,113,559; IPR2016-01459; 411 pages (Filed Apr. 26, 2017).
Dermafocus Exhibit 2019, Declaration of Peter Klopotek Civil Action 15-cv-654-SLR, dated Nov. 2, 2016, in Re U.S. Pat. No. 6,113,559; IPR2016-01459; 1 page (Filed Apr. 26, 2017).
Dermafocus Exhibit 2020, "Our Technology," downloaded from http://jobs.ulthera.com/about on Apr. 10, 2017, in Re U.S. Pat. No. 6,113,559; IPR2016-01459; 4 pages (Filed Apr. 26, 2017).
Dermafocus Exhibit 2021, C. Damianou and K. Hynynen, "Focal Spacing and Near-Field Heating During Pulsed High Temperature Ultrasound Therapy," Ultrasound in Medicine & Biology, vol. 19, No. 9 (1993), 777-787, in Re U.S. Pat. No. 6,113,559; IPR2016-01459; 11 pages (Filed Apr. 26, 2017).
Dermafocus Exhibit 2022, Excerpt from Mosby's Medical Dictionary (5th ed. 1997), in Re U.S. Pat. No. 6,113,559; IPR2016-01459; 5 pages (Filed Apr. 26, 2017).
Dermafocus Exhibit 2023, Excerpt from Miller-Keane Encyclopedia & Dictionary of Medicine, Nursing, & Allied Health (6th ed. 1997), in Re U.S. Pat. No. 6,113,559; IPR2016-01459; 7 pages (Filed Apr. 26, 2017).
Dermafocus Exhibit 2024, Excerpt from Stedman's Concise Medical Dictionary (3 rd ed. 1997), in Re U.S. Pat. No. 6,113,559; IPR2016-01459; 4 pages (Filed Apr. 26, 2017).

(56) References Cited

OTHER PUBLICATIONS

Dermafocus Exhibit 2025, Excerpt from Taber's Cyclopedic Medical Dictionary (18th ed. 1997), in Re U.S. Pat. No. 6,113,559; IPR2016-01459; 9 pages (Filed Apr. 26, 2017).
Dermafocus Exhibit 2026, Bo Eklof et al, "Revision of the CEAP Classification for Chronic Venous Disorders: Consensus Statement," Journal ofVascular Surgery, vol. 40, No. 6 (2004), 1248-1252.el, in Re U.S. Pat. No. 6,113,559; IPR2016-01459; 6 pages (Filed Apr. 26, 2017).
Ulthera, Inc., Reply in Support of Petition for Inter Partes Review in Re U.S. Pat. No. 6,113,559; IPR2016-01459; 33 pages (Filed Aug. 2, 2017).
Ulthera Exhibit 1022, Use of the Argon and Carbon Dioxide Lasers for Treatment of Superficial Venous Varicosities of the Lower Extremity, D. Apfelberg et al., Lasers in Surgery and Medicine, vol. 4.3, pp. 221-231 (1984) (filed Aug. 2, 2017 in re IPR2016-01459).
Ulthera Exhibit 1023, 532-Nanometer Green Laser Beam Treatment of Superficial Varicosities of the Lower Extremities, T. Smith et al., Lasers in Surgery and Medicine, vol. 8.2, pp. 130-134 (1988) (filed Aug. 2, 2017 in re IPR2016-01459).
Ulthera Exhibit 1024, Deposition Transcript of Dr. Mark Palmeri on Jul. 11, 2017 (filed Aug. 2, 2017 in re IPR2016-01459).
Ulthera Exhibit 1025, Ulthera Oral Proceeding Demonstrative Slides (filed Oct. 2, 2017 in re IPR2016-01459).
Dermafocus Exhibit 2027, DermaFocus Oral Proceeding Demonstrative Slides (filed Oct. 2, 2017 in re IPR2016-01459).
PTAB Record of Oral Hearing held Oct. 4, 2017 in Re U.S. Pat. No. 6,113,559; IPR2016-01459; 67 pages (PTAB Document sent to Ulthera on Nov. 1, 2017).
Final Written Decision of Inter Partes Review in Re U.S. Pat. No. 6,113,559; IPR2016-01459; 37 pages [030] (Entered Jan. 19, 2018).

\* cited by examiner

METHODS FOR FACE AND NECK LIFTS

CROSS-REFERENCE TO RELATED APPLICATIONS

This application is a continuation of U.S. application Ser. No. 14/554,571 filed Nov. 26, 2014, issued as U.S. Pat. No. 9,427,601, which is a continuation of U.S. application Ser. No. 13/835,635 filed Mar. 15, 2013, issued as U.S. Pat. No. 8,915,853, which is a continuation of U.S. application Ser. No. 13/494,856 filed Jun. 12, 2012, issued as U.S. Pat. No. 8,444,562, which is a continuation-in-part of U.S. application Ser. No. 11/857,989 filed Sep. 19, 2007, now abandoned, which claims the benefit of priority from U.S. Provisional No. 60/826,199 filed Sep. 19, 2006, each of which are incorporated in its entirety by reference, herein. U.S. application Ser. No. 13/494,856, issued as U.S. Pat. No. 8,444,562, is also a continuation-in-part of U.S. application Ser. No. 12/028,636 filed Feb. 8, 2008, issued as U.S. Pat. No. 8,535,228, which is a continuation-in-part of U.S. application Ser. No. 11/163,151 filed on Oct. 6, 2005, now abandoned, which in turn claims priority to U.S. Provisional Application No. 60/616,755 filed on Oct. 6, 2004, each of which are incorporated in its entirety by reference, herein. Further, U.S. application Ser. No. 12/028,636, issued as U.S. Pat. No. 8,535,228, is a continuation-in-part of U.S. application Ser. No. 11/163,148 filed on Oct. 6, 2005, now abandoned, which in turn claims priority to U.S. Provisional Application No. 60/616,754 filed on Oct. 6, 2004, each of which are incorporated in its entirety by reference, herein. Any and all priority claims identified in the Application Data Sheet, or any correction thereto, are hereby incorporated by reference under 37 CFR 1.57.

FIELD OF INVENTION

Several embodiments of the present invention generally relate to ultrasound treatment and imaging devices for use on any part of the body, and more specifically relate to ultrasound devices having a transducer probe operable to emit and receive ultrasound energy for cosmetic and/or medical treatment and imaging.

BACKGROUND

Subcutaneous tissues such as muscles, tendons, ligaments and cartilage are important connective tissues that provide force and motion, non-voluntary motion, anchoring, stability, and support among other functions. These tissues can cause changes to cosmetic and/or aesthetic appearance, and are prone to wear and injury because of the natural aging process, sports and other activities which put stress on the tissues.

Muscle tissue is capable of contraction and expansion. Skeletal muscle is a fibrous tissue used to generate stress and strain. For example, skeletal muscles in the forehead region can produce frowning and wrinkles. There are several muscles within the forehead region including the epicranius muscle, the corrugator supercilii muscle, and the procerus muscle. These muscles are responsible for movement of the forehead and various facial expressions. Besides muscles, other tissues exist in the forehead region that also can lead to wrinkles and other cosmetic/aesthetic effects on the forehead.

One popular procedure for reducing wrinkles on the forehead is a cosmetic procedure known as a brow lift. During a brow lift, portions of muscle, fat, and other tissues in the forehead region are invasively cut, removed, and/or paralyzed to reduce or eliminate wrinkles from the forehead. For example, traditional brow lifts require an incision beginning at one ear and continuing around the forehead at the hair line to the other ear. Once the incision is made, various tissues (and portions of those tissues) such as muscles or fat are cut, removed, manipulated, or paralyzed to reduce wrinkles. For example, portions of the muscle that causes vertical frown lines between the brows can be removed during a brow lift to reduce or eliminate wrinkles.

A less invasive brow lift procedure is known as an "endoscopic lift." During an endoscopic brow lift, smaller incisions are made along the forehead and an endoscope and surgical cutting tools are inserted within the incisions to cut, remove, manipulate, or paralyze tissue to reduce or eliminate wrinkles from the brow.

Unfortunately, both traditional and endoscopic brow lifts are invasive and require hospital stays.

There are certain treatments to remove or reduce the appearance of wrinkles on the forehead that are less invasive. Such treatments are designed purely to paralyze muscles within the forehead. Paralyzing the muscle prevents it from moving and therefore, prevents wrinkles. One such treatment is the injection of Botulin toxin, a neurotoxin sold under the trademark BOTOX®, into muscle tissue to paralyze the tissue. However, such cosmetic therapy is temporary and requires chronic usage to sustain the intended effects. Further, BOTOX-type treatments may cause permanent paralysis and disfigurement. Finally, these types of treatments are limited in the scope of treatment they provide.

Another area where subcutaneous tissue can be problematic is around the eyes. Specifically, excess fat embedded in the support structure around the lower and upper eyelids can cause eyes to be puffy and give the appearance of fatigue. Moreover, "bags" of excess fat and skin caused by excess fat and loose connective tissue typically form around a person's eyes as she ages. Generally, these problems associated with various tissues around the eyes are cosmetic; however, in certain cases the skin can droop so far down that a patient's peripheral vision is affected.

Besides droopy skin, puffy eyelids, and bags around the eyes, wrinkles can appear that extend from the outer corner of the eye around the side of a patient's face. These wrinkles are known as "crow's feet." Crow's feet are caused in part by the muscle around the eye known as the "orbicularis oculi muscle." Crow's feet can be treated by paralyzing or otherwise incapacitating the orbicularis oculi muscle.

Surgery to remove wrinkles, droopy skin, puffy eyelids, and bags around the eyes is referred to as a "blepharoplasty." During a blepharoplasty procedure, a surgeon removes fat, muscle, or other tissues responsible for the natural effects of aging that appear near a patient's eyes. A blepharoplasty can be limited to the upper eyelids (an "upper lid blepharoplasty"), the lower eyelids (a "lower lid blepharoplasty") or both the upper and lower eyelids.

During a traditional blepharoplasty, an incision is made along the natural lines of a patient's eyelids. In an upper lid blepharoplasty, a surgeon will make the incisions along the creases of the patient's upper eyelids and during a lower lid blepharoplasty; incisions are made just below the patient's eyelashes. Once the incisions are made, the surgeon separates skin from the underlying fatty tissue and muscle before removing the excess fat and unneeded muscle.

Another type of blepharoplasty has developed which is known as a "transconjunctival blepharoplasty." A transconjunctival blepharoplasty typically is only used to remove pockets of fat along the lower eyelids. During a transconjunctival blepharoplasty, three incisions are made along the interior of the lower eyelid and fatty deposits are removed.

Blepharoplasty procedures can have many drawbacks. Most notably, traditional blepharoplasty procedures are fairly invasive and many patients must spend a week or more recovering at home until the swelling and black and blue eyes disappear. Further, most patients who have had a blepharoplasty are irritated by wind for several months after the procedure. Therefore, it would be desirable to provide a less invasive blepharoplasty procedure to improve the appearance of the eye region.

A blepharoplasty procedure alone is typically not the best way to treat crow's feet. Removing crow's feet after procedures to remove excess fat, skin, muscle, and other tissues around the eye is commonly requested by patients to remove all the wrinkles around the eyes. Crow's feet are typically treated by paralyzing the orbicularis oculi muscle with an injection of Botulin toxin, a neurotoxin sold under the trademark BOTOX®. However, such cosmetic therapy is temporary and requires chronic usage to sustain the intended effects. Further, BOTOX-type treatments may cause permanent paralysis and disfigurement. In addition, the animal protein-based formulation for BOTOX-type treatments makes patients more prone to immune reactions. Therefore, it would also be desirable to provide a method of treating the eyes that replaced not only a blepharoplasty, but also eliminated the need for BOTOX-type treatments to remove crow's feet.

Cartilage tissue is yet another subcutaneous tissue that can be treated with ultrasound. Cartilage tissue is thin, rubbery, elastic tissue that comprises numerous body parts and acts as a cushion along the joints. For example, the ears and nose contain cartilage tissue which gives the ears and nose their elastic flexibility. Cartilage tissue also covers the ends of bones in normal joints and acts as a natural shock absorber for the joint and reduces friction between the two bones comprising the joint.

Cartilage is also responsible for many of the complaints that people have about their appearance, specifically their ears and nose. For example, many people complain that their ears stick outward from their head too much or that their ears are simply too big and dislike the appearance of their ears for these reasons. Patients can elect to correct this condition by cutting, removing, or reshaping the cartilage of the ears to re-shape the ears so they do not project as much from the person's head or are smaller.

During ear surgery, cartilage is removed, cut, or sculpted to change the appearance of the ears. One type of ear surgery is known as an "otoplasty" wherein the cartilage within the ears is cut, removed, or otherwise sculpted to reduce the projections of the ears from the head and allow the ears to rest against the patient's head thereby reducing the angle of the ear to the head. In a traditional otoplasty, a surgeon makes an incision in the back of the ear to expose the ear cartilage. Once the incision is made, the surgeon may sculpt or remove the cartilage. In certain cases, large pieces of cartilage are removed during surgery to change the shape and appearance of the ears. Stitches are used to close the incision made during surgery and to help maintain the new shape of the patient's ears.

While effective, traditional ear surgeries such as an otoplasty take several hours and require an overnight hospital stay for the most aggressive procedures. Further, the cartilage can become infected during the surgery and blood clots can form within the ear that must be drawn out if not dissolved naturally. Other problems associated with ear surgery include a recovery period that lasts several days and requires patients to wear bandages around their ears which are uncomfortable.

Further complicating matters is that many patients undergoing ear surgery such as an otoplasty are children between the ages of four to fourteen. The complications noted above that result from traditional surgeries are only magnified in patients this young. It would therefore be desirable to have a method of treating cartilage that is non-invasive to alleviate the disadvantages of a traditional invasive ear surgeries.

Coarse sagging of the skin and facial musculature occurs gradually over time due to gravity and chronic changes in connective tissue generally associated with aging. Invasive surgical treatment to tighten such tissues is common, for example by facelift procedures. In these treatments for connective tissue sagging, a portion of the tissue is usually removed, and sutures or other fasteners are used to suspend the sagging tissue structures. On the face, the Superficial Muscular Aponeurosis System (SMAS) forms a continuous layer superficial to the muscles of facial expression and beneath the skin and subcutaneous fat. Conventional face lift operations involve suspension of the SMAS through such suture and fastener procedures.

It is an object of some embodiments of the present invention to provide the combination of targeted, precise, local heating to a specified temperature region capable of inducing coagulation and/or ablation (thermal injury) to underlying skin and subcutaneous fat. Attempts have included the use of radio frequency (RF) devices that have been used to produce heating and shrinkage of skin on the face with some limited success as a non-invasive alternative to surgical lifting procedures. However, RF is a dispersive form of energy deposition. RF energy is impossible to control precisely within the heated tissue volume and depth, because resistive heating of tissues by RF energy occurs along the entire path of electrical conduction through tissues. Another restriction of RF energy for non-invasive tightening of the SMAS is unwanted destruction of the overlying fat and skin layers. The electric impedance to RF within fat, overlying the suspensory connective structures intended for shrinking, leads to higher temperatures in the fat than in the target suspensory structures. Similarly, midinfrared lasers and other light sources have been used to non-invasively heat and shrink connective tissues of the dermis, again with limited success. However, light is not capable of non-invasive treatment of SMAS because light does not penetrate deeply enough to produce local heating there. Below a depth of approximately 1 mm, light energy is multiply scattered and cannot be focused to achieve precise local heating.

SUMMARY

Methods and systems for ultrasound treatment of tissue are provided. In an embodiment, tissue such as muscle, tendon, fat, ligaments and cartilage are treated with ultrasound energy. The ultrasound energy can be focused, unfocused or defocused and is applied to a region of interest containing at least one of muscle, tendon, ligament or cartilage (MTLC) tissue to achieve a therapeutic effect.

In certain embodiments, various procedures that are traditionally performed through invasive techniques are accomplished by targeting energy such as ultrasound energy at specific subcutaneous tissues. Certain procedures include a brow lift, a blepharoplasty, and treatment of cartilage tissue.

In one embodiment, a method and system for non-invasively treating subcutaneous tissues to perform a brow lift is provided. In an embodiment, a non-invasive brow lift is performed by applying ultrasound energy at specific depths along the brow to ablatively cut, cause tissue to be reabsorbed into the body, coagulate, remove, manipulate, or paralyze subcutaneous tissue such as the corrugator supercilii muscle, the epicranius muscle, and the procerus muscle within the brow to reduce wrinkles.

In one embodiment, ultrasound energy is applied at a region of interest along the patient's forehead. The ultrasound energy is applied at specific depths and is capable of targeting certain subcutaneous tissues within the brow such as muscles and fat. The ultrasound energy targets these tissues and cuts, ablates, coagulates, micro-ablates, manipulates, or causes the subcutaneous tissue to be reabsorbed into the patient's body which effectuates a brow lift non-invasively.

For example, in one embodiment, the corrugator supercilii muscle on the patient's forehead can be targeted and treated by the application of ultrasound energy at specific depths. This muscle or other subcutaneous muscles can be ablated, coagulated, micro-ablated, shaped or otherwise manipulated by the application of ultrasound energy in a non-invasive manner. Specifically, instead of cutting a corrugator supercilii muscle during a classic or endoscopic brow lift, the targeted muscle such as the corrugator supercilii can be ablated, micro-ablated, or coagulated by applying ultrasound energy at the forehead without the need for traditional invasive techniques.

Various embodiments of methods and systems are configured for targeted treatment of subcutaneous tissue in the forehead region in various manners such as through the use of therapy only, therapy and monitoring, imaging and therapy, or therapy, imaging and monitoring. Targeted therapy of tissue can be provided through ultrasound energy delivered at desired depths and locations via various spatial and temporal energy settings. In one embodiment, the tissues of interest are viewed in motion in real time by utilizing ultrasound imaging to clearly view the moving tissue to aid in targeting and treatment of a region of interest on the patient's forehead. Therefore, the physician performing the non-invasive brow lift can visually observe the movement and changes occurring to the subcutaneous tissue during treatment.

In another embodiment, a method and system for performing a non-invasive blepharoplasty by treating various tissues with energy is provided. In an embodiment, a non-invasive blepharoplasty that can effectively treat crow's feet is performed by applying ultrasound energy at specific depths around the patient's eyes to ablate, cut, manipulate, caused to be reabsorbed into the body, and/or paralyze tissue around the eyes to reduce wrinkles including crow's feet, puffiness, and/or sagging skin.

In one embodiment, ultrasound energy is applied at a region of interest around the patient's eyes. The ultrasound energy is applied at specific depths and is capable of targeting certain tissues including various subcutaneous tissues. For example, pockets of fat near the patient's eyelids can be targeted and treated by the application of ultrasound energy at specific depths. These pockets of fat can be ablated and reabsorbed into the body during the treatment. Muscles, skin, or other supporting, connective tissues can be ablated, shaped, or otherwise manipulated by the application of ultrasound energy in a non-invasive manner. Specifically, instead of cutting into the sensitive area around the patient's eyes as is done during a traditional blepharoplasty or transconjunctival blepharoplasty, the targeted tissues can be treated by applying ultrasound energy around the eyes without the need for traditional invasive techniques.

Further, by applying energy at a region of interest that is partially comprised by the orbicularis oculi muscle, the energy can be used to paralyze or otherwise selectively incapacitate or modify this orbicularis oculi muscle tissue. Therefore, the need for redundant BOTOX-type injections is eliminated and the entire eye region can be treated in this non-invasive manner.

In various embodiments, a method and system are configured for targeted treatment of tissue around the eyes in various manners such as through the use of therapy only, therapy and monitoring, imaging and therapy, or therapy, imaging and monitoring. Targeted therapy of tissue can be provided through ultrasound energy delivered at desired depths and locations via various spatial and temporal energy settings.

In another embodiment, the tissues of interest are viewed in motion in real time by utilizing ultrasound imaging to clearly view the moving tissue to aid in targeting and treatment of a region of interest near the patient's eyes. Therefore, the physician performing the non-invasive blepharoplasty can visually observe the movement and changes occurring to the tissue during treatment.

In yet another embodiment, a method and system for treating various cartilage tissues with energy is provided. In an embodiment, a non-invasive otoplasty is performed by applying ultrasound energy at specific depths along the pinna of the ear to ablatively cut, cause tissue to be reabsorbed into the body, or manipulate cartilage tissue within the ear to reduce the angle at which the ears protrude from the head.

In one embodiment, ultrasound energy is targeted to a region of interest along the pinna of the patient's ear. The ultrasound energy is applied at specific depths and is capable of targeting cartilage tissue within the ear such as scapha cartilage and scaphoid fossa which in part, form the pinna of the ear. The ablative cutting, shaping, and manipulating of cartilage can be used to reduce the overall size of the patient's ear or be used to ablate the tissue and cause it to be reabsorbed into the body to perform a non-invasive otoplasty thereby allowing the ears to rest against the head.

In other embodiments, cartilage tissue at other locations of the patient's body can be treated according to the method and system of the present invention. In one such embodiment, nose surgery or a "rhinoplasty" can be performed using targeted ultrasound energy. During a rhinoplasty procedure, energy is applied at specific depths and is capable of targeting cartilage within the nose. The cartilage can be ablatively cut, shaped or otherwise manipulated by the application of ultrasound energy in a non-invasive manner. This cutting, shaping, and manipulating of the cartilage of the nose can be used to cause the cartilage to be reabsorbed into the body, ablate, or coagulate the cartilage of the nose to perform a non-invasive rhinoplasty according to the present invention.

In various embodiments, a method and system are configured for targeted treatment of cartilage tissue in various manners such as through the use of therapy only, therapy and monitoring, imaging and therapy, or therapy, imaging and monitoring. Targeted therapy of tissue can be provided through ultrasound energy delivered at desired depths and locations via various spatial and temporal energy settings. In one embodiment, the cartilage is viewed in motion in real time by utilizing ultrasound imaging to clearly view the cartilage to aid in targeting and treatment of a region of interest. Therefore, the physician or other user can visually observe the movement and changes occurring to the cartilage during treatment.

In any of the embodiments disclosed herein, one or more of the following effects is achieved: a face lift, a brow lift, a chin lift, a wrinkle reduction, a scar reduction, a tattoo removal, a vein removal, sun spot removal, and acne treatment. In various embodiments, the treatment function is one of face lift, a brow lift, a chin lift, an eye treatment, a wrinkle reduction, a scar reduction, a burn treatment, a tattoo removal, a vein removal, a vein reduction, a treatment on a sweat gland, a treatment of hyperhidrosis, sun spot removal, an acne treatment, and a pimple removal. In another embodiment, the device may be used on adipose tissue (e.g., fat).

In any of the embodiments disclosed herein, imaging occurs prior to the therapy, simultaneously with the therapy, or after the therapy. In several of the embodiments described herein, the procedure is entirely cosmetic and not a medical act.

In one embodiment, a method of treating sagging brows includes acoustically coupling an ultrasound probe system to a skin surface on a brow. In one embodiment, the ultrasound probe system includes an imaging element, a therapy element, and a motion mechanism. The motion mechanism is controlled by a control system in communication with the ultrasound probe. The method can include using the ultrasound imaging element to image a region of interest under the skin surface at a fixed depth, the region of interest comprising a tissue comprising a portion of at least one of muscular fascia, fat, and SMAS tissue. In one embodiment, the region of interest at the fixed depth is displayed on a display system, the display system being electronically connected to the ultrasound imaging element. The method includes using the ultrasound therapy element to treat the region of interest. The therapy element is coupled to the motion mechanism within the probe. The therapy element is configured for targeted delivery of ablative ultrasound energy to form a thermal lesion with at least a temperature sufficient to treat at least a portion of the tissue at the fixed depth of up to about 9 mm from the skin surface. The method can include activating the motion mechanism within the probe to form a plurality of the thermal lesions along a line at the fixed depth into the tissue to cause any one of the group consisting of ablation, deactivation, and shrinkage of at least a portion of the tissue. In one embodiment, the plurality of thermal lesions facilitates a tightening of the tissue that leads to a brow lift.

In one embodiment, the imaging element is configured to image with an imaging frequency of between 2 kHz to 75 MHz and the therapy element is configured to treat with a treatment frequency of between 4 MHz and 15 MHz. In one embodiment, the fixed depth of the lesion is within a range of 0 to 5 mm from the skin surface. In one embodiment, the fixed depth of the lesion is within a range of 1 mm to 6 mm from the skin surface. In one embodiment, the activating of the motion mechanism includes communication between and at least two of the group consisting of a control system, an accelerometer, encoder and a position/orientation device.

In one embodiment, a method of treating skin on a face includes providing a probe that emits ultrasound energy, coupling the probe to a skin surface on the face proximate a region comprising subcutaneous fat, muscle, and connective tissue. The method can include emitting and directing ultrasound energy from the probe to specific depths to target the subcutaneous fat, muscle, and connective tissue. In one embodiment, the method includes applying a sufficient amount of ultrasound energy to coagulate at least one of subcutaneous fat, muscle, and connective tissue. In one embodiment, the method includes coagulating a sufficient amount of the subcutaneous fat, muscle, and connective tissue to reduce skin sagging on the face.

In one embodiment, a sufficient amount of ultrasound energy is emitted to ablate the subcutaneous fat, muscle, and connective tissue responsible for wrinkles. In one embodiment, the subcutaneous fat tissue is disposed along the lower eyelid and a lower lid blepharoplasty is performed. In one embodiment, the subcutaneous fat tissue is disposed along the upper eyelid and an upper lid blepharoplasty is performed. In one embodiment, the subcutaneous fat tissue is disposed along both the upper and lower eyelids and both an upper and lower blepharoplasty is performed. In one embodiment, the region is located near an eye region further includes the orbicularis oculi muscle. In one embodiment, the application of ultrasound energy ablates the orbicularis oculi muscle. In one embodiment, the ablation of the orbicularis oculi muscle results in the removal of crow's feet. In one embodiment, the region includes a corrugator supercilii muscle. In one embodiment, the corrugator supercilii muscle is ablated with ultrasound energy at a frequency of 3-7 MHz.

In one embodiment, a method of reducing wrinkles on a brow with a combined imaging and therapy ultrasound transducer includes identifying a treatment area comprising at least one wrinkle in a skin surface and wrinkle causing subcutaneous tissue. In one embodiment, the method includes imaging at least a portion of the treatment area with an ultrasound transducer configured for both imaging and therapy. In one embodiment, the method includes delivering ultrasound energy with the ultrasound transducer through the skin surface and into a portion of the treatment area comprising the wrinkle-causing subcutaneous tissue to cause thermally injury to a portion of the wrinkle-causing subcutaneous tissue, thereby reducing the at least one wrinkle the skin surface.

In one embodiment, delivering ultrasound energy is in a frequency range of about 2 MHz to about 25 MHz. In one embodiment, delivering ultrasound energy is at an energy level sufficient to cause the portion of the wrinkle-causing subcutaneous tissue to reabsorb into the body. In one embodiment, the portion of the wrinkle-causing subcutaneous tissue includes a portion of an epicranius muscle. In one embodiment, the portion of the wrinkle-causing subcutaneous tissue includes a portion of a procerus muscle.

Further areas of applicability will become apparent from the description provided herein. It should be understood that the description and specific examples are intended for purposes of illustration only and are not intended to limit the scope of the embodiments disclosed herein.

BRIEF DESCRIPTION OF THE DRAWINGS

The subject matter of various embodiments of the invention is particularly pointed out in the concluding portion of the specification. Embodiments of the invention, however, both as to organization and method of operation, may be better understood by reference to the following description taken in conjunction with the accompanying drawing figures, in which like parts may be referred to by like numerals. The drawings described herein are for illustration purposes only and are not intended to limit the scope of the present disclosure in any way. Embodiments of the present invention will become more fully understood from the detailed description and the accompanying drawings wherein.

DETAILED DESCRIPTION

Figure 1:
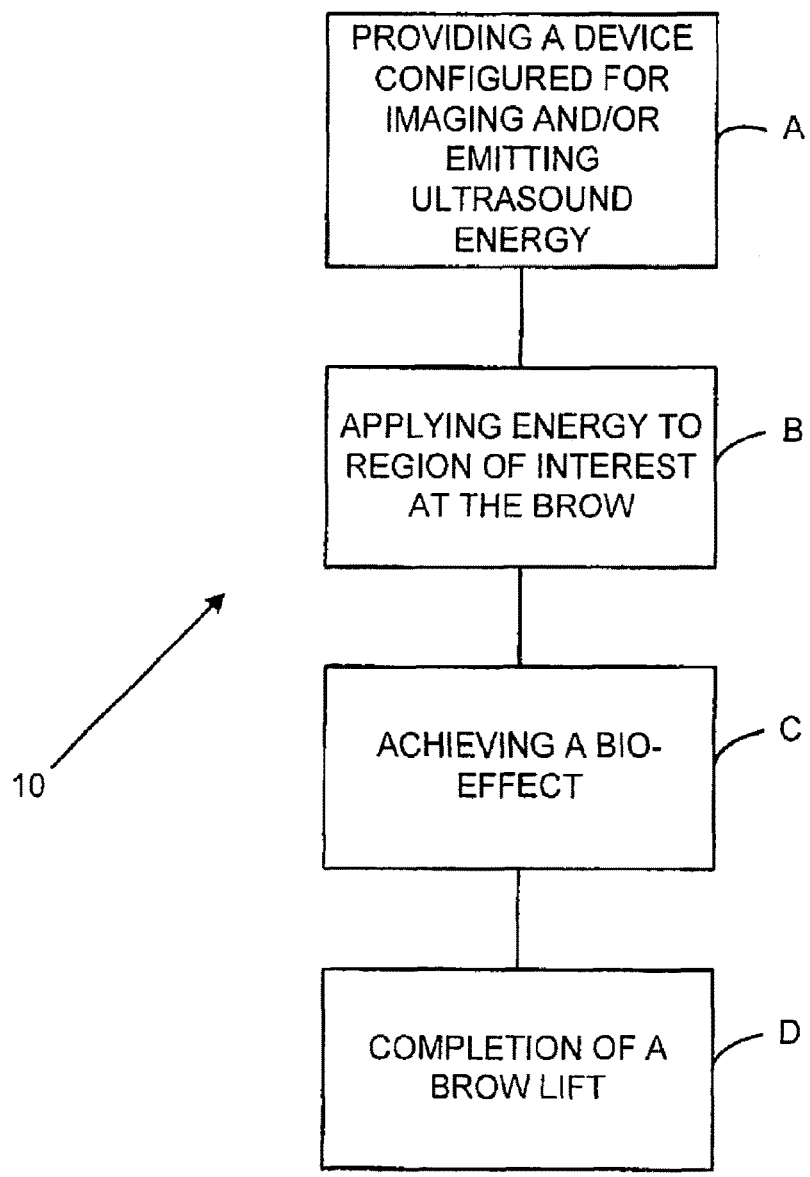
FIG. 1 illustrates a flow chart of the treatment method for performing a brow lift in accordance with an embodiment of the present invention.

The following description sets forth examples of embodiments, and is not intended to limit the present invention(s) or its teachings, applications, or uses thereof. It should be understood that throughout the drawings, corresponding reference numerals indicate like or corresponding parts and features. The description of specific examples indicated in various embodiments of the present invention are intended for purposes of illustration only and are not intended to limit the scope of the invention disclosed herein. Moreover, recitation of multiple embodiments having stated features is not intended to exclude other embodiments having additional features or other embodiments incorporating different combinations of the stated features. Further, features in one embodiment (such as in one figure) may be combined with descriptions (and figures) of other embodiments.

In one embodiment, methods and systems for ultrasound treatment of tissue are configured to provide cosmetic treatment. In various embodiments of the present invention, tissue below or even at a skin surface such as epidermis, dermis, fascia, and superficial muscular aponeurotic system ("SMAS"), are treated non-invasively with ultrasound energy. The ultrasound energy can be focused, unfocused or defocused and applied to a region of interest containing at least one of epidermis, dermis, hypodermis, fascia, and SMAS to achieve a therapeutic effect. In one embodiment, the present invention provides non-invasive dermatological treatment to produce eyebrow lift through tissue coagulation and tightening. In one embodiment, the present invention provides imaging of skin and sub-dermal tissue. Ultrasound energy can be focused, unfocused or defocused, and applied to any desired region of interest, including adipose tissue. In one embodiment, adipose tissue is specifically targeted.

In various embodiments, certain cosmetic procedures that are traditionally performed through invasive techniques are accomplished by targeting energy, such as ultrasound energy, at specific subcutaneous tissues. In several embodiments, methods and systems for non-invasively treating subcutaneous tissues to perform a brow lift are provided; however, various other cosmetic treatment applications, such as face lifts, acne treatment and/or any other cosmetic treatment application, can also be performed with the cosmetic treatment system. In one embodiment, a system integrates the capabilities of high resolution ultrasound imaging with that of ultrasound therapy, providing an imaging feature that allows the user to visualize the skin and sub-dermal regions of interest before treatment. In one embodiment, the system allows the user to place a transducer module at optimal locations on the skin and provides feedback information to assure proper skin contact. In one embodiment, the therapeutic system provides an ultrasonic transducer module that directs acoustic waves to the treatment area. This acoustic energy heats tissue as a result of frictional losses during energy absorption, producing a discrete zone of coagulation.

The present disclosure may be described herein in terms of various functional components and processing steps. For simplicity, the next part of the present disclosure illustrates three methods and systems: a method and system for performing a brow lift, a method and system for performing a blepharoplasty, and a method and system for treating cartilage; however, such methods and systems can be suitably applied and/or for other tissue applications. Further, while specific hardware and software components are mentioned and described throughout, other components configured to perform the same function can also be utilized.

Method and System for Performing a Brow Lift

With reference to FIGS. 1-8 and according to one embodiment, a method and system is provided for treating tissue along a patient's forehead with focused, unfocused or defocused energy to elevate the patient's eyebrows and reduce wrinkles to perform a brow lift. In an embodiment, the energy used is ultrasound energy. In other embodiments, the energy is laser energy or radio frequency energy. In certain embodiments, the energy is ultrasound energy combined with other forms of energy such as laser or radio frequency energy. The method will be referred to as method 10 throughout. In an embodiment, with particular reference to FIG. 3, the treated tissue region 1 comprises subcutaneous tissue 2 and can comprise muscle, tendon, ligament or cartilage tissue (MTLC), among other types of tissue. It should be noted that references throughout this specification to tissue 1 include subcutaneous tissue 2 and references to subcutaneous tissue 2 include tissue 1.

Figure 2:
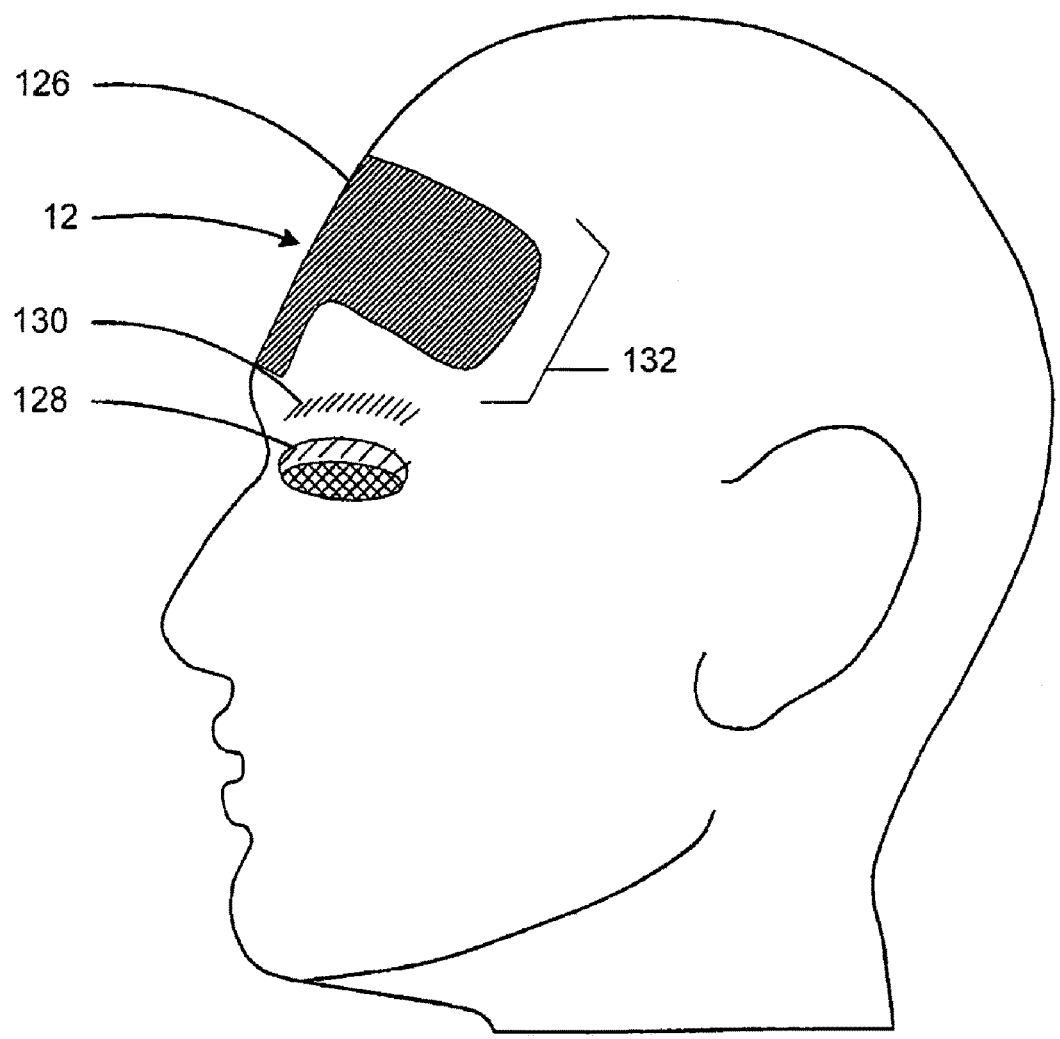
FIG. 2 illustrates a patient's head and the location of the muscles that can be treated during a brow lift in accordance with embodiments of the present invention.

Subcutaneous tissue 2 is wrinkle generating subcutaneous tissue located within a Region of Interest (ROI) 12, e.g., as illustrated in FIG. 2, which is on a patient's forehead or forehead region in an embodiment. ROI 12 may comprise an inner treatment region, a superficial region, a subcutaneous region of interest and/or any other region of interest in between an inner treatment region, a superficial region, and/or a subcutaneous region within a patient, and/or combinations thereof.

As depicted in the embodiment shown in FIG. 1, method 10 broadly comprises the following steps A-D. First, in step A, a system that emits energy such as ultrasound energy is provided. In one embodiment, this system is also configured to obtain images. At step B, energy is applied to a region of interest which comprises the patient's forehead region. The energy is applied until a certain bio-effect is achieved at step C. Upon the completion of bio-effects at step C, a brow lift is completed at step D.

The bio-effects may produce a clinical outcome such as a brow lift which can comprise elevating the patient's eyebrows and reducing wrinkles on the patient's brow or forehead region. The clinical outcome may be the same as traditional invasive surgery techniques, and may comprise the removal of wrinkles through a brow lift or replacement of BOTOX-type treatment. The term "BOTOX-type treatment" is meant to include treating the muscles and other tissue 1 and subcutaneous tissue 2 within the forehead with muscle relaxant drugs. One drug is sold under the trademark BOTOX®. and is produced by the Allergan Corporation of Irvine, Calif. Other drugs include the DYSPORT®. drug produced by Ipsen, Inc. of Milford, Mass. or the VISTABEL®. drug also produced by the Allergan Corporation.

FIG. 2 depicts an embodiment where method 10 is used to perform a brow lift by targeting wrinkle generating subcutaneous tissue 2. Wrinkles can be partially or completely removed by applying ultrasound energy at ROI 12 along the patient's forehead at levels causing the desired bio-effects. As noted above, the bio-effects can comprise ablating, micro-ablating, coagulating, severing, partially incapacitating, shortening, removing, or otherwise manipulating tissue 1 or subcutaneous tissue 2 to achieve the desired effect. As part of removing the subcutaneous tissue 2, method 10 can be used to ablate, micro-ablate, or coagulate a specific tissue. Further, in one embodiment, muscle 3 (such as the corrugator supercilii muscle) can be paralyzed and permanently disabled and method 10 can be utilized to replace toxic BOTOX®. injections either completely or reduce the amount of BOTOX-type injections.

When method 10 is used in this manner, certain subcutaneous tissues such as muscles are incapacitated and paralyzed or rendered incapable of movement. In one embodiment, the muscles within ROI 12 may be either cut, ablated, coagulated, or micro-ablated in a manner such that the muscles may be no longer able of movement and be permanently paralyzed due to the bio-effects from the application of energy such as ultrasound energy. The paralysis of the muscles may reduce or eliminate wrinkles on the tissue. Unlike traditional BOTOX-type injections, the paralysis may be permanent and the wrinkles may not reappear after treatment. Therefore, repeated treatments as with BOTOX-type treatments are not necessary. Method 10 may be used on any area of the body of a patient to replace traditional BOTOX-type injections. Examples include the forehead or neck area, or around the eyes to remove wrinkles referred to as "crow's feet."

With continued reference to FIG. 2 and in an embodiment, the use of ultrasound energy 21 may replace the need for any invasive surgery to perform a brow lift. In this embodiment, a transducer may be coupled to, or positioned near a brow 126 and ultrasound energy may be emitted and targeted to specific depths within ROI 12, which may produce various bio-effects. These bio-effects may have the same effect as traditional invasive techniques without traditional or endoscopic surgery. For example, instead of making an incision across brow 126 to cut a particular muscle such as the corrugator supercilii muscle or SMAS, the ultrasound energy can be applied at ROI 12 to cut and/or remove a portion of the corrugator supercilii muscle or permanently paralyze and disable the corrugator supercilii muscle or SMAS 8 and achieve the same results as traditional invasive brow lifts.

Method 10 may be used to perform any type of brow lift. For example, an endobrow or open brow lift of just the brow 126 may be performed. In this procedure, ROI 12 may comprise the upper eyelids 128 and eyebrows 130. Alternatively, the brow lift may limit the ROI 12 to just the forehead muscles 132. In yet another embodiment, method 10 may be utilized in a similar manner to replace traditional surgical techniques to perform an entire face lift.

Turning now to the embodiment depicted in FIGS. 3-5, energy such as ultrasound energy 21 is delivered at specific depths below the skin of a patient to treat tissue 1 and subcutaneous tissue 2. Certain subcutaneous tissues 2 which may be treated by method 10 may comprise muscles 3, fascia 7, the Superficial Muscular Aponeurotic System ("SMAS") 8, fat 9, as well as ligament and cartilage tissue.

The application of energy to ROI 12 may produce certain desired bio-effects on tissue 1 and/or subcutaneous tissue 2 by affecting these tissues that are responsible for wrinkles along brow 126. The bio-effects may comprise, but are not limited to, ablating, coagulating, microablating, severing, partially incapacitating, rejuvenating, shortening, or removing tissue 1 and/or subcutaneous tissue 2 either instantly or over longer time periods. Specific bio-effects may be used to treat different subcutaneous tissues 2 to produce different treatments as described in greater detail below.

Figure 3:
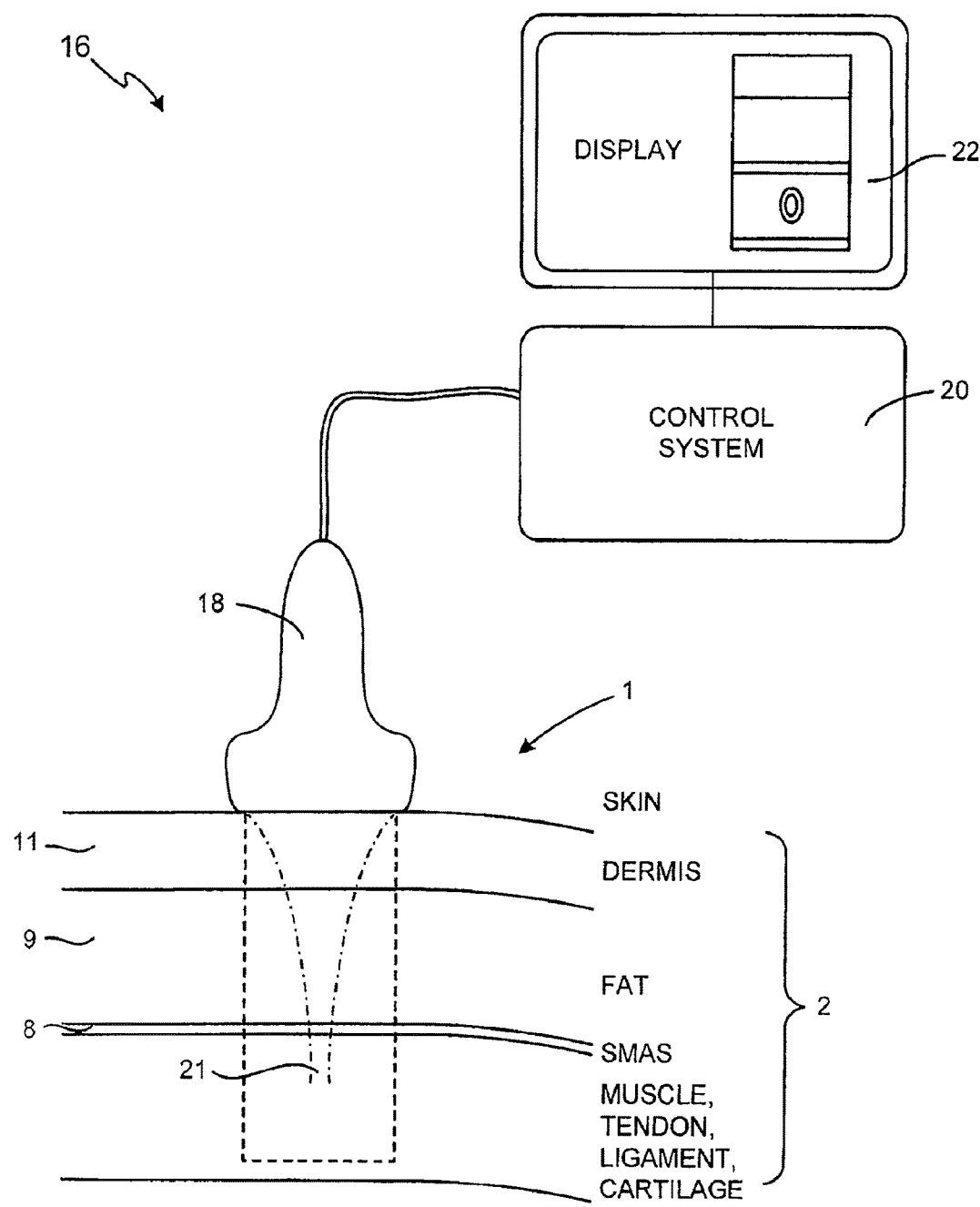
FIG. 3 illustrates a schematic diagram of an ultrasound treatment system configured to treat subcutaneous tissue during a brow lift in accordance with an embodiment of the present invention.
Figure 4:
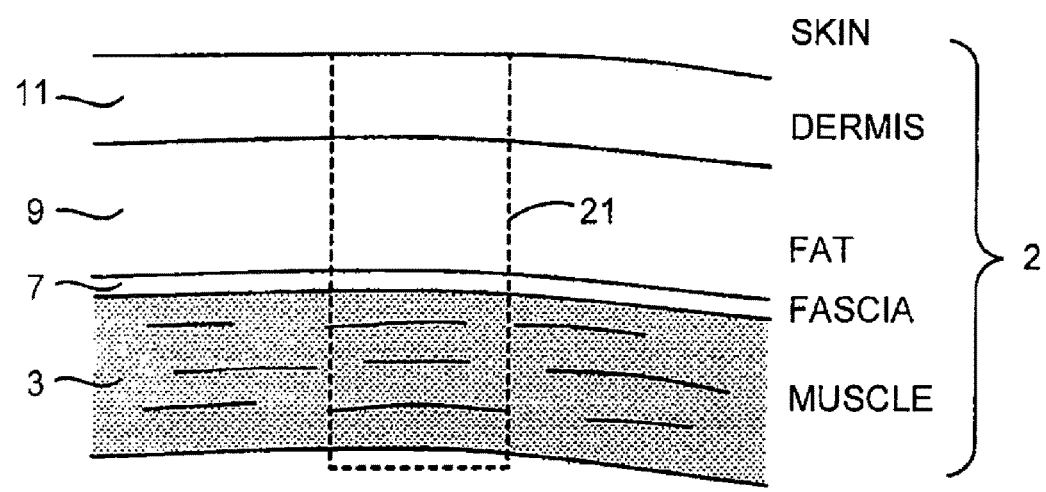
FIG. 4 illustrates various layers of subcutaneous tissue that the can be treated or imaged during a brow lift in accordance with an embodiment of the present invention.
Figure 5:
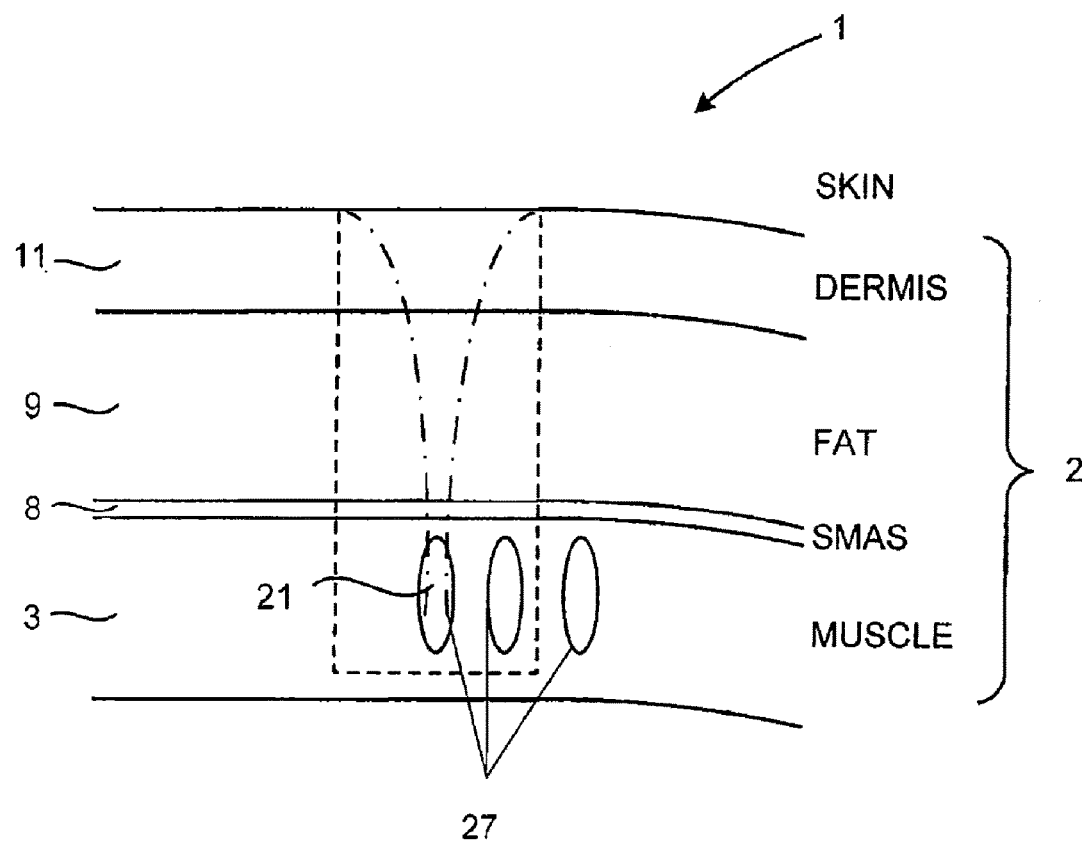
FIG. 5 illustrates a layer of muscle tissue being treated during a brow lift in accordance with an embodiment of the present invention.

In an embodiment, with reference to FIGS. 3-5, various different tissues 1 or subcutaneous tissues 2 may be treated by method 10 to produce different bio-effects. In order to treat a specific subcutaneous tissue 2 to achieve a desired bio-effect, ultrasound energy 21 may be directed to a specific depth within ROI 12 to reach the targeted subcutaneous tissue 2. For example, if it is desired to cut muscle 3 such as the corrugator supercilii muscle (by applying ultrasound energy 21 at ablative or coagulative levels), which is approximately 15 mm below the surface of the skin, ultrasound energy 21 may be provided at ROI 12 at a level to reach 15 mm below the skin at an ablative or coagulative level which may be capable of ablating or coagulating muscle 3.

In an embodiment, the energy level for ablating tissue such as muscle 3 is in the range of approximately 0.1 joules to 10 joules to create an ablative lesion. Further, the amount of time energy such as ultrasound energy 21 is applied at these power levels to create a lesion varies in the range from approximately 1 millisecond to several minutes. The frequency of the ultrasound energy is in the range between approximately 2-12 MHz and more specifically in the range of approximately 3-7 MHz. Certain times are in the range of approximately 1 millisecond to 200 milliseconds. In an embodiment where a legion is being cut into the corrugator supercilii muscle, approximately 1.5 joules of power is applied for about 40 milliseconds. Applying ultrasound energy 21 in this manner can cause ablative lesions in the range of approximately 0.1 cubic millimeters to about 1000 cubic millimeters. A smaller lesion can be in the range of about 0.1 cubic millimeters to about 3 cubic millimeters. Cutting the corrugator supercilii muscle in this manner may paralyze and permanently disable the corrugator supercilii muscle.

An example of ablating muscle 3 is depicted in FIG. 5 which depicts a series of lesions 27 cut into muscle 3. Besides ablating or coagulating muscle 3, other bio-effects may comprise incapacitating, partially incapacitating, severing, rejuvenating, removing, ablating, micro-ablating, coagulating, shortening, cutting, manipulating, or removing tissue 1 either instantly or over time and/or other effects, and/or combinations thereof. In an embodiment, muscle 3 can comprise the frontalis muscle, the corrugator supercilii muscle, the epicranius muscle, or the procerus muscle.

Different tissues 1 and subcutaneous tissues 2 within the ROI 12 may have different acoustic properties. For example, the corrugator supercilii muscle might have different acoustic properties than the frontalis muscle or fat disposed along the brow. These different acoustic properties affect the amount of energy applied to ROI 12 to cause certain bio-effects to the corrugator supercilii muscle than may be required to achieve the same or similar bio-effects for the frontalis muscle. These acoustic properties may comprise the varied acoustic phase velocity (speed of sound) and its potential anisotropy, varied mass density, acoustic impedance, acoustic absorption and attenuation, target size and shape versus wavelength, and direction of incident energy, stiffness, and the reflectivity of tissue 1 and subcutaneous tissues 2, among many others. Depending on the acoustic properties of a particular tissue 1 or subcutaneous tissue 2 being treated, the application of ultrasound energy 21 at ROI 12 may be adjusted to best compliment the acoustic property of tissue 1 or subcutaneous tissue 2 being targeted.

Depending at least in part upon the desired bio-effect and the subcutaneous tissue 2 being treated, method 10 may be used with an extracorporeal, non-invasive, partially invasive, or invasive procedure. Also, depending at least in part upon the specific bio-effect and subcutaneous tissue 2 targeted, there may be temperature increases within ROI 12 which may range from approximately 0-60° C. or heating, cavitation, steaming, and/or vibro-acoustic stimulation, and/or combinations thereof.

Besides producing various bio-effects to tissue 1, method 10 and the associated ultrasound system may also be used for imaging. The imaging may be accomplished in combination with the treatments described herein, or it may be accomplished as a separate function to locate tissue 1 or subcutaneous tissue 2 to be targeted. In an embodiment, the imaging of ROI 12 may be accomplished in real time as the treatment is being administered. This may assist visualization of certain moving subcutaneous tissue 2 during treatment. In other embodiments, the user may simply know where the specific subcutaneous tissue 2 is based on experience and not require imaging.

Throughout this application, reference has been made to treating a single layer of tissue 1 at any given time. It should be noted that two or more layers of tissue (both the skin and subcutaneous tissue 2) may be treated at the same time and fall within the scope of this disclosure. In this embodiment, the skin may be treated along with subcutaneous tissues 2. In other embodiments where two or more layers of tissue are treated, muscle 3, ligaments 5, and SMAS 8 can be treated simultaneously.

In another embodiment, method 10 can be used to assist in delivery of various fillers and other medicines to ROI 12. According to this embodiment, ultrasound energy 21 assists in forcing the fillers and medicants into tissue 1 and subcutaneous tissue 2 at ROI 12. Hyaluronic acid can be delivered to ROI 12 in this manner. The application of ultrasound energy 21 to ROI 12 causes surrounding tissues to absorb the fillers such as hyaluronic acid by increasing the temperature at ROI 12 and through the mechanical effects of ultrasound such as cavitation and streaming. Utilizing ultrasound energy 21 to effectuate the delivery of medicants and fillers is described in U.S. patent application Ser. No. 11/163,177 entitled "Method and System for Treating Acne and Sebaceous Glands" which is been incorporated by reference in its entirety, herein.

Figure 6:
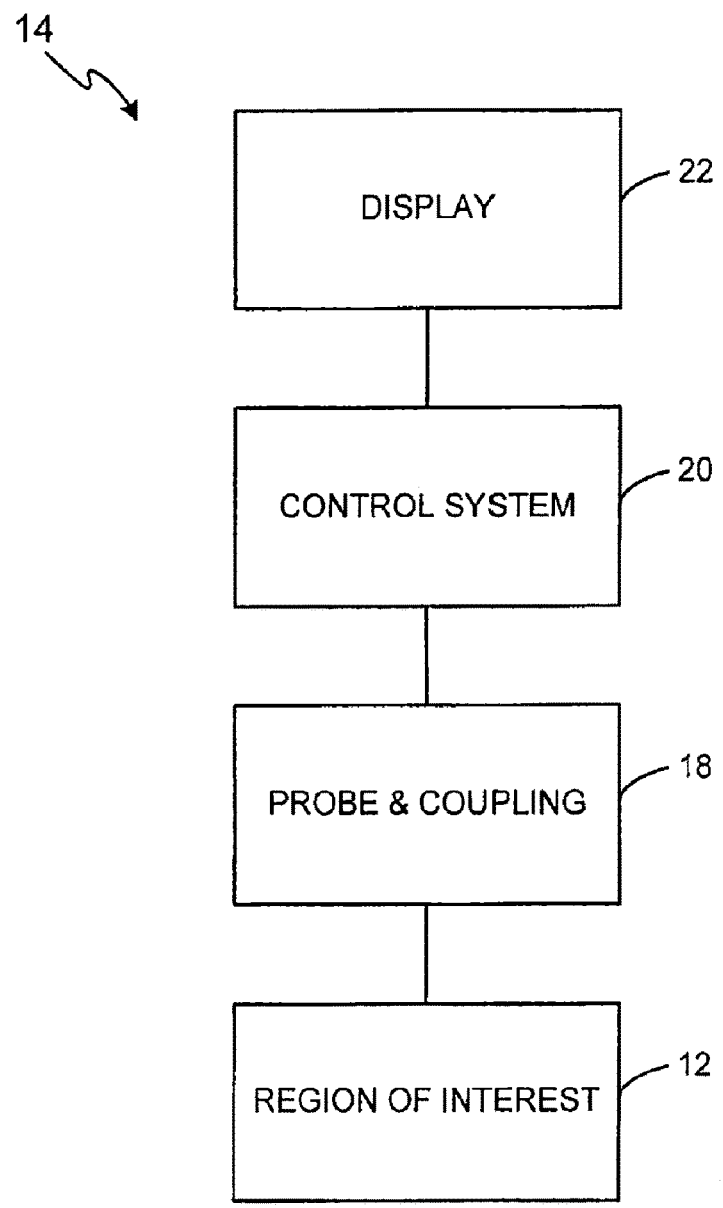
FIG. 6 illustrates a block diagram of a treatment system for performing a brow lift in accordance with an embodiment of the present invention.

Turning now to the embodiment depicted in FIGS. 6-8, an system 14 for emitting energy to effectuate a brow lift is an ultrasound system 16 that may be capable of emitting ultrasound energy 21 that is focused, unfocused or defocused to treat tissue 1 and subcutaneous tissue 2 at ROI 12. System 14 may comprise a probe 18, a control system 20, and a display 22. System 14 may be used to delivery energy to, and monitor, ROI 12. Certain embodiments of systems may be disclosed in U.S. patent application Ser. No. 11/163, 177 entitled "Method and System for Treating Acne and Sebaceous Glands," U.S. patent application Ser. No. 10/950, 112 entitled "Method and System for Combined Ultrasound Treatment", and U.S. Patent Application No. 60/826,039 entitled "Method and System for Non-Ablative Acne Treatment", each of which are hereby incorporated by reference in their entirety.

With reference to FIG. 7, an embodiment of a probe 18 may be a transducer 19 capable of emitting ultrasound energy 21 into ROI 12. This may heat ROI 12 at a specific depth to target a specific tissue 1 or subcutaneous tissue 2 causing that tissue to be ablated, micro-ablated, coagulated, incapacitated, partially incapacitated, rejuvenated, shortened, paralyzed, or removed. Certain tissues that are targeted comprise the corrugator supercilii muscle, the frontalis muscle, the procerus muscle, and/or the epicranius muscle or other muscle disposed along the patient's forehead.

A coupling gel may be used to couple probe 18 to ROI 12 at the patient's forehead. Ultrasound energy 21 may be emitted in various energy fields in this embodiment. With additional reference to FIG. 7A and FIG. 7B and in this embodiment, the energy fields may be focused, defocused, and/or made substantially planar by transducer 19, to provide many different effects. Energy may be applied in a C-plane or C-scan. For example, in one embodiment, a generally substantially planar energy field may provide a heating and/or pretreatment effect, a focused energy field may provide a more concentrated source of heat or hypothermal effect, and a non-focused energy field may provide diffused heating effects. It should be noted that the term "non-focused" as used throughout encompasses energy that is unfocused or defocused.

In another embodiment, a transducer 19 may be capable of emitting ultrasound energy 21 for imaging or treatment or combinations thereof. In an embodiment, transducer 19 may be configured to emit ultrasound energy 21 at specific depths in ROI 12 to target a specific tissue such as a corrugator supercilii muscle as described below. In this embodiment of FIG. 7, transducer 19 may be capable of emitting unfocused or defocused ultrasound energy 21 over a wide area in ROI 12 for treatment purposes.

Transducer 19 may comprise one or more transducers for facilitating treatment. Transducer 19 may further comprise one or more transduction elements 26, e.g., elements 26A or 26B (see FIGS. 7A and 7B). The transduction elements 26 may comprise piezoelectrically active material, such as lead zirconante titanate (PZT), or other piezoelectrically active material such as, but not limited to, a piezoelectric ceramic, crystal, plastic, and/or composite materials, as well as lithium niobate, lead titanate, barium titanate, and/or lead metaniobate. In addition to, or instead of, a piezoelectrically active material, transducer 19 may comprise any other materials configured for generating radiation and/or acoustical energy. Transducer 19 may also comprise one or more matching and/or backing layers configured along with the transduction element 26, such as being coupled to the piezoelectrically active material. Transducer 19 may also be configured with single or multiple damping elements along the transduction element 26.

In an embodiment, the thickness of the transduction element 26 of transducer 19 may be configured to be uniform. That is, the transduction element 26 may be configured to have a thickness that is generally substantially the same throughout.

In another embodiment, the transduction element 26 may also be configured with a variable thickness, and/or as a multiple damped device. For example, the transduction element 26 of transducer 19 may be configured to have a first thickness selected to provide a center operating frequency of a lower range, for example from approximately 1 kHz to 3 MHz. The transduction element 26 may also be configured with a second thickness selected to provide a center operating frequency of a higher range, for example from approximately 3 to 100 MHz or more.

In yet another embodiment, transducer 19 may be configured as a single broadband transducer excited with two or more frequencies to provide an adequate output for raising the temperature within ROI 12 to the desired level. Transducer 19 may also be configured as two or more individual transducers, wherein each transducer 19 may comprise a transduction element 26. The thickness of the transduction elements 26 may be configured to provide center-operating frequencies in a desired treatment range. For example, in an embodiment, transducer 19 may comprise a first transducer 19 configured with a first transduction element 26A having a thickness corresponding to a center frequency range of approximately 1 MHz to 3 MHz, and a second transducer 19 configured with a second transduction element 26B having a thickness corresponding to a center frequency of approximately 3 MHz to 100 MHz or more. Various other ranges of thickness for a first and/or second transduction element 26 can also be realized.

Moreover, in an embodiment, any variety of mechanical lenses or variable focus lenses, e.g. liquid-filled lenses, may also be used to focus and or defocus the energy field. For example, with reference to the embodiments depicted in FIGS. 7A and 7B, transducer 19 may also be configured with an electronic focusing array 24 in combination with one or more transduction elements 26 to facilitate increased flexibility in treating ROI 12. Array 24 may be configured in a manner similar to transducer 19. That is, array 24 may be configured as an array of electronic apertures that may be operated by a variety of phases via variable electronic time delays, for example, T1, T2, T3 . . . Tj. By the term "operated," the electronic apertures of array 24 may be manipulated, driven, used, and/or configured to produce and/or deliver energy in a manner corresponding to the phase variation caused by the electronic time delay. For example, these phase variations may be used to deliver defocused beams, planar beams, and/or focused beams, each of which may be used in combination to achieve different physiological effects in ROI 12.

Transduction elements 26 may be configured to be concave, convex, and/or planar. For example, in the embodiment depicted in FIG. 7A, transduction elements 26A and 26B are configured to be concave in order to provide focused energy for treatment of ROI 12. Additional embodiments are disclosed in U.S. patent application Ser. No. 10/944,500, entitled "System and Method for Variable Depth Ultrasound Treatment," incorporated herein by reference in its entirety.

Figure 7A:
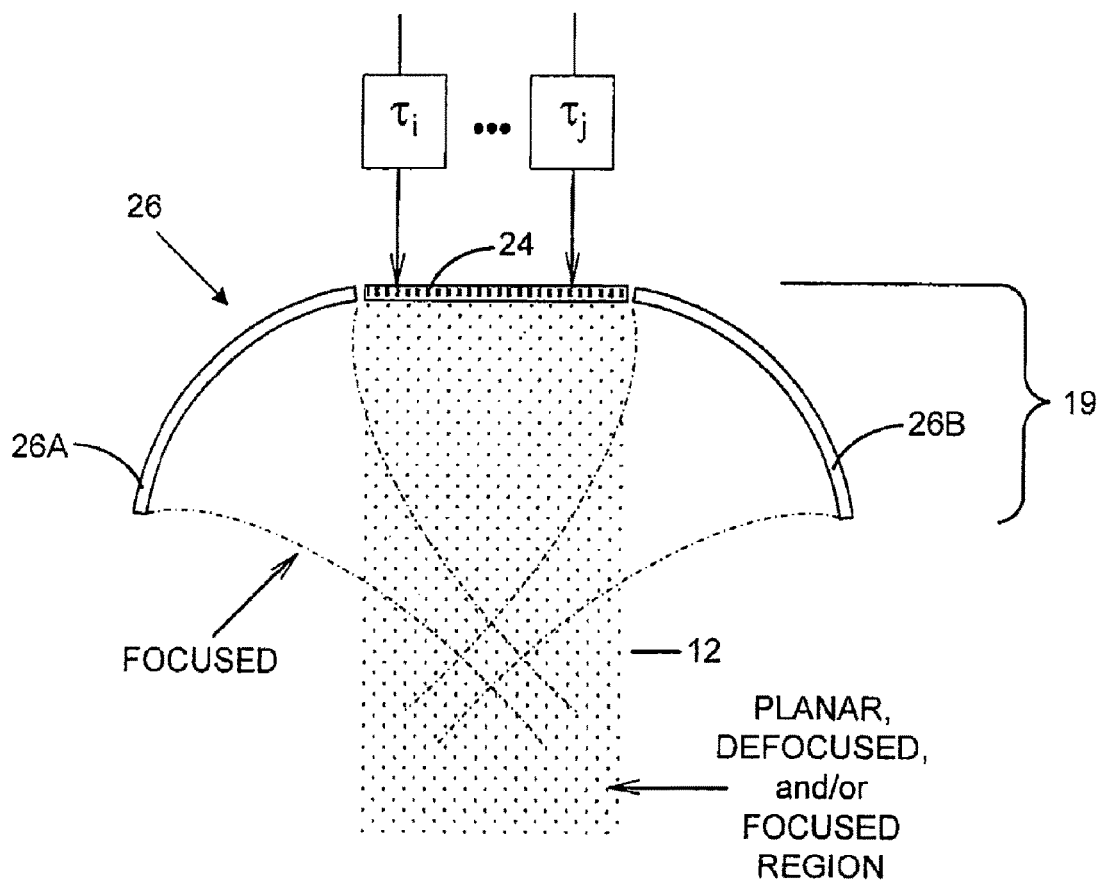
FIGS. 7A, 7B, 7C, 7D, and 7E illustrate cross-sectional diagrams of an transducer used in a system used to effectuate a brow lift in accordance with various embodiments of the present invention.
Figure 7B:
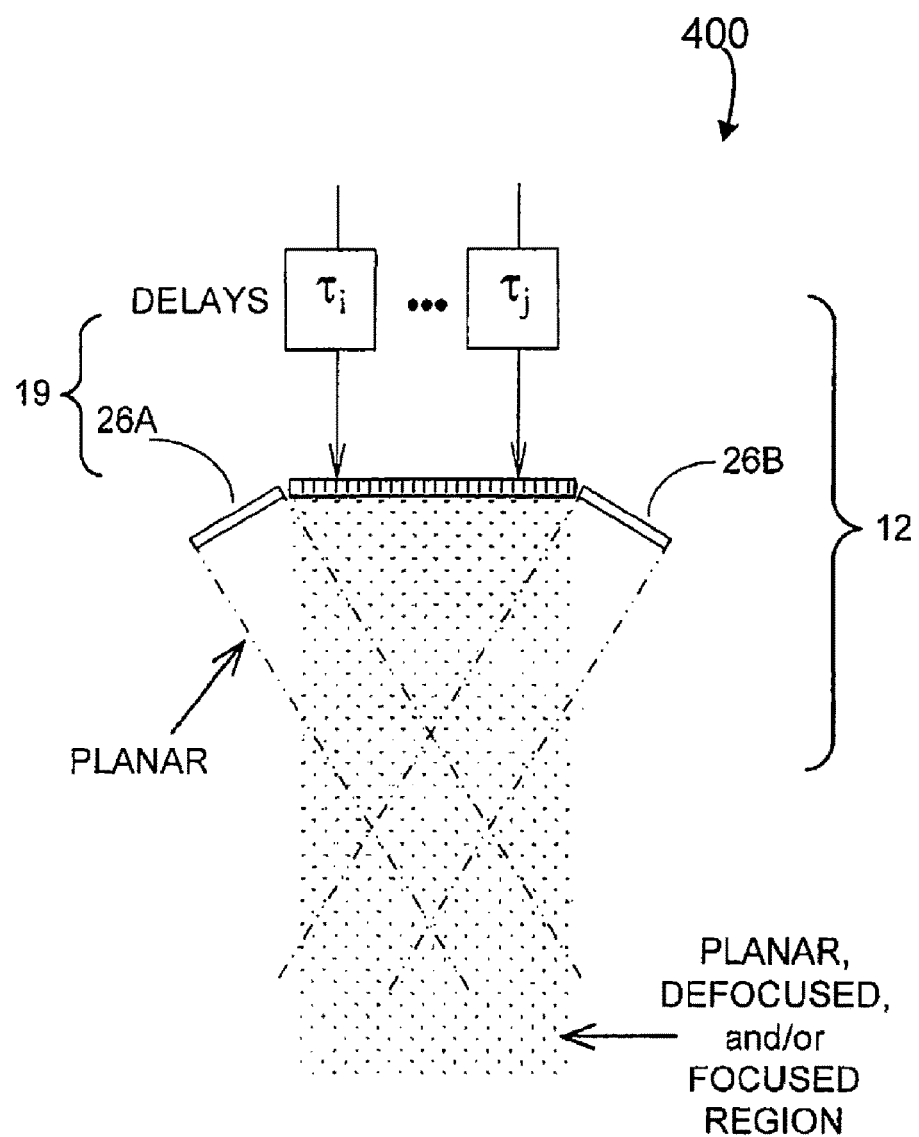

In another embodiment, depicted in FIG. 7B, transduction elements 26A and 26B may be configured to be substantially flat in order to provide substantially uniform energy to ROI 12. While FIGS. 7A and 7B depict embodiments with transduction elements 26 configured as concave and substantially flat, respectively, transduction elements 26 may be configured to be concave, convex, and/or substantially flat. In addition, transduction elements 26 may be configured to be any combination of concave, convex, and/or substantially flat structures. For example, a first transduction element 26 may be configured to be concave, while a second transduction element 26 may be configured to be substantially flat.

Moreover, transduction element 26 can be any distance from the patient's skin. In that regard, it can be far away from the skin disposed within a long transducer or it can be just a few millimeters from the surface of the patient's skin. In certain embodiments, positioning the transduction element 26 closer to the patient's skin is better for emitting ultrasound at high frequencies. Moreover, both three and two dimensional arrays of elements can be used in the present invention.

Figure 7C:
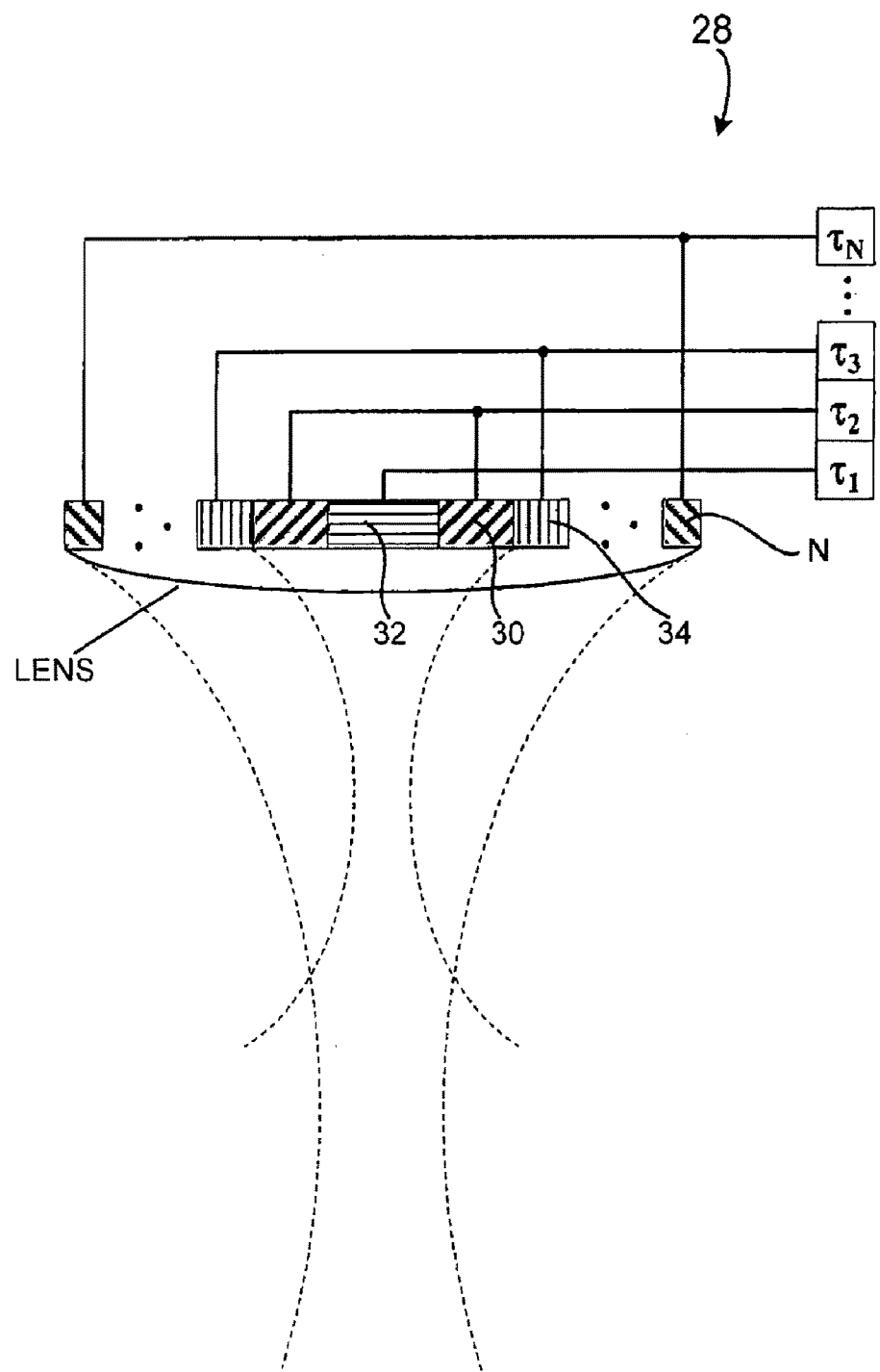
Figure 7D:
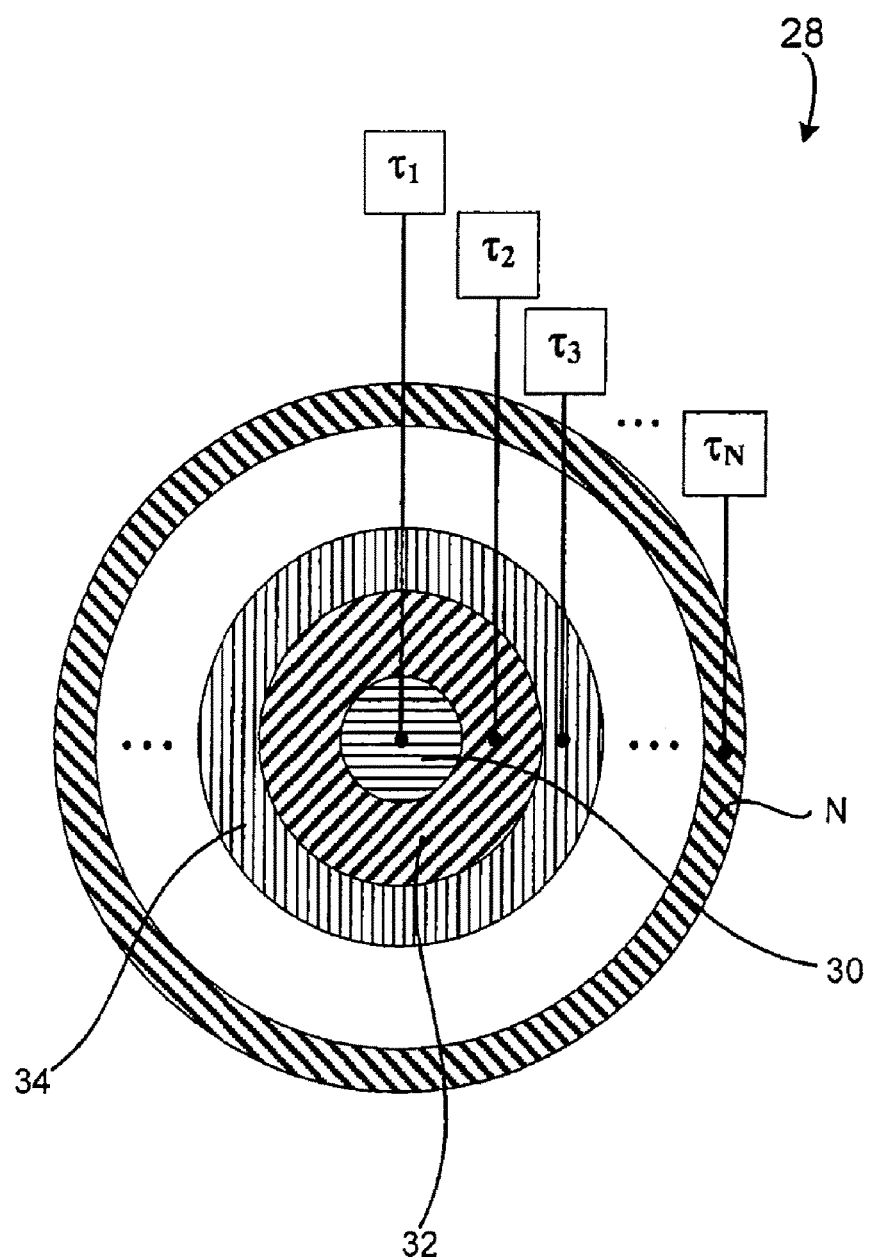

With reference to FIGS. 7C and 7D, transducer 19 may also be configured as an annular array to provide planar, focused and/or defocused acoustical energy. For example, in an embodiment, an annular array 28 may comprise a plurality of rings 30, 32, 34 to N. Rings 30, 32, 34 to N may be mechanically and electrically isolated into a set of individual elements, and may create planar, focused, or defocused waves. For example, such waves can be centered on-axis, such as by methods of adjusting corresponding transmit and/or receive delays, T1, T2, T3 . . . TN. An electronic focus may be suitably moved along various depth positions, and may enable variable strength or beam tightness, while an electronic defocus may have varying amounts of defocusing. In an embodiment, a lens and/or convex or concave shaped annular array 28 may also be provided to aid focusing or defocusing such that any time differential delays can be reduced. Movement of annular array 28 in one, two or three-dimensions, or along any path, such as through use of probes and/or any conventional robotic arm mechanisms, may be implemented to scan and/or treat a volume or any corresponding space within ROI 12.

Figure 7E:
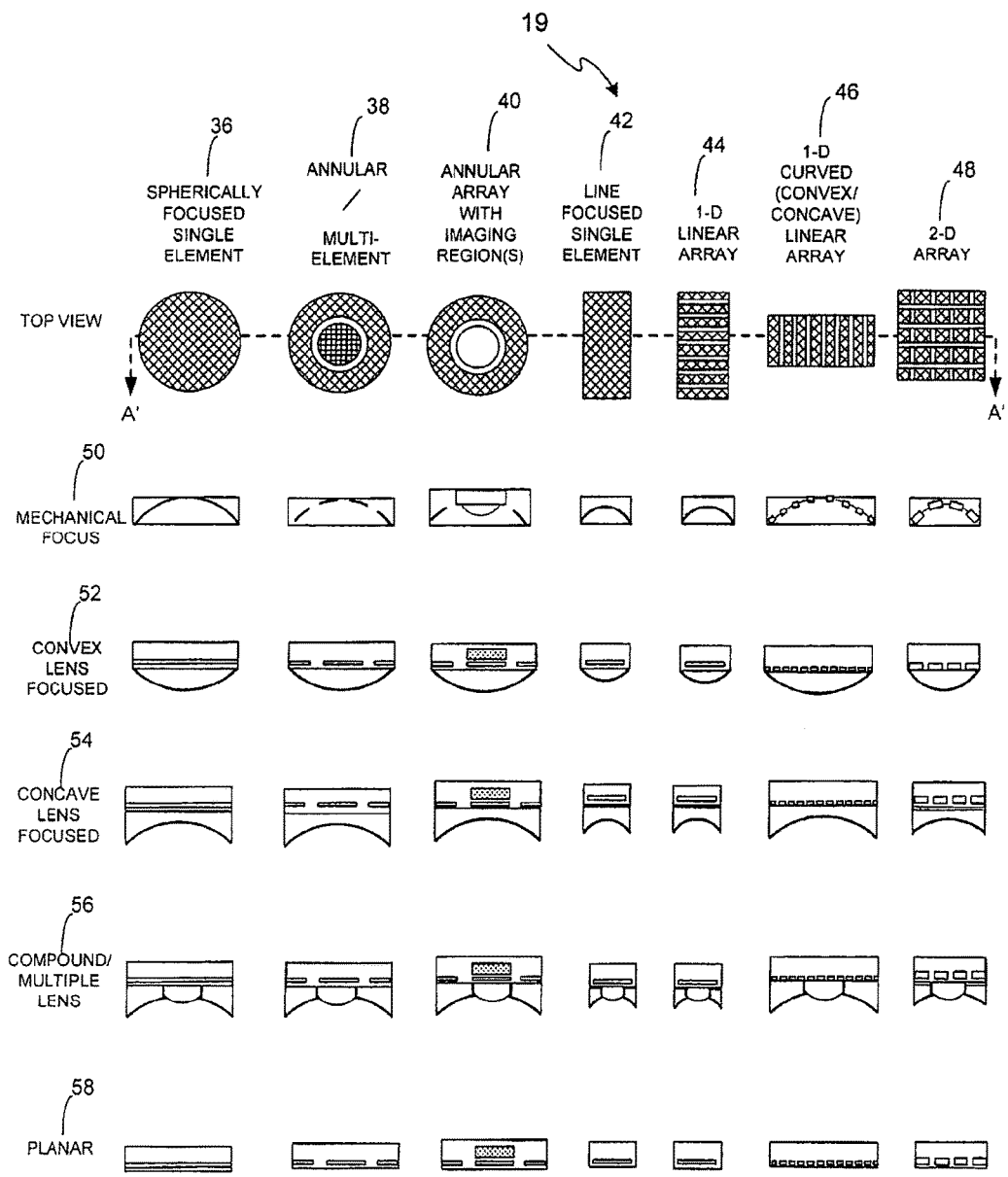

With reference to FIG. 7E, another transducer 19 can be configured to comprise a spherically focused single element 36, annular/multi-element 38, annular with imaging region (s) 40, line-focused single element 42, 1-D linear array 44, 1-D curved (convex/concave) linear array 46, and/or 2-D array 48, with mechanical focus 50, convex lens focus 52, concave lens focus 54, compound/multiple lens focused 56, and/or planar array form 58 to achieve focused, unfocused, or defocused sound fields for both imaging and/or therapy.

Transducer 19 may further comprise a reflective surface, tip, or area at the end of the transducer 19 that emits ultrasound energy 21. This reflective surface may enhance, magnify, or otherwise change ultrasound energy 21 emitted from system 14.

In an embodiment, suction is used to attach probe 18 to the patient's body. In this embodiment, a negative pressure differential is created and probe 18 attaches to the patient's skin by suction. A vacuum-type device is used to create the suction and the vacuum device can be integral with, detachable, or completely separate from probe 18. The suction attachment of probe 18 to the skin and associated negative pressure differential ensures that probe 18 is properly coupled to the patient's skin. Further, the suction-attachment also reduces the thickness of the tissue to make it easier to reach the targeted tissue. In other embodiments, a coupling gel is used to couple probe 18 to the patient's skin. The coupling gel can include medicines and other drugs and the application of ultrasound energy 21 can facilitate transdermal drug delivery.

Figure 8A:
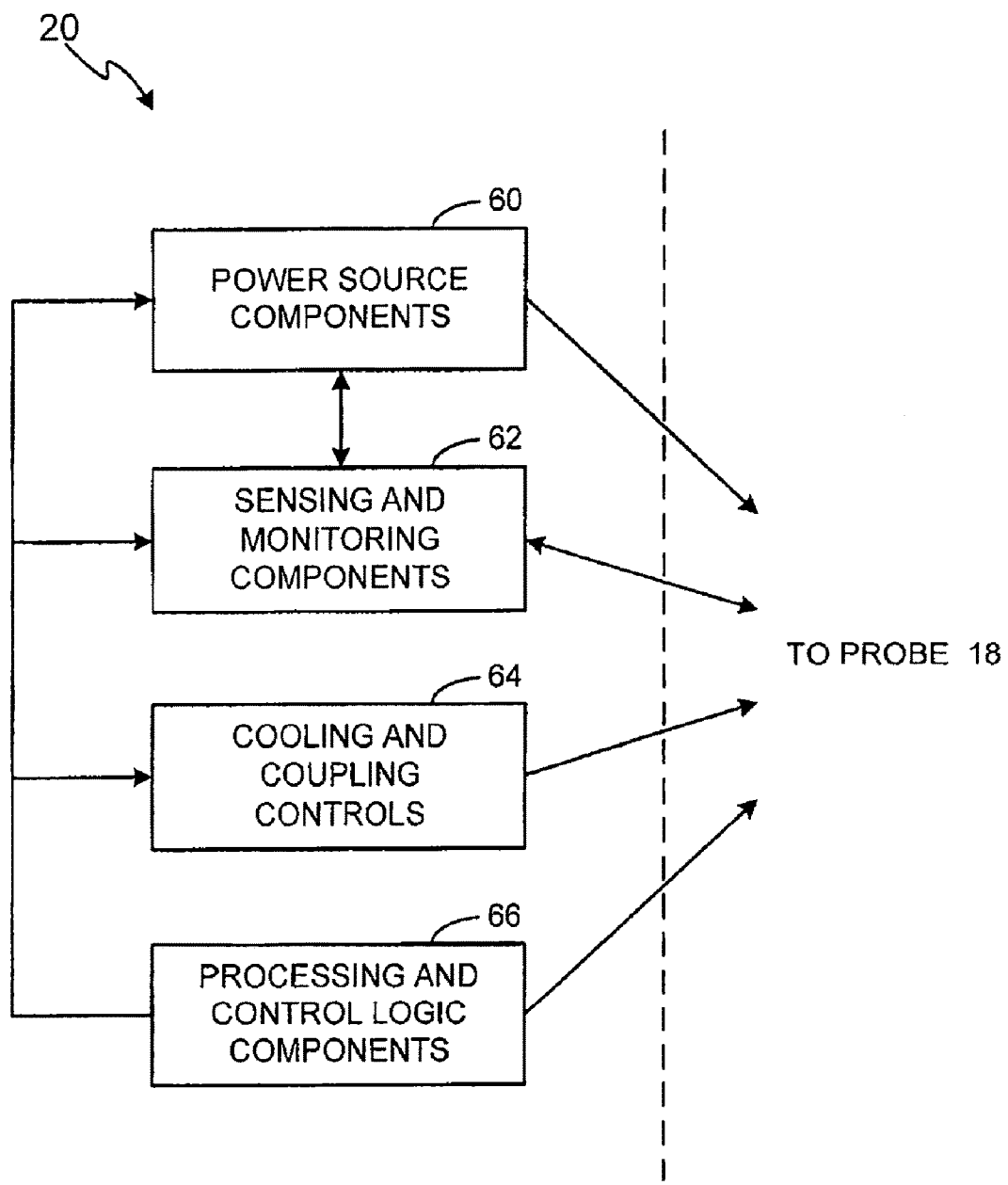
FIGS. 8A, 8B, and 8C illustrate block diagrams of an control system used in a system for effectuating a brow lift in accordance with embodiments of the present invention.
Figure 8B:
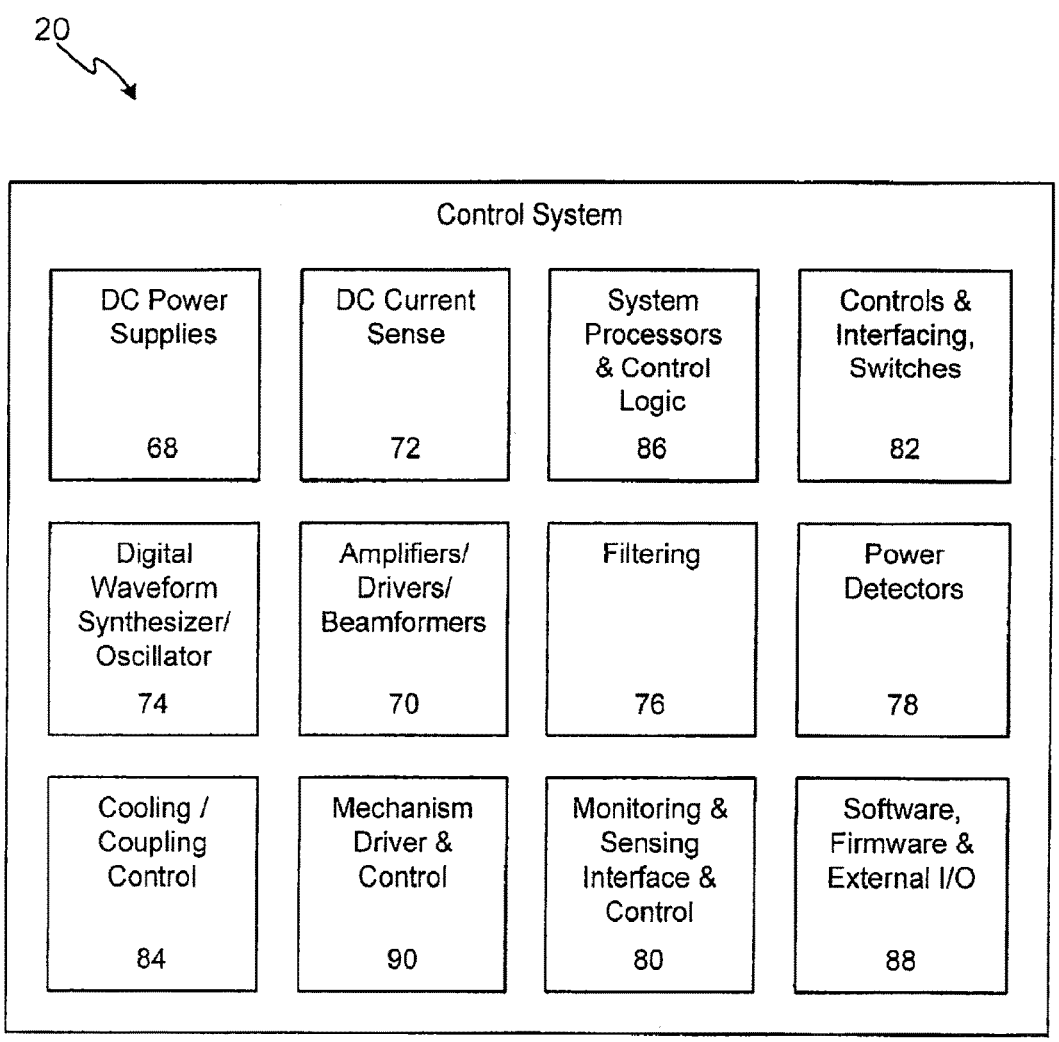
Figure 8C:
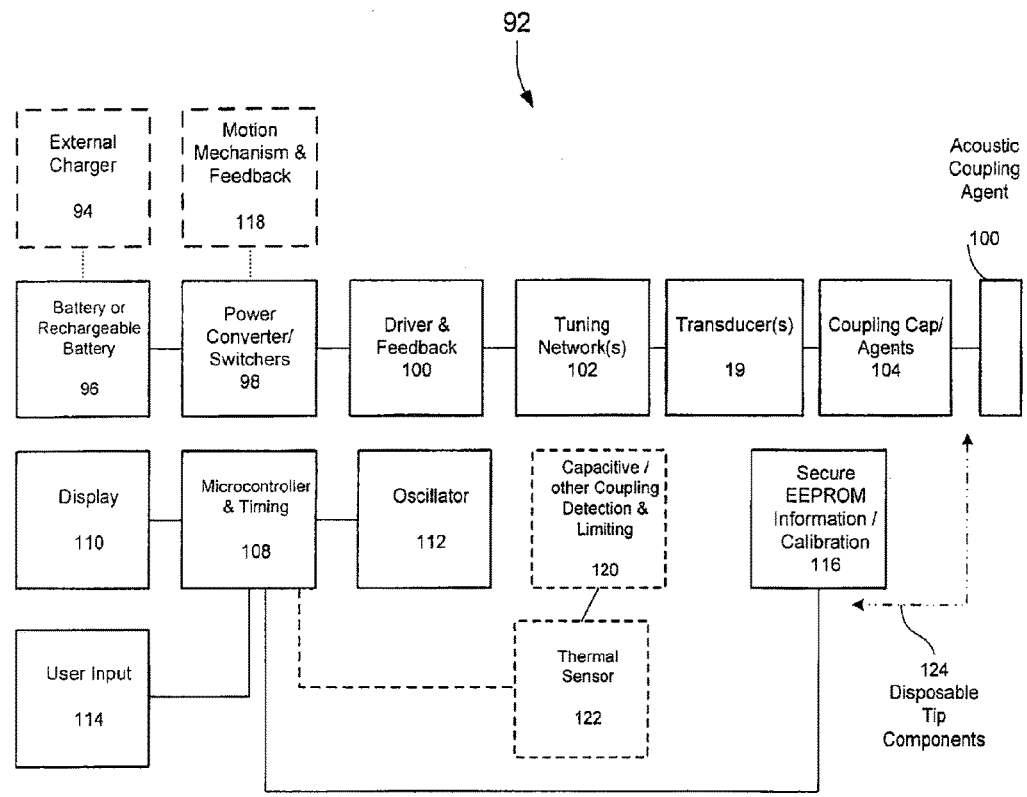

An probe 18 may be suitably controlled and operated in various manners by control system 20 as depicted in FIGS. 8A-8C which also relays and processes images obtained by transducer 19 to display 22. In the embodiment depicted in FIGS. 8A-8C, control system 20 may be capable of coordination and control of the entire treatment process to achieve the desired therapeutic effect on tissue 1 and subcutaneous tissue 2 within ROI 12. For example, in an embodiment, control system 20 may comprise power source components 60, sensing and monitoring components 62, cooling and coupling controls 64, and/or processing and control logic components 66. Control system 20 may be configured and optimized in a variety of ways with more or less subsystems and components to implement the therapeutic system for controlled targeting of the desired tissue 1 or subcutaneous tissue 2, and the embodiments in FIGS. 8A-8C are merely for illustration purposes.

For example, for power sourcing components 60, control system 20 may comprise one or more direct current (DC) power supplies 68 capable of providing electrical energy for the entire control system 20, including power required by a transducer electronic amplifier/driver 70. A DC current sense device 72 may also be provided to confirm the level of power entering amplifiers/drivers 70 for safety and monitoring purposes, among others.

In an embodiment, amplifiers/drivers 70 may comprise multi-channel or single channel power amplifiers and/or drivers. In an embodiment for transducer array configurations, amplifiers/drivers 70 may also be configured with a beamformer to facilitate array focusing. An beamformer may be electrically excited by an oscillator/digitally controlled waveform synthesizer 74 with related switching logic.

Power sourcing components 60 may also comprise various filtering configurations 76. For example, switchable harmonic filters and/or matching may be used at the output of amplifier/driver 70 to increase the drive efficiency and effectiveness. Power detection components 78 may also be included to confirm appropriate operation and calibration. For example, electric power and other energy detection components 78 may be used to monitor the amount of power entering probe 18.

Various sensing and monitoring components 62 may also be suitably implemented within control system 20. For example, in an embodiment, monitoring, sensing, and interface control components 80 may be capable of operating with various motion detection systems implemented within probe 18, to receive and process information such as acoustic or other spatial and temporal information from ROI 12. Sensing and monitoring components 62 may also comprise various controls, interfacing, and switches 82 and/or power detectors 78. Such sensing and monitoring components 62 may facilitate open-loop and/or closed-loop feedback systems within treatment system 14.

In an embodiment, sensing and monitoring components 62 may further comprise a sensor that may be connected to an audio or visual alarm system to prevent overuse of system 14. In this embodiment, the sensor may be capable of sensing the amount of energy transferred to the skin, and/or the time that system 14 has been actively emitting energy. When a certain time or temperature threshold has been reached, the alarm may sound an audible alarm, or cause a visual indicator to activate to alert the user that a threshold has been reached. This may prevent overuse of the system 14. In an embodiment, the sensor may be operatively connected to control system 20 and force control system 20, to stop emitting ultrasound energy 21 from transducer 19.

In an embodiment, a cooling/coupling control system 84 may be provided, and may be capable of removing waste heat from probe 18. Furthermore the cooling/coupling control system 84 may be capable of providing a controlled temperature at the superficial tissue interface and deeper into tissue, and/or provide acoustic coupling from probe 18 to ROI 12. Such cooling/coupling control systems 84 can also be capable of operating in both open-loop and/or closed-loop feedback arrangements with various coupling and feedback components.

Additionally, an control system 20 may further comprise a system processor and various digital control logic 86, such as one or more of microcontrollers, microprocessors, field-programmable gate arrays, computer boards, and associated components, including firmware and control software 88, which may be capable of interfacing with user controls and interfacing circuits as well as input/output circuits and systems for communications, displays, interfacing, storage, documentation, and other useful functions. System software 88 may be capable of controlling all initialization, timing, level setting, monitoring, safety monitoring, and all other system functions required to accomplish user-defined treatment objectives. Further, various control switches 90 may also be suitably configured to control operation.

With reference to FIG. 8C, an transducer 19 may be controlled and operated in various manners by a hand-held format control system 92. An external battery charger 94 can be used with rechargeable-type batteries 96 or the batteries can be single-use disposable types, such as M-sized cells. Power converters 98 produce voltages suitable for powering a driver/feedback circuit 100 with tuning network 102 driving transducer 19 which is coupled to the patient via one or more acoustic coupling caps 104. Cap 104 can be composed of at least one of a solid media, semi-solid e.g. gelatinous media, and/or liquid media equivalent to an acoustic coupling agent (contained within a housing). Cap 104 is coupled to the patient with an acoustic coupling agent 106. In addition, a microcontroller and timing circuits 108 with associated software and algorithms provide control and user interfacing via a display 110, oscillator 112, and other input/output controls 114 such as switches and audio devices. A storage element 116, such as an Electrically Erasable Programmable Read-Only Memory ("EEPROM"), secure EEPROM, tamper-proof EEPROM, or similar device holds calibration and usage data. A motion mechanism with feedback 118 can be suitably controlled to scan the transducer 19, if desirable, in a line or two-dimensional pattern and/or with variable depth. Other feedback controls comprise a capacitive, acoustic, or other coupling detection means and/or limiting controls 120 and thermal sensor 122. A combination of the secure EEPROM with at least one of coupling caps 104, transducer 19, thermal sensor 122, coupling detectors, or tuning network. Finally, an transducer can further comprise a disposable tip 124 that can be disposed of after contacting a patient and replaced for sanitary reasons.

With reference again to FIG. 3, an system 14 also may comprise display 22 capable of providing images of ROI 12 in certain embodiments where ultrasound energy 21 may be emitted from transducer 19 in a manner suitable for imaging. In an embodiment, display 22 is a computer monitor. Display 22 may be capable of enabling the user to facilitate localization of the treatment area and surrounding structures, e.g., identification of subcutaneous tissue 2. In an alternative embodiment, the user may know the location of the specific subcutaneous tissue 2 to be treated based at lest in part upon prior experience or education.

After localization, ultrasound energy 21 is delivered at a depth, distribution, timing, and energy level to achieve the desired therapeutic effect at ROI 12 to treat tissue 1. Before, during and/or after delivery of ultrasound energy 21, monitoring of the treatment area and surrounding structures may be conducted to further plan and assess the results and/or provide feedback to control system 20, and to a system operator via display 22. In an embodiment, localization may be facilitated through ultrasound imaging that may be used to define the position of a desired tissue 1 or subcutaneous tissue 2 in ROI 12.

For ultrasound energy 21 delivery, transducer 19 may be mechanically and/or electronically scanned to place treatment zones over an extended area in ROI 12. A treatment depth may be adjusted between a range of approximately 1 to 30 millimeters, and/or the greatest depth of tissue 1 or subcutaneous tissue 2. Such delivery of energy may occur through imaging of the targeted tissue 1, and then applying ultrasound energy 21 at known depths over an extended area without initial or ongoing imaging.

The ultrasound beam from transducer 19 may be spatially and/or temporally controlled at least in part by changing the spatial parameters of transducer 19, such as the placement, distance, treatment depth and transducer 19 structure, as well as by changing the temporal parameters of transducer 19, such as the frequency, drive amplitude, and timing, with such control handled via control system 20. Such spatial and temporal parameters may also be suitably monitored and/or utilized in open-loop and/or closed-loop feedback systems within ultrasound system 16.

Finally, it should be noted that while this disclosure is directed primarily to using ultrasound energy 21 to conduct procedures non-invasively, that the method and system for performing a brow lift described above can also utilize energy such as ultrasound energy 21 to assist in invasive procedures. For example, ultrasound energy 21 can be used to ablate subcutaneous tissues 2 and tissues 1 during an invasive procedure. In this regard, ultrasound energy 21 can be used for invasive and minimally invasive procedures.

Method and System for Performing a Blepharoplasty

With reference to FIGS. 9-16 and in accordance with an embodiment, a method and system are provided for treating tissue around the eyes with focused, unfocused or defocused energy to perform a non-invasive blepharoplasty. In an embodiment, the energy used is ultrasound energy. In other embodiments, the energy is laser energy or radio frequency energy. In certain embodiments, the energy is ultrasound energy combined with other forms of energy such as laser or radio frequency energy. The method will be referred to as method 110 throughout. In an embodiment, the treated tissue region comprises skin and subcutaneous tissue 12 comprising muscle, tendon, ligament or cartilage tissue ("MTLC"), other fibrous tissue, fascial tissue, and/or connective tissue and any other types of tissue. It should be noted that references throughout this specification to tissue 11 include subcutaneous tissue 12.

Figure 9:
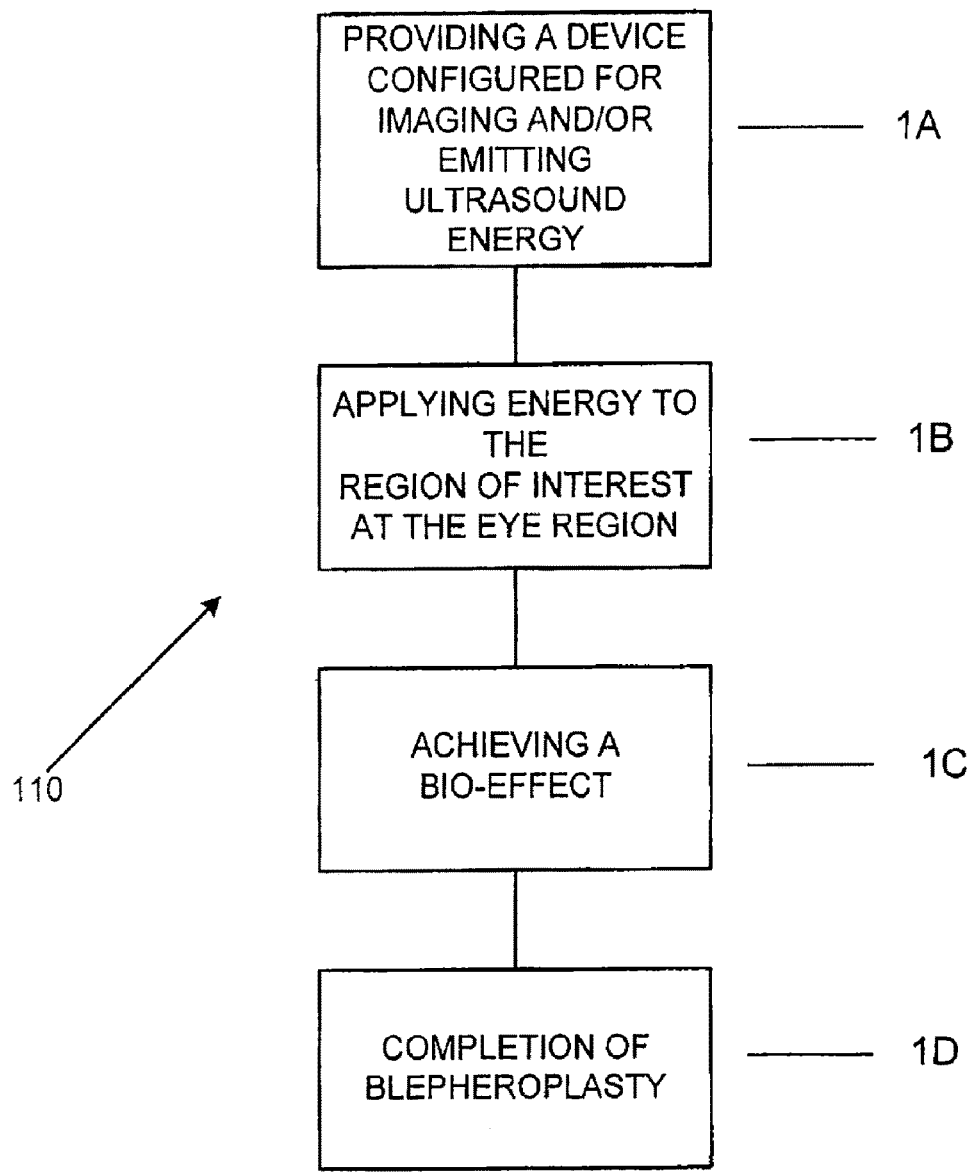
FIG. 9 illustrates a flow chart of the treatment method for performing a blepharoplasty in accordance with an embodiment of the present invention.

As depicted in the embodiment shown in FIG. 9, method 110 broadly comprises the following steps 1A-1D. First, in step 1A, a system that emits energy such as ultrasound energy is provided. In one embodiment with reference to FIG. 12, this system is also configured to obtain images. At step 1B, energy is applied to a Region of Interest ("ROI") which is part of or near the patient's eyes, or eye region which includes the eye sockets, eyelids, cheeks, the area below the eyes, and the area around the side of the patient's face adjacent to the eyes. The energy is applied until a certain bio-effect is achieved at step 1C. The bio-effects at step 1C reduce the laxity of the tissue around the eyes and thus, reduce wrinkles. Upon the completion of bio-effects at step 1C, a blepharoplasty is achieved at step 1D.

Figure 10A:
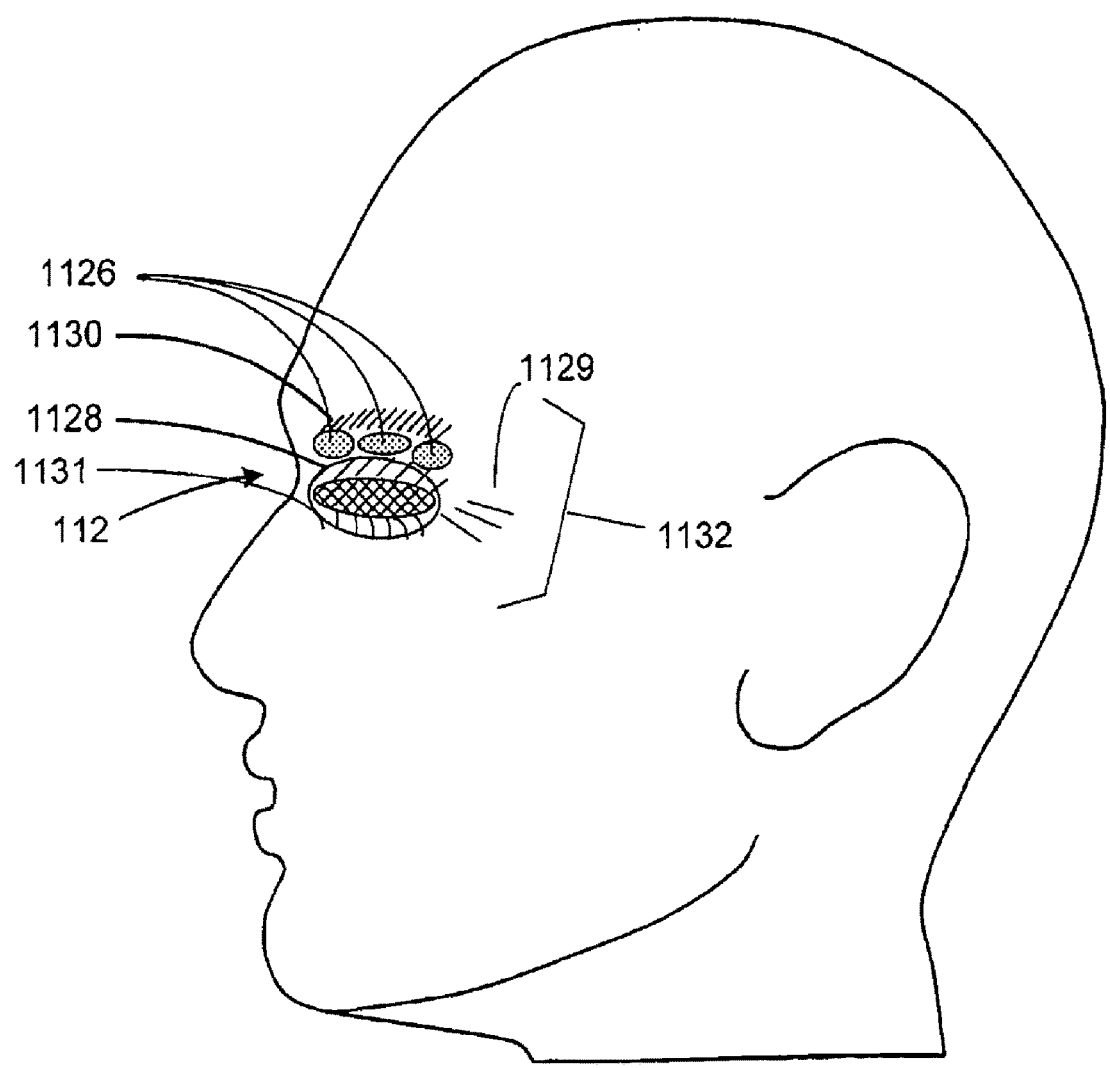
FIGS. 10A and 10B illustrate a patient's head and the location of the tissues that can be treated during a blepharoplasty in accordance with embodiments of the present invention.
Figure 10B:
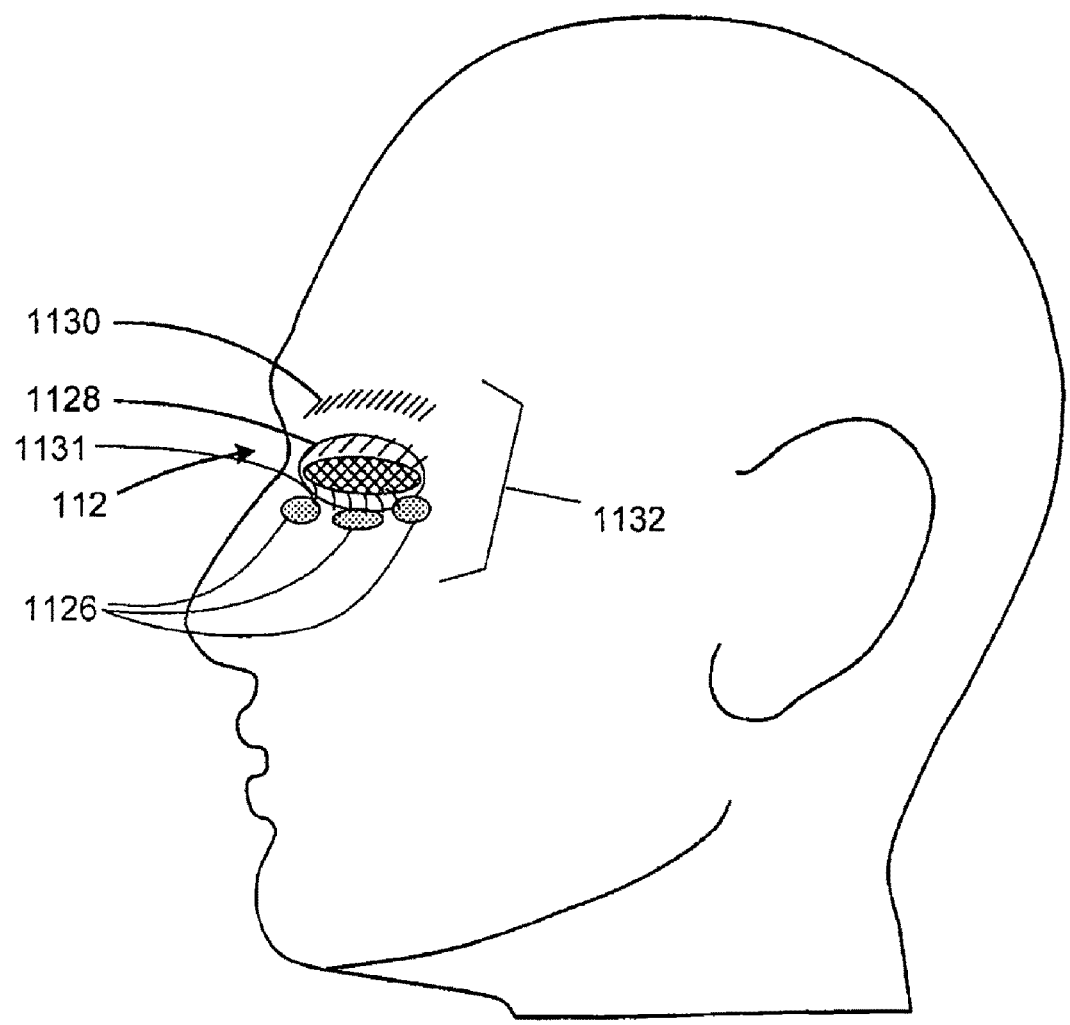

Turning now to FIGS. 10A and 10B, method 110 is used to perform a non-invasive blepharoplasty by ablating portions of fat, muscle, and other subcutaneous and/or connective tissues at the ROI located around a patient's eyes. As part of ablating portions of subcutaneous tissues, method 110 ablates or micro-ablates tissue and subcutaneous tissues comprising, but not limited to, fat and muscle. By ablating and treating these subcutaneous tissues, wrinkles on the skin and sagging skin are removed because the subcutaneous foundation for the skin is treated. Further, in one embodiment, the muscle can be paralyzed and method 110 can be utilized to replace toxic BOTOX®. injections to remove any crow's feet 1129 located adjacent to the patient's eyes. Method 110 can be used to supplement or replace BOTOX-type treatments in this manner. The term "BOTOX-type treatment" or "BOTOX-type injections" are meant to include treating the muscles and other tissue 1 and subcutaneous tissue 2 within the forehead with muscle relaxant drugs. One drug is sold under the trademark BOTOX®. and is produced by the Allergan Corporation of Irvine, Calif. Other drugs include the DYSPORT®. drug produced by Ipsen, Inc. of Milford, Mass. or the VISTABEL®. drug also produced by the Allergan Corporation.

FIG. 10A shows one embodiment where method 110 is used to perform a non-invasive upper lid blepharoplasty and to remove crow's feet 1129 around a patient's eye region 1132. As used throughout, eye region 1132 is meant to encompass the area around the eyes including the eye sockets, the orbital septum, lower and upper eyelids, eyebrows, and the area directly adjacent to the corners of the eye where crow's feet 1129 form. In this embodiment, pockets of fat 1126 around the upper eyelid 1128 can be removed or otherwise ablated, coagulated, or treated as noted herein. Further, muscle can also be caused to be reabsorbed into the body (thus removed) as can other tissue or subcutaneous tissue.

Tissue such as fat pockets 1126 is caused to be reabsorbed into the body by applying energy such as ultrasound energy at specific depths below the surface of the skin at levels where the targeted tissue is ablated, micro-ablated, or coagulated. For example, if fat pockets 1126 are located fifteen millimeters from the surface of the skin, ultrasound energy 121 is applied at a depth of fifteen millimeters at ablative levels to destroy and cause fat pockets 1126 to be reabsorbed into the body. Portions of muscle can also be ablated and subsequently reabsorbed into the ROI 112 as well (effectively removing the reabsorbed tissue from the ROI).

Ultrasound energy 121 can be applied at various frequencies, power levels, and times to target and effect subcutaneous tissue 112. Certain frequencies include anywhere in the range of approximately 2-12 MHz and more specifically in the range of approximately 3-7 MHz. Certain time frames to create ablative lesions within subcutaneous tissue 21 are in the range of approximately a few milliseconds to several minutes. Further, certain power ranges to create ablative lesions in subcutaneous tissue 12 are in the range of approximately 0.1 joules to 10 joules. Applying ultrasound energy 121 in this manner produces ablative lesions in subcutaneous tissue in the range of approximately 0.1 cubic millimeters to a 1000 cubic millimeters. Certain smaller lesions are in the range of approximately 0.1 cubic millimeters to 3 cubic millimeters.

In an embodiment, the application of ultrasound energy 121 to ROI 112 also causes the regeneration, remodeling, and shrinkage of tissue 12. With respect to regeneration and remodeling, the application of ultrasound energy 121 to ROI 112 causes thermal and mechanical affects which cause injury to subcutaneous tissues 12 and tissues 11. These injuries to tissues 11 and subcutaneous tissues 12 cause various chemical processes that lead to certain protein's repair and regeneration. Certain proteins comprise, but are not necessary limited to, collagen, myosin, elastin, and actin. In addition to proteins, fat calls are affected. As these proteins and fat are being repaired and regenerated, the amount of tissue 11 and subcutaneous tissues 12 are increased. This overall increase in tissue mass can cause voids or pockets in tissue 12 to be filled with the excess subcutaneous tissue 12 which also reduces wrinkles at ROI 12.

FIG. 10B shows one embodiment for a lower lid blepharoplasty where pockets of fat 1126 around a lower eyelid 1131 are ablated, micro-ablated, or coagulated and caused to be reabsorbed into the body by the application of ultrasound energy as described above. Further, portions of muscle can also be caused to be reabsorbed into the body as can other subcutaneous tissue by similar methods. When fat and other subcutaneous tissue is reabsorbed into the body, puffiness around the eyes is reduced as on of the bio-effects achieved by the application of ultrasound energy.

With continued reference to FIGS. 10A-10B, in an embodiment, transducer 119 may be coupled to or positioned near the eye region 1132 and ultrasound energy 121 may be emitted from probe 118 at specific depths within ROI 112 which may produce various bio-effects. These bio-effects may have the same effect as traditional invasive techniques and can comprise ablating, micro-ablating, coagulating, severing, or cutting, partially incapacitating, shortening or removing tissue 11 from ROI 112. These bio-effects have the same effects as a traditional blepharoplasty procedure but accomplish a blepharoplasty in a non-invasive manner.

For example, instead of making an incision across the eyelids 1130 and 1131 to remove fat pockets 1126, ultrasound energy 121 can be applied at ROI 12 to ablate, coagulate, and/or cause fat to be reabsorbed into the body such as fat pockets 1126 or muscle and achieve the same results as traditional invasive blepharoplasty procedures or a traditional transconjunctival blepharoplasty. Method 110 may be used to perform any type of blepharoplasty including an upper lid blepharoplasty, a lower lid blepharoplasty, or a transconjunctival blepharoplasty.

In one embodiment, method 110 can be used to replace traditional BOTOX-type treatments and other medicants or fillers as described below. In other embodiments, method 10 can be use to assist in transdermal drug delivery of BOTOX-type drugs and other medicines, medicants and fillers. In these embodiments, the application of ultrasound energy 121 to the ROI increases the temperature at ROI 112. This increased temperature assists in the transdermal delivery of BOTOX-type drugs. In other embodiments, the application of ultrasound energy to the ROI causes mechanical effects such as cavitation and streaming which essentially helps "push" the medicines into the patient's tissue.

In one embodiment, method 110 can also be effectively used to remove crow's feet 1129. Crow's feet 1129 can be removed by paralyzing the orbicularis oculi muscle which is typically accomplished with BOTOX-type injections. Applying ultrasound energy 121 at specific depths to contact the orbicularis oculi muscle can incapacitate or otherwise paralyze the orbicularis oculi muscle. The orbicularis oculi muscle including the orbital part, the palpebral part, and the orbicularis oculi muscle can be treated in accordance with the present invention. For example, in one embodiment, ultrasound energy can be applied at the ROI to make several lesions in the orbicularis oculi muscle which incapacitates and paralyzes the muscle. With the orbicularis oculi muscle paralyzed, crow's feet 1129 disappear just as they would with traditional BOTOX-type injections that paralyze the orbicularis oculi muscle.

When method 110 is utilized to replace traditional BOTOX-type injections, the muscles are incapacitated to a point where they are paralyzed or rendered incapable of movement. In one embodiment, the muscles within the ROI may be either ablated, micro-ablated, or coagulated in a manner such that the muscles may be no longer be capable of movement, and be permanently paralyzed due to the bio-effects from the application of energy such as ultrasound energy 121. The paralysis of the muscles may reduce or eliminate wrinkles on the tissue such as crow's feet 1129. Unlike traditional BOTOX-type injections, the paralysis may be permanent and the wrinkles may not reappear after treatment. Therefore, repeated treatments as with BOTOX-type treatments are not necessary. Method 110 may be used on any area of the patient's body to replace traditional BOTOX-type injections.

In another embodiment, method 110 can be used to perform a combination blepharoplasty and midcheek lift. The ability to utilize energy such as ultrasound energy to perform face lifts such as a midcheek lift is described in patent application Ser. No. 11/163,151 entitled "Method and System For Noninvasive Face Lifts and Deep Tissue Tightening" which is herein incorporated in its entirety by reference. In this procedure, ultrasound energy is applied below the eyes to ablate or coagulate subcutaneous tissue and move tissue and subcutaneous tissue upwards to perform a midcheek lift. In this embodiment, both this procedure and a blepharoplasty can be completed utilizing ultrasound energy to target and ablate or coagulate subcutaneous tissue such as fibro-muscular tissue.

In an embodiment where a midcheek lift is being performed in conjunction with a blepharoplasty, imaging can take place as discussed above to monitor the effects on the tissue. Therefore, the operator of the system can vary the amount of ultrasound energy being emitted from the system if necessary.

In another embodiment, method 110 can be used to assist in delivery of various fillers and other medicines to ROI 112. According to this embodiment, ultrasound energy 121 assists in forcing the fillers and medicants into tissue 11 and subcutaneous tissue 12 at ROI 112. Hyaluronic acid can be delivered to ROI 112 in this manner. The application of ultrasound energy 121 to ROI 112 causes surrounding tissues to absorb the fillers such as hyaluronic acid by increasing the temperature at ROI 112 thereby increasing absorption and through the mechanical effects of ultrasound such as cavitation and streaming. Utilizing ultrasound energy 21 to effectuate the delivery of medicants and fillers is described in U.S. patent application Ser. No. 11/163,177 entitled "Method and System for Treating Acne and Sebaceous Glands" which has been incorporated by reference in its entirety.

Figure 11:
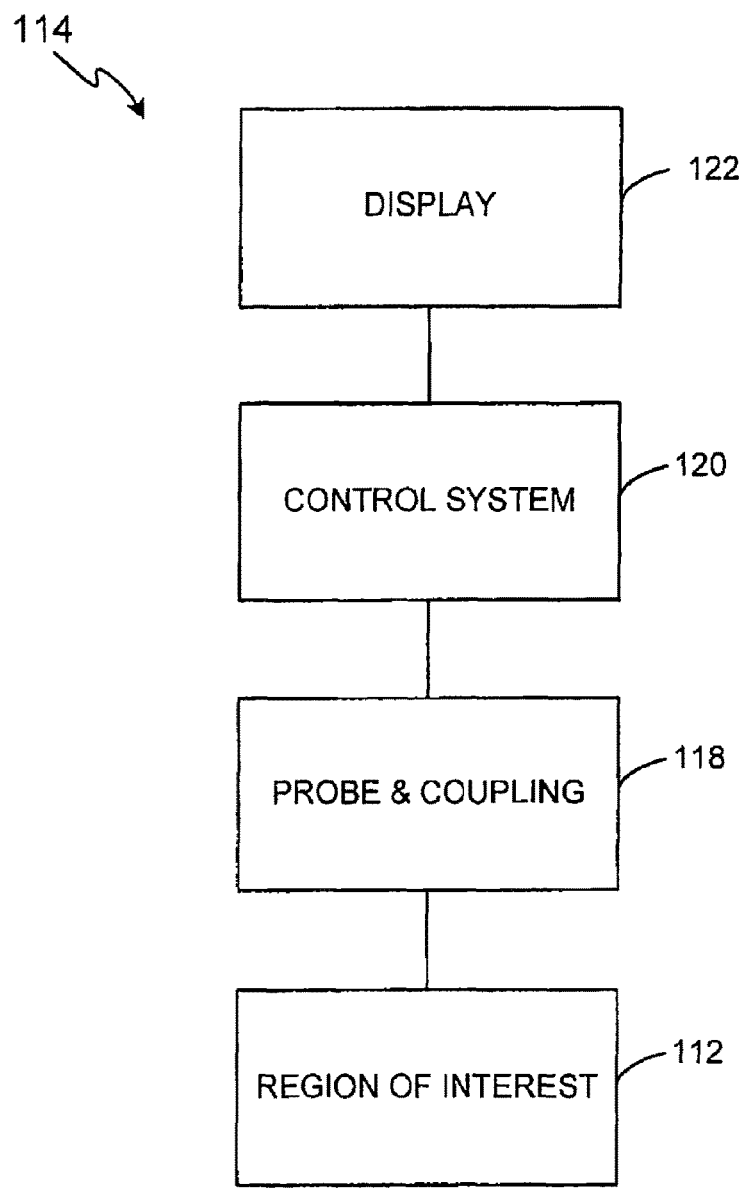
FIG. 11 illustrates a schematic diagram of an ultrasound treatment system configured to treat tissue during a blepharoplasty in accordance with an embodiment of the present invention.
Figure 12:
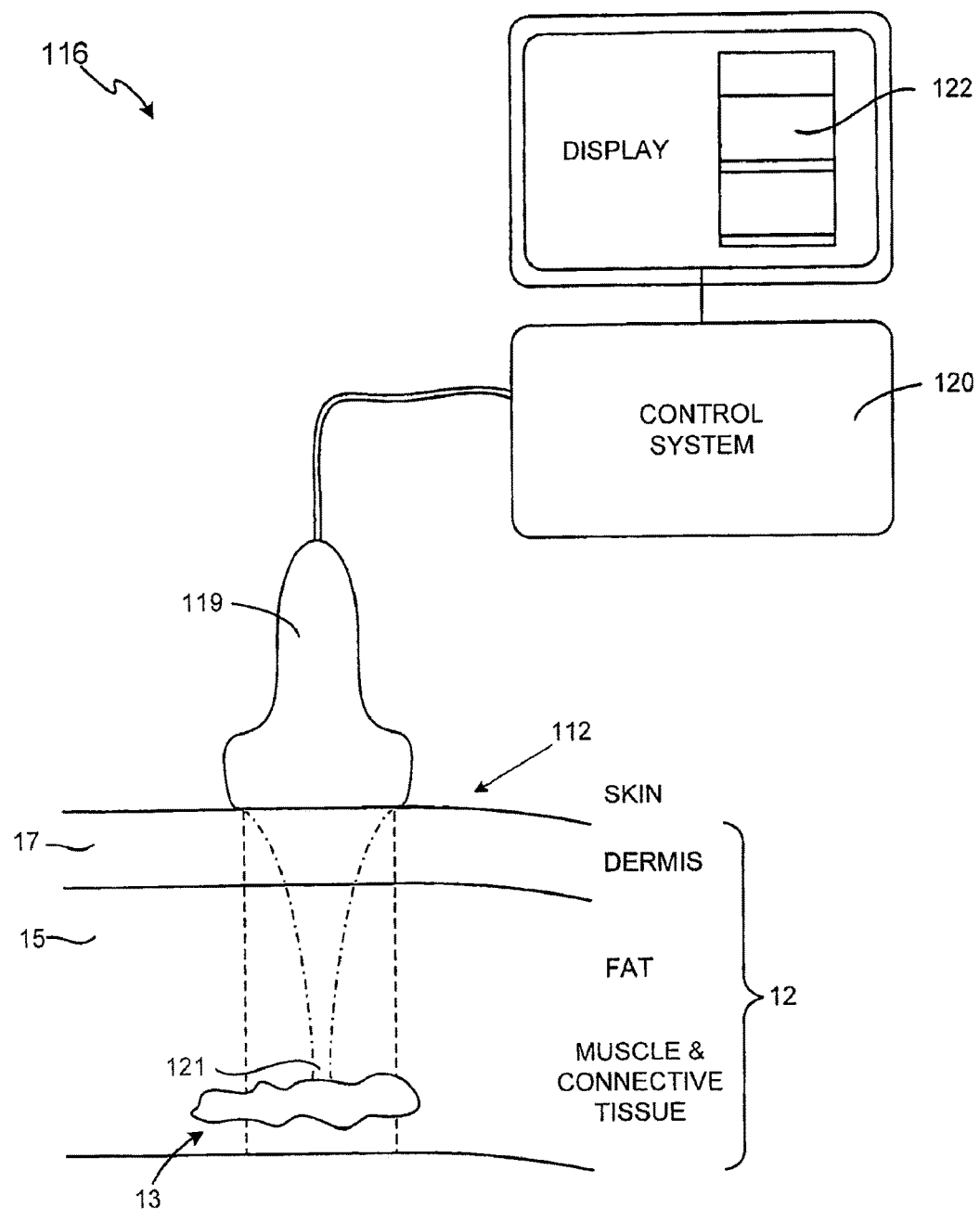
FIG. 12 illustrates a schematic diagram of an ultrasound treatment system configured to treat subcutaneous tissue during a blepharoplasty in accordance with an embodiment of the present invention.

In an embodiment depicted in FIGS. 11-12, a system is an ultrasound system 116 that may be capable of emitting ultrasound energy 121 that is focused, unfocused or defocused to treat tissue 11 at ROI 112. System 114 may comprise a probe 118, a control system 120, and a display 122. System 114 may be used to deliver energy to, and monitor, ROI 112. Certain embodiments of systems may be disclosed in U.S. patent application Ser. No. 11/163,177 entitled "Method and System for Treating Acne and Sebaceous Glands," U.S. patent application Ser. No. 10/950,112 entitled "Method and System for Combined Ultrasound Treatment", and U.S. Patent Application No. 60/826,039 entitled "Method and System for Non-Ablative Acne Treatment", all of which are hereby incorporated by reference in their entirety.

Figure 13:
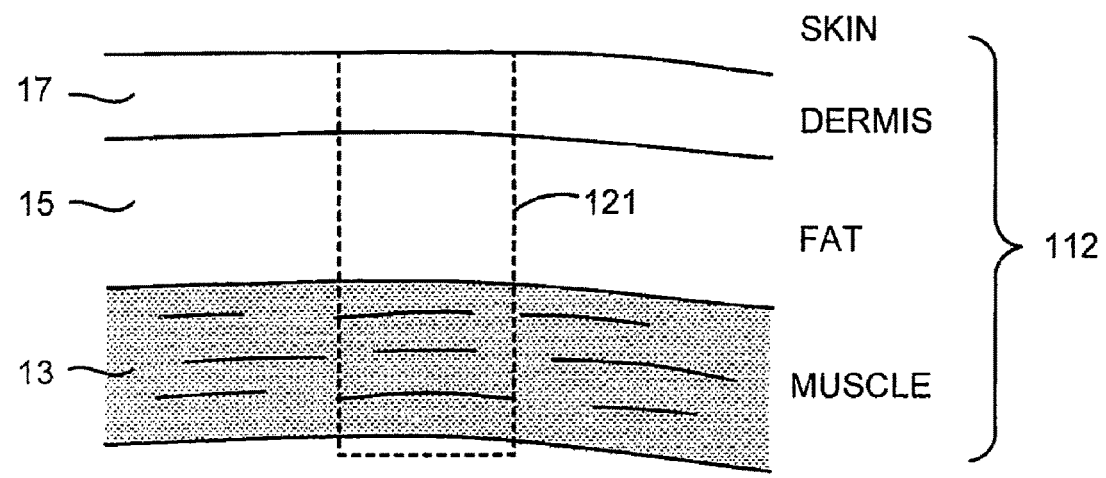
FIG. 13 illustrates various layers of tissue that the can be treated or imaged during a blepharoplasty in accordance with embodiments of the present invention.
Figure 14:
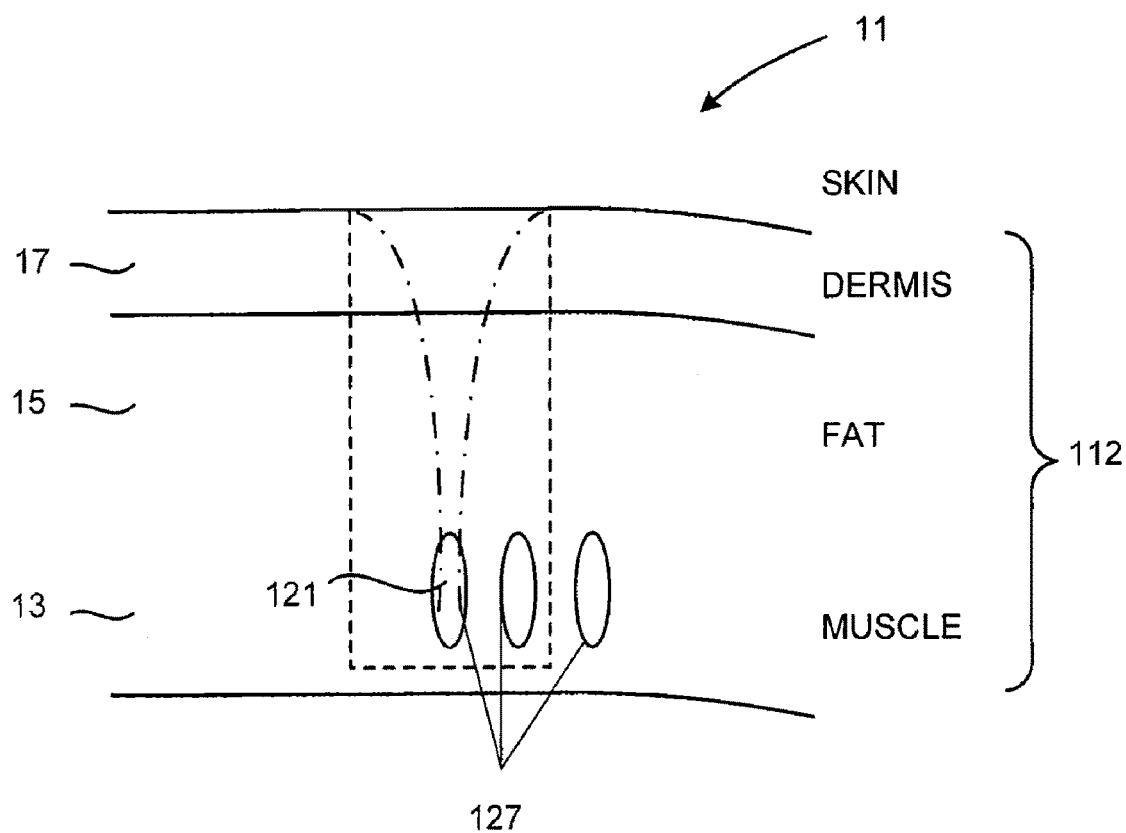
FIG. 14 illustrates a layer of muscle or other relevant tissue being treated during a blepharoplasty in accordance with an embodiment of the present invention.

Moreover, with reference to FIGS. 12-14, various different tissues 11 or subcutaneous tissues 12 may be treated by method 110 to produce different bio-effects in an embodiment of the present invention. In order to treat a specific subcutaneous tissue 12 to achieve a desired bio-effect, ultrasound energy 121 from system 114 may be directed to a specific depth within ROI 112 to reach the targeted subcutaneous tissue 12. For example, if it is desired to cut muscle 13 (by applying ultrasound energy 121 at ablative levels), which is approximately 15 mm below the surface of the skin, ultrasound energy 121 from ultrasound system 116 may be provided at ROI 112 at a level to reach 15 mm below the skin at an ablative level which may be capable of ablating muscle 13. An example of ablating muscle 13 is depicted in FIG. 14 which depicts a series of lesions 127 ablated into muscle 13. Besides ablating muscle 13, other bio-effects may comprise incapacitating, partially incapacitating, severing, rejuvenating, removing, ablating, micro-ablating, shortening, manipulating, or removing tissue 11 either instantly or over time, and/or other effects, and/or combinations thereof.

Depending at least in part upon the desired bio-effect and the subcutaneous tissue 12 being treated, method 110 may be used with an extracorporeal, non-invasive, partially invasive, or invasive procedure. Also, depending at least in part upon the specific bio-effect and tissue 11 targeted, there may be temperature increases within ROI 112 which may range from approximately 0-60° C. or heating, cavitation, steaming, and/or vibro-accoustic stimulation, and/or combinations thereof.

Besides producing various bio-effects to tissue 11, method 110 and ultrasound system 116 may also be used for imaging. The imaging may be accomplished in combination with the treatments described herein, or it may be accomplished as a separate function to locate tissue 11 or subcutaneous tissue 12 to be targeted. In an embodiment, the imaging of ROI 112 may be accomplished in real time as the treatment is being administered. This may assist visualization of certain moving subcutaneous tissue 12 during treatment. In other embodiments, the user may simply know where the specific subcutaneous tissue 12 is based on experience and not require imaging.

In an embodiment depicted in FIGS. 12-14, ultrasound energy 121 is delivered at specific depths at and below the skin of a patient to treat subcutaneous tissue 12. Subcutaneous tissue 12 which may also be treated by method 110 may comprise muscles 13, fat 15, and various connective tissue. Other subcutaneous tissues 12 which may be treated may comprise muscle fascia, ligament, dermis 17, and various other tissues, such as the Superficial Muscular Aponeurotic System ("SMAS"), and other fibro-muscular tissues. Subcutaneous tissue 12 may be located within ROI 112 on a patient's body that may be desired to be treated such as the patient's eye region. In one embodiment, the area around the orbital septum is treated. ROI 112 may comprise an inner treatment region, a superficial region, a subcutaneous region of interest and/or any other region of interest in between an inner treatment region, a superficial region, and/or a subcutaneous region within a patient, and/or combinations thereof.

The application of energy to ROI 112 may produce certain desired bio-effects on tissue 11 and/or subcutaneous tissue 12. The bio-effects may comprise, but are not limited to, ablating, micro-ablating, coagulating, severing or cutting, partially incapacitating, rejuvenating, shortening, or removing tissue 12 either instantly or over longer time periods by causing the tissue to be reabsorbed into the body. Specific bio-effects may be used to treat different tissues 11 to produce different treatments as described in greater detail below. These effects on subcutaneous tissue 12 also enable the skin to be tighter and not sag as its support layer of subcutaneous tissue 12 has been treated by method 110.

Different tissues 11 and subcutaneous tissues 12 within ROI 112 may have different acoustic properties. For example, muscle 13 might have different acoustic properties than fascia or dermis 17. These different acoustic properties affect the amount of energy applied to ROI 112 to cause certain bio-effects to muscle 13 than may be required to achieve the same or similar bio-effects for fascia. These acoustic properties may comprise the varied acoustic phase velocity (speed of sound) and its potential anisotropy, varied mass density, acoustic impedance, acoustic absorption and attenuation, target size and shape versus wavelength, and direction of incident energy, stiffness, and the reflectivity of subcutaneous tissues 12, among many others. Depending on the acoustic properties of a particular tissue 11 or subcutaneous tissue 12 being treated, the application of ultrasound energy 121 at ROI 112 may be adjusted to best compliment the acoustic property of tissue 11 or subcutaneous tissue 12 being targeted and treated.

In an embodiment, suction is used to attach probe 118 to the patient's body. In this embodiment, a negative pressure differential is created and probe 118 attaches to the patient's skin by suction. A vacuum-type device is used to create the suction and the vacuum device can be integral with, detachable, or completely separate from probe 118. The suction attachment of probe 118 to the skin and associated negative pressure differential ensures that probe 118 is properly coupled to skin 185. Further, the suction-attachment also reduces the thickness of the tissue to make it easier to reach the targeted tissue. In other embodiments, a coupling gel is used to couple probe 118 to the patient's skin 185. The coupling gel can include medicines and other drugs and the application of ultrasound energy 121 can facilitate transdermal drug delivery.

With additional reference to FIG. 15, an embodiment of a probe 118 may be a transducer 119 capable of emitting ultrasound energy 121 into ROI 112. This may heat ROI 112 at a specific depth to target a specific tissue 11 or subcutaneous tissue 12 and causing that tissue to be ablated, micro-ablated, incapacitated, coagulated, partially incapacitated, rejuvenated, shortened, paralyzed, or caused to be reabsorbed into the body. A coupling gel may be used to couple probe 118 to ROI 112. Ultrasound energy 121 may be emitted in various energy fields in this embodiment. With additional reference to FIG. 15A and FIG. 15B, the energy fields may be focused, defocused, and/or made substantially planar by transducer 119 to provide many different effects. For example, energy may be applied in a C-plane or C-scan. In one embodiment, a generally substantially planar energy field may provide a heating and/or pretreatment effect, a focused energy field may provide a more concentrated source of heat or hyperthermal effect, and a non-focused energy field may provide diffused heating effects. It should be noted that the term "non-focused" as used throughout encompasses energy that is unfocused or defocused.

Moreover, transduction element 126 can be any distance from the patient's skin. In that regard, it can be far away from the skin disposed within a long transducer or it can be just a few millimeters from the surface of the patient's skin. In certain embodiments, positioning the transduction element 126 closer to the patient's skin is better for emitting ultrasound at high frequencies. Moreover, both three and two dimensional arrays of elements can be used in the present invention.

In another embodiment, a transducer 119 may be capable of emitting ultrasound energy 121 for imaging or treatment or combinations thereof. In an embodiment, transducer 119 may be configured to emit ultrasound energy 121 at specific depths in ROI 112 as described below. In this embodiment of FIG. 112, transducer 119 may be capable of emitting unfocused or defocused ultrasound energy 121 over a wide area in ROI 112 for treatment purposes.

Figure 15A:
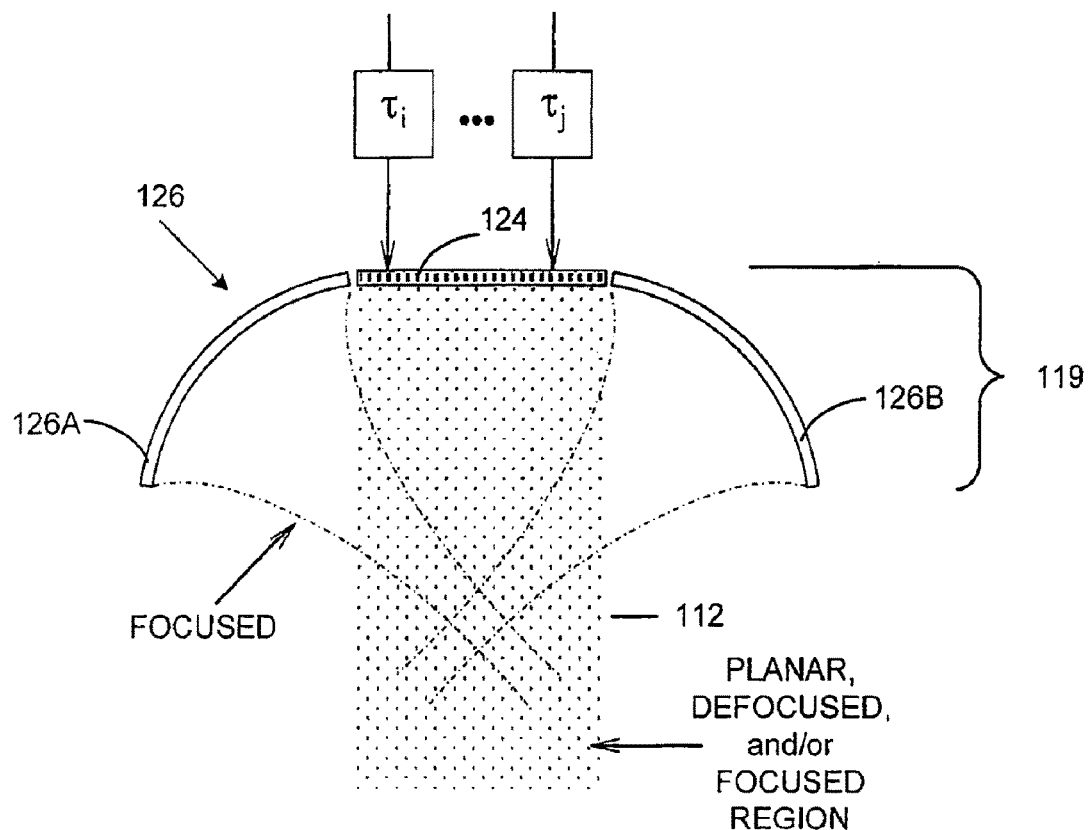
FIGS. 15A, 15B, 15C, 15D, and 15E illustrate cross-sectional diagrams of an transducer used in a system used to effectuate a blepharoplasty in accordance with various embodiments of the present invention.
Figure 15B:
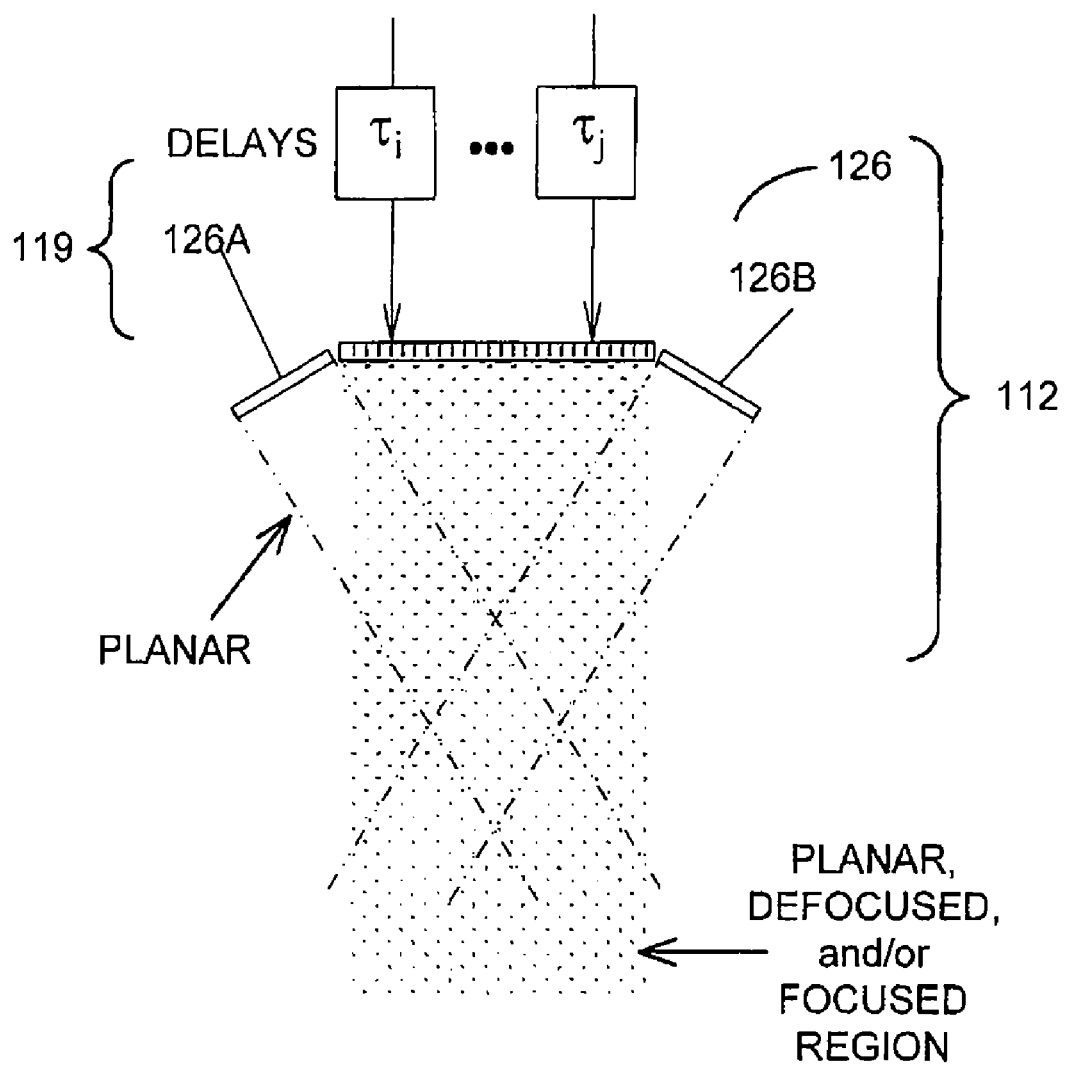

With continued reference to FIGS. 15A and 15B, transducer 119 may comprise one or more transducers for facilitating treatment. Transducer 119 may further comprise one or more transduction elements 126, e.g., elements 126A or 126B. The transduction elements 126 may comprise piezoelectrically active material, such as lead zirconante titanate (PZT), or other piezoelectrically active material such as, but not limited to, a piezoelectric ceramic, crystal, plastic, and/or composite materials, as well as lithium niobate, lead titanate, barium titanate, and/or lead metaniobate. In addition to, or instead of, a piezoelectrically active material, transducer 119 may comprise any other materials configured for generating radiation and/or acoustical energy. Transducer 119 may also comprise one or more matching and/or backing layers configured along with the transduction element 126, such as being coupled to the piezoelectrically active material. Transducer 119 may also be configured with single or multiple damping elements along the transduction element 126.

In an embodiment, the thickness of the transduction element 126 of transducer 119 may be configured to be uniform. That is, the transduction element 126 may be configured to have a thickness that is generally substantially the same throughout.

In another embodiment, the transduction element 126 may also be configured with a variable thickness, and/or as a multiple damped device. For example, the transduction element 126 of transducer 119 may be configured to have a first thickness selected to provide a center operating frequency of a lower range, for example from approximately 1 kHz to 3 MHz in one embodiment and between 15 kHz to 3 MHZ in another embodiment. The transduction element 126 may also be configured with a second thickness selected to provide a center operating frequency of a higher range, for example from approximately 3 to 100 MHz or more.

In yet another embodiment, transducer 119 may be configured as a single broadband transducer excited with two or more frequencies to provide an adequate output for raising the temperature within ROI 112 to the desired level. Transducer 119 may also be configured as two or more individual transducers, wherein each transducer 119 may comprise a transduction element 126. The thickness of the transduction elements 126 may be configured to provide center-operating frequencies in a desired treatment range. For example, in an embodiment, transducer 119 may comprise a first transducer 119 configured with a first transduction element 126A having a thickness corresponding to a center frequency range of approximately 1 MHz to 3 MHz, and a second transducer 119 configured with a second transduction element 126B having a thickness corresponding to a center frequency of approximately 3 MHz to 100 MHz or more. Various other ranges of thickness for a first and/or second transduction element 126 can also be realized.

Moreover, in an embodiment, any variety of mechanical lenses or variable focus lenses, e.g. liquid-filled lenses, may also be used to focus and or defocus the energy field. For example, with reference to the embodiments depicted in FIGS. 15A and 15B, transducer 119 may also be configured with an electronic focusing array 124 in combination with one or more transduction elements 126 to facilitate increased flexibility in treating ROI 12. Array 124 may be configured in a manner similar to transducer 119. That is, array 124 may be configured as an array of electronic apertures that may be operated by a variety of phases via variable electronic time delays, for example, T1, T2, T3 . . . Tj. By the term "operated," the electronic apertures of array 124 may be manipulated, driven, used, and/or configured to produce and/or deliver energy in a manner corresponding to the phase variation caused by the electronic time delay. For example, these phase variations may be used to deliver defocused beams, planar beams, and/or focused beams, each of which may be used in combination to achieve different physiological effects in ROI 112.

Transduction elements 126 may be configured to be concave, convex, and/or planar. For example, in the embodiment depicted in FIG. 15A, transduction elements 126A and 126B are configured to be concave in order to provide focused energy for treatment of ROI 112. Additional embodiments are disclosed in U.S. patent application Ser. No. 10/944,500, entitled "System and Method for Variable Depth Ultrasound Treatment", incorporated herein by reference in its entirety.

In another embodiment depicted in FIG. 15B, transduction elements 126A and 126B may be configured to be substantially flat in order to provide substantially uniform energy to ROI 112. While FIGS. 15A and 15B depict embodiments with transduction elements 126 configured as concave and substantially flat, respectively, transduction elements 126 may be configured to be concave, convex, and/or substantially flat. In addition, transduction elements 126 may be configured to be any combination of concave, convex, and/or substantially flat structures. For example, a first transduction element 126 may be configured to be concave, while a second transduction element 126 may be configured to be substantially flat.

Figure 15C:
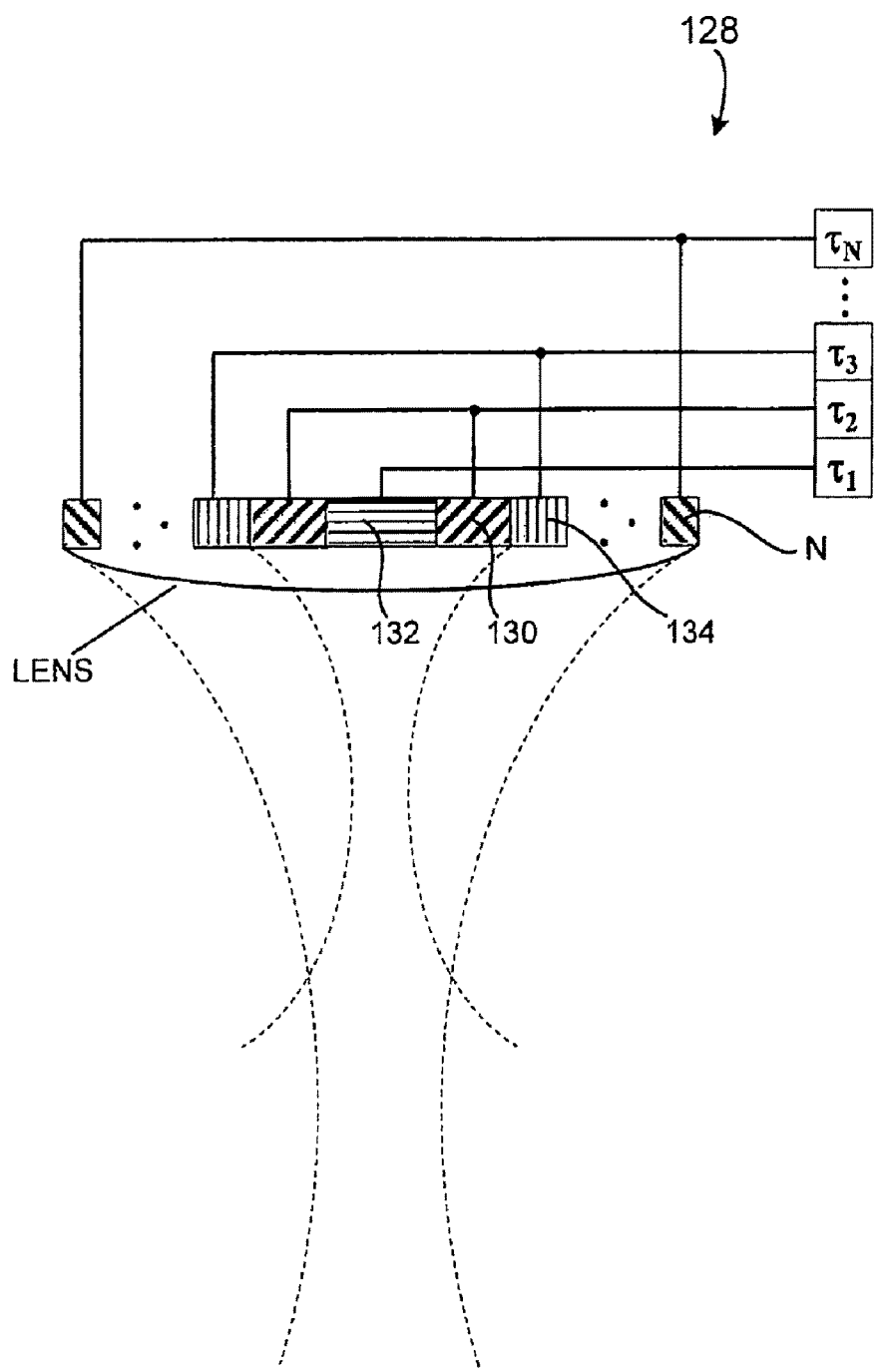
Figure 15D:
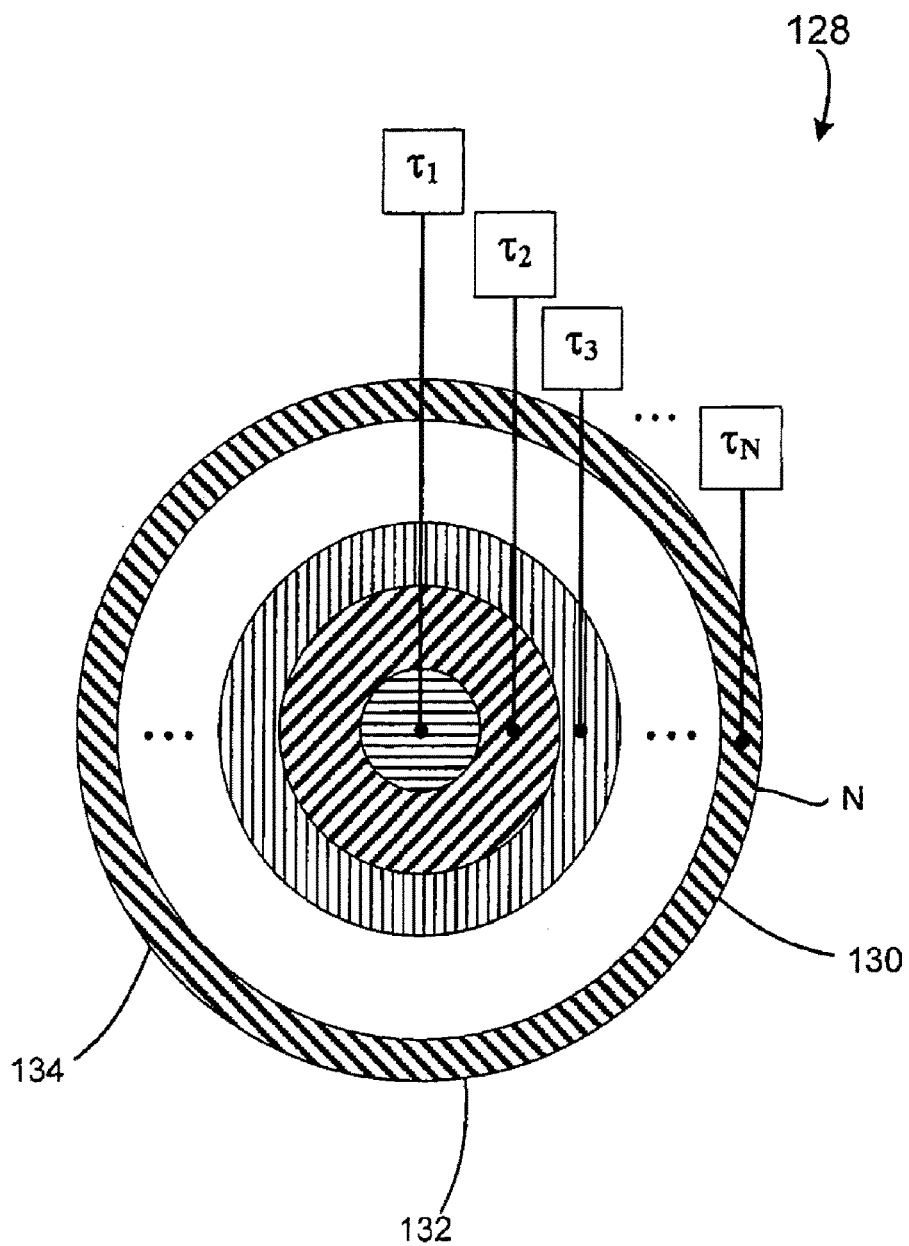

With reference to FIGS. 15C and 15D, transducer 119 may also be configured as an annular array to provide planar, focused and/or defocused acoustical energy. For example, in an embodiment, an annular array 128 may comprise a plurality of rings 130, 132, 134 to N. Rings 130, 132, 134 to N may be mechanically and electrically isolated into a set of individual elements, and may create planar, focused, or defocused waves. For example, such waves can be centered on-axis, such as by methods of adjusting corresponding transmit and/or receive delays, T1, T2, T3 . . . TN. An electronic focus may be suitably moved along various depth positions, and may enable variable strength or beam tightness, while an electronic defocus may have varying amounts of defocusing. In an embodiment, a lens and/or convex or concave shaped annular array 128 may also be provided to aid focusing or defocusing such that any time differential delays can be reduced. Movement of annular array 128 in one, two or three-dimensions, or along any path, such as through use of probes and/or any conventional robotic arm mechanisms, may be implemented to scan and/or treat a volume or any corresponding space within ROI 1 12.

Figure 15E:
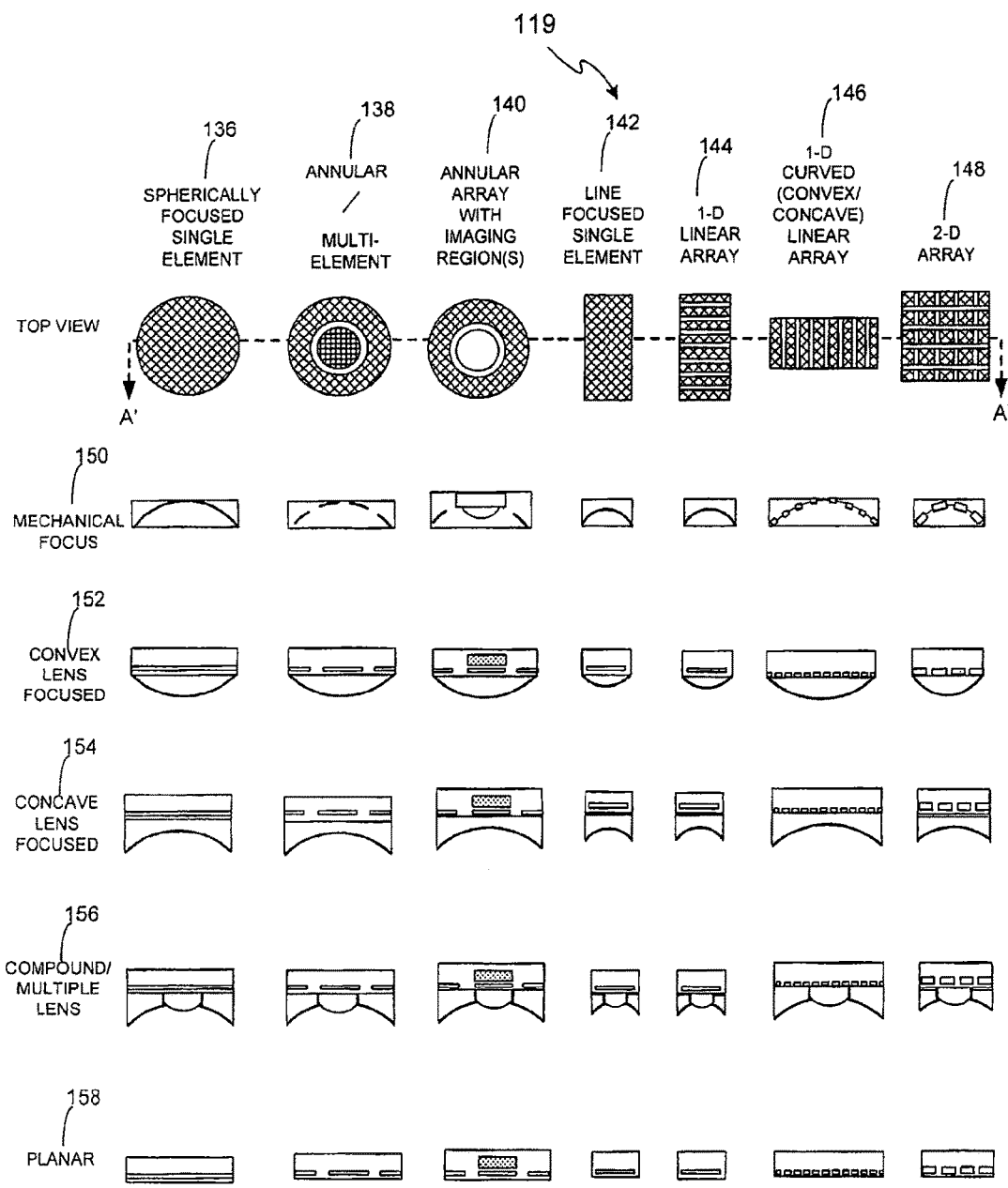

With reference to FIG. 15E, another transducer 119 can be configured to comprise a spherically focused single element 136, annular/multi-element 138, annular with imaging region(s) 140, line-focused single element 142, 1-D linear array 144, 1-D curved (convex/concave) linear array 146, and/or 2-D array 148, with mechanical focus 150, convex lens focus 152, concave lens focus 154, compound/multiple lens focused 156, and/or planar array form 158 to achieve focused, unfocused, or defocused sound fields for both imaging and/or therapy.

Transducer 119 may further comprise a reflective surface, tip, or area at the end of the transducer 119 that emits ultrasound energy 121. This reflective surface may enhance, magnify, or otherwise change ultrasound energy 121 emitted from system 114.

Figure 16A:
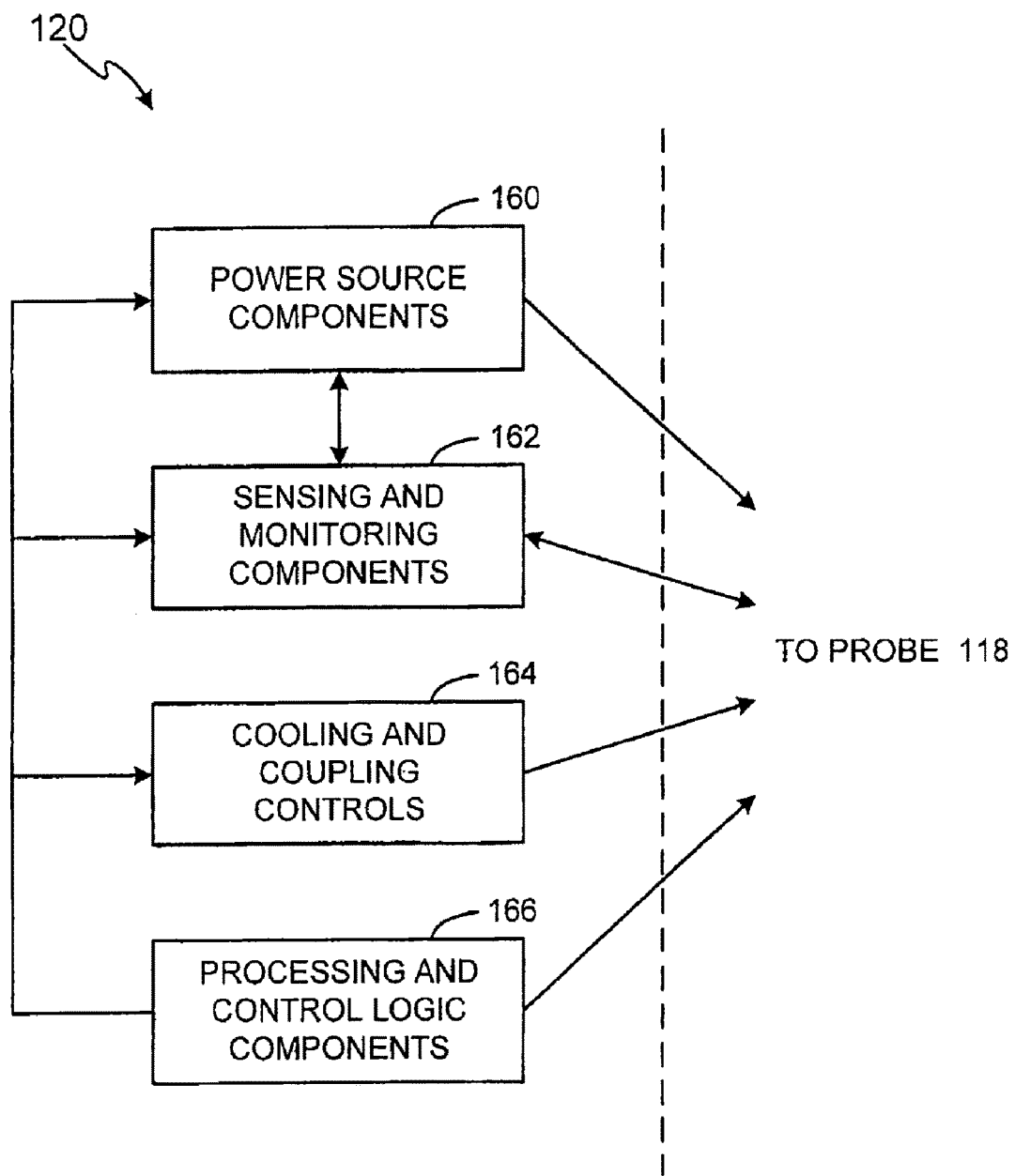
FIGS. 16A, 16B, and 16C illustrate block diagrams of an control system used in a system used to effectuate a blepharoplasty in accordance with embodiments of the present invention.
Figure 16B:
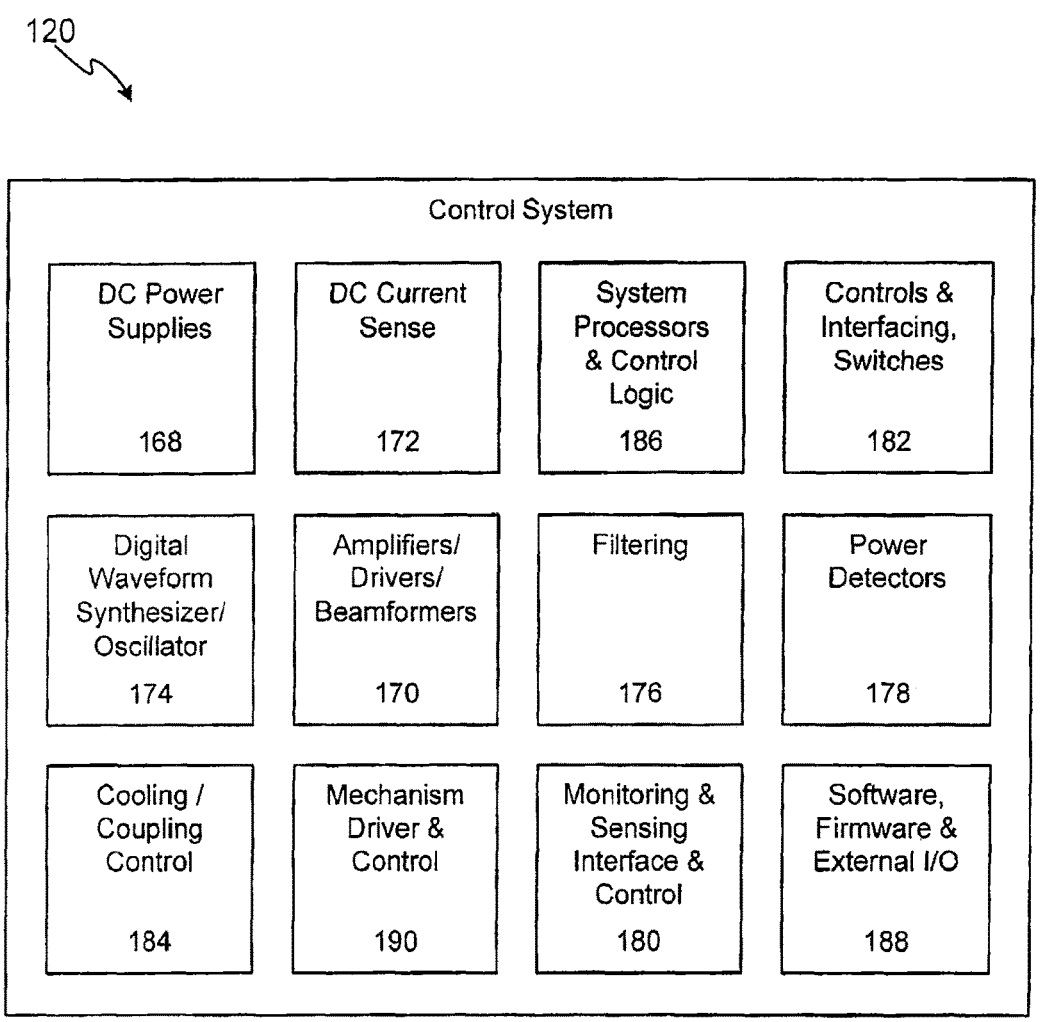
Figure 16C:
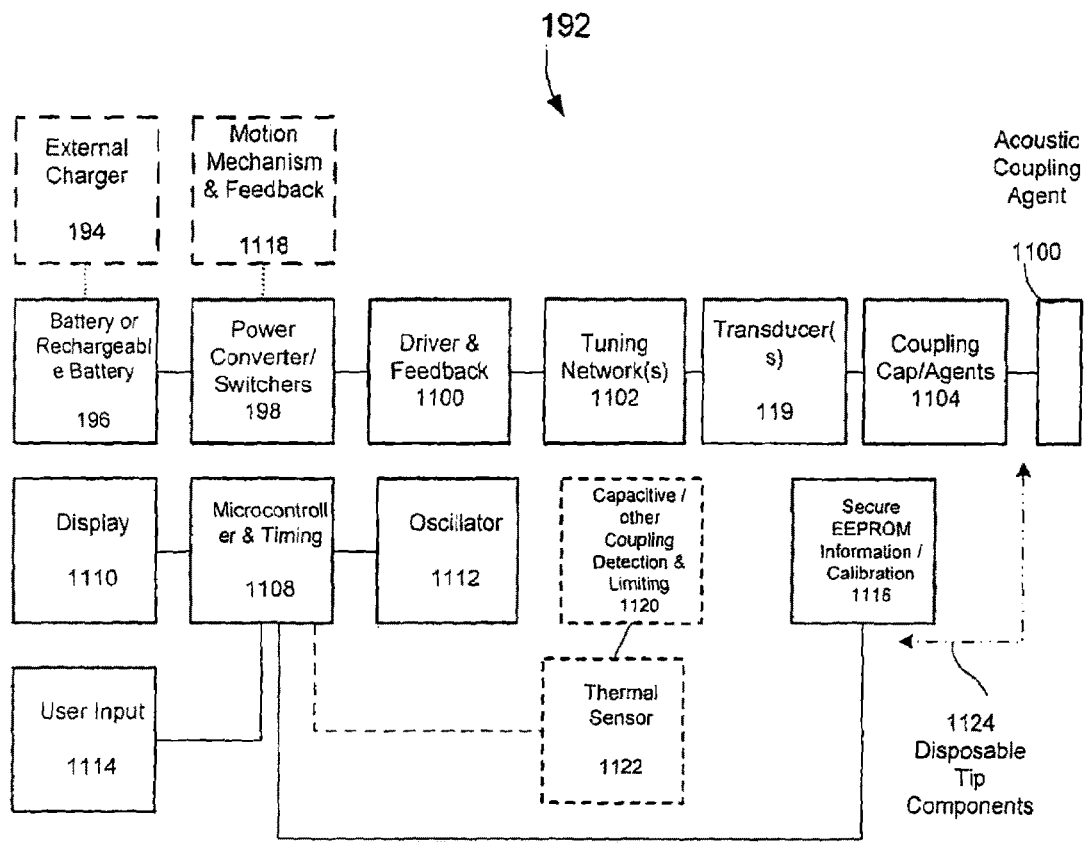

An embodiment of a probe 118 may be suitably controlled and operated in various manners by control system 120 as depicted in FIGS. 16A-16C which also relays processes images obtained by transducer 119 to display 122. In the embodiment depicted in FIGS. 16A-16C, control system 120 may be capable of coordination and control of the entire treatment process to achieve the desired therapeutic effect in tissue 11 within ROI 112. In an embodiment, control system 120 may comprise power source components 160, sensing and monitoring components 162, cooling and coupling controls 164, and/or processing and control logic components 166. Control system 120 may be configured and optimized in a variety of ways with more or less subsystems and components to implement the therapeutic system for controlled targeting of the desired tissue 11 or subcutaneous tissue 12, and the embodiments in FIGS. 16A-16C are merely for illustration purposes.

For example, for power sourcing components 160, control system 120 may comprise one or more direct current (DC) power supplies 168 capable of providing electrical energy for the entire control system 120, including power required by a transducer electronic amplifier/driver 170. A DC current sense device 172 may also be provided to confirm the level of power entering amplifiers/drivers 170 for safety and monitoring purposes, among others.

In an embodiment, amplifiers/drivers 170 may comprise multi-channel or single channel power amplifiers and/or drivers. In an embodiment for transducer array configurations, amplifiers/drivers 170 may also be configured with a beamformer to facilitate array focusing. An beamformer may be electrically excited by an oscillator/digitally controlled waveform synthesizer 174 with related switching logic.

Power sourcing components 160 may also comprise various filtering configurations 176. For example, switchable harmonic filters and/or matching may be used at the output of amplifier/driver 170 to increase the drive efficiency and effectiveness. Power detection components 178 may also be included to confirm appropriate operation and calibration. For example, electric power and other energy detection components 178 may be used to monitor the amount of power entering probe 118.

Various sensing and monitoring components 162 may also be suitably implemented within control system 120. For example, in an embodiment, monitoring, sensing, and interface control components 180 may be capable of operating with various motion detection systems implemented within probe 118, to receive and process information such as acoustic or other spatial and temporal information from ROI 112. Sensing and monitoring components 162 may also comprise various controls, interfacing, and switches 182 and/or power detectors 178. Such sensing and monitoring components 162 may facilitate open-loop and/or closed-loop feedback systems within treatment system 114.

In an embodiment, sensing and monitoring components 162 may further comprise a sensor that may be connected to an audio or visual alarm system to prevent overuse of system 114. In this embodiment, the sensor may be capable of sensing the amount of energy transferred to the skin, and/or the time that system 114 has been actively emitting energy. When a certain time or temperature threshold has been reached, the alarm may sound an audible alarm, or cause a visual indicator to activate to alert the user that a threshold has been reached. This may prevent overuse of system 114. In an embodiment, the sensor may be operatively connected to control system 120 and force control system 20, to stop emitting ultrasound energy 121 from transducer 119.

In an embodiment, a cooling/coupling control system 184 may be provided, and may be capable of removing waste heat from probe 118. Furthermore the cooling/coupling control system 184 may be capable of providing a controlled temperature at the superficial tissue interface and deeper into tissue, and/or provide acoustic coupling from probe 118 to ROI 112. Such cooling/coupling control systems 184 can also be capable of operating in both open-loop and/or closed-loop feedback arrangements with various coupling and feedback components.

Additionally, an embodiment of a control system 120 may further comprise a system processor and various digital control logic 186, such as one or more of microcontrollers, microprocessors, field-programmable gate arrays, computer boards, and associated components, including firmware and control software 188, which may be capable of interfacing with user controls and interfacing circuits as well as input/output circuits and systems for communications, displays, interfacing, storage, documentation, and other useful functions. System software 188 may be capable of controlling all initialization, timing, level setting, monitoring, safety monitoring, and all other system functions required to accomplish user-defined treatment objectives. Further, various control switches 190 may also be suitably configured to control operation.

With reference to FIG. 16C, an embodiment of a transducer 119 may be controlled and operated in various manners by a hand-held format control system 192. An external battery charger 194 can be used with rechargeable-type batteries 196 or the batteries can be single-use disposable types, such as AA-sized cells. Power converters 198 produce voltages suitable for powering a driver/feedback circuit 1100 with tuning network 1102 driving transducer 119 which is coupled to the patient via one or more acoustic coupling caps 1104. Cap 1104 can be composed of at least one of a solid media, semi-solid e.g. gelatinous media, and/or liquid media equivalent to an acoustic coupling agent (contained within a housing). Cap 1104 is coupled to the patient with an acoustic coupling agent 1106. In addition, a microcontroller and timing circuits 1108 with associated software and algorithms provide control and user interfacing via a display 1110, oscillator 1112, and other input/output controls 1114 such as switches and audio devices. A storage element 1116, such as an Electrically Erasable Programmable Read-Only Memory ("EEPROM"), secure EEPROM, tamper-proof EEPROM, or similar device holds calibration and usage data. A motion mechanism with feedback 1118 can be suitably controlled to scan the transducer 119, if desirable, in a line or two-dimensional pattern and/or with variable depth. Other feedback controls comprise a capacitive, acoustic, or other coupling detection means and/or limiting controls 1120 and thermal sensor 1122. A combination of the secure EEPROM with at least one of coupling caps 1104, transducer 119, thermal sensor 1122, coupling detectors, or tuning network may also be used. Finally, an transducer can further comprise a disposable tip 1124 that can be disposed of after contacting a patient and replaced for sanitary reasons.

With reference again to FIGS. 11-12, an embodiment of a system 114 also may comprise display 122 capable of providing images of ROI 112 in certain embodiments where ultrasound energy 121 may be emitted from transducer 119 in a manner suitable for imaging. Display 122 may be capable of enabling the user to facilitate localization of the treatment area and surrounding structures, e.g., identification of subcutaneous tissue 12. In an alternative embodiment, the user may know the location of the specific subcutaneous tissue 12 to be treated based at least in part upon prior experience or education.

After localization, ultrasound energy 121 is delivered at a depth, distribution, timing, and energy level to achieve the desired therapeutic effect at ROI 112 to treat tissue 11. Before, during, and/or after delivery of ultrasound energy 121, monitoring of the treatment area and surrounding structures may be conducted to further plan and assess the results and/or provide feedback to control system 120, and to a system operator via display 122. In an embodiment, localization may be facilitated through ultrasound imaging that may be used to define the position of a desired tissue 11 in ROI 112.

For ultrasound energy 121 delivery, transducer 119 may be mechanically and/or electronically scanned to place treatment zones over an extended area in ROI 112. A treatment depth may be adjusted between a range of approximately 0 to 30 millimeters, and/or the greatest depth of tissue 1 and/or subcutaneous tissue 12. Such delivery of energy may occur through imaging of the targeted tissue 11, and then applying ultrasound energy 121 at known depths over an extended area without initial or ongoing imaging.

The ultrasound beam from transducer 119 may be spatially and/or temporally controlled at least in part by changing the spatial parameters of transducer 119, such as the placement, distance, treatment depth, and transducer 119 structure, as well as by changing the temporal parameters of transducer 119, such as the frequency, drive amplitude, and timing, with such control handled via control system 120. Such spatial and temporal parameters may also be suitably monitored and/or utilized in open-loop and/or closed-loop feedback systems within ultrasound system 116.

Throughout this application, reference has been made to treating a single layer of tissue 11 or subcutaneous tissue 12 at any given time. It should be noted that two or more layers of tissue may be treated at the same time and fall within the scope of this disclosure. In certain embodiments where two or more layers of tissue are treated, muscle 13, ligaments 15, and other fibro-muscular layers of tissue can be treated simultaneously.

Finally, it should be noted that while this disclosure is directed primarily to using ultrasound energy 121 to conduct procedures non-invasively, that the method and system for performing a blepharoplasty described above can also utilize energy such as ultrasound energy 121 to assist in invasive procedures. For example, ultrasound energy 121 can be used to ablate subcutaneous tissues 12 and tissues 11 during an invasive procedure. In this regard, ultrasound energy 121 can be used for invasive and minimally invasive procedures.

Method and System for Treating Cartilage Tissue

With reference to FIGS. 17-24, another method and system are provided for treating tissue with focused, unfocused or defocused energy. In an embodiment, the energy used is ultrasound energy. In other embodiments, the energy is laser energy or radio frequency energy. In certain embodiments, the energy is ultrasound energy combined with other forms of energy such as laser or radio frequency energy. In an embodiment, the energy used is ultrasound energy and the tissue treated is cartilage tissue. The method will be referred to as method 210 throughout. In an embodiment, the treated tissue region 21 comprises subcutaneous tissue 22 and can comprise muscle, tendon, ligament or cartilage tissue (MTLC), among other types of tissue.

Figure 17:
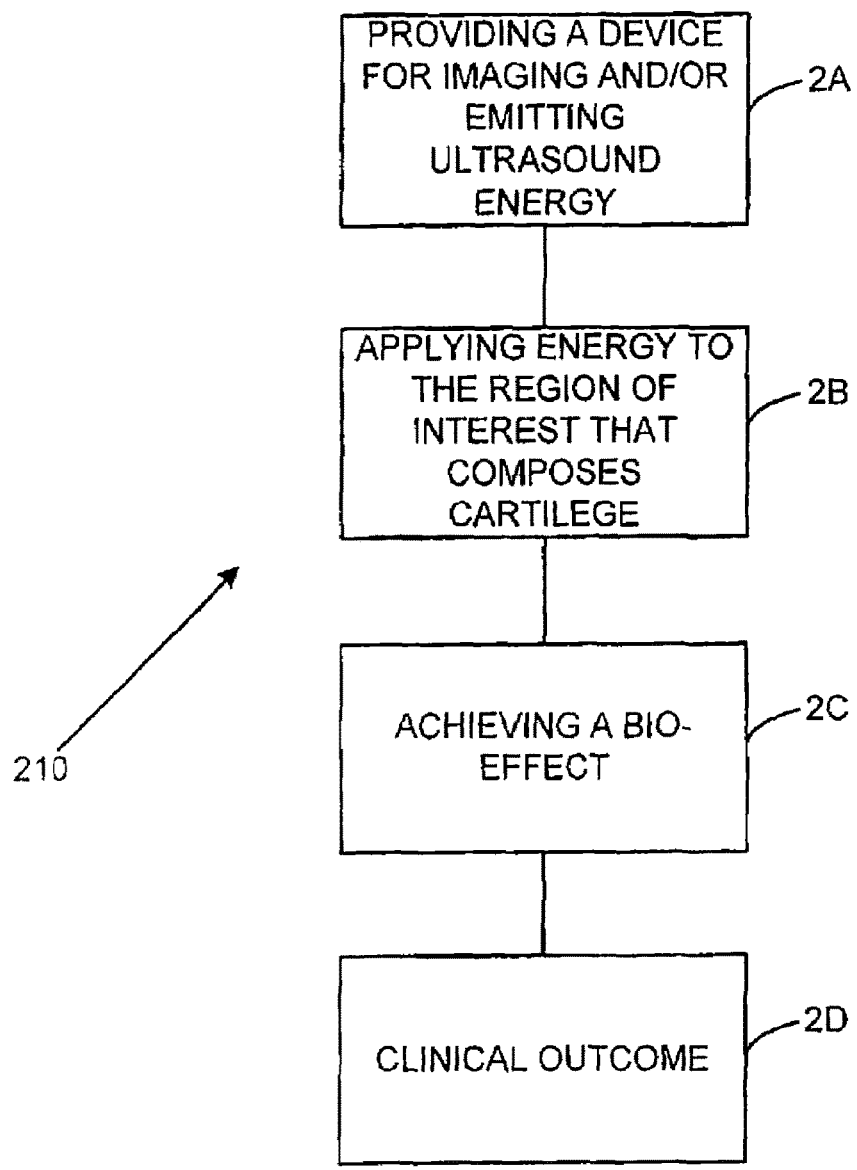
FIG. 17 illustrates a flow chart of the treatment method for treating cartilage in accordance with an embodiment of the present invention.

As depicted in the embodiment shown in FIG. 17, method 10 broadly comprises the following steps 2A-2D. First, at step 2A, a system that emits energy such as ultrasound energy is provided. At step 2B, energy is applied to a Region of Interest ("ROI") which comprises any area of a body that comprises cartilage. Certain ROIs include the nose, ears, soft palate, joint sockets such as the knee, elbow, shoulders, hips, and any other area of the body that comprises cartilage. The energy is applied until a specific bio-effect is achieved at step 2C through cutting, reabsorbing or manipulating the cartilage. Certain bio-effects achieved by cutting, reabsorbing or manipulating the cartilage at step 2C can comprise, but are not limited to, incapacitating, partially incapacitating, rejuvenating, ablating, micro-ablating, modifying, shortening, coagulating, paralyzing, or causing the cartilage to be reabsorbed into the body. As used throughout, the term "ablate" means to destroy or coagulate tissue at ROI 212. The term "micro-ablate" means to ablate on a smaller scale. Upon the completion of bio-effects at step 2C, cartilage is treated and a clinical outcome such as an otoplasty or rhinoplasty is achieved at step 2D.

Figure 19:
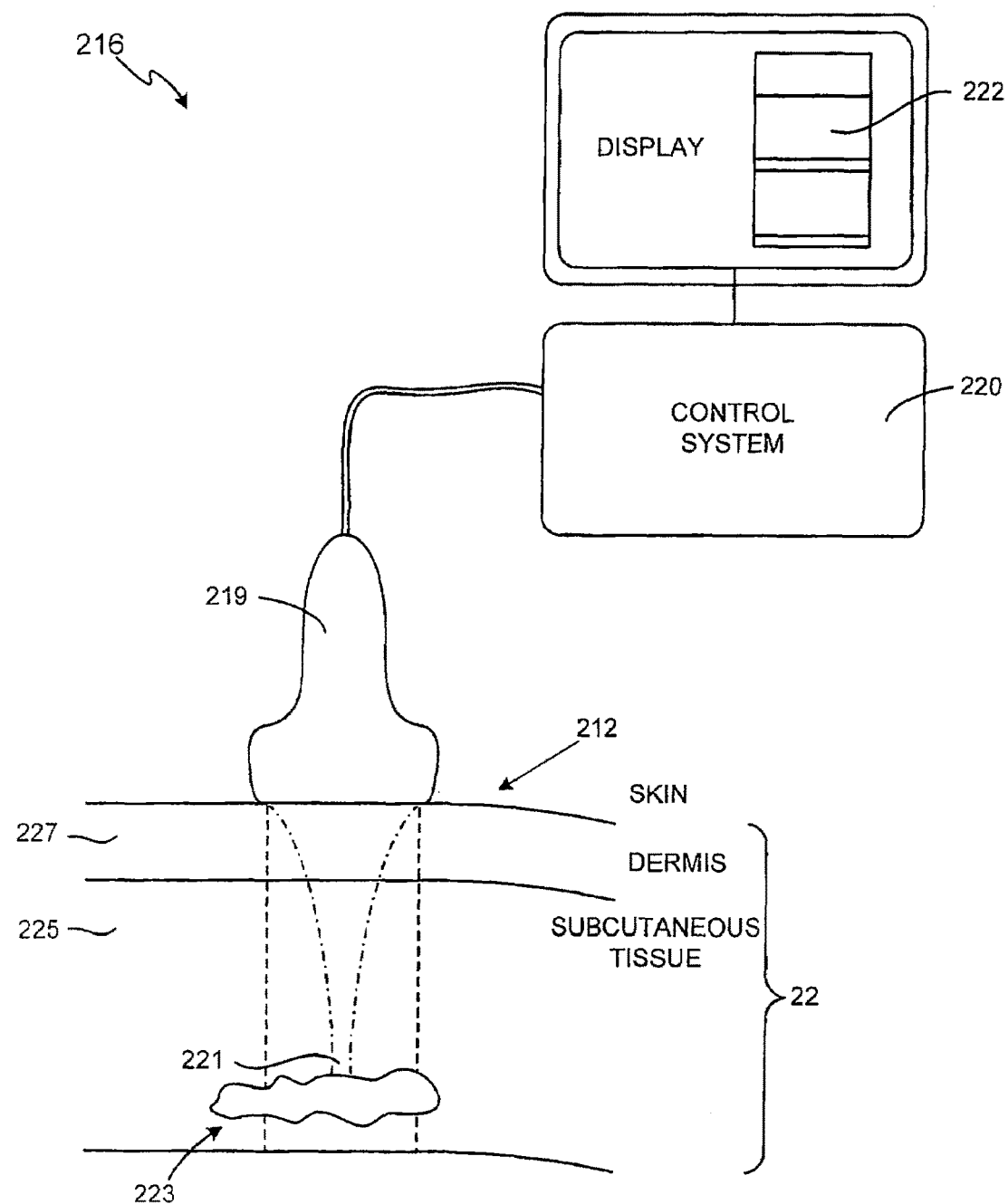
FIG. 19 illustrates a schematic diagram of a treatment system configured to treat cartilage tissue in accordance with an embodiment of the present invention.
Figure 20:
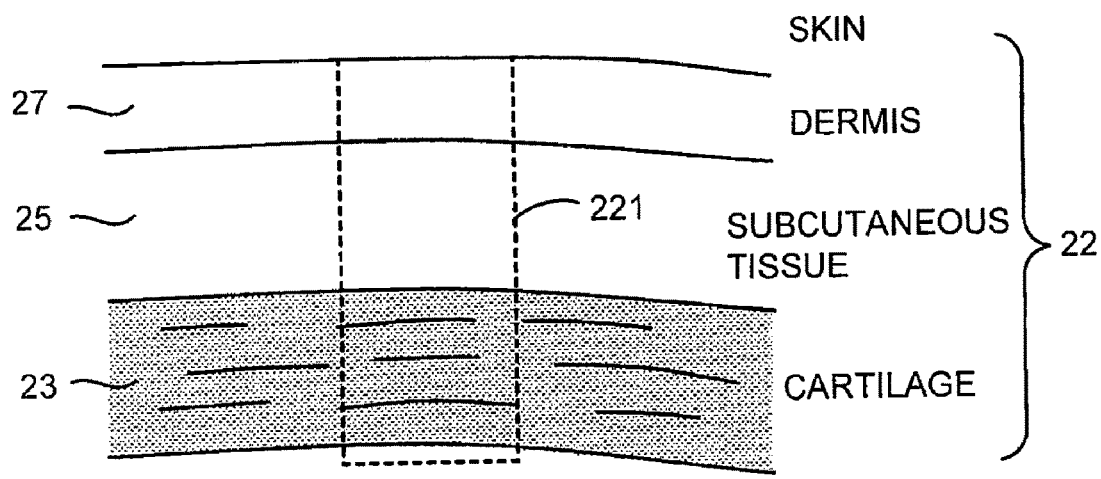
FIG. 20 illustrates various layers of tissue and cartilage tissue that the can be treated or imaged in accordance with an embodiment of the present invention.

In an embodiment, depicting in FIGS. 19-21, energy such as ultrasound energy 221 is delivered at specific depths below a patient's skin to treat tissue 21, subcutaneous tissue 22, and cartilage 23. Certain depths are in the range of approximately 0.1-100 millimeters. The exact depth depends upon the location of cartilage 23 and the general location of ROI 212. For example, an ear with relatively shallow cartilage 23 may require that ultrasound energy 221 reach a depth in the range of approximately 50 microns to 3 millimeters.

Besides depth, ultrasound energy 221 is delivered at specific frequencies, powers, application times, temperatures, and penetrate certain depths within ROI 212 to achieve various effects on cartilage 23. Moreover, the lesion shape (when ultrasound energy 221 is applied at ablative levels) also varies depending on the type of procedure being conducted and the time ultrasound energy 221 is applied.

For example, a broad time range for applying ultrasound energy 221 is anytime time frame approximately between 1 millisecond and 10 minutes. Certain time frames include 50 milliseconds to 30 seconds to soften cartilage 23 in an ear. Ablating cartilage in the ear may require ultrasound energy 221 to be applied for a longer time frame such as 100 milliseconds to 5 minutes depending on the depth of cartilage 23 and the power of ultrasound 221.

The frequency of ultrasound energy 221 can also very greatly depending on the type and location of tissue 21 and subcutaneous tissue 22. A broad frequency range is approximately between 1-25 MHz and ranges within this range can For example, to penetrate deep into the knee joint to target cartilage 23 in the knee joint may require a frequency in the range of approximately 2-8 MHz. An ear on the other hand may only require a frequency of 5-25 MHz.

In various embodiments, certain power levels to cause ablation of cartilage 23 comprise, but are not limited to, 250 watts to 5000 watts. The temperature range to cause ablative lesions is approximately between 45°-100° C. in an embodiment. However, longer time periods could be used with more powerful ultrasound energy or vice-versa to create ablative lesions at ROI 212.

In various embodiments, certain lesion sizes that can be produced using method 210 are in the approximate range of 0.1 cubic millimeters to a 1000 cubic millimeters depending on the desired result and the location of ROI 212. For example, a smaller lesion is in the approximate range of 0.1 cubic millimeters to 3 cubic millimeters. One lesion is on a patient's nose and may be in the approximate range of 5 cubic millimeters to 1000 cubic millimeters. This type of lesion can effectuate removing a portion of cartilage 23 from the nose.

Subcutaneous tissue 22, which may be treated by method 210, may comprise cartilage 23 and other ligament and muscle tissue. Other subcutaneous tissues 22 which may be treated may comprise various subcutaneous tissues 22, and dermis 27, muscle fascia or tissue comprising Superficial Muscular Aponeurotic System or "SMAS." Subcutaneous tissue 22 may be located within ROI 212 on a patient's body that may be desired to be treated such as areas that contain cartilage 23. In various embodiments, certain ROI 212's are the patient's ears and nose. In other embodiments, other areas with cartilage 23 can be ROI 212. These areas include locations between the joints that contain cartilage 23 such as the elbows, knees, shoulders, and any other joint. ROI 212 may further comprise an inner treatment region, a superficial region, a subcutaneous region of interest and/or any other region of interest in between an inner treatment region, a superficial region, and/or any other areas.

Figure 18:
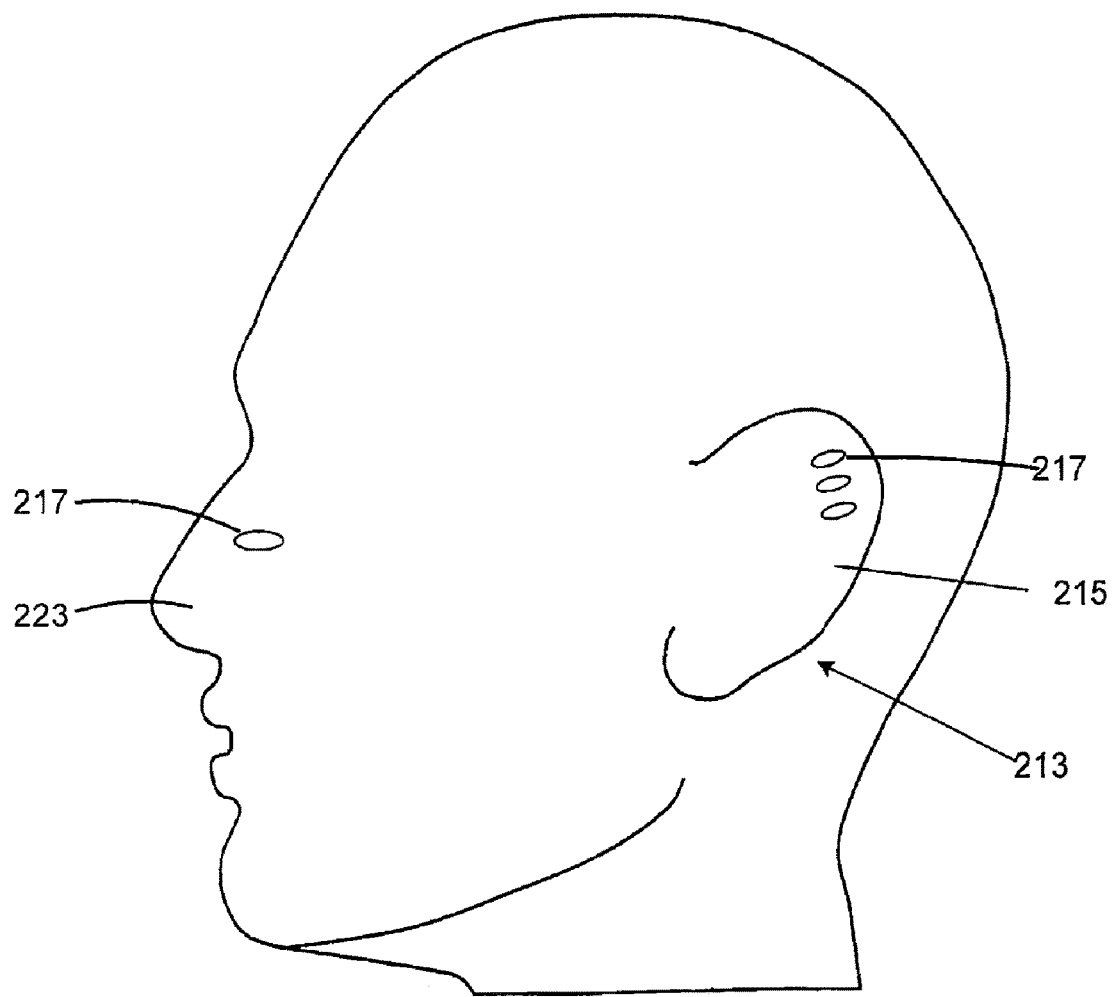
FIG. 18 illustrates a patient's head and the location of the cartilage that can be treated in accordance with embodiments of the present invention.

FIG. 18 depicts certain embodiments of ROI 212's that can be treated. Energy such as ultrasound energy may be applied to the patient's ear 213 and to specific regions of ear 213 such as the pinna 215. In this embodiment, incisions 217 are created by applying energy at ablative levels at pinna 215. Incisions 217 enable cartilage 23 that comprises pinna 215 to more easily rest backwards towards the patient's head. In this manner, an otoplasty procedure can be performed non-invasively.

In another similar embodiment depicted in FIG. 18, cartilage 23 that defines the patient's nose 223 can be treated by method 210. In this embodiment, energy may be applied to specific ROI 212 at nose 223 to ablate cartilage 23. As depicted in this embodiment, incisions 217 are created by the application of energy at ablative levels. The incisions cause cartilage 23 within nose 223 to loose rigidity. This loss of rigidity allows a surgeon or other operator to adjust nose 223. The use of method 210 can be used alone or to assist more traditional surgical techniques in sculpting nose 223. This enables the adjustment of nose 223 and can be a substitute for a traditional nose surgery such as a rhinoplasty.

Figure 21:
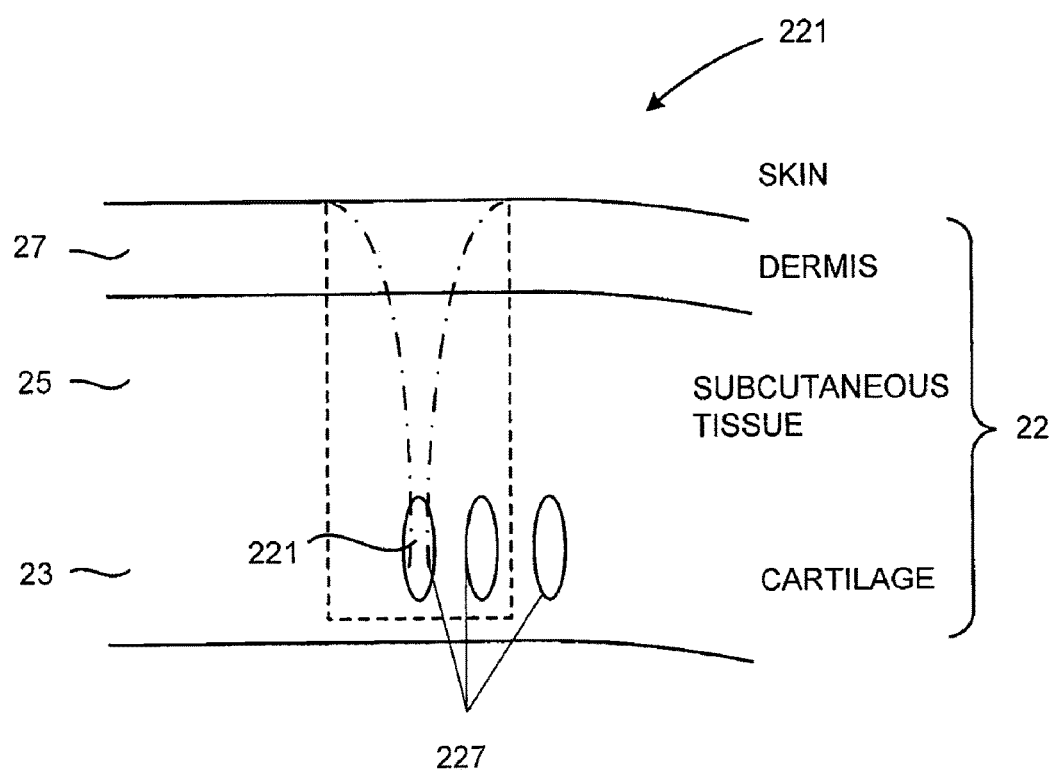
FIG. 21 illustrates a layer of cartilage tissue being treated in accordance with an embodiment of the present invention.

In another embodiment, with reference to FIGS. 17-21, various different subcutaneous tissues 22 or cartilage 23 may be treated by method 210 to produce different bio-effects. In order to treat a specific subcutaneous tissue 22 or cartilage 23 to achieve a desired bio-effect, ultrasound energy 221 from system 214 may be directed to a specific depth within ROI 212 to reach the targeted subcutaneous tissue 22 or cartilage 23. For example, if it is desired to cut cartilage 23, which is 15 mm below the surface of the skin, ultrasound energy 221 from ultrasound system 216 may be provided at ROI 212 at a level to reach up to and approximately 15 mm below the skin (the exact depth will vary though depending on the location of ROI 212) at an ablative level which may be capable of cutting cartilage 23. An example of cutting cartilage 23 is depicted in FIG. 21 which depicts a series of lesions 227 cut into cartilage 23. Besides cutting cartilage 23, other bio-effects may comprise incapacitating, partially incapacitating, severing, rejuvenating, removing, ablating, micro-ablating, shortening, manipulating, or removing cartilage 23 either instantly or over time, and/or other effects, and/or combinations thereof.

Depending at least in part upon the desired bio-effect and the subcutaneous tissue 22 or cartilage 23 being treated, method 210 may be used with an extracorporeal, non-invasive, partially invasive, or invasive procedure. Also, depending at least in part upon the specific bio-effect and subcutaneous tissue 22 targeted, there may be temperature increases within ROI 212 which may range approximately from 0-60° C. or any suitable range for heating, cavitation, steaming, and/or vibro-accoustic stimulation, and/or combinations thereof.

All known types of cartilage 23 can be targeted and treated according to method 210. Certain types of cartilage 23 comprise scaphoid cartilage and helix cartilage of an ear 213. Other types of cartilage 23 are found in a patient's nose 223 when method 210 is used to treat cartilage 23 within nose 223 as described below include, but are not necessarily limited to, the major alar cartilage, the septal nasal cartilage, the accessory nasal cartilage, and minor alar cartilage.

Numerous procedures to ears 213 that are typically done surgically to remove cartilage 23 from ears 213 to reduce the overall size of ears 13 can also be accomplished using method 210. Certain embodiments of procedures include, but are not necessarily limited to, a conchal floor reduction, a conchal post wall reduction, an antihelix reduction, a scapha reduction, and a helix reduction.

In certain embodiments where cartilage 23 within ear 213 is treated with ultrasound energy 221, cartilage 23 may be ablated, coagulated, and completely reabsorbed into the body or it can be ablated to form one or more incisions within ear 213. In one embodiment, ear surgery such as an otoplasty is performed to adjust ears 213 which may protrude further from the patient's head than desired. The amount of protrusion of ears 213 from the patient's head can be corrected by cutting cartilage 23 that comprises pinna 215 of ears 213. In this embodiment, pinna 215 of ears 213 is ROI 212 and ultrasound energy 221 is used to ablate, coagulate, or cut cartilage 23 that comprises pinna 215 of ears 213.

When cartilage 23 is disposed in ears 213 or nose 223, method 210 can further comprise the step of utilizing a mechanical device after treatment to shape and form cartilage 23. For example, during a Rhinoplasty, a clamp may be placed on the patient's nose 223 to help shape nose 223 following method 210. Clamps, pins, and other mechanical devices can be used to shape cartilage 23 in other areas of the body too such as ears 213. Notably, following treatment of ears 213, mechanical clamps or another similar device can be attached to the ears and used to push the ears in a certain direction. Once cartilage 23 has been softened, ablated, or otherwise affected by method 210, it is more malleable and ears 213 are easier to force backwards (or forwards) in a particular direction.

Different subcutaneous tissues 22 within ROI 212 may have different acoustic properties. For example, cartilage 23 might have different acoustic properties than muscle or fascia. These different acoustic properties affect the amount of energy applied to ROI 212 to cause certain bio-effects to cartilage 23 than may be required to achieve the same or similar bio-effects for fascia. These acoustic properties may comprise the varied acoustic phase velocity (speed of sound) and its potential anisotropy, varied mass density, acoustic impedance, acoustic absorption and attenuation, target size and shape versus wavelength and direction of incident energy, stiffness, and the reflectivity of subcutaneous tissues 22 such as cartilage 23, among many others. Depending on the acoustic properties of a particular subcutaneous tissue 22 or cartilage 23 being treated, the application of ultrasound energy 221 at ROI 212 may be adjusted to best compliment the acoustic property of the subcutaneous tissue 22 or cartilage 23 being targeted. Certain acoustic ranges comprise, but are not limited to, approximately 1 and 2 Mrayls.

In certain embodiments of procedures, method 210 can be used for cartilage regeneration. Removing a portion of cartilage 23 from a patient will initiate cartilage regeneration in that ROI 212. In this regard, traditionally invasive procedures that effectuate cartilage 23 regeneration can be performed non-invasively using energy such as ultrasound energy 221. In these embodiments, ultrasound energy 221 is applied at ablative levels at the ROI 12 to remove a portion of cartilage 23. Removing a portion of cartilage 23 enables cartilage regeneration to occur. One procedure that can be accomplished with cartilage regeneration is microfracture surgery.

During microfracture surgery, cartilage 23 is applied at ablative levels to target cartilage 23 or other subcutaneous tissues 22 near cartilage 23 in the knee joint. Applying ultrasound energy 221 at ablative levels near the knee joint causes one or more fractures in cartilage 23 or other subcutaneous tissue 22 such as bones. When bones or other subcutaneous tissues 22 are targeted, sufficient ultrasound energy 221 is applied to ablate those tissues. These fractures result in cartilage 23 re-growing in the place of the ablated subcutaneous tissues 22 and a non-invasive microfracture surgery is performed.

In another embodiment, cartilage 23 between the joints is treated with method 210. In this regard, swollen or otherwise injured cartilage 23 responsible for osteoarthritis, rheumatoid arthritis, and juvenile rheumatoid arthritis can be treated with method 210. For example, ROI 212 may be along a patient's knees to treat cartilage 23 that serves as a cushion in a patient's knee socket. Alternatively, ROI 212 can be disposed on a patient's shoulder area to treat cartilage 23 disposed on the shoulder joint. In these embodiments, ultrasound energy 221 may not be applied at ablative levels, e.g., between 250 watts to 5000 watts at temperatures between 45° C. to 100° C., but at levels that produce enough heat at ROI 212 to reduce swelling and the size of cartilage 23 within these joints.

In yet another embodiment, cartilage, muscle, and other tissue responsible for snoring and/or sleep apnea are treated by method 210. These tissues are typically located in and around the hard palate and the soft palate. In this embodiment, cartilage 23, and other MTLC tissue are treated with ultrasound energy 221 at ablative levels to be destroyed or reabsorbed into the body and thus unblock restricted airways that are responsible for snoring and/or sleep apnea. In one embodiment, transducer 219 is placed on the exterior of patient's body to treat ROI 212 at the neck around the Adam's apple. In another embodiment, transducer 219 is configured to be inserted within the oral cavity at the patient's mouth and to treat cartilage 23 and other MTLC tissue internally.

In another embodiment, method 210 can be used to assist in delivery of various fillers and other medicines to ROI 212. According to this embodiment, ultrasound energy 221 assists in forcing the fillers and medicants into tissue 21 and subcutaneous tissue 22 at ROI 12. Hyaluronic acid can be delivered to ROI 212 in this manner. The application of ultrasound energy 221 to ROI 212 causes surrounding tissues to absorb the fillers such as hyaluronic acid by increasing the temperature at ROI 212 and through the mechanical effects of ultrasound such as cavitation and streaming. Utilizing ultrasound energy 221 to effectuate the delivery of medicants and fillers is described in U.S. patent application Ser. No. 11/163,177 entitled "Method and System for Treating Acne and Sebaceous Glands" which is incorporated by reference in its entirety.

Figure 22:
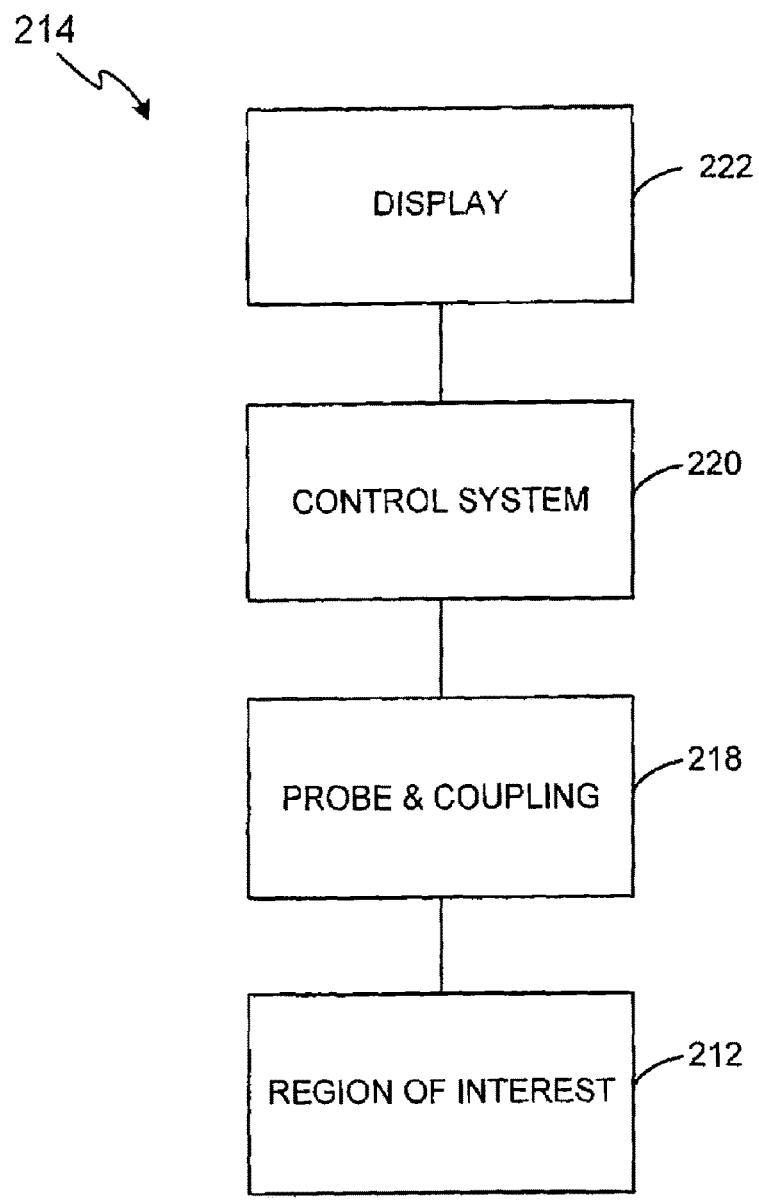
FIG. 22 illustrates a block diagram of a treatment system used to treat cartilage in accordance with an embodiment of the present invention.

As depicted in the embodiment of the system shown in FIG. 22, a system 214 used for method 210 is an ultrasound system 216 that may be capable of emitting ultrasound energy 221 that is focused, unfocused or defocused to treat cartilage 23 at ROI 212. System 214 may comprise a probe 218, a control system 220, and a display 222. System 214 may be used to delivery energy to, and monitor ROI 212. Certain embodiments of systems are disclosed in U.S. patent application Ser. No. 11/163,177 entitled "Method and System for Treating Acne and Sebaceous Glands," U.S. patent application Ser. No. 10/950,112 entitled "Method and System for Combined Ultrasound Treatment", and U.S. Patent Application No. 60/826,039 entitled "Method and System for Non-Ablative Acne Treatment", each of which are hereby incorporated by reference in its entirety.

With additional reference to FIGS. 23A-23E, an embodiment of a probe 218 may be a transducer 219 capable of emitting ultrasound energy 221 into ROI 212. This may heat ROI 212 at a specific depth to target a specific tissue 21 or cartilage 23 causing that tissue 21 or cartilage 23 to be incapacitated, partially incapacitated, rejuvenated, ablated, modified, micro-ablated, shortened, coagulated, paralyzed, or reabsorbed into the body. A coupling gel may be used to couple probe 218 to ROI 212. Ultrasound energy 221 may be emitted in various energy fields in this embodiment. With additional reference to FIG. 23A and FIG. 23B, the energy fields may be focused, defocused, and/or made substantially planar by transducer 219, to provide many different effects. Energy may be applied in a C-plane or C-scan. For example, in one embodiment, a generally substantially planar energy field may provide a heating and/or pretreatment effect, a focused energy field may provide a more concentrated source of heat or hypothermal effect, and a non-focused energy field may provide diffused heating effects. It should be noted that the term "non-focused" as used throughout encompasses energy that is unfocused or defocused. Further, in one embodiment (as depicted in FIG. 19) the application of ultrasound energy may provide imaging or ROI 212.

Figure 23A:
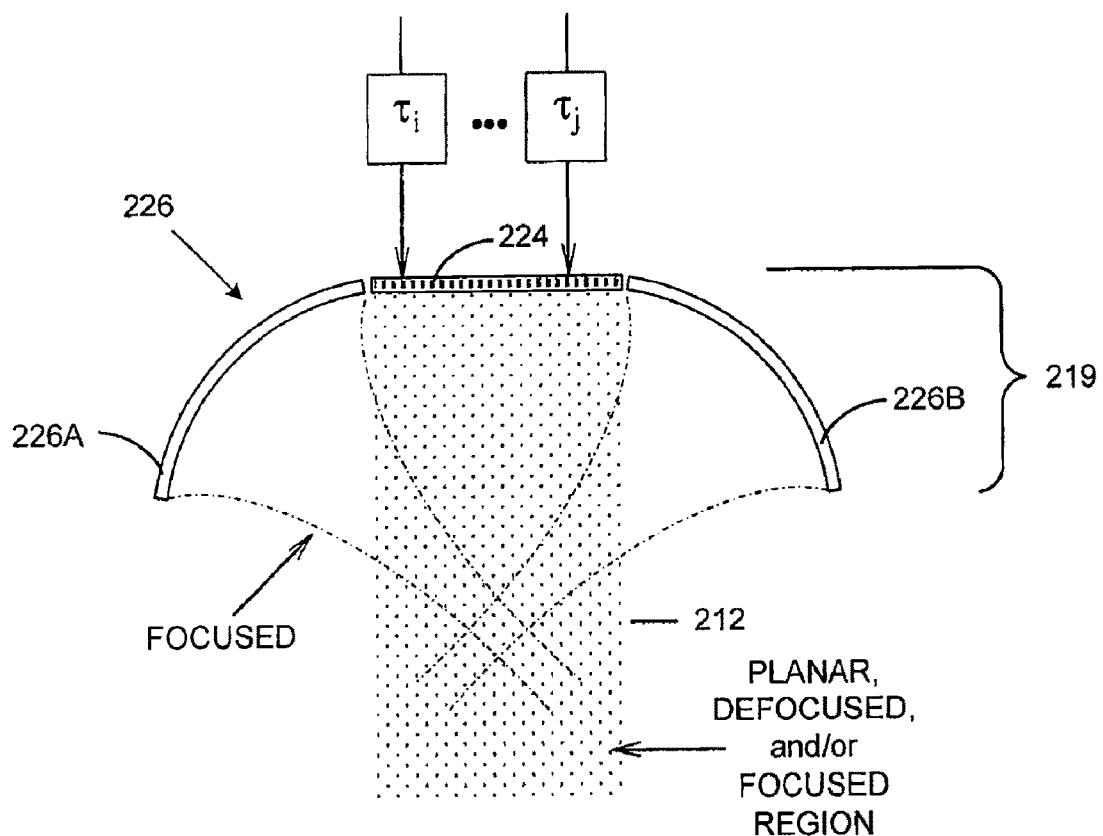
FIGS. 23A, 23B, 23C, 23D, and 23E illustrate cross-sectional diagrams of an transducer used in a system used to treat cartilage in accordance with various embodiments of the present invention.
Figure 23B:
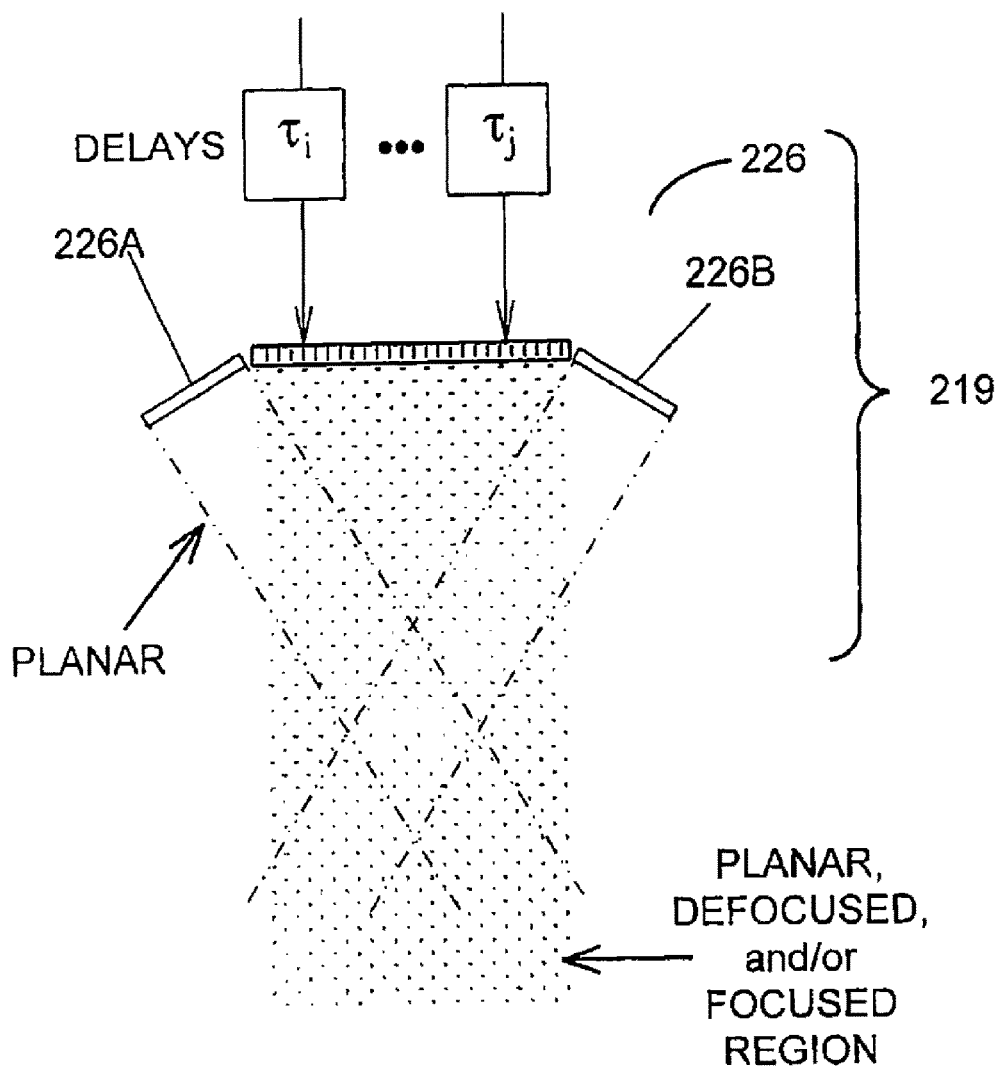

With continued reference to FIGS. 23A and 23B, transducer 219 may comprise one or more transducers for facilitating treatment. Transducer 219 may further comprise one or more transduction elements 226, e.g., elements 226A or 226B. The transduction elements 226 may comprise piezoelectrically active material, such as lead zirconante titanate (PZT), or other piezoelectrically active material such as, but not limited to, a piezoelectric ceramic, crystal, plastic, and/or composite materials, as well as lithium niobate, lead titanate, barium titanate, and/or lead metaniobate. In addition to, or instead of, a piezoelectrically active material, transducer 219 may comprise any other materials configured for generating radiation and/or acoustical energy. Transducer 219 may also comprise one or more matching and/or backing layers configured along with the transduction element 226, such as being coupled to the piezoelectrically active material. Transducer 219 may also be configured with single or multiple damping elements along the transduction element 226.

In an embodiment, the thickness of the transduction element 226 of transducer 219 may be configured to be uniform. That is, the transduction element 226 may be configured to have a thickness that is generally substantially the same throughout.

As depicted in the embodiment shown in FIGS. 23A and 23B, transduction element 226 may also be configured with a variable thickness, and/or as a multiple damped device. For example, the transduction element 226 of transducer 219 may be configured to have a first thickness selected to provide a center operating frequency of a lower range, for example from approximately 1 kHz to 3 MHz. The transduction element 226 may also be configured with a second thickness selected to provide a center operating frequency of a higher range, for example from approximately 3 to 100 MHz or more.

In yet another embodiment, transducer 19 may be configured as a single broadband transducer excited with two or more frequencies to provide an adequate output for raising the temperature within ROI 212 to the desired level. Transducer 219 may also be configured as two or more individual transducers, wherein each transducer 219 may comprise a transduction element 226. The thickness of the transduction elements 226 may be configured to provide center-operating frequencies in a desired treatment range. For example, in an embodiment, transducer 219 may comprise a first transducer 219 configured with a first transduction element 226A having a thickness corresponding to a center frequency range of approximately 1 MHz to 3 MHz, and a second transducer 19 configured with a second transduction element 226B having a thickness corresponding to a center frequency of approximately 3 MHz to 100 MHz or more. Various other ranges of thickness for a first and/or second transduction element 226 can also be realized.

Moreover, any variety of mechanical lenses or variable focus lenses, e.g. liquid-filled lenses, may also be used to focus and or defocus the energy field. For example, with reference to FIGS. 23A and 23B, transducer 219 may also be configured with an electronic focusing array 224 in combination with one or more transduction elements 226 to facilitate increased flexibility in treating ROI 212. Array 224 may be configured in a manner similar to transducer 219. That is, array 224 may be configured as an array of electronic apertures that may be operated by a variety of phases via variable electronic time delays, for example, T1, T2, T3 ... Tj. By the term "operated," the electronic apertures of array 224 may be manipulated, driven, used, and/or configured to produce and/or deliver energy in a manner corresponding to the phase variation caused by the electronic time delay. For example, these phase variations may be used to deliver defocused beams, planar beams, and/or focused beams, each of which may be used in combination to achieve different physiological effects in ROI 212.

Transduction elements 226 may be configured to be concave, convex, and/or planar. For example, as depicted in FIG. 23A, transduction elements 226A and 226B are configured to be concave in order to provide focused energy for treatment of ROI 212. Additional embodiments are disclosed in U.S. patent application Ser. No. 10/944,500, entitled "System and Method for Variable Depth Ultrasound Treatment", incorporated herein by reference in its entirety.

In another embodiment, depicted in FIG. 23B, transduction elements 226A and 226B may be configured to be substantially flat in order to provide substantially uniform energy to ROI 212. While FIGS. 23A and 23B depict embodiments with transduction elements 226 configured as concave and substantially flat, respectively, transduction elements 226 may be configured to be concave, convex, and/or substantially flat. In addition, transduction elements 226 may be configured to be any combination of concave, convex, and/or substantially flat structures. For example, a first transduction element 226 may be configured to be concave, while a second transduction element 226 may be configured to be substantially flat.

Moreover, transduction element 226 can be any distance from the patient's skin. In that regard, it can be far away from the skin disposed within a long transducer or it can be just a few millimeters from the surface of the patient's skin. In certain embodiments, positioning the transduction element 26 closer to the patient's skin is better for emitting ultrasound at high frequencies. Moreover, both three and two dimensional arrays of elements can be used in the present invention.

Figure 23C:
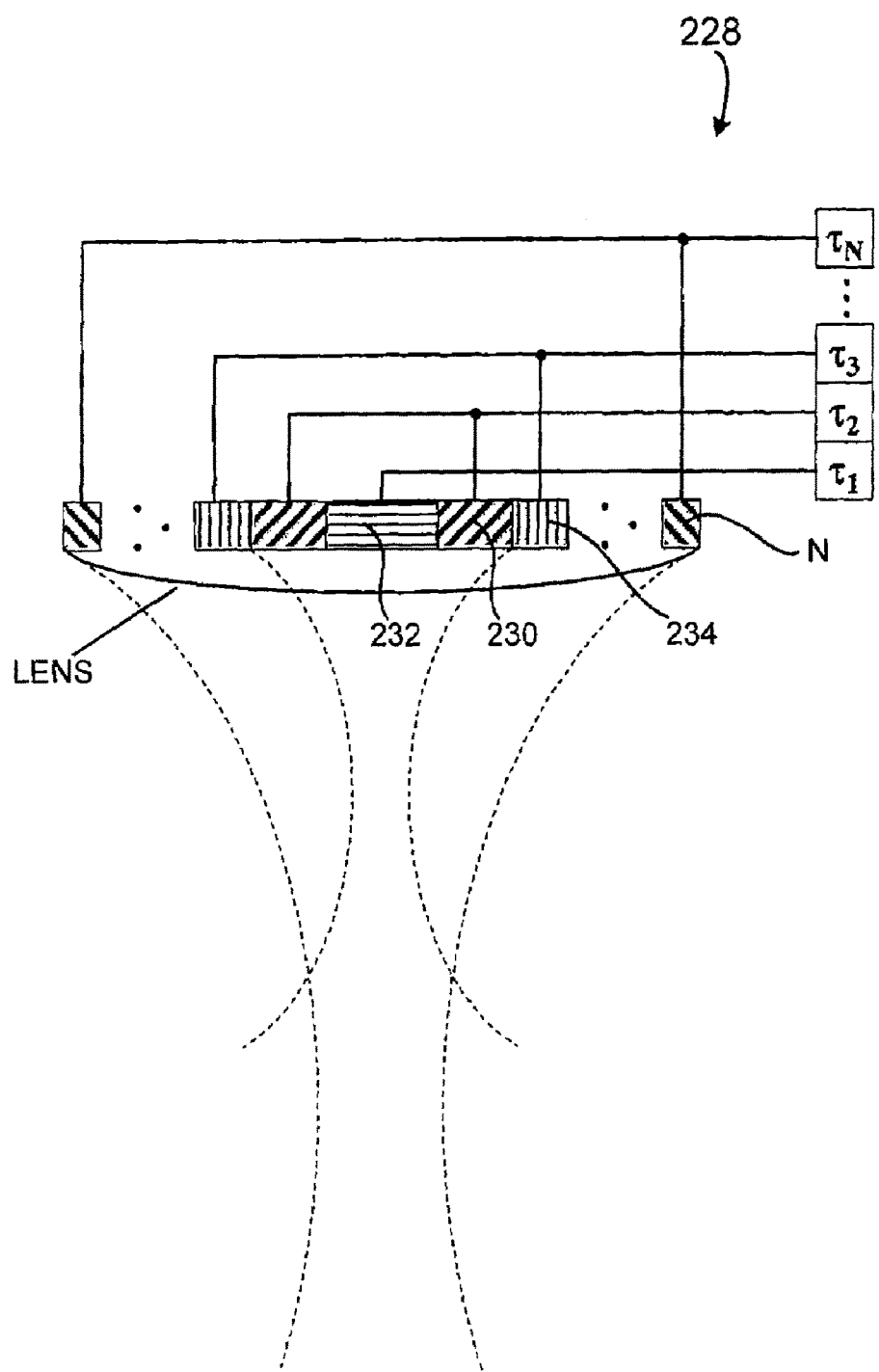
Figure 23D:
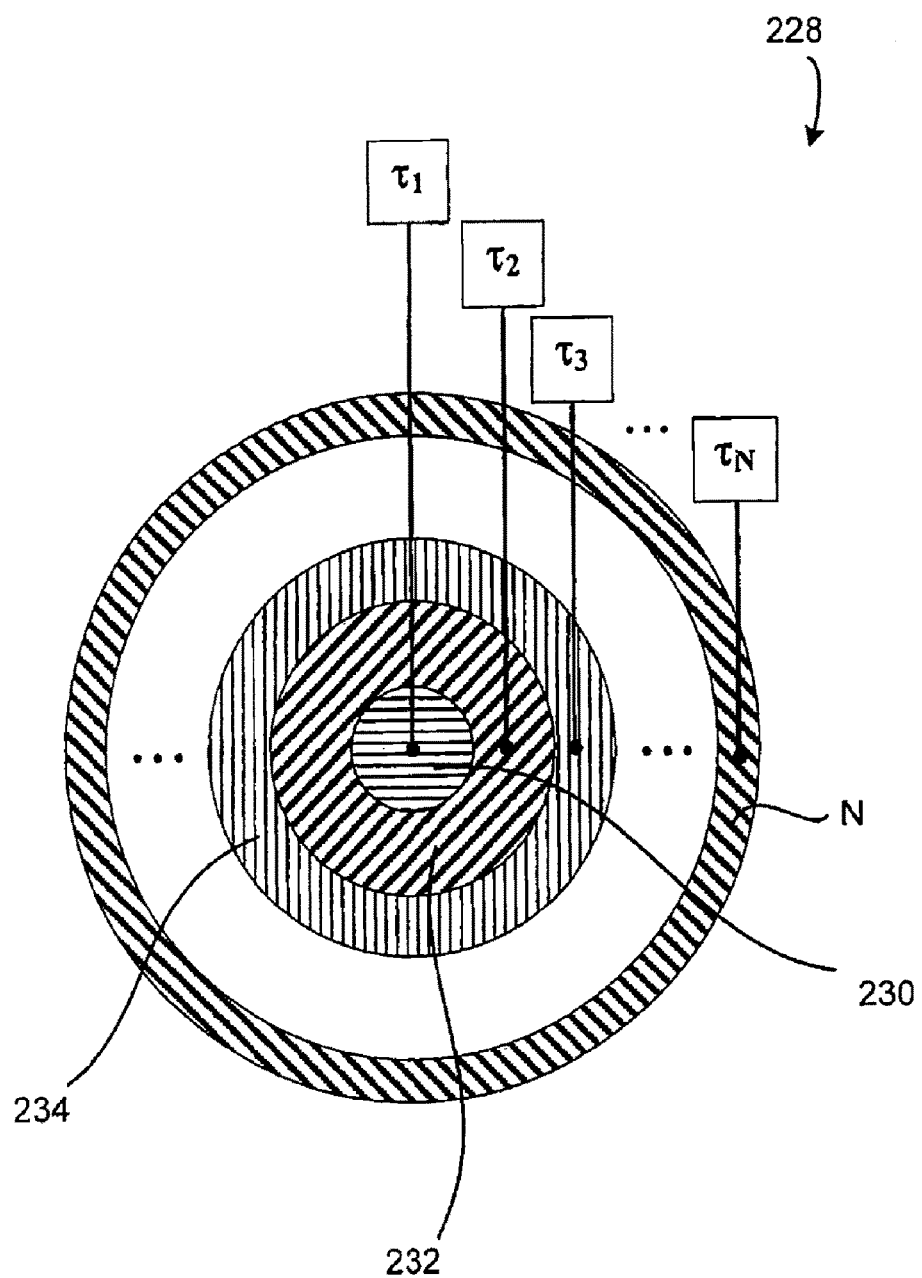

With reference to FIGS. 23C and 23D, transducer 219 may also be configured as an annular array to provide planar, focused and/or defocused acoustical energy. For example, in an embodiment, an annular array 228 may comprise a plurality of rings 230, 232, 234 to N. Rings 230, 232, 234 to N may be mechanically and electrically isolated into a set of individual elements, and may create planar, focused, or defocused waves. For example, such waves can be centered on-axis, such as by methods of adjusting corresponding transmit and/or receive delays, T1, T2, T3 ... TN. An electronic focus may be suitably moved along various depth positions, and may enable variable strength or beam tightness, while an electronic defocus may have varying amounts of defocusing. In an embodiment, a lens and/or convex or concave shaped annular array 228 may also be provided to aid focusing or defocusing such that any time differential delays can be reduced. Movement of annular array 228 in one, two or three-dimensions, or along any path, such as through use of probes and/or any conventional robotic arm mechanisms, may be implemented to scan and/or treat a volume or any corresponding space within ROI 212.

Figure 23E:
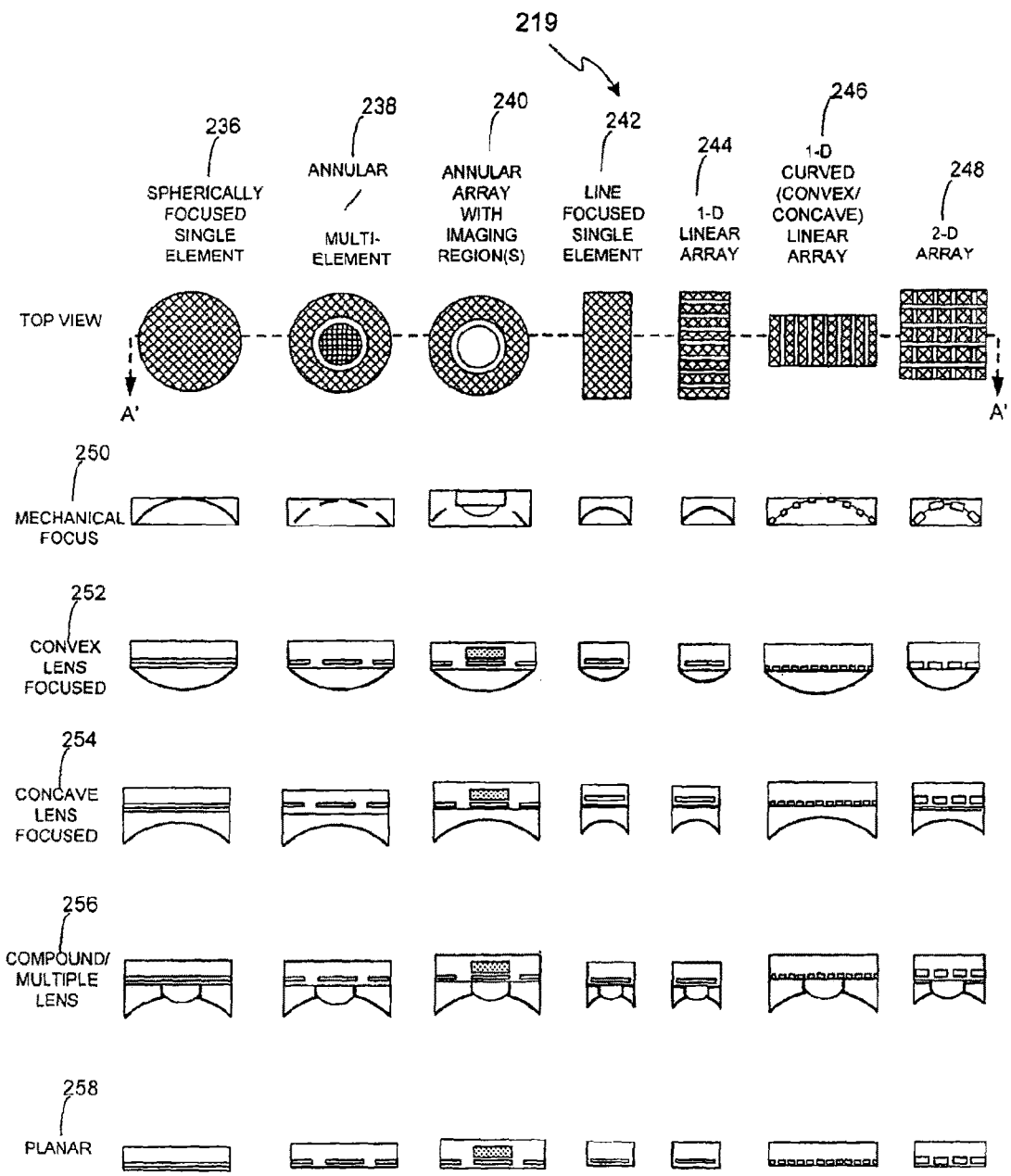

With reference to FIG. 23E, another transducer 219 can be configured to comprise a spherically focused single element 236, annular/multi-element 238, annular with imaging region(s) 240, line-focused single element 242, 1-D linear array 244, 1-D curved (convex/concave) linear array 246, and/or 2-D array 248, with mechanical focus 250, convex lens focus 252, concave lens focus 254, compound/multiple lens focused 256, and/or planar array form 258 to achieve focused, unfocused, or defocused sound fields for both imaging and/or therapy.

Transducer 219 may further comprise a reflective surface, tip, or area at the end of the transducer 219 that emits ultrasound energy 221. This reflective surface may enhance, magnify, or otherwise change ultrasound energy 221 emitted from system 214.

In an embodiment, suction is used to attach probe 218 to the patient's body. In this embodiment, a negative pressure differential is created and probe 218 attaches to the patient's skin by suction. A vacuum-type device is used to create the suction and the vacuum device can be integral with, detachable, or completely separate from probe 218. The suction attachment of probe 18 to the skin and associated negative pressure differential ensures that probe 18 is properly coupled to the patient's skin. Further, the suction-attachment also reduces the thickness of the tissue to make it easier to reach the targeted tissue. In other embodiments, a coupling gel is used to couple probe 218 to the patient's skin. The coupling gel can include medicines and other drugs and the application of ultrasound energy 221 can facilitate transdermal drug delivery.

Figure 24A:
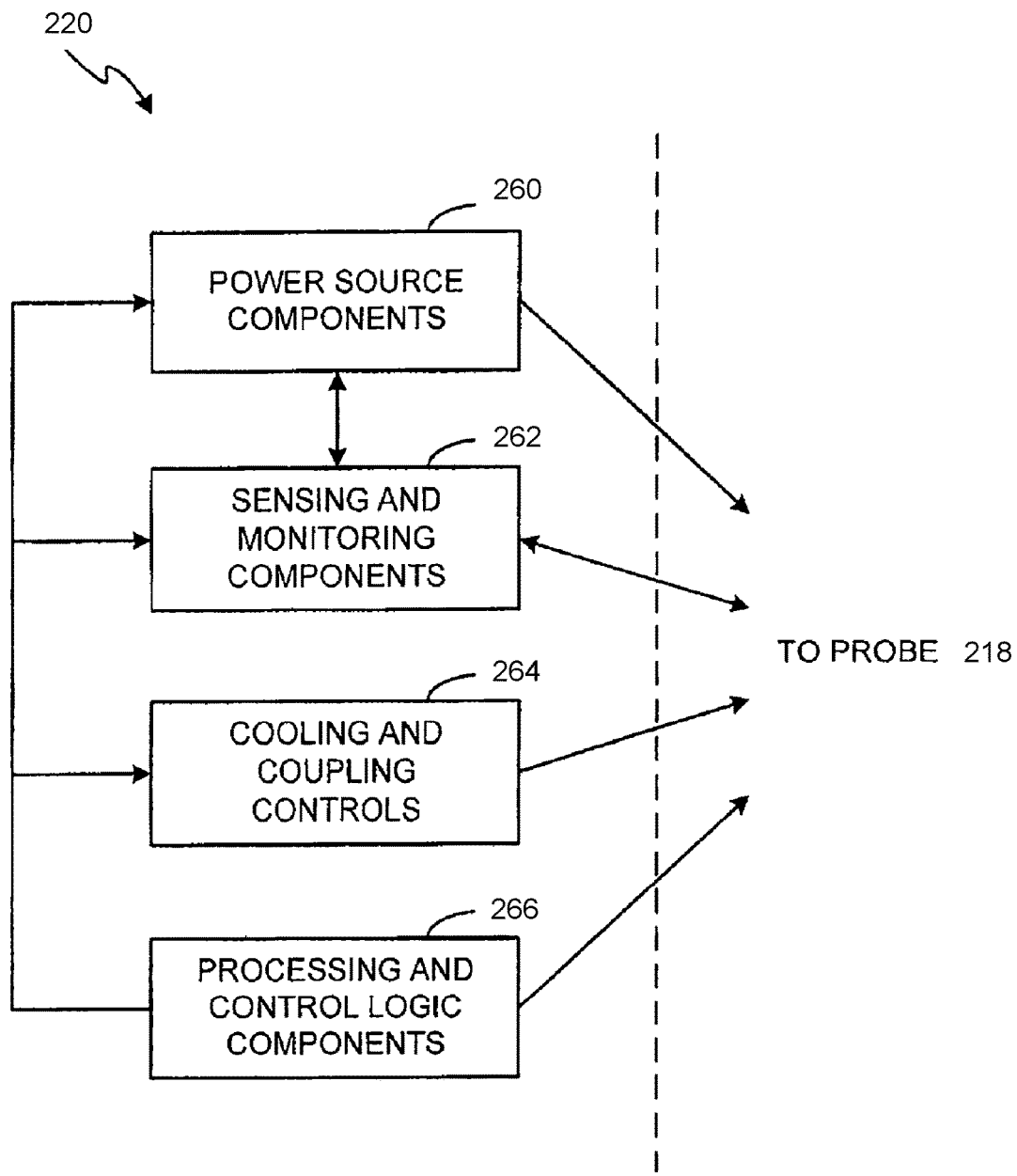
FIGS. 24A, 24B and 24C illustrate block diagrams of an control system used in a system used to treat cartilage in accordance with embodiments of the present invention.
Figure 24B:
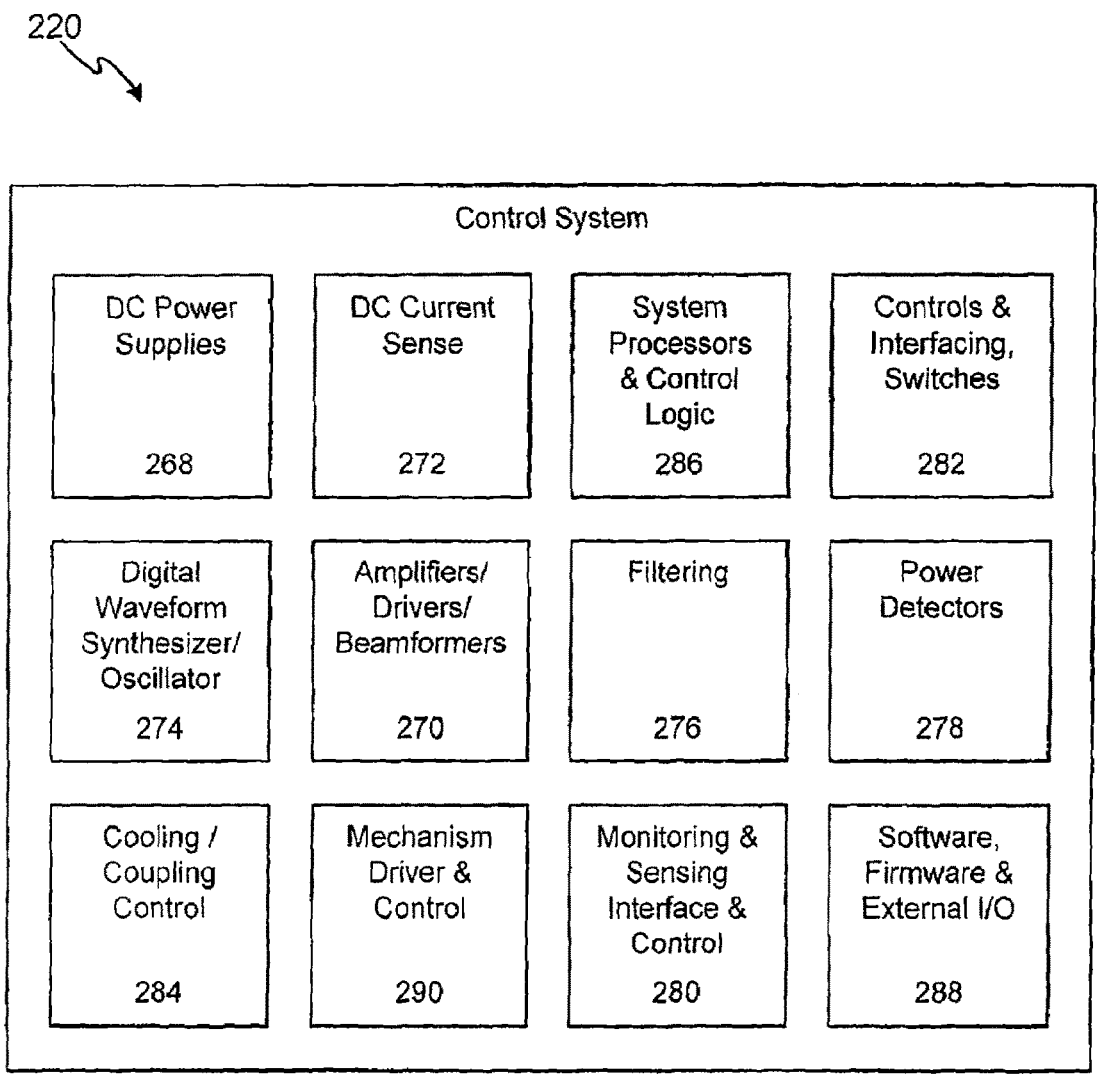
Figure 24C:
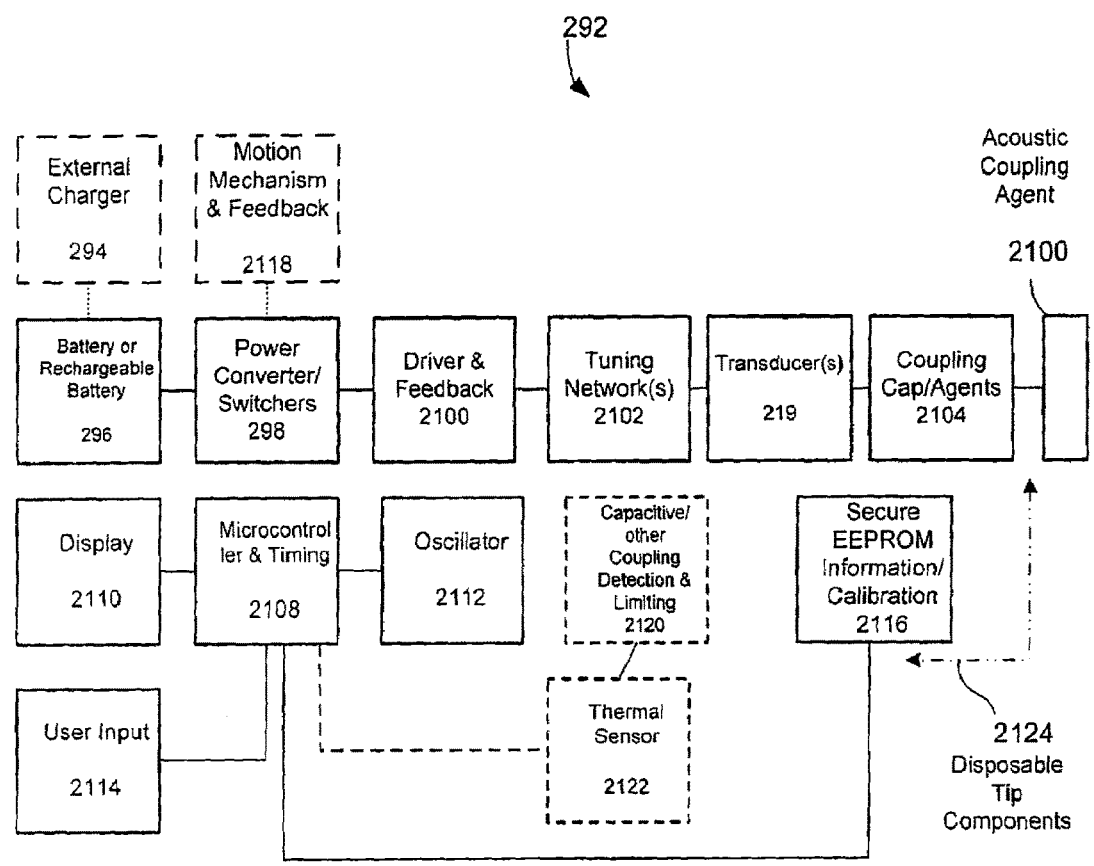

Turning now to FIGS. 24A-24C, an probe 218 may be suitably controlled and operated in various manners by control system 220 which also relays processes images obtained by transducer 219 to display 222. Control system 220 may be capable of coordination and control of the entire treatment process to achieve the desired therapeutic effect on tissue 21 within ROI 212. In an embodiment, control system 220 may comprise power source components 260, sensing and monitoring components 262, cooling and coupling controls 264, and/or processing and control logic components 266. Control system 220 may be configured and optimized in a variety of ways with more or less subsystems and components to implement the therapeutic system for controlled targeting of the desired tissue 21, and the embodiments in FIGS. 24A-24C are merely for illustration purposes.

For example, for power sourcing components 260, control system 220 may comprise one or more direct current (DC) power supplies 268 capable of providing electrical energy for entire control system 220, including power required by a transducer electronic amplifier/driver 270. A DC current sense device 272 may also be provided to confirm the level of power entering amplifiers/drivers 270 for safety and monitoring purposes, among others.

In an embodiment, amplifiers/drivers 270 may comprise multi-channel or single channel power amplifiers and/or drivers. In an embodiment for transducer array configurations, amplifiers/drivers 270 may also be configured with a beamformer to facilitate array focusing. An beamformer may be electrically excited by an oscillator/digitally controlled waveform synthesizer 274 with related switching logic.

Power sourcing components 260 may also comprise various filtering configurations 276. For example, switchable harmonic filters and/or matching may be used at the output of amplifier/driver 270 to increase the drive efficiency and effectiveness. Power detection components 278 may also be included to confirm appropriate operation and calibration. For example, electric power and other energy detection components 278 may be used to monitor the amount of power entering probe 218.

Various sensing and monitoring components 262 may also be suitably implemented within control system 220. For example, in an embodiment, monitoring, sensing, and interface control components 280 may be capable of operating with various motion detection systems implemented within probe 218, to receive and process information such as acoustic or other spatial and temporal information from ROI 212. Sensing and monitoring components 262 may also comprise various controls, interfacing, and switches 282 and/or power detectors 278. Such sensing and monitoring components 262 may facilitate open-loop and/or closed-loop feedback systems within treatment system 214.

In an embodiment, sensing and monitoring components 262 may further comprise a sensor that may be connected to an audio or visual alarm system to prevent overuse of system 214. In this embodiment, the sensor may be capable of sensing the amount of energy transferred to the skin, and/or the time that system 214 has been actively emitting energy. When a certain time or temperature threshold has been reached, the alarm may sound an audible alarm, or cause a visual indicator to activate to alert the user that a threshold has been reached. This may prevent overuse of the system 214. In an embodiment, the sensor may be operatively connected to control system 220 and force control system 220, to stop emitting ultrasound energy 221 from transducer 219.

In an embodiment, a cooling/coupling control system 284 may be provided, and may be capable of removing waste heat from probe 218. Furthermore the cooling/coupling control system 284 may be capable of providing a controlled temperature at the superficial tissue interface and deeper into tissue, and/or provide acoustic coupling from probe 218 to ROI 212. Such cooling/coupling control systems 284 can also be capable of operating in both open-loop and/or closed-loop feedback arrangements with various coupling and feedback components.

Additionally, an control system 220 may further comprise a system processor and various digital control logic 286, such as one or more of microcontrollers, microprocessors, field-programmable gate arrays, computer boards, and associated components, including firmware and control software 288, which may be capable of interfacing with user controls and interfacing circuits as well as input/output circuits and systems for communications, displays, interfacing, storage, documentation, and other useful functions. System software 288 may be capable of controlling all initialization, timing, level setting, monitoring, safety monitoring, and all other system functions required to accomplish user-defined treatment objectives. Further, various control switches 290 may also be suitably configured to control operation.

With reference to FIG. 24C, an transducer 219 may be controlled and operated in various manners by a hand-held format control system 292. An external battery charger 294 can be used with rechargeable-type batteries 296 or the batteries can be single-use disposable types, such as AA-sized cells. Power converters 298 produce voltages suitable for powering a driver/feedback circuit 2100 with tuning network 2102 driving transducer 219 coupled to the patient via one or more acoustic coupling caps 2104. The cap 2104 can be composed of at least one of a solid media, semi-solid e.g. gelatinous media, and/or liquid media equivalent to an acoustic coupling agent (contained within a housing). The cap 2104 is coupled to the patient with an acoustic coupling agent 2106. In addition, a microcontroller and timing circuits 2108 with associated software and algorithms provide control and user interfacing via a display 2110, oscillator 2112, and other input/output controls 2114 such as switches and audio devices. A storage element 2116, such as an Electrically Erasable Programmable Read-Only Memory ("EEPROM"), secure EEPROM, tamper-proof EEPROM, or similar device holds calibration and usage data in an embodiment. A motion mechanism with feedback 118 can be suitably controlled to scan the transducer 219, if desirable, in a line or two-dimensional pattern and/or with variable depth. Other feedback controls comprises a capacitive, acoustic, or other coupling detection means and/or limiting controls 2120 and thermal sensor 2122. A combination of the secure EEPROM with at least one of coupling caps 2104, transducer 219, thermal sensor 2122, coupling detectors, or tuning network. Finally, an transducer can further comprise a disposable tip 2124 that can be disposed of after contacting a patient and replaced for sanitary reasons.

With reference again to FIGS. 19 and 22, an system 214 also may comprise display 222 capable of providing images of the ROI 212 in certain embodiments where ultrasound energy 221 may be emitted from transducer 219 in a manner suitable for imaging. Display 222 may be capable of enabling the user to facilitate localization of the treatment area and surrounding structures, e.g., identification of MLTC tissue. In these embodiments, the user can observe the effects to cartilage 23 in real-time as they occur. Therefore, the user can see the size of lesions within cartilage 23 created or the amount of cartilage 23 ablated and ensure that the correct amount of cartilage 23 is treated. In an alternative embodiment, the user may know the location of the specific MLTC tissue to be treated based at lest in part upon prior experience or education.

After localization, ultrasound energy 221 is delivered at a depth, distribution, timing, and energy level to achieve the desired therapeutic effect at ROI 12 to treat cartilage 23. Before, during and/or after delivery of ultrasound energy 221, monitoring of the treatment area and surrounding structures may be conducted to further plan and assess the results and/or providing feedback to control system 220, and to a system operator via display 222. In an embodiment, localization may be facilitated through ultrasound imaging that may be used to define the position of cartilage 23 in ROI 212.

For ultrasound energy 221 delivery, transducer 219 may be mechanically and/or electronically scanned to place treatment zones over an extended area in ROI 212. A treatment depth may be adjusted between a range of approximately 1 to 30 millimeters, and/or the greatest depth of subcutaneous tissue 22 or cartilage 23 being treated. Such delivery of energy may occur through imaging of the targeted cartilage 23, and then applying ultrasound energy 221 at known depths over an extended area without initial or ongoing imaging.

In certain embodiments, the delivery of ultrasound energy 221 to ROI 212 may be accomplished by utilizing specialized tools that are designed for a specific ROI 212. For example, if ROI 212 comprises cartilage 23 within the ear, a specialized tool that further comprises transducer 219 configured to fit within the patient's ear can be used. In this embodiment, the transducer 219 is attached to a probe, package, or another device configured to easily fit within a patient's ear canal and deliver ultrasound energy 221 to the ear. Similarly, other types of probes 219 or equipment can be utilized to deliver ultrasound energy 221 to a patient's nose of if cartilage 23 is located within or comprises the nose. In these embodiments, transducer 219 is configured to be inserted within the nasal orifice or the ear canal.

The ultrasound beam from transducer 219 may be spatially and/or temporally controlled at least in part by changing the spatial parameters of transducer 219, such as the placement, distance, treatment depth and transducer 219 structure, as well as by changing the temporal parameters of transducer 219, such as the frequency, drive amplitude, and timing, with such control handled via control system 220. Such spatial and temporal parameters may also be suitably monitored and/or utilized in open-loop and/or closed-loop feedback systems within ultrasound system 216.

Finally, it should be noted that while this disclosure is directed primarily to using ultrasound energy 221 to conduct procedures non-invasively, that the method and system for treating cartilage described above can also utilize energy such as ultrasound energy 221 to assist in invasive procedures. For example, ultrasound energy 221 can be used to ablate subcutaneous tissues 22 and tissues 21 during an invasive procedure. In this regard, ultrasound energy 221 can be used for invasive or minimally invasive procedures.

Present embodiments may be described herein in terms of various functional components and processing steps. It should be appreciated that such components and steps may be realized by any number of hardware components configured to perform the specified functions. For example, other embodiments may employ various medical treatment devices, visual imaging and display devices, input terminals and the like, which may carry out a variety of functions under the control of one or more control systems or other control devices. In addition, embodiments may be practiced in any number of medical contexts and that the embodiments relating to a system as described herein are merely indicative of applications for the disclosed subject matter. For example, the principles, features and methods discussed may be applied to any medical application. Further, various aspects of the present disclosure may be suitably applied to other applications, such as other medical or industrial applications.

In various embodiments, the different numbers of removable transducer modules can be configured for different or variable ultrasonic parameters. For example, in various non-limiting embodiments, the ultrasonic parameter can relate to transducer geometry, size, timing, spatial configuration, frequency, variations in spatial parameters, variations in temporal parameters, coagulation formation, controlled necrosis areas or zones, depth, width, absorption coefficient, refraction coefficient, tissue depths, and/or other tissue characteristics. In various embodiments, a variable ultrasonic parameter may be altered, or varied, in order to effect the formation of a lesion for the desired cosmetic approach. In various embodiments, a variable ultrasonic parameter may be altered, or varied, in order to effect the formation of a lesion for the desired clinical approach. By way of example, one variable ultrasonic parameter relates to aspects of configurations associated with tissue depth. For example, some non-limiting embodiments of removable transducer modules can be configured for a tissue depth of 1 mm, 1.5 mm, 2 mm, 3 mm, 4.5 mm, 6 mm, less than 3 mm, between 3 mm and 4.5 mm, more than more than 4.5 mm, more than 6 mm, and anywhere in the ranges of 0-3 mm, 0-4.5 mm, 0-25 mm, 0-100 mm, and any depths therein. In one embodiment, an ultrasonic system is provided with two transducer modules, in which the first module applies treatment at a depth of about 4.5 mm and the second module applies treatment at a depth of about 3 mm. An optional third module that applies treatment at a depth of about 1.5-2 mm is also provided. In some embodiments, a system and/or method comprises the use of removable transducers that treat at different depths is provided (e.g., a first depth in the range of about 1-4 mm below the skin surface and a second depth at about 4-7 mm below the skin surface). A combination of two or more treatment modules is particularly advantageous because it permits treatment of a patient at varied tissue depths, thus providing synergistic results and maximizing the clinical results of a single treatment session. For example, treatment at multiple depths under a single surface region permits a larger overall volume of tissue treatment, which results in enhanced collagen formation and tightening. Additionally, treatment at different depths affects different types of tissue, thereby producing different clinical effects that together provide an enhanced overall cosmetic result. For example, superficial treatment may reduce the visibility of wrinkles and deeper treatment may induce formation of more collagen growth. In some embodiments, treatment of different depths is used to treat different layers of tissue, e.g., epidermal tissue, the superficial dermal tissue, the mid-dermal tissue, and the deep dermal tissue. In another embodiment, treatment at different depths treats different cell types (e.g., dermal cells, fat cells). The combined treatment of different cell types, tissue types or layers, in, for example, a single therapeutic session, are advantageous in several embodiments.

Although treatment of a subject at different depths in one session may be advantageous in some embodiments, sequential treatment over time may be beneficial in other embodiments. For example, a subject may be treated under the same surface region at one depth in week 1, a second depth in week 2, etc. The new collagen produced by the first treatment may be more sensitive to subsequent treatments, which may be desired for some indications. Alternatively, multiple depth treatment under the same surface region in a single session may be advantageous because treatment at one depth may synergistically enhance or supplement treatment at another depth (due to, for example, enhanced blood flow, stimulation of growth factors, hormonal stimulation, etc.).

In several embodiments, different transducer modules provide treatment at different depths. In several embodiments, a system comprising different transducers, each having a different depth, is particularly advantageous because it reduces the risk that a user will inadvertently select an incorrect depth. In one embodiment, a single transducer module can be adjusted or controlled for varied depths. Safety features to minimize the risk that an incorrect depth will be selected can be used in conjunction with the single module system.

In several embodiments, a method of treating the lower face and neck area (e.g., the submental area) is provided. In several embodiments, a method of treating (e.g., softening) mentolabial folds is provided. In other embodiments, a method of blepharoplasty and/or treating the eye region is provided. Upper lid laxity improvement and periorbital lines and texture improvement will be achieved by several embodiments by treating at variable depths. In one embodiment, a subject is treated with about 40-50 lines at depths of 4.5 and 3 mm. The subject is optionally treated with about 40-50 lines at a depth of about 1.5-2 mm. The subject is optionally treated with about 40-50 lines at a depth of about 6 mm. By treating at varied depths in a single treatment session, optimal clinical effects (e.g., softening, tightening) can be achieved.

In several embodiments, the treatment methods described herein are non-invasive cosmetic procedures. In some embodiments, the methods can be used in conjunction with invasive procedures, such as surgical facelifts or liposuction, where skin tightening is desired. In several embodiments, the systems and methods described herein do not cavitate or produce shock waves. In one embodiment, treatment destroys fat cells, while leaving other types of tissue intact. In some embodiments, cooling is not necessary and not used. In some embodiments, cell necrosis is promoted (rather than reduced) via ablation. In some embodiments, treatment does not irritate or scar a dermis layer, but instead affects tissue subdermally. In several embodiments, the transducer has a single emitter. In other embodiments, a plurality of emitters is used. In several embodiments, treatment is performed without puncturing the skin (e.g., with needles) and without the need to suction, pinch or vacuum tissue. In other embodiments, suctioning, pinching or vacuuming is performed. In several embodiments, the lesions that are formed do not overlap. In several embodiments, the treatment employs a pulse duration of 10-60 milliseconds (e.g., about 20 milliseconds) and emits between about 1,000-5,000 W/cm$^2$ (e.g., 2,500 W/cm$^2$). In several embodiments, the energy flux is about 1.5-5.0 J/cm$^2$. In several embodiments, efficacy is produced using 20-500 lines of treatment (e.g., 100-250 lines). In one embodiment, each line takes about 0.5 to 2 seconds to deliver. In one embodiment, each line contains multiple individual lesions which may or may not overlap.

In one embodiment, an transducer module is configured with a treatment frequency of approximately 4 MHz, a treatment depth of approximately 4.5 mm and an imaging depth range of roughly 0-8 mm. In various embodiments, the treatment frequencies can be in the range of 4-5 MHz, 4.2-4.9 MHz, 4.3-4.7 MHz, 4.3 MHz, 4.7 MHz, or other frequencies. In various embodiments, the treatment depth can be in the range of approximately 4-5 mm, 4.3 mm-4.7 mm, and/or 4.4 mm-4.6 mm. In one embodiment, an emitter-receiver module 200 is configured with a treatment frequency of approximately 7 MHz, a treatment depth of approximately 3.0 mm and an imaging depth range of roughly 0-8 mm. In various embodiments, the treatment frequencies can be in the range of 7-8 MHz, 7.2-7.8 MHz, 7.3-7.7 MHz, 7.3 MHz, 477 MHz, 7.5 MHz, or other frequencies. In various embodiments, the treatment depth can be in the range of approximately 4-5 mm, 4.3 mm-4.7 mm, and/or 4.4 mm-4.6 mm. In one embodiment, transducer module is configured with a treatment frequency of approximately 7 MHz, a treatment depth of approximately 4.5 mm and an imaging depth range of roughly 0-8 mm. In various embodiments, the treatment frequencies can be in the range of 7-8 MHz, 7.2-7.8 MHz, 7.3-7.7 MHz, 7.3 MHz, 477 MHz, 7.5 MHz, or other frequencies. In various embodiments, the treatment depth can be in the range of approximately 4-5 mm, 4.3 mm-4.7 mm, and/or 4.4 mm-4.6 mm.

Various embodiments of the system can comprise a radio frequency (hereinafter "RF") driver circuit which can deliver and/or monitor power going to the transducer. In one embodiment, a therapy subsystem can control an acoustic power of the transducer. In one embodiment, the acoustic power can be from a range of 1 watt (hereinafter "W") to about 100 W in a frequency range from about 1 MHz to about 10 MHz, or from about 10 W to about 50 W at a frequency range from about 3 MHz to about 8 MHz. In one embodiment, the acoustic power and frequencies are about 40 W at about 4.3 MHz and about 30 W at about 7.5 MHz. An acoustic energy produced by this acoustic power can be between about 0.01 joule (hereinafter "J") to about 10 J or about 2 J to about 5 J. In one embodiment, the acoustic energy is in a range less than about 3 J. In various embodiments, the acoustic energy is approximately 0.2 J-2.0 J, 0.2 J, 0.4 J, 1.2 J, 2.0 J or other values. In one embodiment, the amount of energy deliverable is adjustable.

In various embodiments the system can control a time on for the transducer. In one embodiment, the time on can be from about 1 millisecond (hereinafter "ms") to about 100 ms or about 10 ms to about 50 ms. In one embodiment, time on periods can be about 30 ms for a 4.3 MHz emission and about 30 ms for a 7.5 MHz emission.

Embodiments of the present invention may be described herein in terms of various functional components and processing steps. It should be appreciated that such components and steps may be realized by any number of hardware components configured to perform the specified functions. For example, embodiments of the present invention may employ various medical treatment devices, visual imaging and display devices, input terminals and the like, which may carry out a variety of functions under the control of one or more control systems or other control devices. In addition, embodiments of the present invention may be practiced in any number of medical contexts and that some embodiments relating to a method and system for noninvasive face lift and deep tissue tightening as described herein are merely indicative of some applications for the invention. For example, the principles, features and methods discussed may be applied to any tissue, such as in one embodiment, a SMAS-like muscular fascia, such as platysma, temporal fascia, and/or occipital fascia, or any other medical application.

Further, various aspects of embodiments of the present invention may be suitably applied to other applications. Some embodiments of the system and method of the present invention may also be used for controlled thermal injury of various tissues and/or noninvasive facelifts and deep tissue tightening. Certain embodiments of systems and methods are disclosed in U.S. patent application Ser. No. 12/028,636 filed Feb. 8, 2008 to which priority is claimed and which is incorporated herein by reference in its entirety, along with each of applications to which it claims priority. Certain embodiments of systems and methods for controlled thermal injury to various tissues are disclosed in U.S. patent application Ser. No. 11/163,148 filed on Oct. 5, 2005 to which priority is claimed and which is incorporated herein by reference in its entirety as well as the provisional application to which that application claims priority to (U.S. Provisional Application No. 60/616,754 filed on Oct. 6, 2004). Certain embodiments of systems and methods for non-invasive facelift and deep tissue tightening are disclosed in U.S. patent application Ser. No. 11/163,151 filed on Oct. 6, 2005, to which priority is claimed and which is incorporated herein by reference in its entirety as well as the provisional application to which that application claims priority to (U.S. Provisional Application No. 60/616,755 filed on Oct. 6, 2004).

In accordance with some embodiments of the present invention, a method and system for noninvasive face lifts and deep tissue tightening are provided. For example, in accordance with an embodiment, with reference to FIG. 25, a treatment system 2100 (or otherwise referred to as a cosmetic treatment system or CTS) configured to treat a region of interest 2106 (or otherwise referred to as a treatment zone) comprises a control system 2102 (or otherwise referred to as a control module or control unit), an imaging/therapy probe with acoustic coupling 2104 (or otherwise referred to as a probe, probe system, hand wand, emitter/receiver module, removable transducer module), and a display system 2108 (or otherwise referred to as display or interactive graphical display). Control system 2102 and display system 2108 can comprise various configurations for controlling probe 2102 and overall system 2100 functionality, such as, for example, a microprocessor with software and a plurality of input/output devices, system and devices for controlling electronic and/or mechanical scanning and/or multiplexing of transducers, a system for power delivery, systems for monitoring, systems for sensing the spatial position of the probe and/or transducers, and/or systems for handling user input and recording treatment results, among others. Imaging/therapy probe 2104 can comprise various probe and/or transducer configurations. For example, probe 2104 can be configured for a combined dual-mode imaging/therapy transducer, coupled or co-housed imaging/therapy transducers, or simply a separate therapy probe and an imaging probe.

In accordance with an embodiment, treatment system 2100 is configured for treating tissue above, below and/or in the SMAS region by first, imaging of region of interest 2106 for localization of the treatment area and surrounding structures, second, delivery of ultrasound energy at a depth, distribution, timing, and energy level to achieve the desired therapeutic effect, and third to monitor the treatment area before, during, and after therapy to plan and assess the results and/or provide feedback. According to another embodiment of the present invention, treatment system 2100 is configured for controlled thermal injury of human superficial tissue based on treatment system 2100's ability to controllably create thermal lesions of conformally variable shape, size, and depth through precise spatial and temporal control of acoustic energy deposition.

As to the treatment of the SMAS region (or SMAS 507), connective tissue can be permanently tightened by thermal treatment to temperatures about 60 degrees Celsius or higher. Upon ablating, collagen fibers shrink immediately by approximately 30% of their length. The shrunken fibers can produce tightening of the tissue, wherein the shrinkage should occur along the dominant direction of the collagen fibers. Throughout the body, collagen fibers are laid down in connective tissues along the lines of chronic stress (tension). On the aged face, neck and/or body, the collagen fibers of the SMAS region are predominantly oriented along the lines of gravitational tension. Shrinkage of these fibers results in tightening of the SMAS in the direction desired for correction of laxity and sagging due to aging. The treatment comprises the ablation of specific regions of the SMAS region and similar suspensory connective tissues.

In addition, the SMAS region varies in depth and thickness at different locations, e.g., between 0.5 mm to 5 mm or more. On the face and other parts of the body, important structures such as nerves, parotid gland, arteries and veins are present over, under or near the SMAS region. Tightening of the SMAS in certain locations, such as the preauricular region associated with sagging of the cheek to create jowls, the frontal region associated with sagging brows, mandibular region associated with sagging neck, can be conducted. Treating through localized heating of regions of the SMAS or other suspensory subcutaneous connective tissue structures to temperatures of about 60-90° C., without significant damage to overlying or distal/underlying tissue, i.e., proximal tissue, as well as the precise delivery of therapeutic energy to SMAS regions, and obtaining feedback from the region of interest before, during, and after treatment can be suitably accomplished through treatment system 2100.

To further illustrate an embodiments of a method and system 2200, with reference to FIGS. 26A-26F, imaging of a region of interest 2206, such as by imaging a region 2222 and displaying images 2224 of the region of interest 2206 on a display 2208, to facilitate localization of the treatment area and surrounding structures can initially be conducted. Next, delivery of ultrasound energy 2220 at a suitably depth, distribution, timing, and energy level to achieve the desired therapeutic effect of thermal injury or ablation to treat SMAS region 2216 (or otherwise referred to as SMAS) can be suitably provided by probe 2204 (or otherwise referred to as module, or emitter-receiver module) through control by control system 2202. Monitoring of the treatment area and surrounding structures before, during, and after therapy, i.e., before, during, and after the delivery of ultrasound energy to SMAS region 2216, can be provided to plan and assess the results and/or provide feedback to control system 2202 and a system user.

Ultrasound imaging and providing of images 2224 can facilitate safe targeting of the SMAS layer 2216. For example, with reference to FIG. 26B, specific targeting for the delivery of energy can be better facilitated to avoid heating vital structures such as the facial nerve (motor nerve) 2234, parotid gland (which makes saliva) 2236, facial artery 2238, and trigeminal nerve (for sensory functions) 2232 among other regions. Further, use of imaging with targeted energy delivery to provide a limited and controlled depth of treatment can minimize the chance of damaging deep structures, such as for example, the facial nerve that lies below the parotid, which is typically 10 mm thick.

Figure 26A:
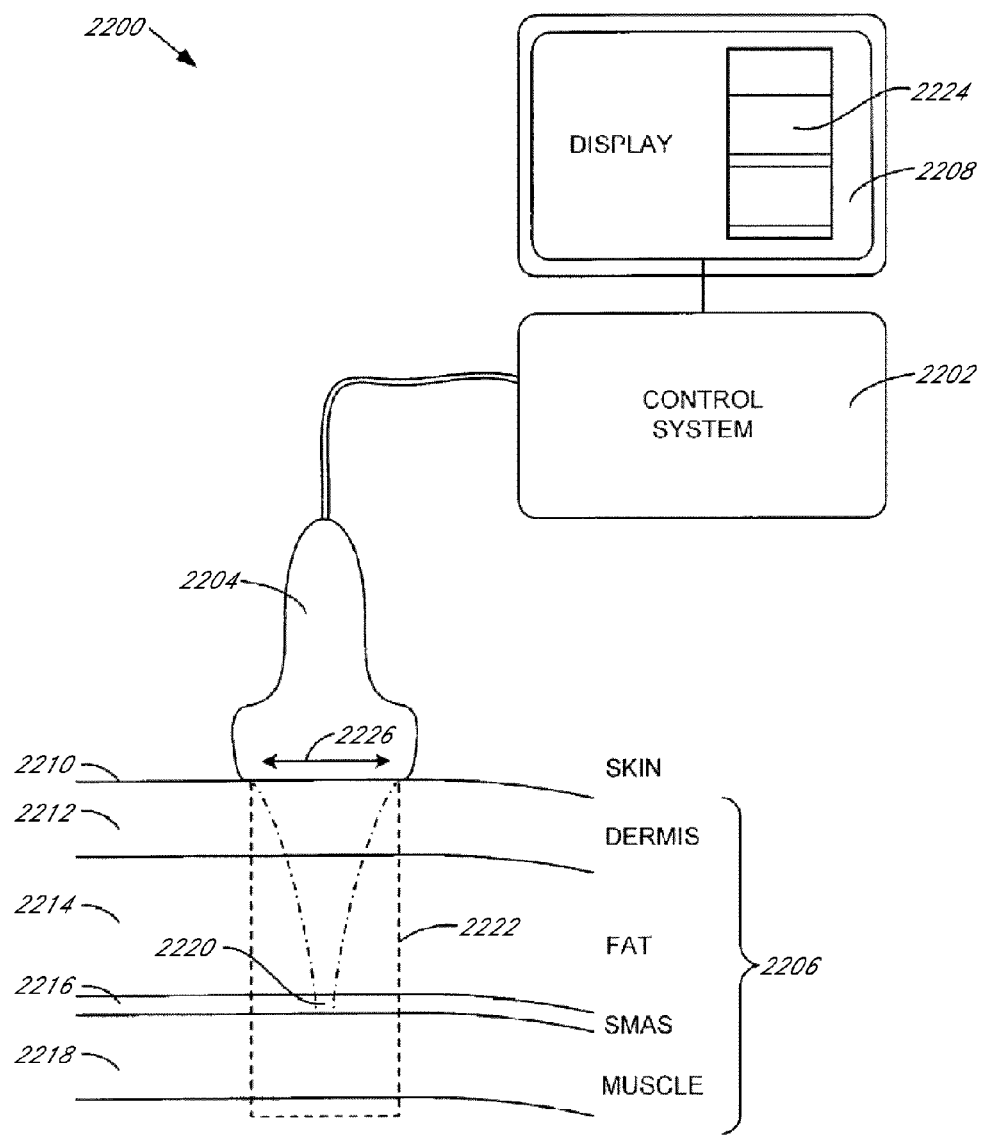
FIGS. 26A-26F illustrates schematic diagrams of an ultrasound imaging/therapy and monitoring system for treating the SMAS layer in accordance with various embodiments of the present invention.
Figure 26B:
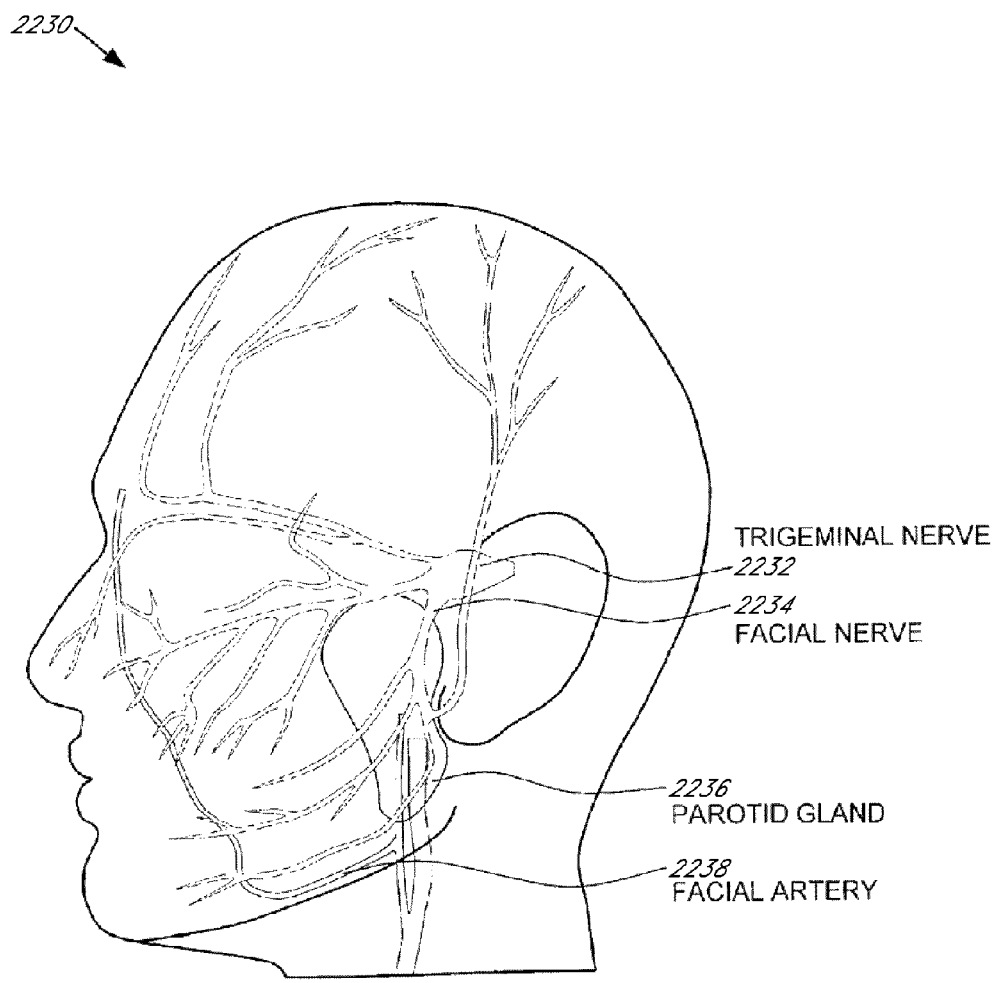
Figure 26C:
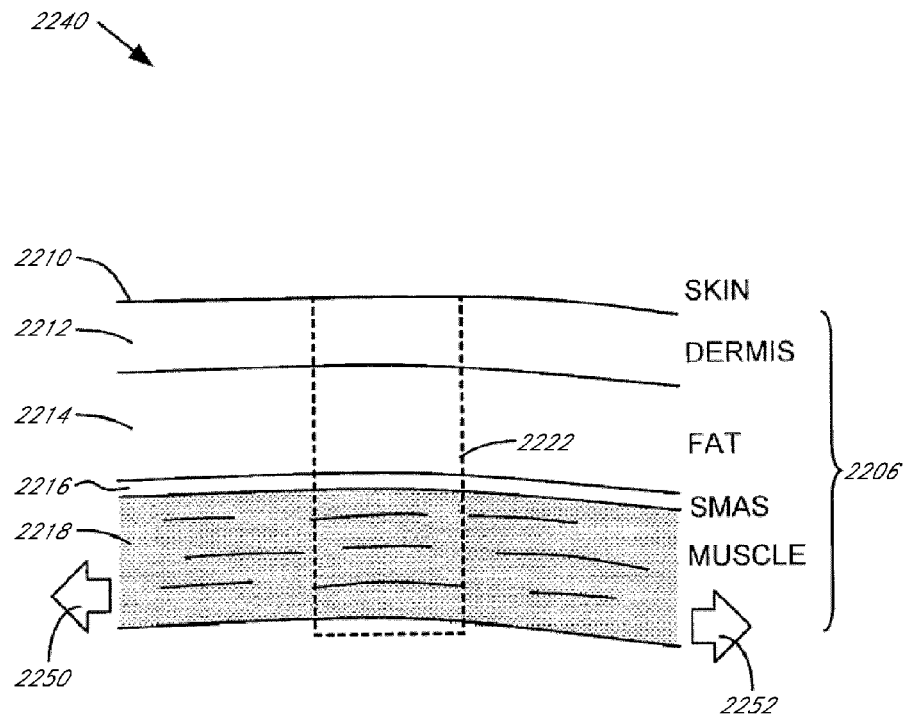

In accordance with an embodiment, with reference to FIG. 26C, ultrasound imaging of region 2222 of the region of interest 2206 can also be used to delineate SMAS layer 2216 as the superficial, echo-dense layer overlying facial muscles 2218. Such muscles can be seen via imaging region 2222 by moving muscles 2218, for example by extensional flexing of muscle layer 2218 generally towards directions 2250 and 2252. Such imaging of region 2222 may be further enhanced via signal and image processing. Once SMAS layer 2216 is localized and/or identified, SMAS layer 2216 is ready for treatment.

The delivery of ultrasound energy 2220 at a suitably depth, distribution, timing, and energy level is provided by probe 2204 through controlled operation by control system 2202 to achieve the desired therapeutic effect of thermal injury to treat SMAS region 2216. During operation, probe 2204 can also be mechanically and/or electronically scanned within tissue surface region 2226 to treat an extended area. In addition, spatial control of a treatment depth 2220 (or otherwise referred to as depth) can be suitably adjusted in various ranges, such as between a wide range of approximately 0 to 15 mm, suitably fixed to a few discrete depths, with an adjustment limited to a fine range, e.g. approximately between 3 mm to 9 mm, and/or dynamically adjusted during treatment, to treat SMAS layer 2216 that typically lies at a depth between approximately 5 mm to 7 mm. Before, during, and after the delivery of ultrasound energy to SMAS region 2216, monitoring of the treatment area and surrounding structures can be provided to plan and assess the results and/or provide feedback to control system 2202 and a system user.

Figure 26D:
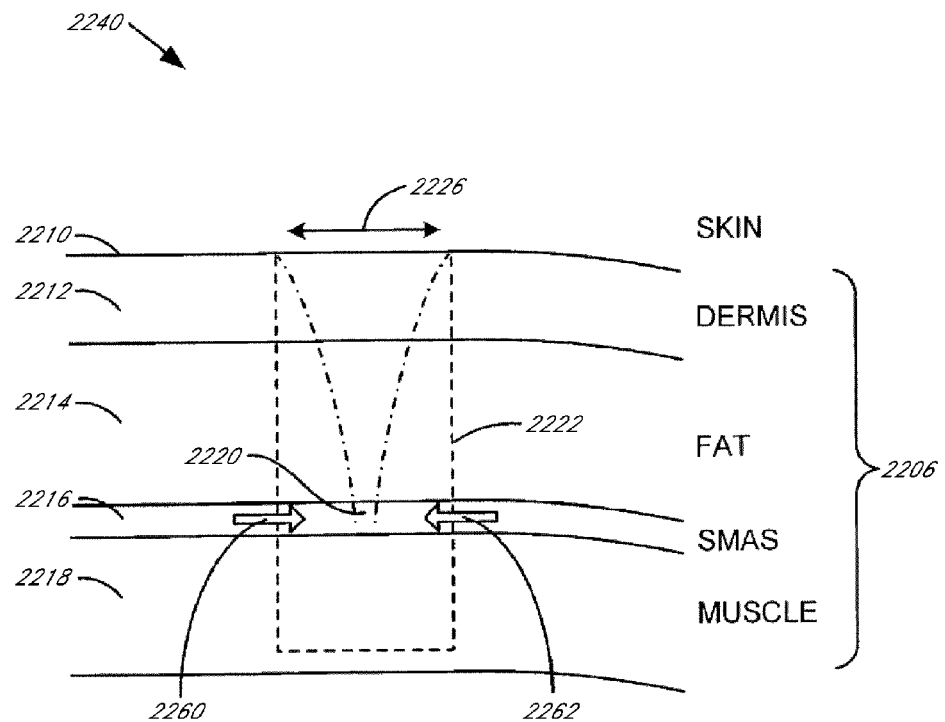

For example, in accordance with an embodiment, with additional reference to FIG. 26D, ultrasound imaging of region 2222 can be used to monitor treatment by watching the amount of shrinkage of SMAS layer 2216 in direction of areas 2260 and 2262, such as in real time or quasi-real time, during and after energy delivery to region 2220. The onset of substantially immediate shrinkage of SMAS layer 2216 is detectable by ultrasound imaging of region 2222 and may be further enhanced via image and signal processing. In one embodiment, the monitoring of such shrinkage can be advantageous because it can confirm the intended therapeutic goal of noninvasive lifting and tissue tightening; in addition, such monitoring may be used for system feedback. In addition to image monitoring, additional treatment parameters that can be suitably monitored in accordance with various other embodiments may include temperature, video, profilometry, strain imaging and/or gauges or any other suitable spatial, temporal and/or other tissue parameters, or combinations thereof.

Figure 26E:
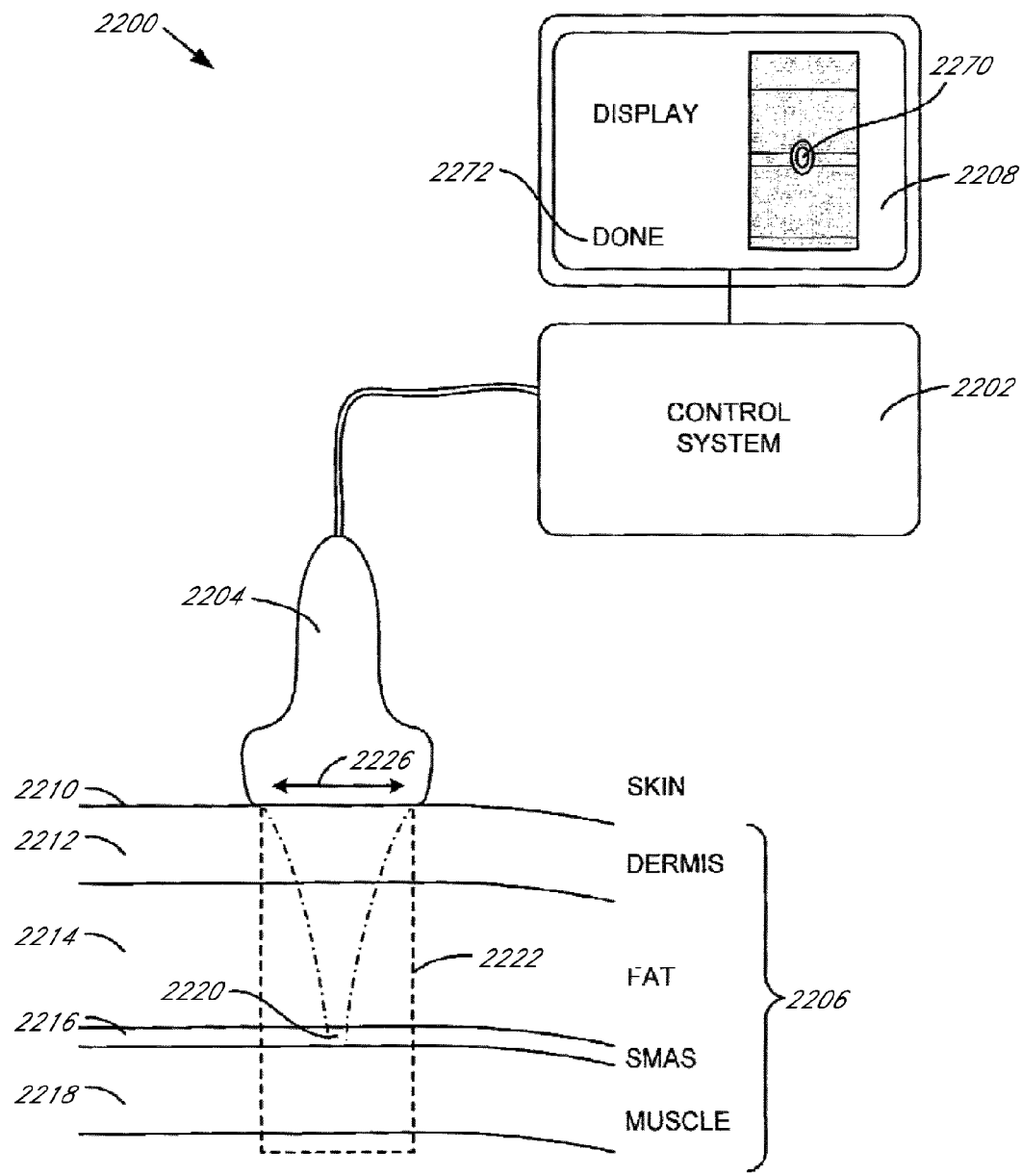

For example, in accordance with an embodiment of the present invention, with additional reference to FIG. 26E, an embodiment of a monitoring method and system 2200 may suitably monitor the temperature profile or other tissue parameters of the region of interest 2206, such as attenuation or speed of sound of treatment region 2222 and suitably adjust the spatial and/or temporal characteristics and energy levels of ultrasound therapy transducer probe 2204. The results of such monitoring techniques may be indicated on display 2208 in various manners, such as, for example, by way of one-, two-, or three-dimensional images of monitoring results 2270, or may comprise an indicator 2272, such as a success, fail and/or completed/done type of indication, or combinations thereof.

Figure 26F:
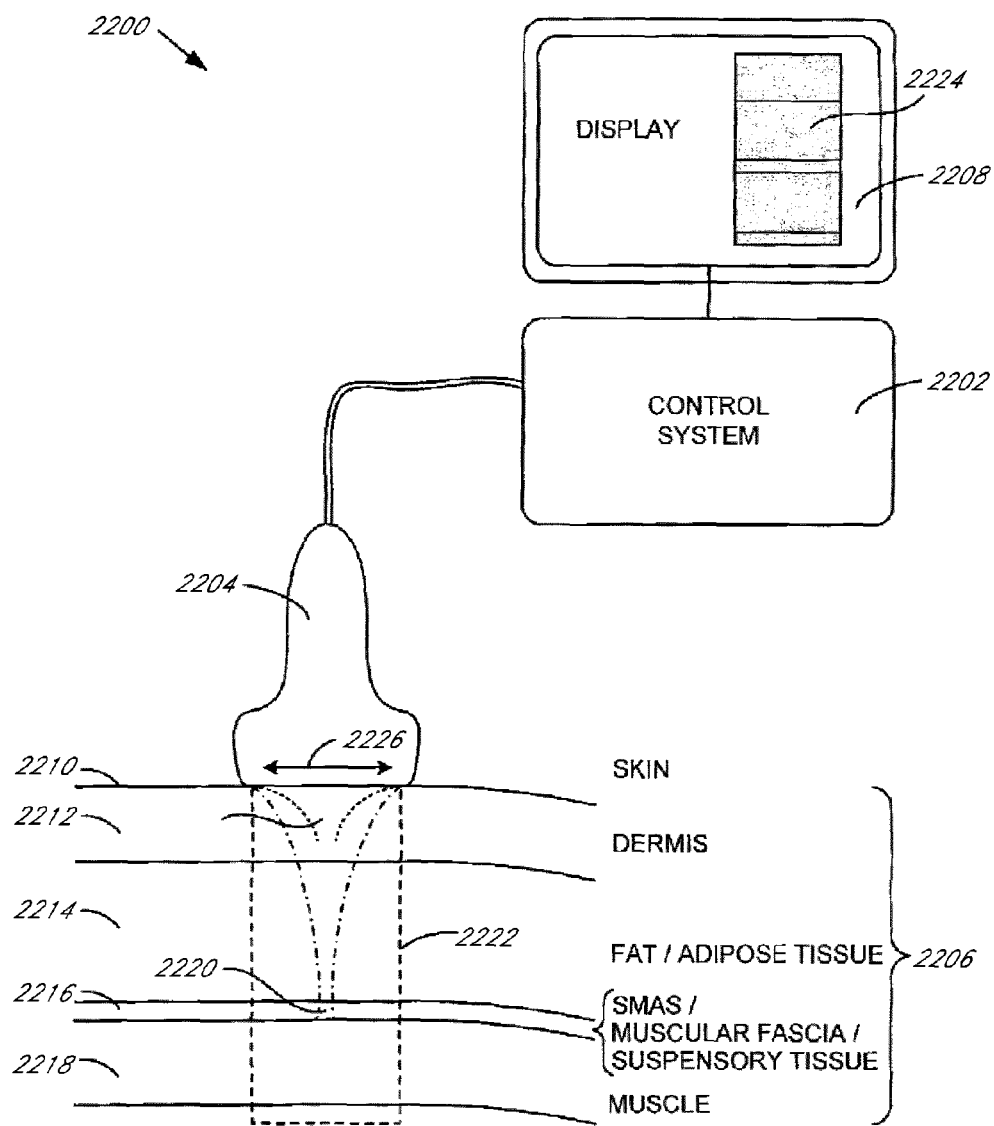

In accordance with another embodiment, with reference to FIG. 26F, the targeting of particular region 2220 within SMAS layer 2216 can be suitably be expanded within region of interest 2206 to include a combination of tissues, such as skin 2210, dermis 2212 2210, fat/adipose tissue 2214 2210, SMAS/muscular fascia/and/or other suspensory tissue 2216 2210, and muscle 2218 2210. Treatment of a combination of such tissues and/or fascia may be treated including at least one of SMAS layer 2216 or other layers of muscular fascia in combination with at least one of muscle tissue, adipose tissue, SMAS and/or other muscular fascia, skin, and dermis, can be suitably achieved by treatment system 2200. For example, treatment of SMAS layer 2216 may be performed in combination with treatment of dermis 2280 by suitable adjustment of the spatial and temporal parameters of probe 2204 within treatment system 2200.

Figure 25:
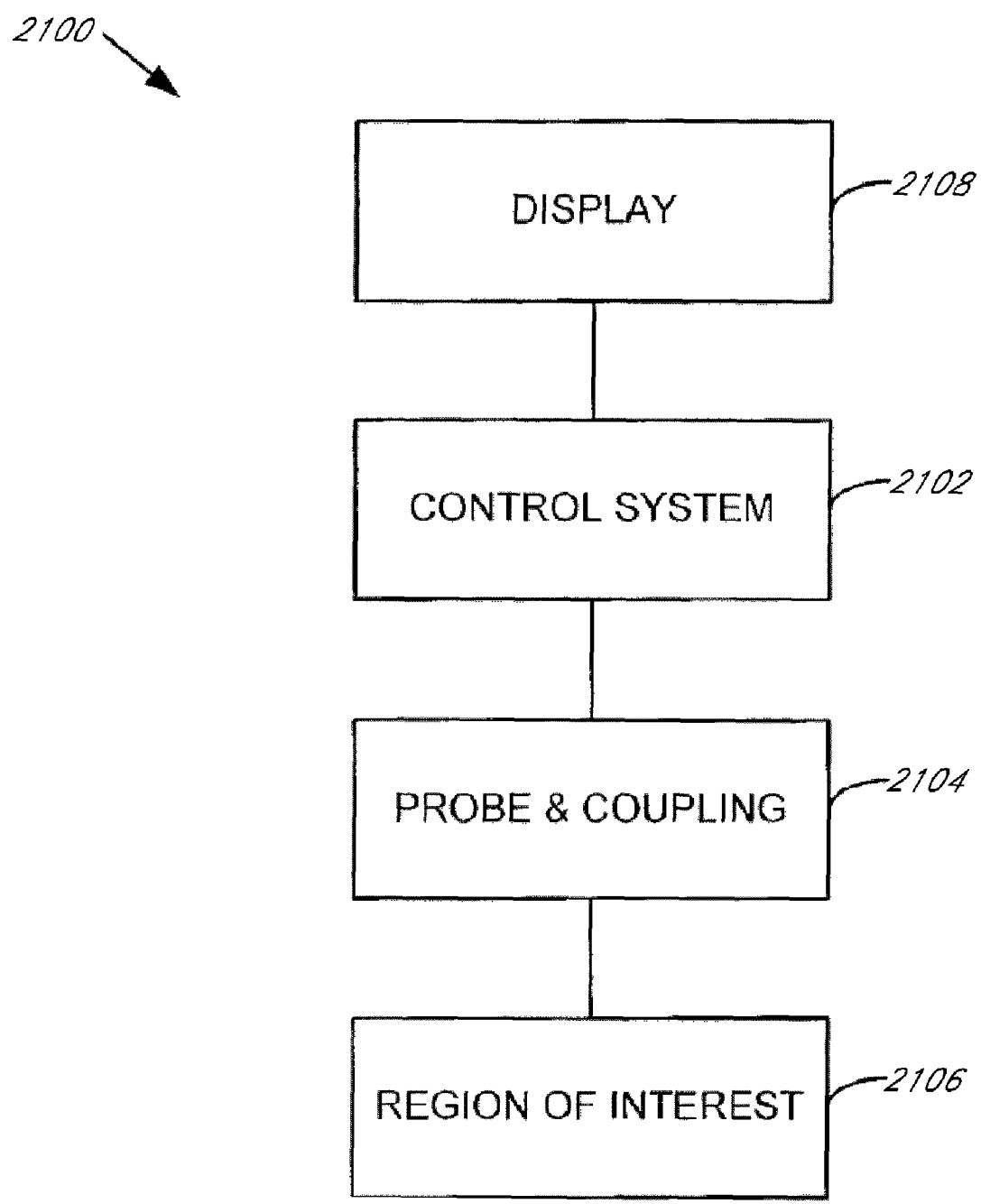
FIG. 25 illustrates a block diagram of a treatment system in accordance with an embodiment of the present invention.

In accordance with various aspects of the present invention, a therapeutic treatment method and system for controlled thermal injury of human superficial tissue to effectuate face lifts, deep tissue tightening, and other procedures is based on the ability to controllably create thermal lesions of conformally variable shape, size, and depth through precise spatial and temporal control of acoustic energy deposition. With reference to FIG. 25, in accordance with an embodiment, a therapeutic treatment system 2200 includes a control system 2102 and a probe system 2104 that can facilitate treatment planning, controlling and/or delivering of acoustic energy, and/or monitoring of treatment conditions to a region of interest 2106. Region-of-interest 2106 is configured within the human superficial tissue comprising from just below the tissue outer surface to approximately 30 mm or more in depth.

Therapeutic treatment system 2100 is configured with the ability to controllably produce conformal lesions of thermal injury in superficial human tissue within region of interest 2106 through precise spatial and temporal control of acoustic energy deposition, i.e., control of probe 2104 is confined within selected time and space parameters, with such control being independent of the tissue. In accordance with an embodiment, control system 2102 and probe system 2104 can be suitably configured for spatial control of the acoustic energy by controlling the manner of distribution of the acoustical energy. For example, spatial control may be realized through selection of the type of one or more transducer configurations insonifying region of interest 2106, selection of the placement and location of probe system 2104 for delivery of acoustical energy relative to region-of-interest 2106, e.g., probe system 2104 being configured for scanning over part or whole of region-of-interest 2106 to produce contiguous thermal injury having a particular orientation or otherwise change in distance from region-of-interest 2106, and/or control of other environment parameters, e.g., the temperature at the acoustic coupling interface can be controlled, and/or the coupling of probe 2104 to human tissue. In addition to the spatial control parameters, control system 2102 and probe system 2104 can also be configured for temporal control, such as through adjustment and optimization of drive amplitude levels, frequency/waveform selections, e.g., the types of pulses, bursts or continuous waveforms, and timing sequences and other energy drive characteristics to control thermal ablation of tissue. The spatial and/or temporal control can also be facilitated through open-loop and closed-loop feedback arrangements, such as through the monitoring of various spatial and temporal characteristics. As a result, control of acoustical energy within six degrees of freedom, e.g., spatially within the X, Y and Z domain, as well as the axis of rotation within the XY, YZ and XZ domains, can be suitably achieved to generate conformal lesions of variable shape, size and orientation.

Figure 38:
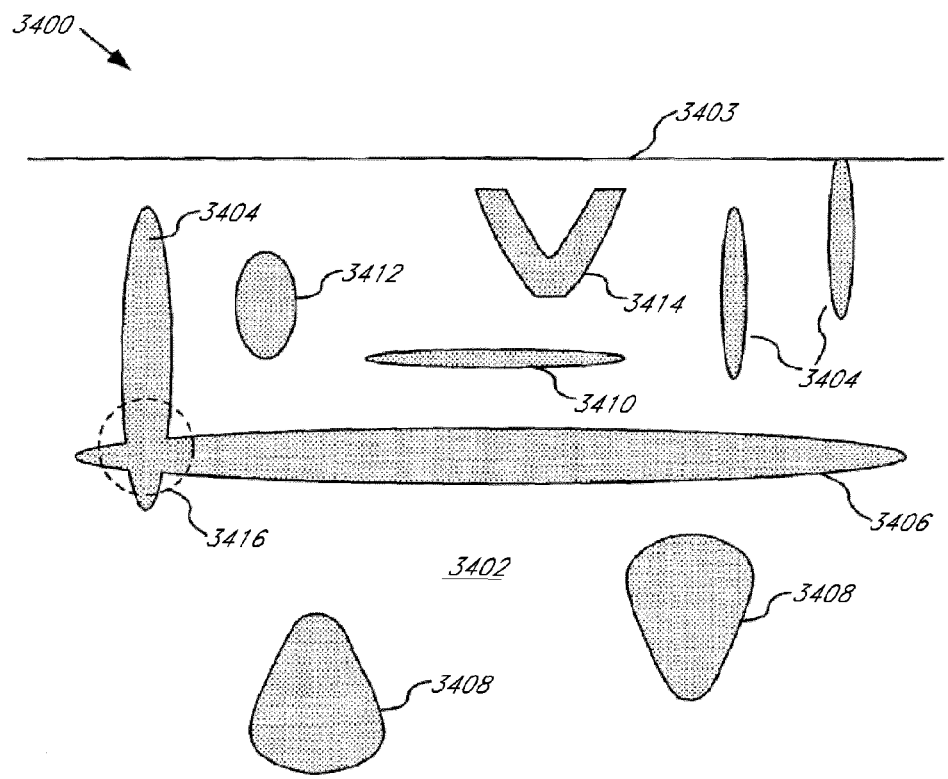
FIG. 38 illustrates a cross sectional diagram of a human superficial tissue region of interest including a plurality of lesions of controlled thermal injury in accordance with an embodiment of the present invention.

For example, through such spatial and/or temporal control, an embodiment of a treatment system 2100 can enable the regions of thermal injury to possess arbitrary shape and size and allow the tissue to be destroyed (ablated) in a controlled manner. With reference to FIG. 38, one or more thermal lesions may be created within a tissue region of interest 3400, with such thermal lesions having a narrow or wide lateral extent, long or short axial length, and/or deep or shallow placement, including up to a tissue outer surface 3403. For example, cigar shaped lesions may be produced in a vertical disposition 3404 and/or horizontal disposition 3406. In addition, raindrop-shaped lesions 3408, flat planar lesions 3410, round lesions 3412 and/or other v-shaped/ellipsoidal lesions 3414 may be formed, among others. For example, mushroom-shaped lesion 3420 may be provided, such as through initial generation of a an initial round or cigar-shaped lesion 3422, with continued application of ablative ultrasound resulting in thermal expansion to further generate a growing lesion 3424, such thermal expansion being continued until raindrop-shaped lesion 3420 is achieved. The plurality of shapes can also be configured in various sizes and orientations, e.g., lesions 3408 could be rotationally oriented clockwise or counterclockwise at any desired angle, or made larger or smaller as selected, all depending on spatial and/or temporal control. Moreover, separate islands of destruction, i.e., multiple lesions separated throughout the tissue region, may also be created over part of or the whole portion within tissue region-of-interest 3400. In addition, contiguous structures and/or overlapping structures 3416 may be provided from the controlled configuration of discrete lesions. For example, a series of one or more crossed-lesions 3418 can be generated along a tissue region to facilitate various types of treatment methods.

The specific configurations of controlled thermal injury are selected to achieve the desired tissue and therapeutic effect(s). For example, any tissue effect can be realized, including but not limited to thermal and non-thermal streaming, cavitational, hydrodynamic, ablative, hemostatic, diathermic, and/or resonance-induced tissue effects. Such effects can be suitably realized at treatment depths over a range of approximately 0-30000 μm within region of interest 2200 to provide a high degree of utility.

Figure 27A:
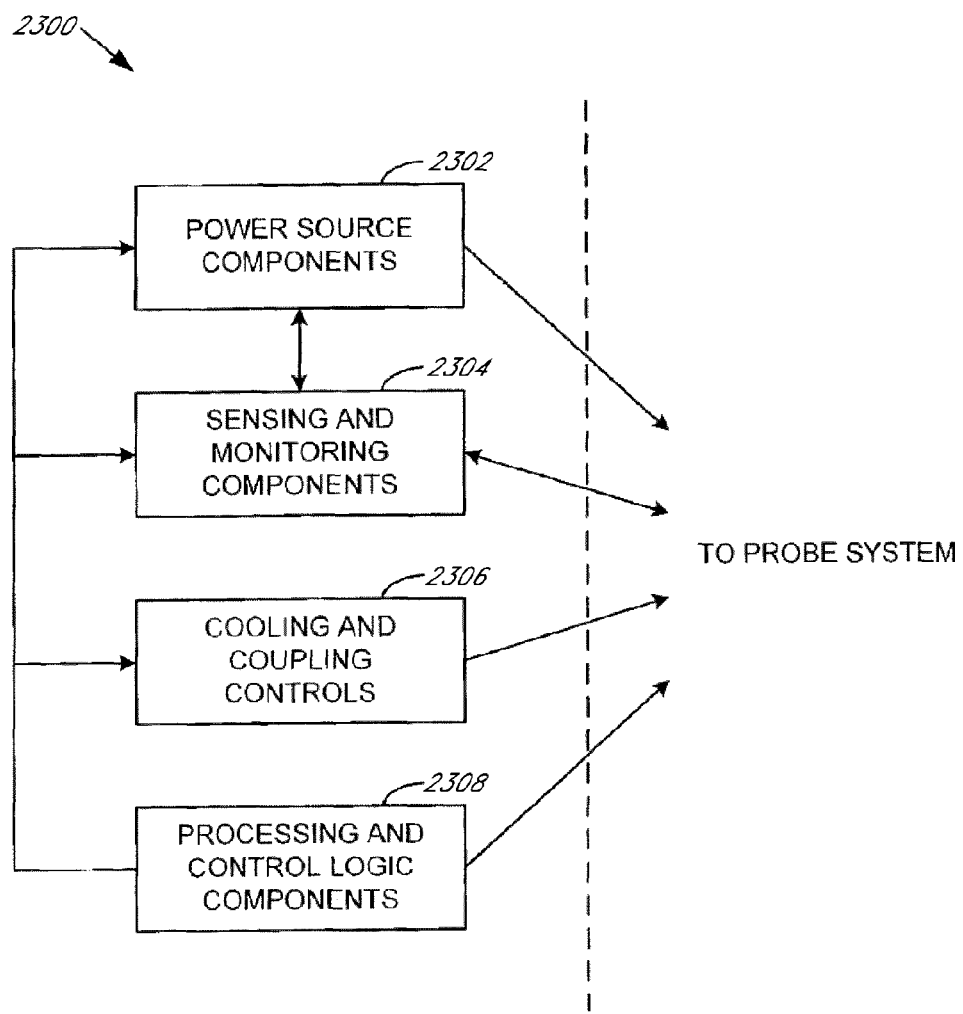
FIGS. 27A and 27B illustrate block diagrams of a control system in accordance with embodiments of the present invention.
Figure 27B:
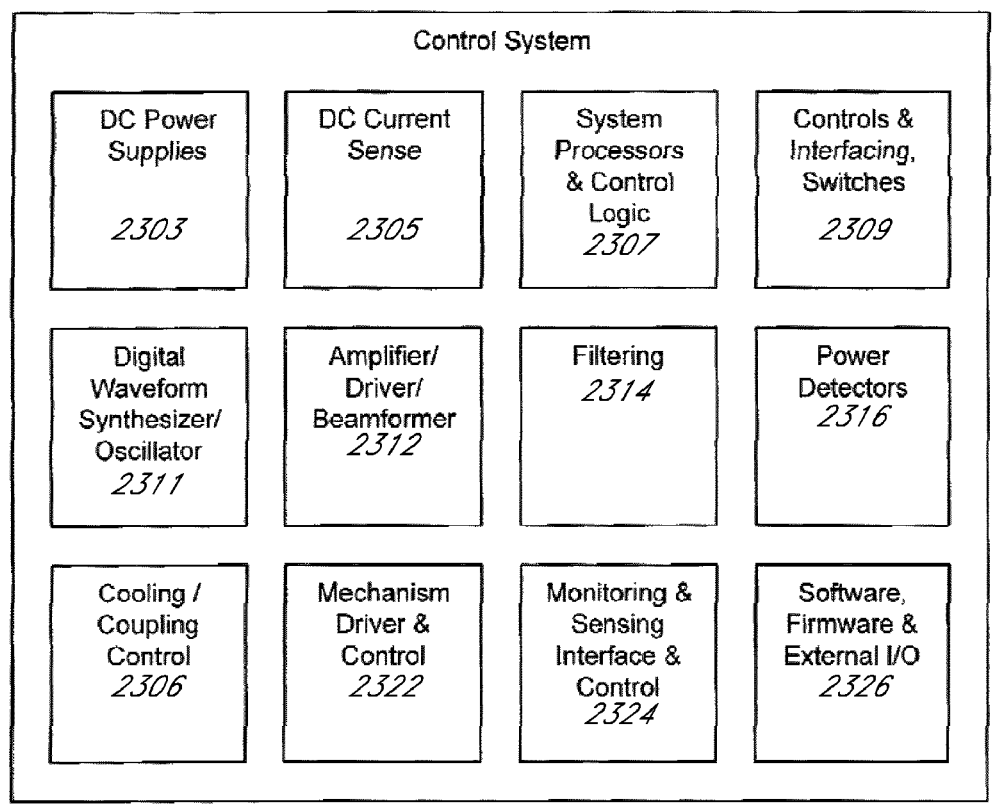

An embodiment of a control system 2202 and display system 2208 may be configured in various manners for controlling probe and system functionality. With reference again to FIGS. 27A and 27B, in accordance with embodiments, a control system 2300 can be configured for coordination and control of the entire therapeutic treatment process for noninvasive face lifts and deep tissue tightening. For example, control system 2300 can suitably comprise power source components 2302, sensing and monitoring components 2304, cooling and coupling controls 2306, and/or processing and control logic components 2308. Control system 2300 can be configured and optimized in a variety of ways with more or less subsystems and components to implement the therapeutic system for controlled thermal injury, and the embodiments in FIGS. 27A and 27B are merely for illustration purposes.

For example, for power sourcing components 2302, control system 2300 can comprise one or more direct current (DC) power supplies 2303 configured to provide electrical energy for entire control system 2300, including power required by a transducer electronic amplifier/driver 2312. A DC current sense device 2305 can also be provided to confirm the level of power going into amplifiers/drivers 2312 for safety and monitoring purposes.

Amplifiers/drivers 2312 can comprise multi-channel or single channel power amplifiers and/or drivers. In accordance with an embodiment for transducer array configurations, amplifiers/drivers 2312 can also be configured with a beamformer to facilitate array focusing. An embodiment of a beamformer can be electrically excited by an oscillator/digitally controlled waveform synthesizer 2310 with related switching logic.

The power sourcing components can also include various filtering configurations 2314. For example, switchable harmonic filters and/or matching may be used at the output of amplifier/driver 2312 to increase the drive efficiency and effectiveness. Power detection components 2316 may also be included to confirm appropriate operation and calibration. For example, electric power and other energy detection components 2316 may be used to monitor the amount of power going to an embodiment of a probe system.

Various sensing and monitoring components 2304 may also be suitably implemented within control system 2300. For example, in accordance with an embodiment, monitoring, sensing and interface control components 2324 may be configured to operate with various motion detection systems implemented within transducer probe 2204 to receive and process information such as acoustic or other spatial and temporal information from a region of interest. Sensing and monitoring components can also include various controls, interfacing and switches 2309 and/or power detectors 2316. Such sensing and monitoring components 2304 can facilitate open-loop and/or closed-loop feedback systems within treatment system 2200.

Still further, monitoring, sensing and interface control components 2324 may comprise imaging systems configured for one-dimensional, two-dimensional and/or three dimensional imaging functions. Such imaging systems can comprise any imaging modality based on at least one of photography and other visual optical methods, magnetic resonance imaging (MRI), computed tomography (CT), optical coherence tomography (OCT), electromagnetic, microwave, or radio frequency (RF) methods, positron emission tomography (PET), infrared, ultrasound, acoustic, or any other suitable method of visualization, localization, or monitoring of a region-of-interest 2106. Still further, various other tissue parameter monitoring components, such as temperature measuring devices and components, can be configured within monitoring, sensing and interface control components 2324, such monitoring devices comprising any modality now known or hereinafter devised.

Cooling/coupling control systems 2306 may be provided to remove waste heat from an embodiment of a probe 2204, provide a controlled temperature at the superficial tissue interface and deeper into tissue, and/or provide acoustic coupling from transducer probe 2204 to region-of-interest 2206. Such cooling/coupling control systems 2306 can also be configured to operate in both open-loop and/or closed-loop feedback arrangements with various coupling and feedback components.

Processing and control logic components 2308 can comprise various system processors and digital control logic 2307, such as one or more of microcontrollers, microprocessors, field-programmable gate arrays (FPGAs), computer boards, and associated components, including firmware and control software 2326, which interfaces to user controls and interfacing circuits as well as input/output circuits and systems for communications, displays, interfacing, storage, documentation, and other useful functions. System software and firmware 2326 controls all initialization, timing, level setting, monitoring, safety monitoring, and all other system functions required to accomplish user-defined treatment objectives. Further, various control switches 2308 can also be suitably configured to control operation.

An embodiment of a transducer probe 2204 can also be configured in various manners and comprise a number of reusable and/or disposable components and parts in various embodiments to facilitate its operation. For example, transducer probe 2204 can be configured within any type of transducer probe housing or arrangement for facilitating the coupling of transducer to a tissue interface, with such housing comprising various shapes, contours and configurations. Transducer probe 2204 can comprise any type of matching, such as for example, electric matching, which may be electrically switchable; multiplexer circuits and/or aperture/element selection circuits; and/or probe identification devices, to certify probe handle, electric matching, transducer usage history and calibration, such as one or more serial EEPROM (memories). Transducer probe 2204 may also comprise cables and connectors; motion mechanisms, motion sensors and encoders; thermal monitoring sensors; and/or user control and status related switches, and indicators such as LEDs. For example, a motion mechanism in probe 2204 may be used to controllably create multiple lesions, or sensing of probe motion itself may be used to controllably create multiple lesions and/or stop creation of lesions, e.g. for safety reasons if probe 2204 is suddenly jerked or is dropped. In addition, an external motion encoder arm may be used to hold the probe during use, whereby the spatial position and attitude of probe 2104 is sent to the control system to help controllably create lesions. Furthermore, other sensing functionality such as profilometers or other imaging modalities may be integrated into the probe in accordance with various embodiments. Moreover, the therapy contemplated herein can also be produced, for example, by transducers disclosed in U.S. application Ser. No. 10/944,499, filed on Sep. 16, 2004, entitled Method And System For Ultrasound Treatment With A Multi-Directional Transducer and U.S. application Ser. No. 10/944,500, filed on Sep. 16, 2004, and entitled System And Method For Variable Depth Ultrasound Treatment, both hereby incorporated by reference.

Figure 28A:
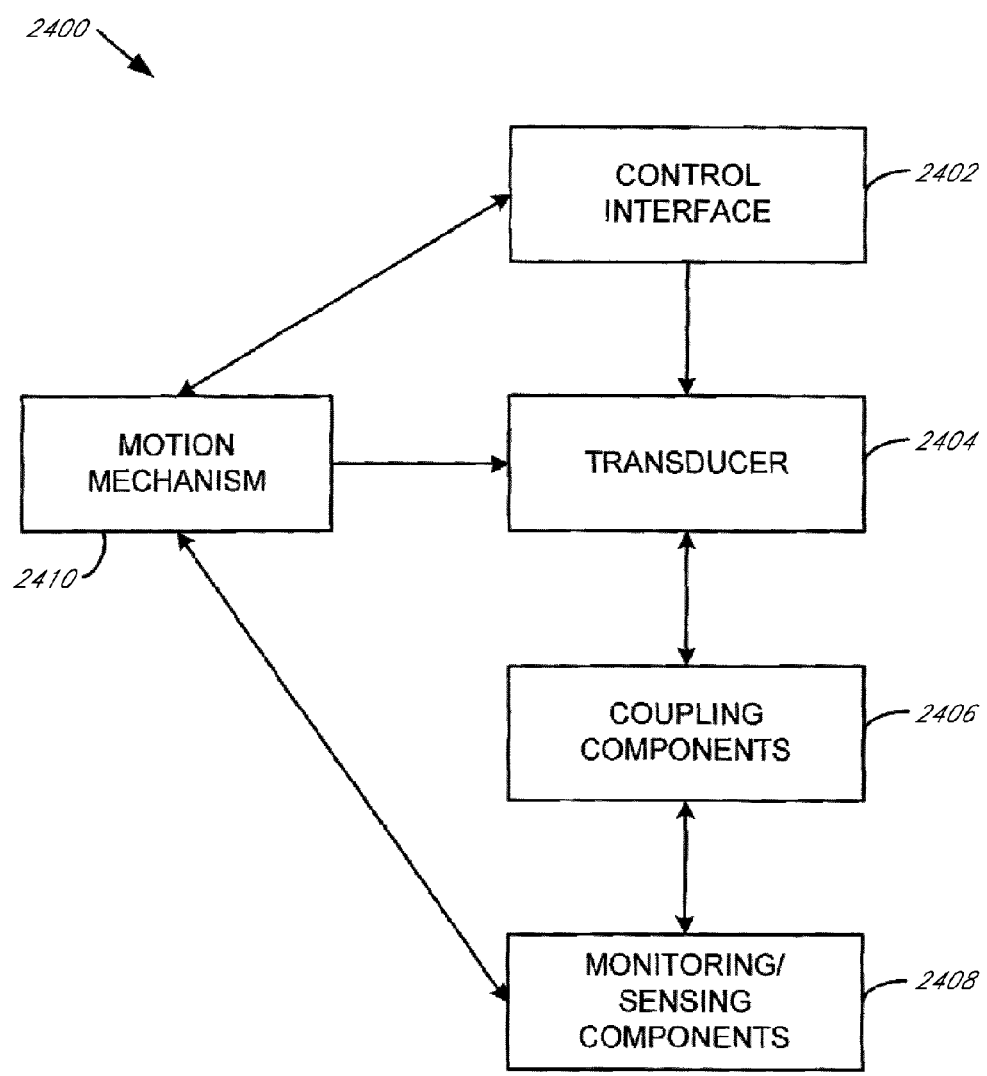
FIGS. 28A and 28B illustrate block diagrams of a probe system in accordance with embodiments of the present invention.
Figure 28B:
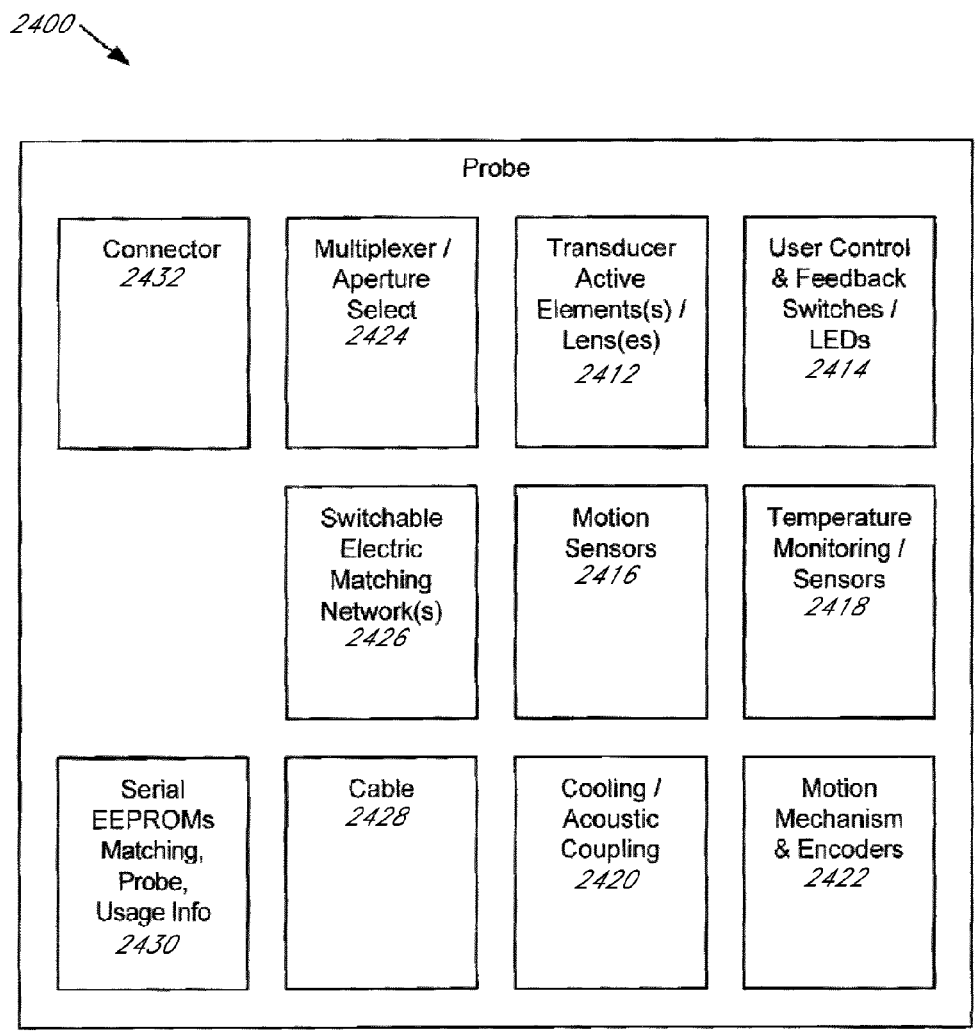

With reference to FIGS. 28A and 28B, in accordance with an embodiment, a transducer probe 2400 can comprise a control interface 2402, a transducer 2404, coupling components 2406, and monitoring/sensing components 2408, and/or motion mechanism 2410. However, transducer probe 2400 can be configured and optimized in a variety of ways with more or less parts and components to provide ultrasound energy for controlled thermal injury, and the embodiment in FIGS. 28A and 28B are merely for illustration purposes. Transducer 2404 can be any transducer configured to produce conformal lesions of thermal injury in superficial human tissue within a region of interest through precise spatial and temporal control of acoustic energy deposition.

Control interface 2402 is configured for interfacing with control system 2300 to facilitate control of transducer probe 2400. Control interface components 2402 can comprise multiplexer/aperture select 2424, switchable electric matching networks 2426, serial EEPROMs and/or other processing components and matching and probe usage information 2430 and interface connectors 2432.

Coupling components 2406 can comprise various devices to facilitate coupling of transducer probe 2400 to a region of interest. For example, coupling components 2406 can comprise cooling and acoustic coupling system 2420 configured for acoustic coupling of ultrasound energy and signals. Acoustic cooling/coupling system 2420 with possible connections such as manifolds may be utilized to couple sound into the region-of-interest, control temperature at the interface and deeper into tissue, provide liquid-filled lens focusing, and/or to remove transducer waste heat. Coupling system 2420 may facilitate such coupling through use of various coupling mediums, including air and other gases, water and other fluids, gels, solids, and/or any combination thereof, or any other medium that allows for signals to be transmitted between transducer active elements 2412 and a region of interest. In addition to providing a coupling function, in accordance with an embodiment, coupling system 2420 can also be configured for providing temperature control during the treatment application. For example, coupling system 2420 can be configured for controlled cooling of an interface surface or region between transducer probe 2400 and a region of interest and beyond by suitably controlling the temperature of the coupling medium. The suitable temperature for such coupling medium can be achieved in various manners, and utilize various feedback systems, such as thermocouples, thermistors or any other device or system configured for temperature measurement of a coupling medium. Such controlled cooling can be configured to further facilitate spatial and/or thermal energy control of transducer probe 2400.

Figure 35:
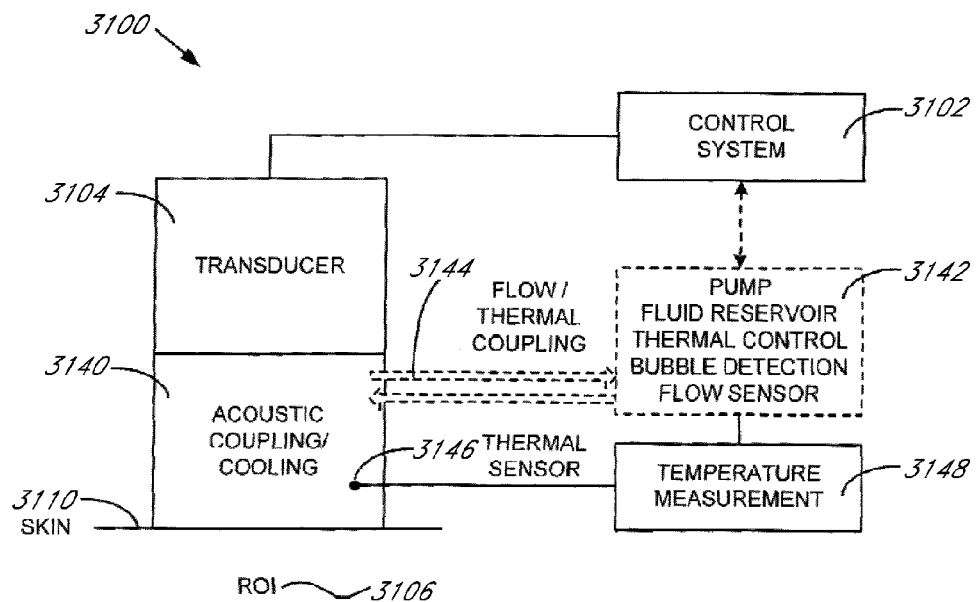
FIG. 35 illustrates a schematic diagram of an acoustic coupling and cooling system in accordance with an embodiment of the present invention.

In accordance with an embodiment, with additional reference to FIG. 35, acoustic coupling and cooling 3140 can be provided to acoustically couple energy and imaging signals from transducer probe 3104 to and from the region of interest 3106, to provide thermal control at the probe to region-of-interest interface 3110 and deeper into tissue, and to remove potential waste heat from the transducer probe at region 3144. Temperature monitoring can be provided at the coupling interface via a thermal sensor 3146 to provide a mechanism of temperature measurement 3148 and control via control system 3102 and a thermal control system 3142. Thermal control may consist of passive cooling such as via heat sinks or natural conduction and convection or via active cooling such as with peltier thermoelectric coolers, refrigerants, or fluid-based systems comprised of pump, fluid reservoir, bubble detection, flow sensor, flow channels/tubing 3144 and thermal control 3142.

With continued reference to FIGS. 28A-28B, monitoring and sensing components 2408 can comprise various motion and/or position sensors 2416, temperature monitoring sensors 2418, user control and feedback switches 2414 and other like components for facilitating control by control system 2300, e.g., to facilitate spatial and/or temporal control through open-loop and closed-loop feedback arrangements that monitor various spatial and temporal characteristics.

Motion mechanism 2410 (or otherwise referred to as a movement mechanism) can comprise manual operation, mechanical arrangements, or some combination thereof. For example, a motion mechanism 2422 can be suitably controlled by control system 2300, such as through the use of accelerometers, encoders or other position/orientation devices 2416 to determine and enable movement and positions of transducer probe 2400. Linear, rotational or variable movement can be facilitated, e.g., those depending on the treatment application and tissue contour surface.

Transducer 2404 can comprise one or more transducers configured for treating of SMAS layers and targeted regions. Transducer 2404 can also comprise one or more transduction elements and/or lenses 2412. The transduction elements can comprise a piezoelectrically active material, such as lead zirconante titanate (PZT), or any other piezoelectrically active material, such as a piezoelectric ceramic, crystal, plastic, and/or composite materials, as well as lithium niobate, lead titanate, barium titanate, and/or lead metaniobate. In addition to, or instead of, a piezoelectrically active material, transducer 2404 can comprise any other materials configured for generating radiation and/or acoustical energy. Transducer 2404 can also comprise one or more matching layers configured along with the transduction element such as coupled to the piezoelectrically active material. Acoustic matching layers and/or damping may be employed as necessary to achieve the desired electroacoustic response.

In accordance with an embodiment, the thickness of the transduction element of transducer 2404 can be configured to be uniform. That is, a transduction element 2412 can be configured to have a thickness that is substantially the same throughout. In accordance with another embodiment, the thickness of a transduction element 2412 can also be configured to be variable. For example, transduction element(s) 2412 of transducer 2404 can be configured to have a first thickness selected to provide a center operating frequency of approximately 2 kHz to 75 MHz, such as for imaging applications. Transduction element 2412 can also be configured with a second thickness selected to provide a center operating frequency of approximately 2 to 400 MHz, and typically between 4 MHz and 15 MHz for therapy application. Transducer 2404 can be configured as a single broadband transducer excited with at least two or more frequencies to provide an adequate output for generating a desired response. Transducer 2404 can also be configured as two or more individual transducers, wherein each transducer comprises one or more transduction element. The thickness of the transduction elements can be configured to provide center-operating frequencies in a desired treatment range.

For example, transducer 2404 can comprise a first transducer configured with a first transduction element having a thickness corresponding to a center frequency range of approximately 1 kHz to 3 MHz, and a second transducer configured with a second transduction element having a thickness corresponding to a center frequency of approximately 3 MHz to 100 MHz or more.

Figure 29:
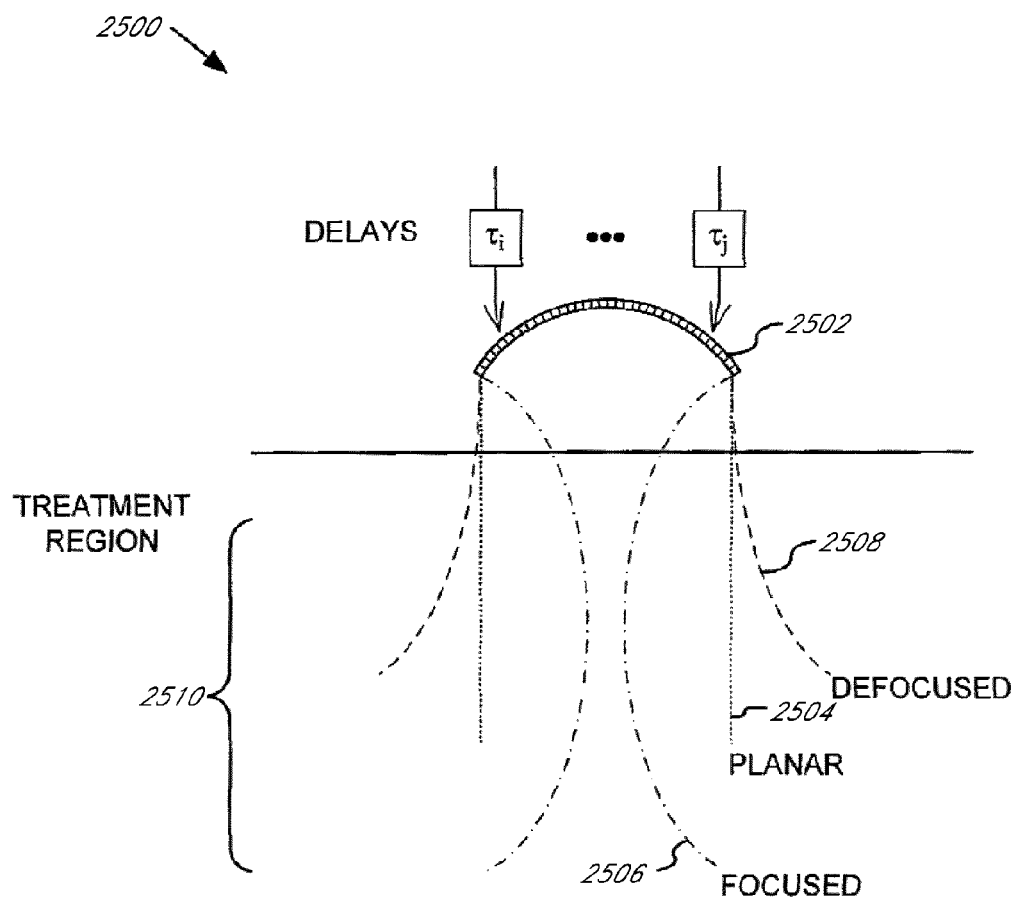
FIG. 29 illustrates a cross-sectional diagram of a transducer in accordance with an embodiment of the present invention.

Transducer 2404 may be composed of one or more individual transducers in any combination of focused, planar, or unfocused single-element, multi-element, or array transducers, including 1-D, 2-D, and annular arrays; linear, curvilinear, sector, or spherical arrays; spherically, cylindrically, and/or electronically focused, defocused, and/or lensed sources. For example, with reference to an embodiment depicted in FIG. 29, transducer 2500 can be configured as an acoustic array to facilitate phase focusing. That is, transducer 2500 can be configured as an array of electronic apertures that may be operated by a variety of phases via variable electronic time delays. By the term "operated," the electronic apertures of transducer 2500 may be manipulated, driven, used, and/or configured to produce and/or deliver an energy beam corresponding to the phase variation caused by the electronic time delay. For example, these phase variations can be used to deliver defocused beams, planar beams, and/or focused beams, each of which may be used in combination to achieve different physiological effects in a region of interest 2510. Transducer 2500 may additionally comprise any software and/or other hardware for generating, producing and or driving a phased aperture array with one or more electronic time delays.

Transducer 2500 can also be configured to provide focused treatment to one or more regions of interest using various frequencies. In order to provide focused treatment, transducer 2500 can be configured with one or more variable depth devices to facilitate treatment. For example, transducer 2500 may be configured with variable depth devices disclosed in U.S. patent application Ser. No. 10/944,500, entitled "System and Method for Variable Depth Ultrasound", filed on Sep. 16, 2004, having at least one common inventor and a common Assignee as the present application, and incorporated herein by reference. In addition, transducer 2500 can also be configured to treat one or more additional ROI 2510 through the enabling of sub-harmonics or pulse-echo imaging, as disclosed in U.S. patent application Ser. No. 10/944,499, entitled "Method and System for Ultrasound Treatment with a Multi-directional Transducer", filed on Sep. 16, 2004, having at least one common inventor and a common Assignee as the present application, and also incorporated herein by reference.

Moreover, any variety of mechanical lenses or variable focus lenses, e.g. liquid-filled lenses, may also be used to focus and or defocus the sound field. For example, with reference to embodiments depicted in FIGS. 30A and 30B, transducer 2600 may also be configured with an electronic focusing array 2604 in combination with one or more transduction elements 2606 to facilitate increased flexibility in treating ROI 2610 (or 65 as shown in FIGS. 12-14). Array 2604 may be configured in a manner similar to transducer 2502. That is, array 2604 can be configured as an array of electronic apertures that may be operated by a variety of phases via variable electronic time delays, for example, $T_1$, $T_2 \ldots T_j$. By the term "operated," the electronic apertures of array 2604 may be manipulated, driven, used, and/or configured to produce and/or deliver energy in a manner corresponding to the phase variation caused by the electronic time delay. For example, these phase variations can be used to deliver defocused beams, planar beams, and/or focused beams, each of which may be used in combination to achieve different physiological effects in ROI 2610.

Transduction elements 2606 may be configured to be concave, convex, and/or planar. For example, in an embodiment depicted in FIG. 30A, transduction elements 2606 are configured to be concave in order to provide focused energy for treatment of ROI 2610. Additional embodiments are disclosed in U.S. patent application Ser. No. 10/944,500, entitled "Variable Depth Transducer System and Method", and again incorporated herein by reference.

Figure 30A:
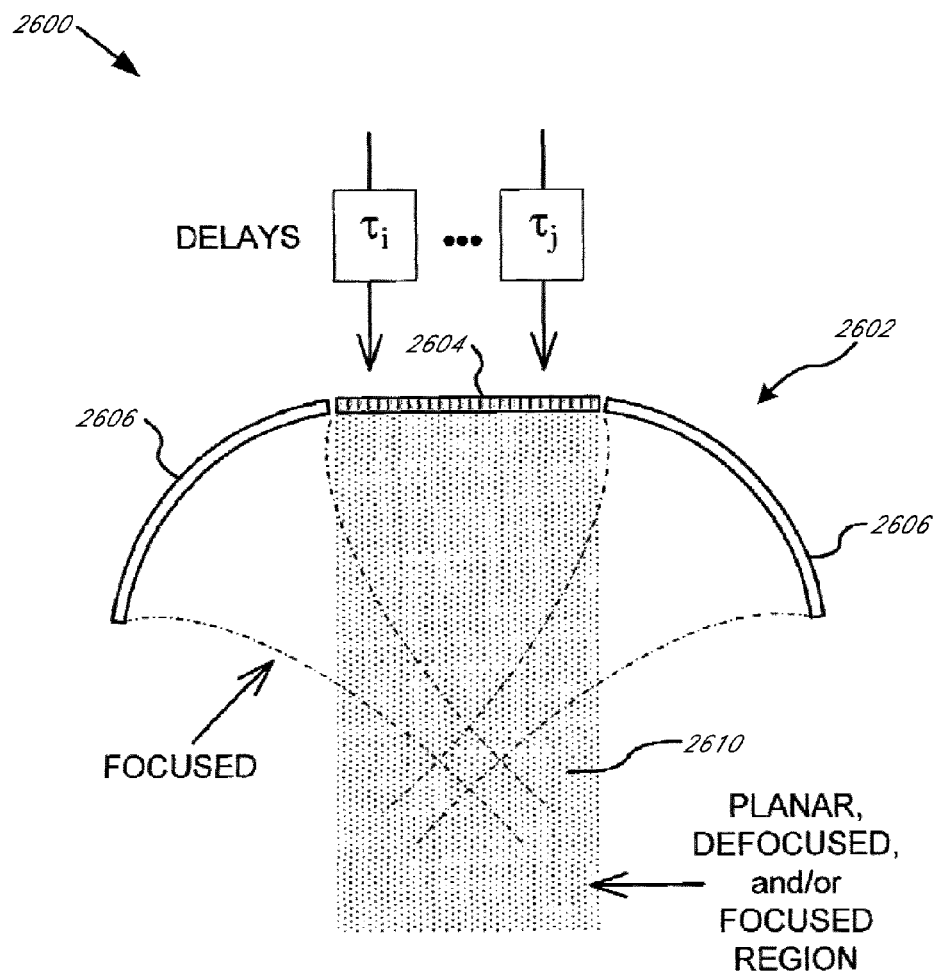
FIGS. 30A and 30B illustrate cross-sectional diagrams of a transducer in accordance with embodiments of the present invention.
Figure 30B:
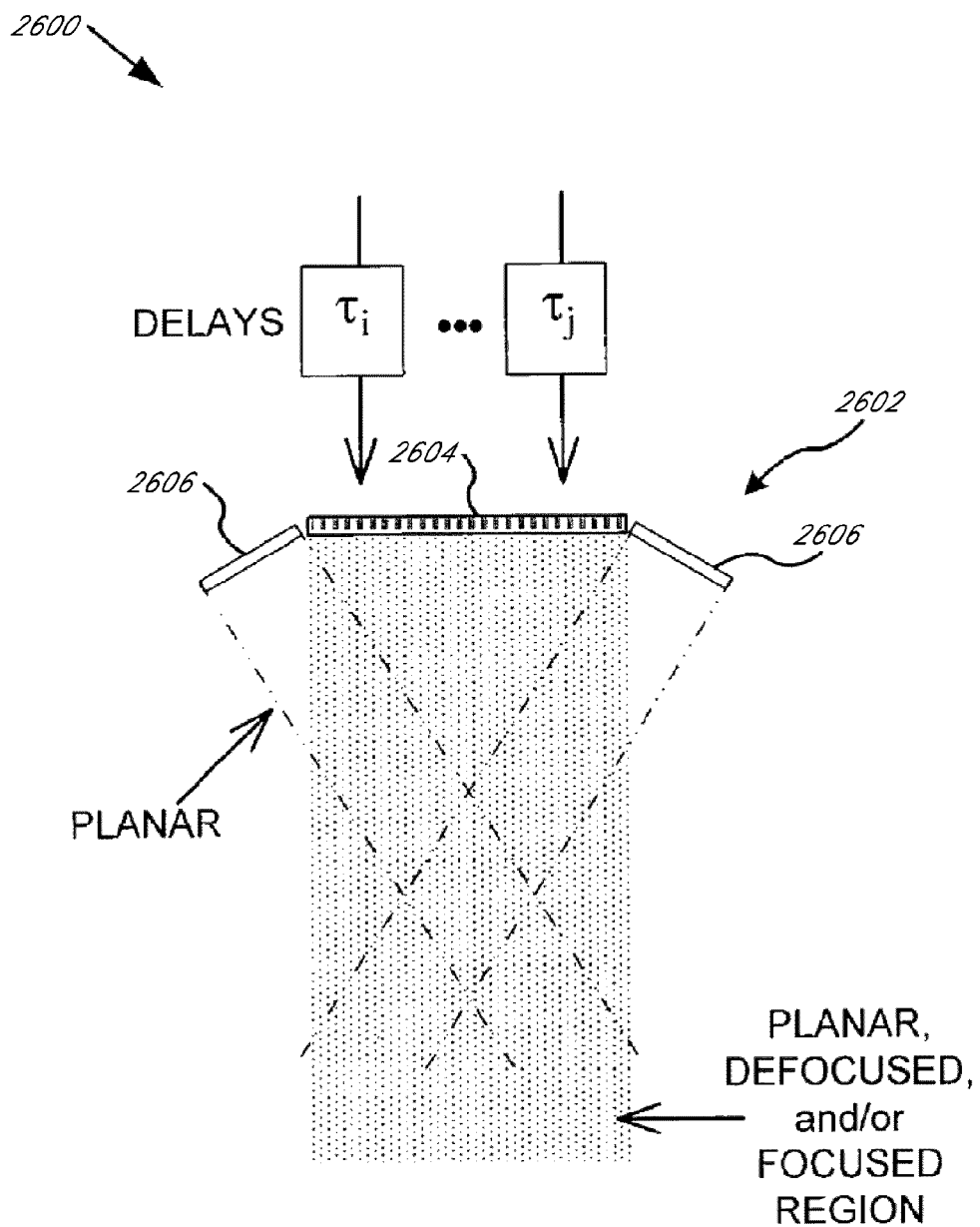

In another embodiment, depicted in FIG. 30B, transduction elements 2606 can be configured to be substantially flat in order to provide substantially uniform energy to ROI 2610. While FIGS. 30A and 30B depict embodiments with transduction elements 2604 configured as concave and substantially flat, respectively, transduction elements 2604 can be configured to be concave, convex, and/or substantially flat. In addition, transduction elements 2604 can be configured to be any combination of concave, convex, and/or substantially flat structures. For example, a first transduction element can be configured to be concave, while a second transduction element can be configured to be substantially flat.

Figure 32A:
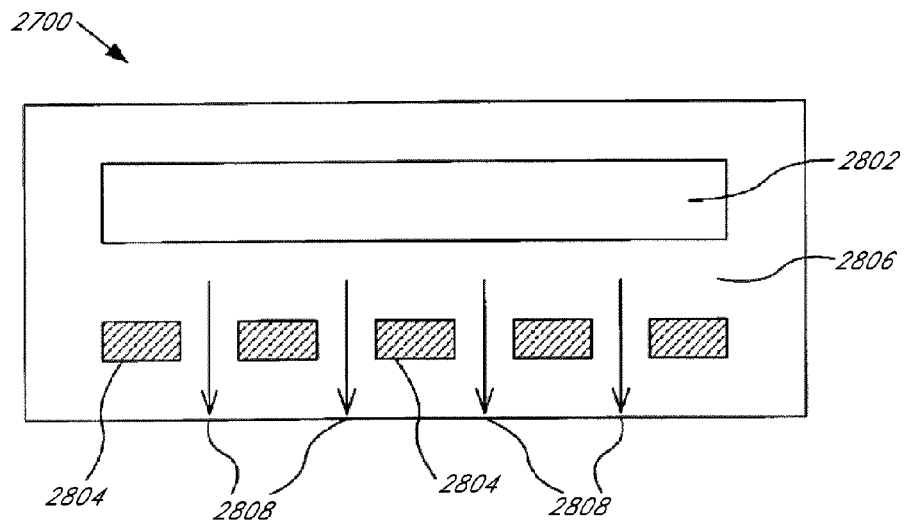
FIGS. 32A and 32B illustrate cross-sectional diagrams of a transducer in accordance with another embodiment of the present invention.
Figure 32B:
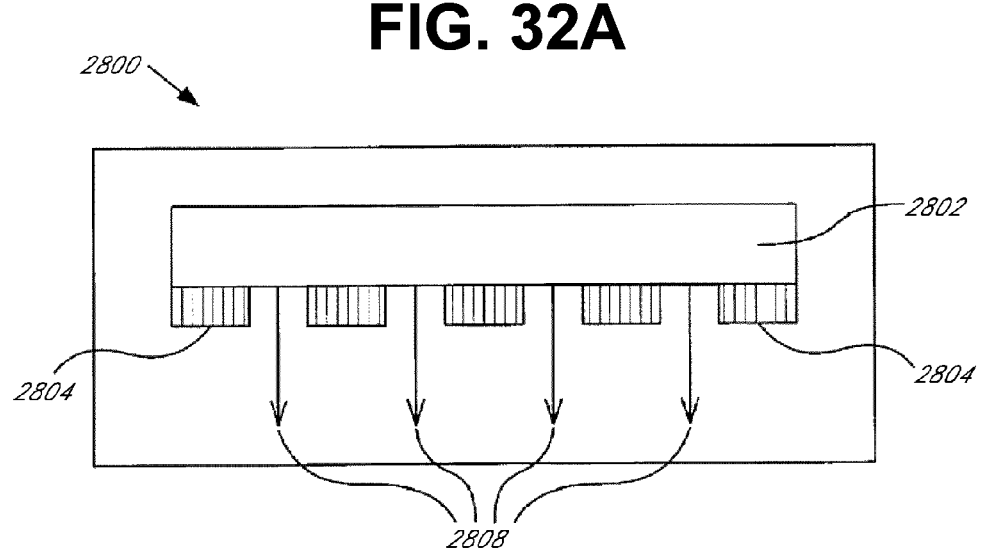

With reference to FIGS. 32A and 32B, transducer 2404 can be configured as single-element arrays, wherein a single-element 2802, e.g., a transduction element of various structures and materials, can be configured with a plurality of masks 2804, such masks comprising ceramic, metal or any other material or structure for masking or altering energy distribution from element 2802, creating an array of energy distributions 2808. Masks 2804 can be coupled directly to element 2802 or separated by a standoff 2806, such as any suitably solid or liquid material.

Figure 34A:
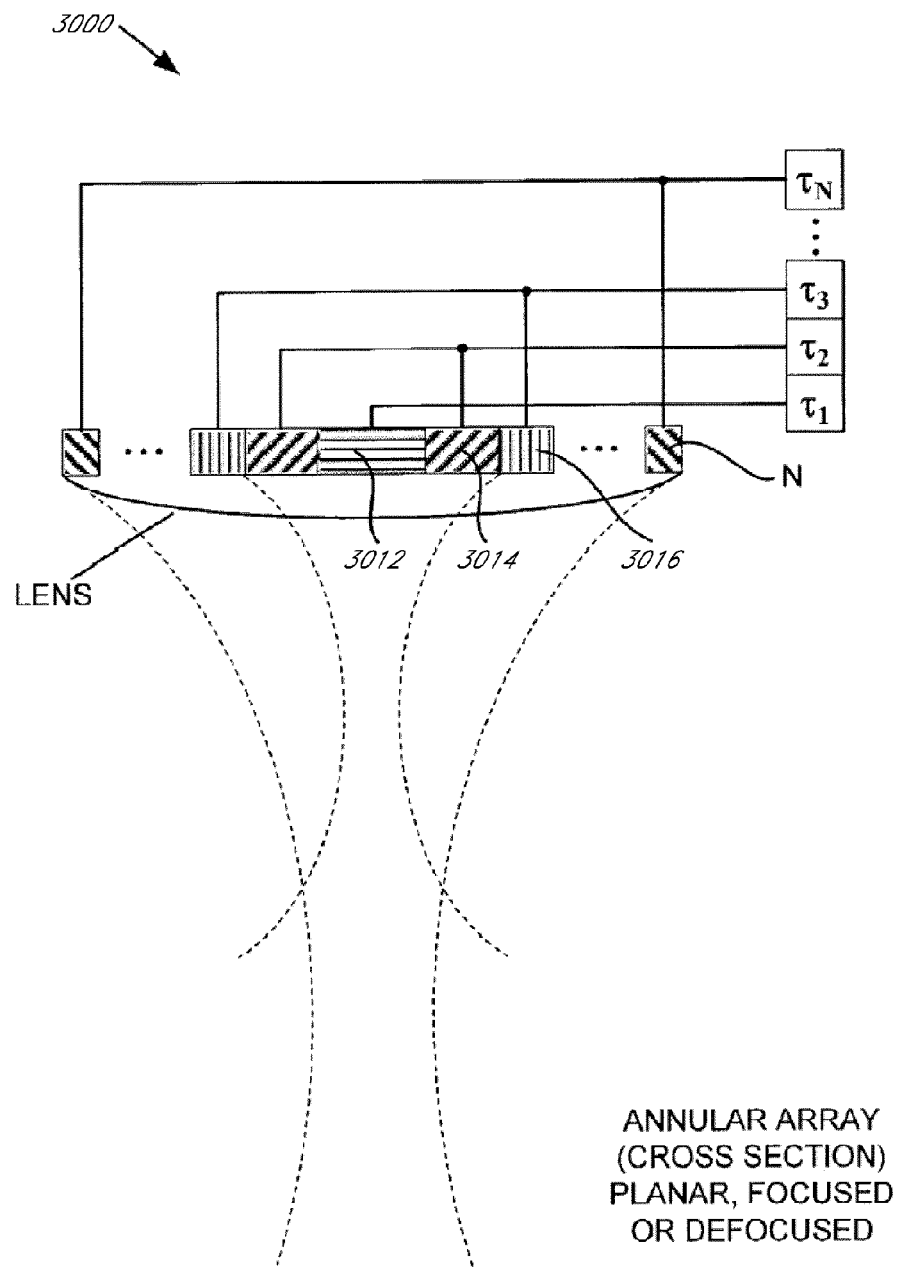
FIGS. 34A-34F illustrate cross-sectional diagrams of transducers in accordance with other embodiments of the present invention.
Figure 34B:
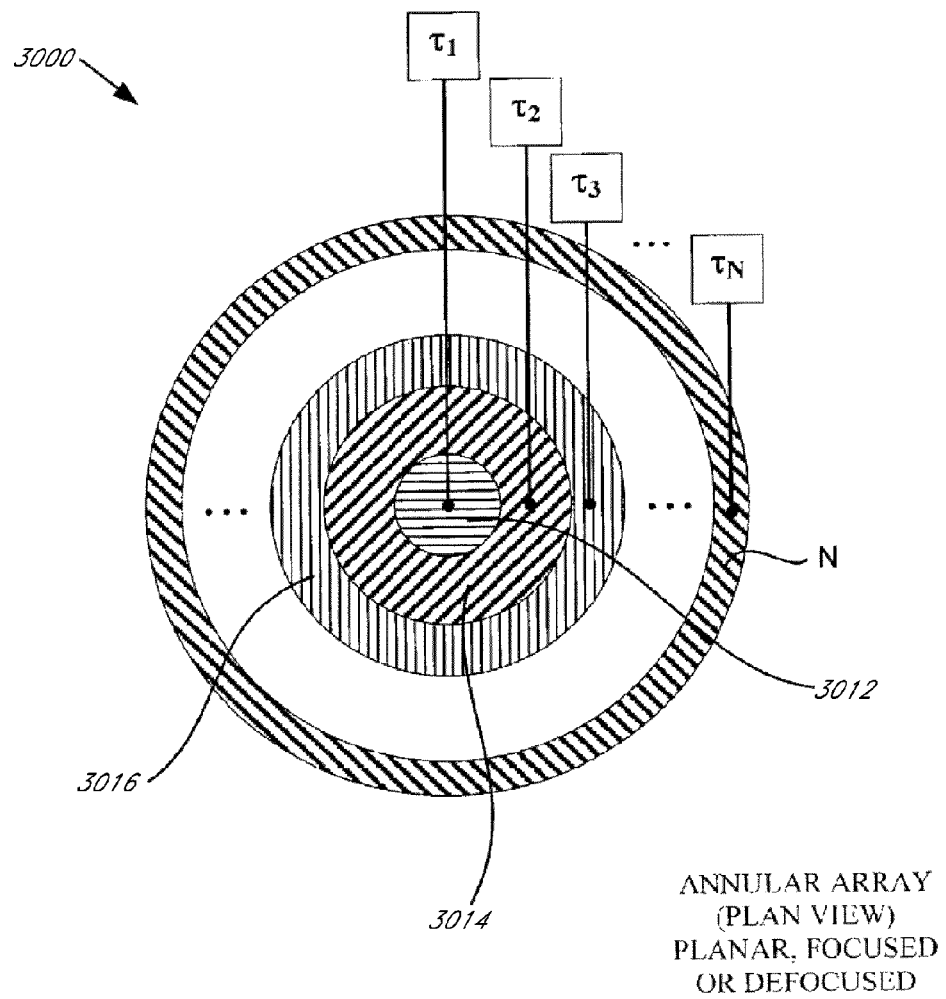
Figure 34C:
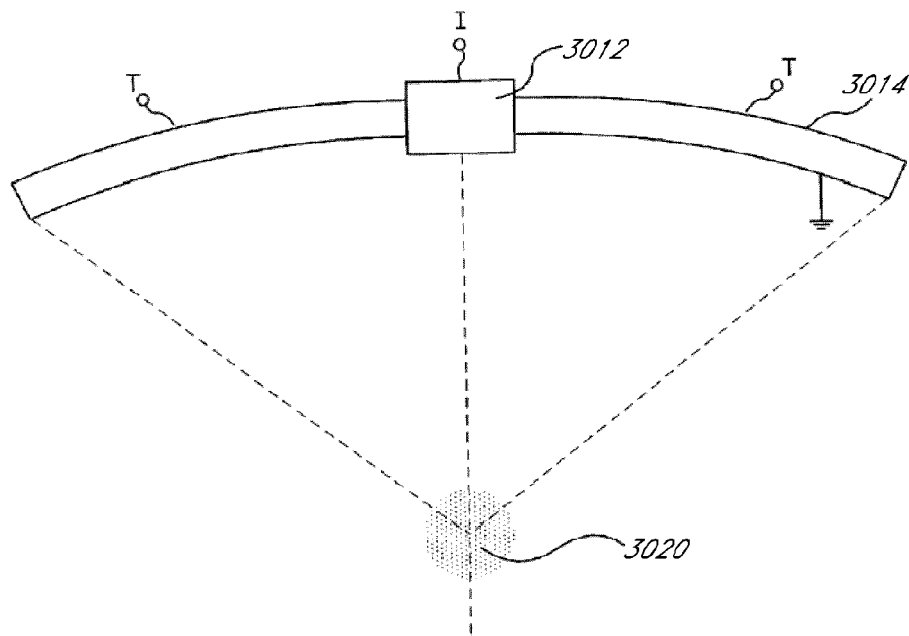
Figure 34D:
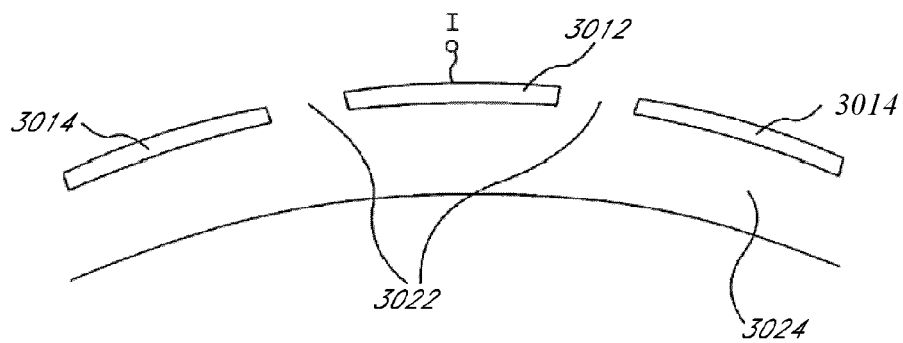
Figure 34E:
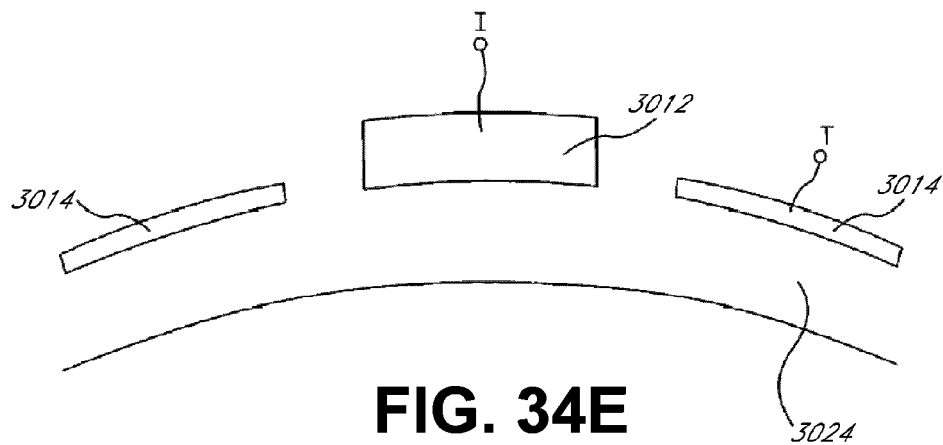

An embodiment of a transducer 2404 can also be configured as an annular array to provide planar, focused and/or defocused acoustical energy. For example, with reference to FIGS. 34A and 34B, in accordance with an embodiment, an annular array 3000 can comprise a plurality of rings 3012, 3014, 3016 to N. Rings 3012, 3014, 3016 to N can be mechanically and electrically isolated into a set of individual elements, and can create planar, focused, or defocused waves. For example, such waves can be centered on-axis, such as by methods of adjusting corresponding transmit and/or receive delays, $\tau 1, \tau 2, \tau 3 \ldots \tau N$. An electronic focus can be suitably moved along various depth positions, and can enable variable strength or beam tightness, while an electronic defocus can have varying amounts of defocusing. In accordance with an embodiment, a lens and/or convex or concave shaped annular array 3000 can also be provided to aid focusing or defocusing such that any time differential delays can be reduced. Movement of annular array 2800 in one, two or three-dimensions, or along any path, such as through use of probes and/or any conventional robotic arm mechanisms, may be implemented to scan and/or treat a volume or any corresponding space within a region of interest.

Transducer 2404 can also be configured in other annular or non-array configurations for imaging/therapy functions. For example, with reference to FIGS. 34C-34F, a transducer can comprise an imaging element 3012 configured with therapy element(s) 3014. Elements 3012 and 3014 can comprise a single-transduction element, e.g., a combined imaging/transducer element, or separate elements, can be electrically isolated 3022 within the same transduction element or between separate imaging and therapy elements, and/or can comprise standoff 3024 or other matching layers, or any combination thereof. For example, with particular reference to FIG. 34F, a transducer can comprise an imaging element 3012 having a surface 3028 configured for focusing, defocusing or planar energy distribution, with therapy elements 3014 including a stepped-configuration lens configured for focusing, defocusing, or planar energy distribution.

With a better understanding of the various transducer structures, and with reference again to FIG. 38, how the geometric configuration of the transducer or transducers that contributes to the wide range of lesioning effects can be better understood. For example, cigar-shaped lesions 3404 and 3406 may be produced from a spherically focused source, and/or planar lesions 3410 from a flat source. Concave planar sources and arrays can produce a "V-shaped" or ellipsoidal lesion 3414. Electronic arrays, such as a linear array, can produce defocused, planar, or focused acoustic beams that may be employed to form a wide variety of additional lesion shapes at various depths. An array may be employed alone or in conjunction with one or more planar or focused transducers. Such transducers and arrays in combination produce a very wide range of acoustic fields and their associated benefits. A fixed focus and/or variable focus lens or lenses may be used to further increase treatment flexibility. A convex-shaped lens, with acoustic velocity less than that of superficial tissue, may be utilized, such as a liquid-filled lens, gel-filled or solid gel lens, rubber or composite lens, with adequate power handling capacity; or a concave-shaped, low profile, lens may be utilized and composed of any material or composite with velocity greater than that of tissue. While the structure of transducer source and configuration can facilitate a particular shaped lesion as suggested above, such structures are not limited to those particular shapes as the other spatial parameters, as well as the temporal parameters, can facilitate additional shapes within any transducer structure and source.

In accordance with various embodiments of the present invention, transducer 2404 may be configured to provide one, two and/or three-dimensional treatment applications for focusing acoustic energy to one or more regions of interest. For example, as discussed above, transducer 2404 can be suitably diced to form a one-dimensional array, e.g., transducer 2602 comprising a single array of sub-transduction elements.

Figure 33:
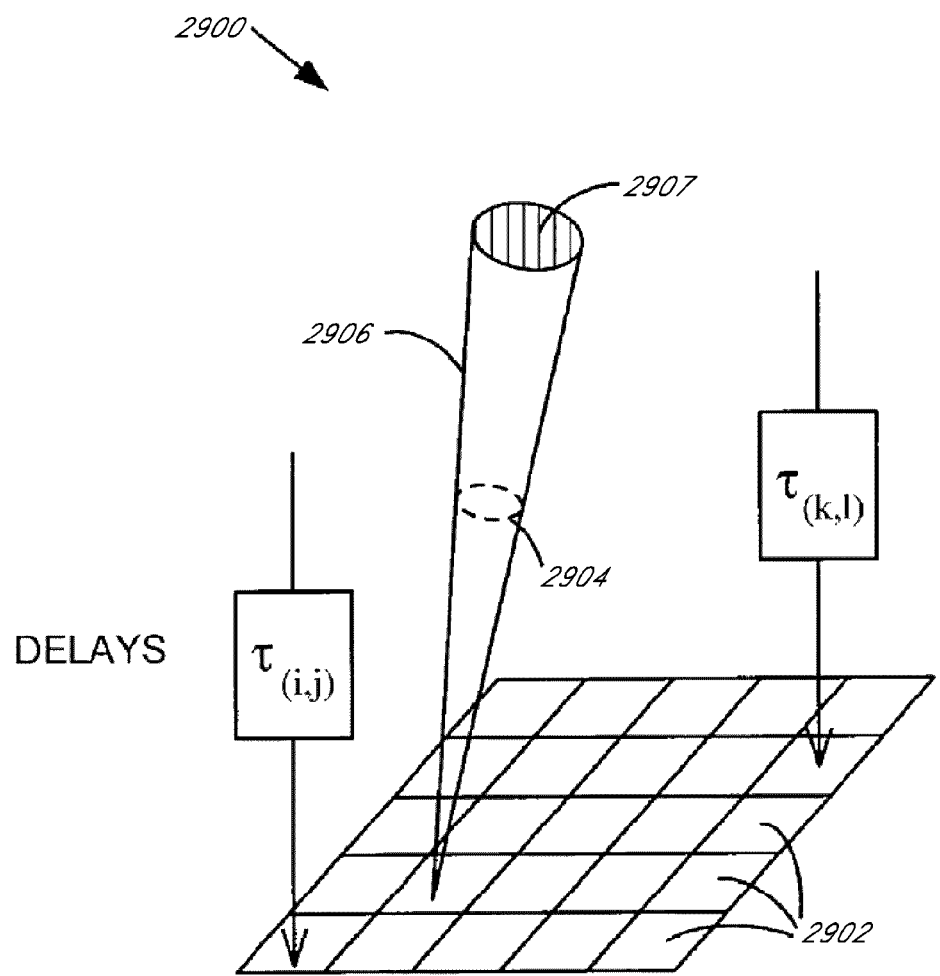
FIG. 33 illustrates a transducer configured as a two-dimensional array for ultrasound treatment in accordance with an embodiment of the present invention.

In accordance with another embodiment, transducer 2404 may be suitably diced in two-dimensions to form a two-dimensional array. For example, with reference to FIG. 33, an embodiment with two-dimensional array 2900 can be suitably diced into a plurality of two-dimensional portions 2902. Two-dimensional portions 2902 can be suitably configured to focus on the treatment region at a certain depth, and thus provide respective slices 2904, 2907 of the treatment region. As a result, the two-dimensional array 2900 can provide a two-dimensional slicing of the image place of a treatment region, thus providing two-dimensional treatment.

In accordance with another embodiment, transducer 2404 may be suitably configured to provide three-dimensional treatment. For example, to provide-three dimensional treatment of a region of interest, with reference again to FIG. 23, a three-dimensional system can comprise a transducer within probe 104 configured with an adaptive algorithm, such as, for example, one utilizing three-dimensional graphic software, contained in a control system, such as control system 102. The adaptive algorithm is suitably configured to receive two-dimensional imaging, temperature and/or treatment or other tissue parameter information relating to the region of interest, process the received information, and then provide corresponding three-dimensional imaging, temperature and/or treatment information.

In accordance with an embodiment, with reference again to FIG. 33, a three-dimensional system can comprise a two-dimensional array 2900 configured with an adaptive algorithm to suitably receive 2904 slices from different image planes of the treatment region, process the received information, and then provide volumetric information 2906, e.g., three-dimensional imaging, temperature and/or treatment information. Moreover, after processing the received information with the adaptive algorithm, the two-dimensional array 2900 may suitably provide therapeutic heating to the volumetric region 2906 as desired.

In accordance with other embodiments, rather than utilizing an adaptive algorithm, such as three-dimensional software, to provide three-dimensional imaging and/or temperature information, a three-dimensional system can comprise a single transducer 2404 configured within a probe arrangement to operate from various rotational and/or translational positions relative to a target region.

Figure 31:
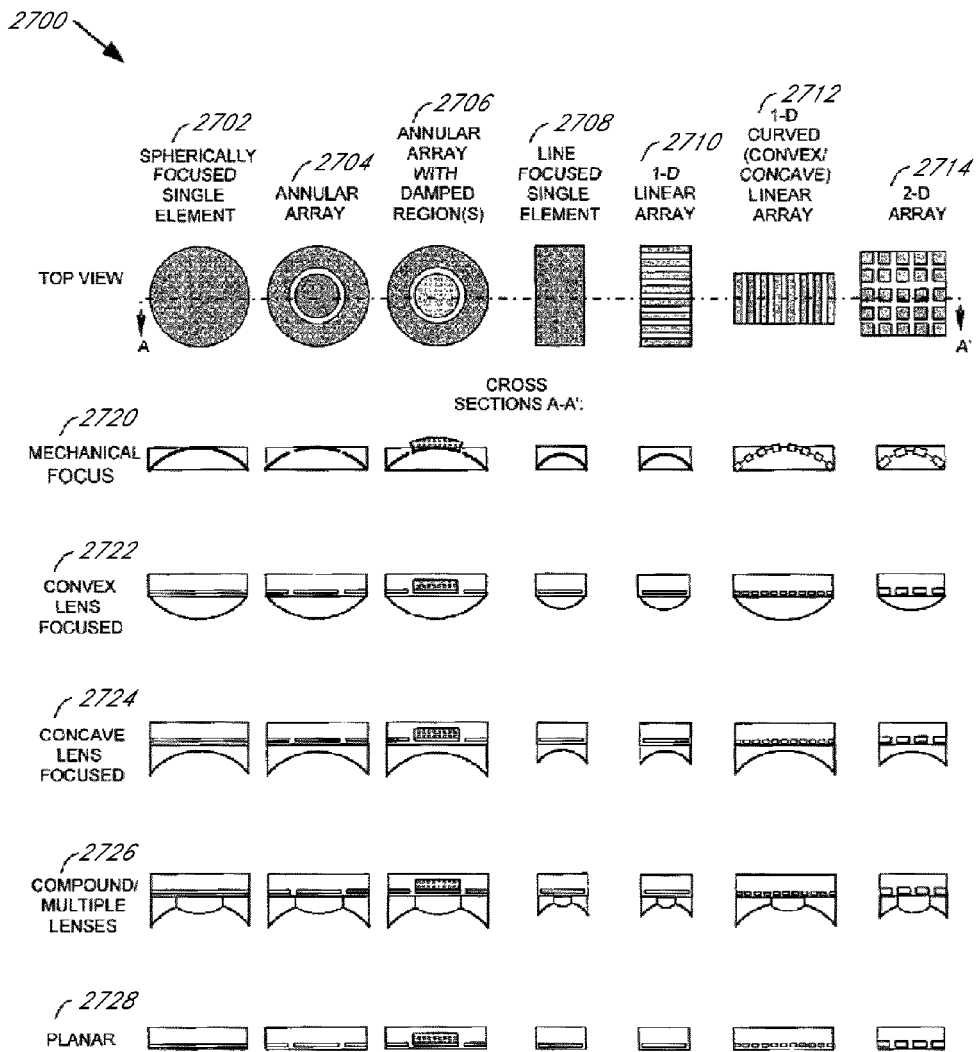
FIG. 31 illustrates transducer configurations for ultrasound treatment in accordance with various embodiments of the present invention.
Figure 34F:
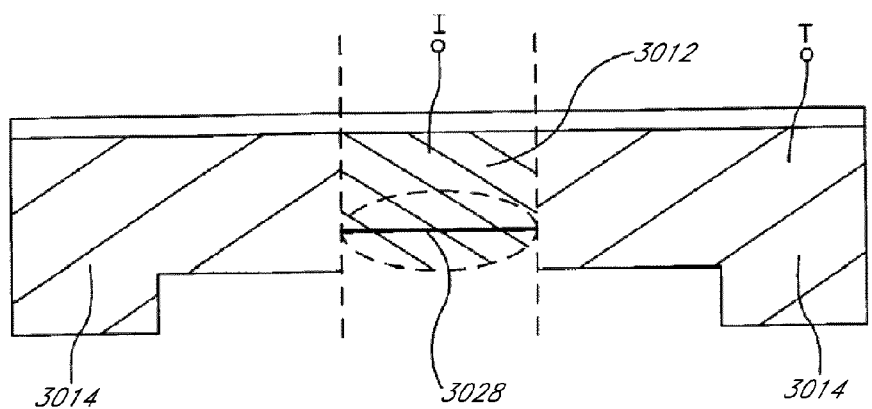

To further illustrate the various structures for transducer 2404, with reference to FIG. 31, ultrasound therapy transducer 2700 can be configured for a single focus, an array of foci, a locus of foci, a line focus, and/or diffraction patterns. Transducer 2700 can also comprise single elements, multiple elements, annular arrays, one-, two-, or three-dimensional arrays, broadband transducers, and/or combinations thereof, with or without lenses, acoustic components, and mechanical and/or electronic focusing. Transducers configured as spherically focused single elements 2702, annular arrays 2704, annular arrays with damped regions 2706, line focused single elements 2708, 1-D linear arrays 2710, 1-D curvilinear arrays in concave or convex form, with or without elevation focusing, 2-D arrays, and 3-D spatial arrangements of transducers may be used to perform therapy and/or imaging and acoustic monitoring functions. For any transducer configuration, focusing and/or defocusing may be in one plane or two planes via mechanical focus 2720, convex lens 2722, concave lens 2724, compound or multiple lenses 2726, planar form 2728, or stepped form, such as illustrated in FIG. 34F. Any transducer or combination of transducers may be utilized for treatment. For example, an annular transducer may be used with an outer portion dedicated to therapy and the inner disk dedicated to broadband imaging wherein such imaging transducer and therapy transducer have different acoustic lenses and design, such as illustrated in FIGS. 34C-34F.

Moreover, such transduction elements 2700 may comprise a piezoelectrically active material, such as lead zirconante titanate (PZT), or any other piezoelectrically active material, such as a piezoelectric ceramic, crystal, plastic, and/or composite materials, as well as lithium niobate, lead titanate, barium titanate, and/or lead metaniobate. Transduction elements 2700 may also comprise one or more matching layers configured along with the piezoelectrically active material. In addition to or instead of piezoelectrically active material, transduction elements 2700 can comprise any other materials configured for generating radiation and/or acoustical energy. A means of transferring energy to and from the transducer to the region of interest is provided.

Figure 36:
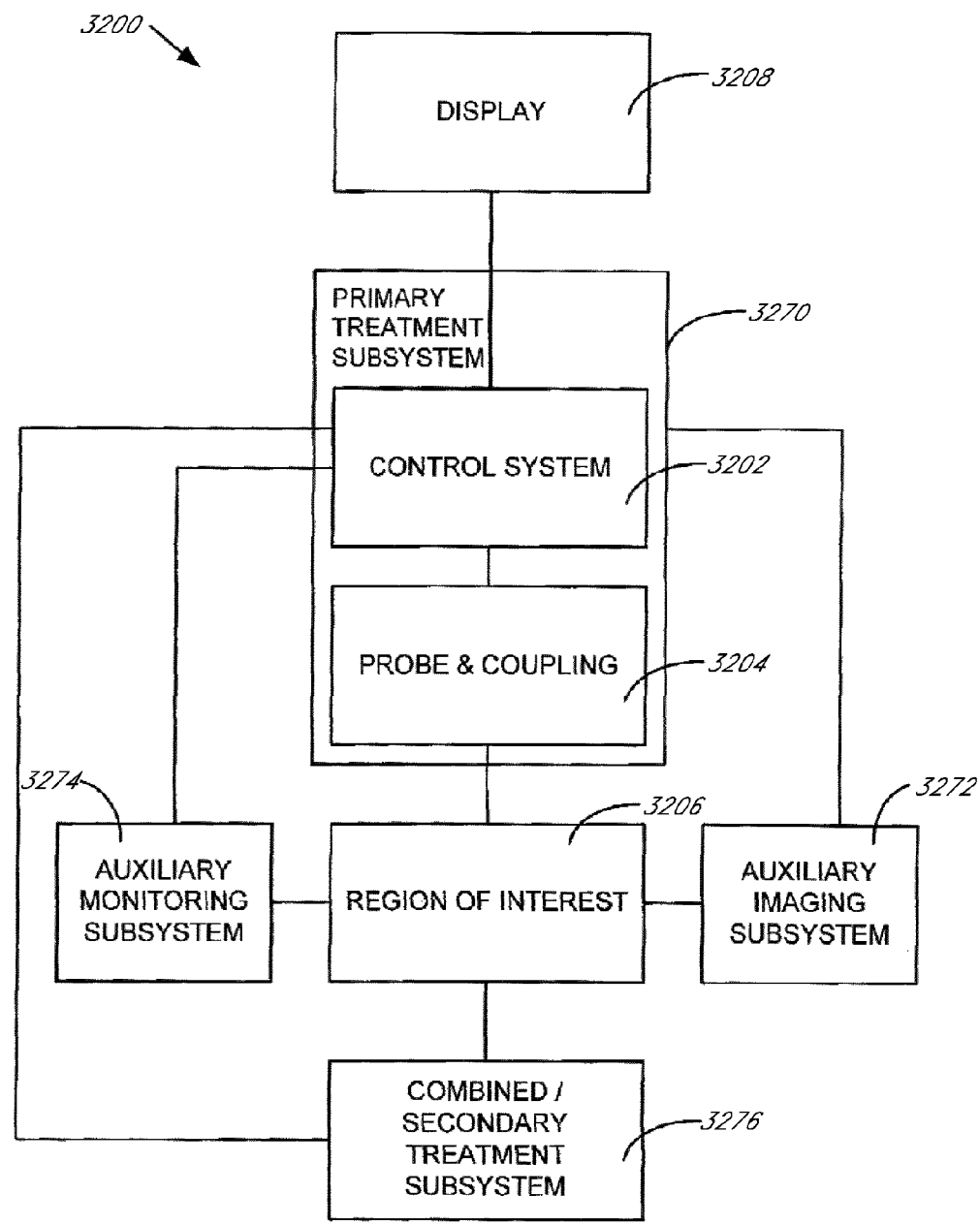
FIG. 36 illustrates a block diagram of a treatment system comprising an ultrasound treatment subsystem combined with additional subsystems and methods of treatment monitoring and/or treatment imaging as well as a secondary treatment subsystem in accordance with an embodiment of the present invention.

In accordance with another embodiment, with reference to FIG. 36, a treatment system 2200 can be configured with and/or combined with various auxiliary systems to provide additional functions. For example, an embodiment of a treatment system 3200 for treating a region of interest 3206 can comprise a control system 3202, a probe 3204, and a display 3208. Treatment system 3200 further comprises an auxiliary imaging modality 3274 and/or auxiliary monitoring modality 3272 may be based upon at least one of photography and other visual optical methods, magnetic resonance imaging (MRI), computed tomography (CT), optical coherence tomography (OCT), electromagnetic, microwave, or radio frequency (RF) methods, positron emission tomography (PET), infrared, ultrasound, acoustic, or any other suitable method of visualization, localization, or monitoring of SMAS layers within region-of-interest 3206, including imaging/monitoring enhancements. Such imaging/monitoring enhancement for ultrasound imaging via probe 3204 and control system 3202 could comprise M-mode, persistence, filtering, color, Doppler, and harmonic imaging among others. Further, in several embodiments an ultrasound treatment system 3270, as a primary source of treatment, may be combined or substituted with another source of treatment 3276, including radio frequency (RF), intense pulsed light (IPL), laser, infrared laser, microwave, or any other suitable energy source.

Figure 37:
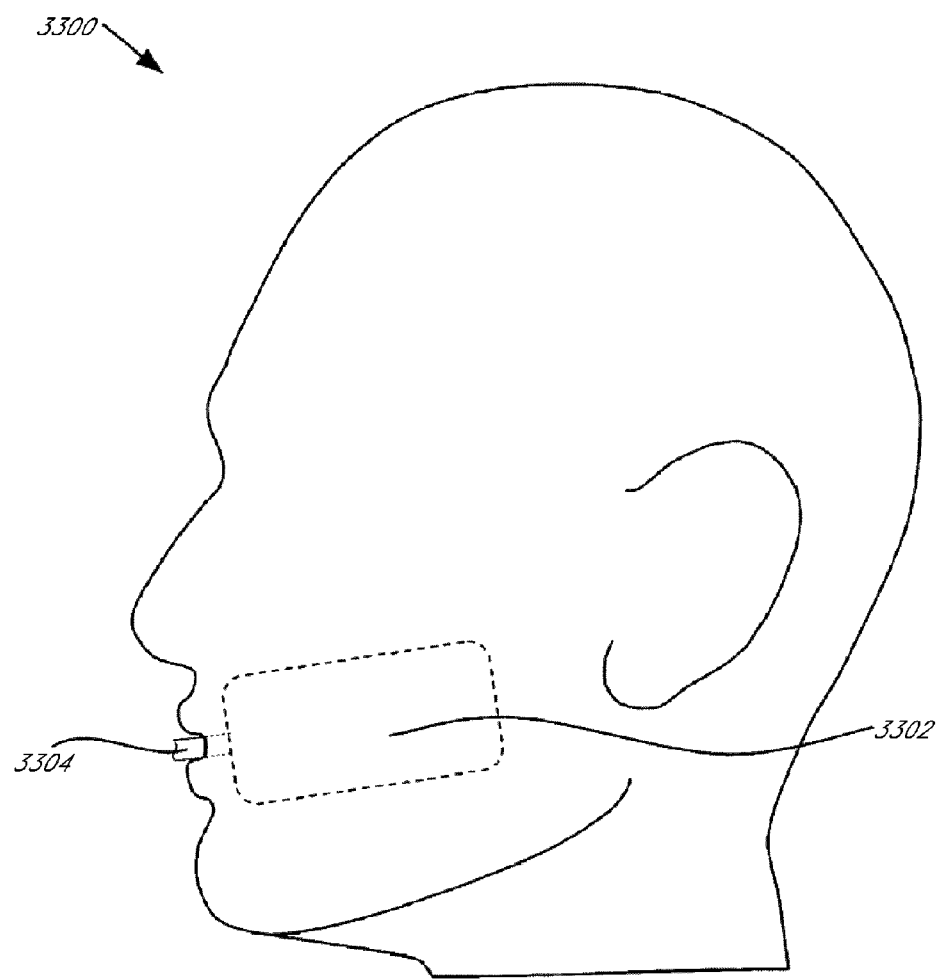
FIG. 37 illustrates a schematic diagram with imaging, therapy, or monitoring being provided with one or more active or passive oral inserts in accordance with an embodiment of the present invention.

In accordance with another embodiment, with reference to FIG. 37, treatment composed of imaging, monitoring, and/or therapy to a region of interest may be further aided, augmented, and/or delivered with passive or active devices 3304 within the oral cavity. For example, if passive or active device 3304 is a second transducer or acoustic reflector acoustically coupled to the cheek lining it is possible to obtain through transmission, tomographic, or round-trip acoustic waves which are useful for treatment monitoring, such as in measuring acoustic speed of sound and attenuation, which are temperature dependent; furthermore such a transducer could be used to treat and/or image. In addition an active, passive, or active/passive object 3304 may be used to flatten the skin, and/or may be used as an imaging grid, marker, or beacon, to aid determination of position. A passive or active device 3304 may also be used to aid cooling or temperature control. Natural air in the oral cavity may also be used as passive device 3304 whereby it may be utilized to as an acoustic reflector to aid thickness measurement and monitoring function.

During operation of an embodiment of a treatment system, a lesion configuration of a selected size, shape, orientation is determined. Based on that lesion configuration, one or more spatial parameters are selected, along with suitable temporal parameters, the combination of which yields the desired conformal lesion. Operation of the transducer can then be initiated to provide the conformal lesion or lesions. Open and/or closed-loop feedback systems can also be implemented to monitor the spatial and/or temporal characteristics, and/or other tissue parameter monitoring, to further control the conformal lesions.

Figure 39:
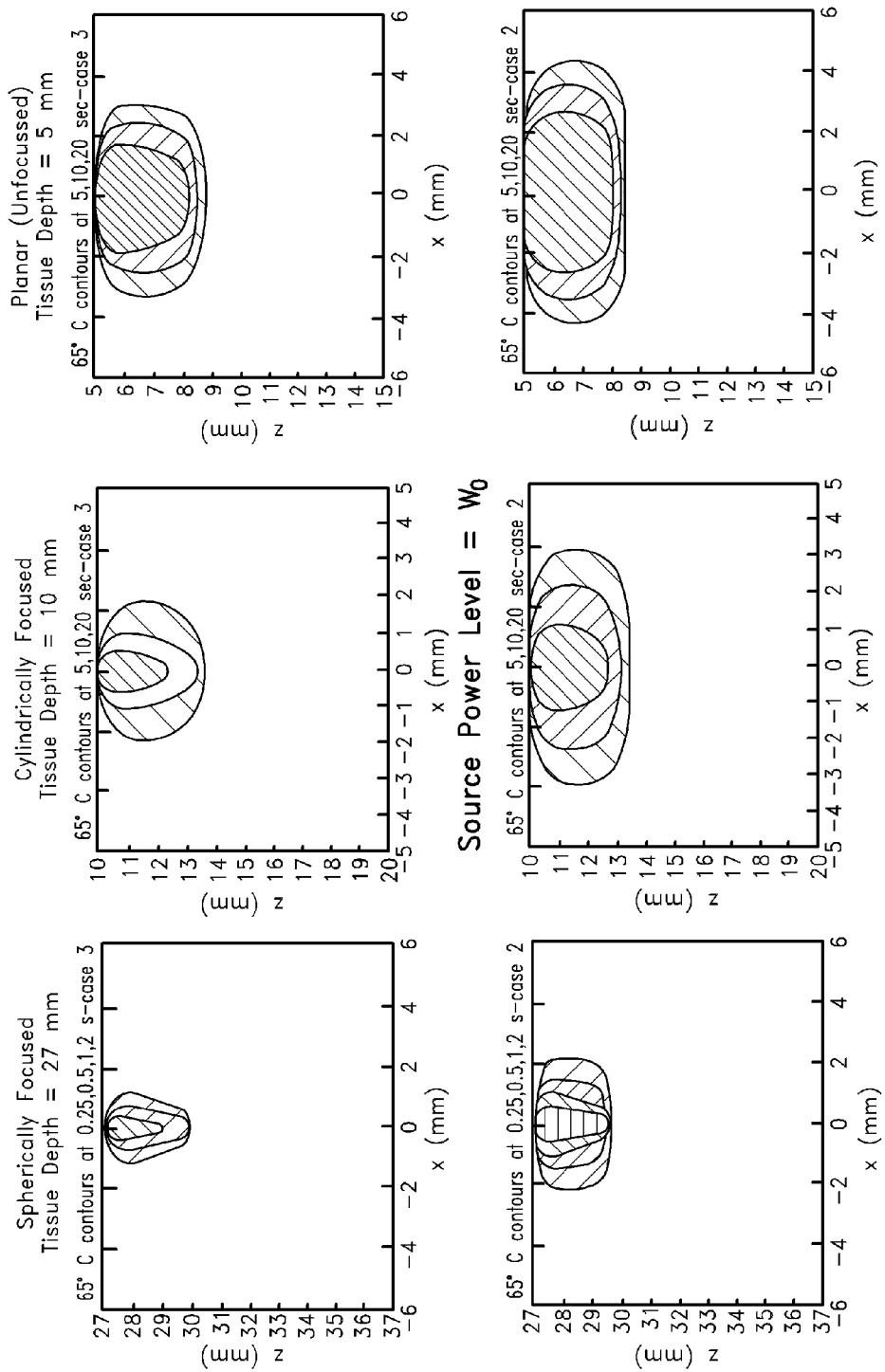
FIG. 39 illustrates a diagram of simulation results for various spatially controlled configurations in accordance with embodiments of the present invention.
Figure 40:
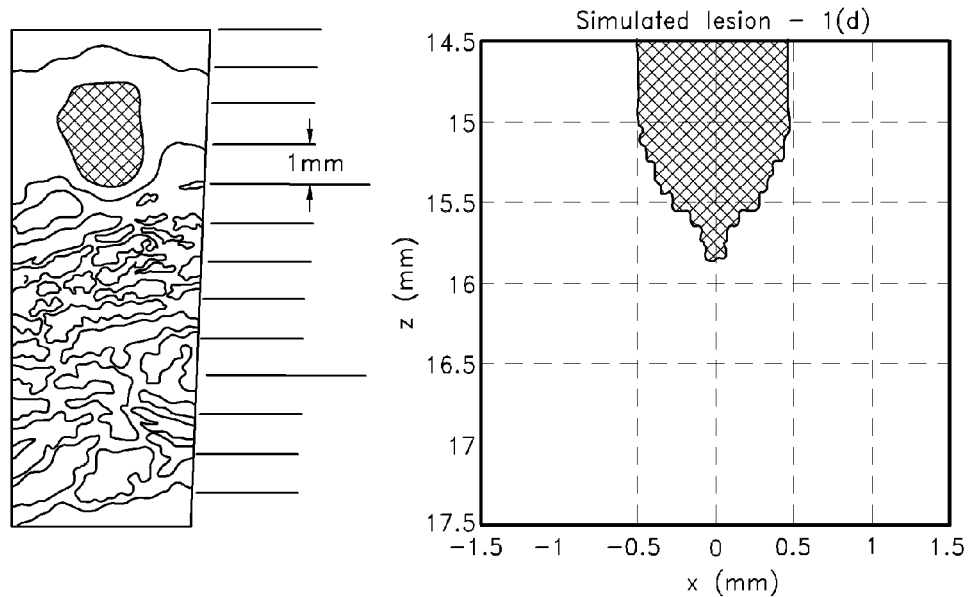
FIG. 40 illustrates an diagram of simulation results of a pair of lesioning and simulation results in accordance with the present invention.
Figure 40:
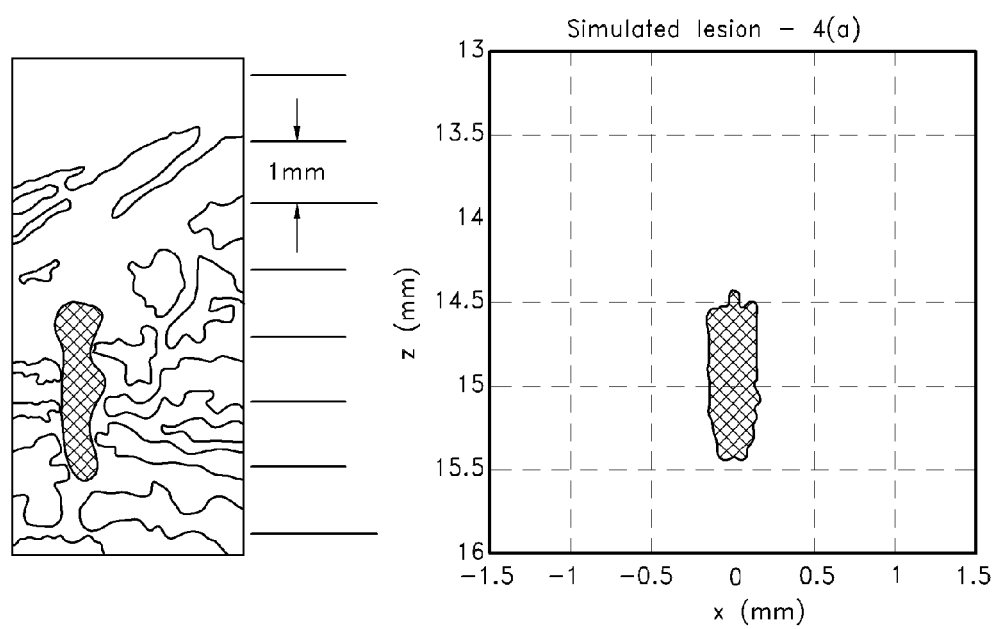
Figure 41:
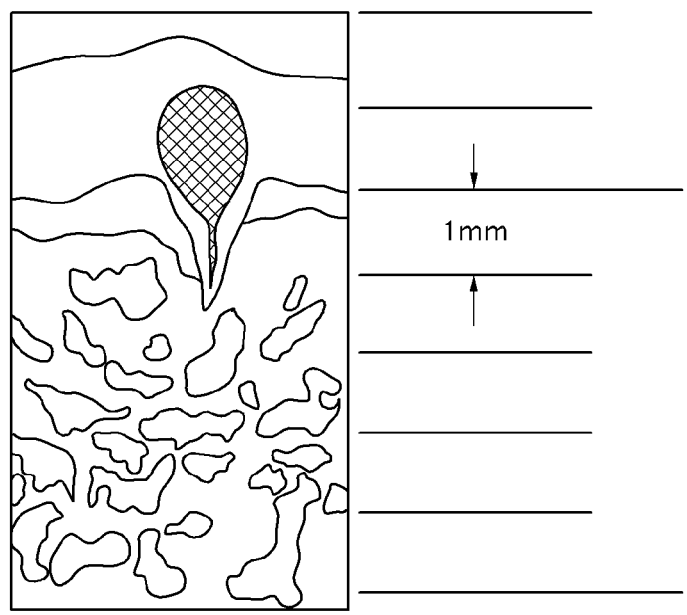
FIG. 41 illustrates another diagram of simulation results of a pair of lesioning results in accordance with the present invention.
Figure 41:
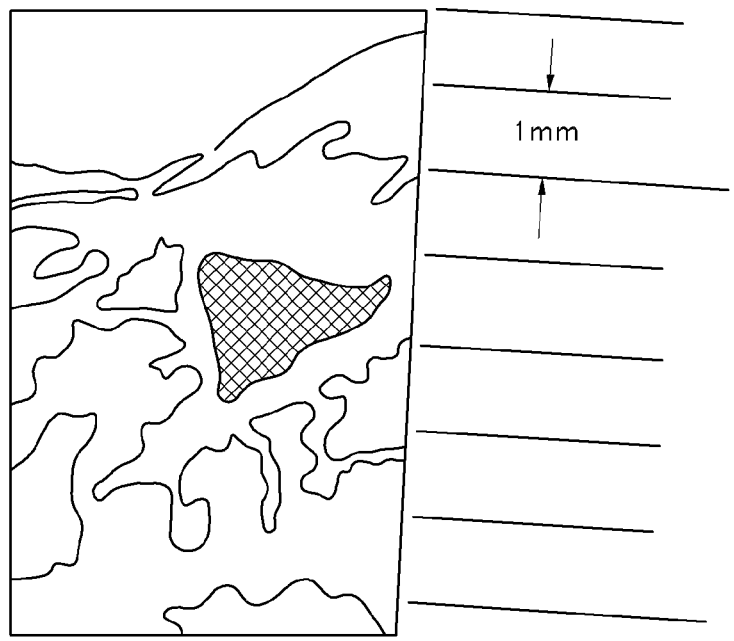

With reference to FIG. 39, a collection of simulation results, illustrating thermal lesion growth over time are illustrated. Such lesion growth was generated with a spherically focused, cylindrically focused, and planar (unfocused) source at a nominal source acoustic power level, $W_0$ and twice that level, $2 W_0$, but any configurations of transducer can be utilized as disclosed herein. The thermal contours indicate where the tissue reached 65° C. for different times. The contour for the cylindrically focused source is along the short axis, or so-called elevation plane. The figure highlights the different shapes of lesions possible with different power levels and source geometries. In addition, with reference to FIG. 40, a pair of lesioning and simulation results is illustrated, showing chemically stained porcine tissue photomicrographs adjacent to their simulation results. In addition, with reference to FIG. 41, another pair of lesioning results is illustrated, showing chemically stained porcine tissue photomicrographs, highlighting a tadpole shaped lesion and a wedge shaped lesion.

In summary, adjustment of the acoustic field spatial distribution via transducer type and distribution, such as size, element configuration, electronic or mechanical lenses, acoustic coupling and/or cooling, combined with adjustment of the temporal acoustic field, such as through control of transmit power level and timing, transmit frequency and/or drive waveform can facilitate the achieving of controlled thermal lesions of variable size, shape, and depths. Moreover, the restorative biological responses of the human body can further cause the desired effects to the superficial human tissue.

The citation of references herein does not constitute admission that those references are prior art or have relevance to the patentability of the teachings disclosed herein. All references cited in the Description section of the specification are hereby incorporated by reference in their entirety for all purposes. In the event that one or more of the incorporated references, literature, and similar materials differs from or contradicts this application, including, but not limited to, defined terms, term usage, described techniques, or the like, this application controls.

Some embodiments and the examples described herein are examples and not intended to be limiting in describing the full scope of compositions and methods of these invention. Equivalent changes, modifications and variations of some embodiments, materials, compositions and methods can be made within the scope of the present invention, with substantially similar results.

What is claimed is:

1. A method of lifting skin tissue, the method comprising:
   positioning a portion of an ultrasound probe on a skin surface, the ultrasound probe comprising a movement mechanism and at least one piezoelectric ultrasound therapy element,
   using the at least one piezoelectric ultrasound therapy element to treat a region of interest under the skin surface, the region of interest comprising a tissue comprising at least one of the group consisting of: a muscle, a muscular fascia, a fat tissue, and a superficial muscular aponeurosis system (SMAS) tissue;
   wherein the at least one piezoelectric ultrasound therapy element is coupled to the movement mechanism within the ultrasound probe;
   wherein the at least one piezoelectric ultrasound therapy element is configured for targeted delivery of ultrasound energy to form a thermal focus with at least a temperature sufficient to treat at least a portion of the tissue at a fixed depth under the skin surface; and
   activating the movement mechanism within the ultrasound probe to move the at least one piezoelectric ultrasound therapy element to form a plurality of the thermal foci at the fixed depth to treat at least the SMAS tissue in the region of interest,
   wherein the plurality of thermal foci results in a tissue lift.

2. The method of claim 1, wherein positioning a portion of the ultrasound probe on the skin surface comprises positioning the portion of the ultrasound probe on at least one of the group consisting of: a forehead, an eyelid, a nose, a cheek, an ear, a mouth, and a chin.

3. The method of claim 1, wherein positioning a portion of the ultrasound probe on the skin surface comprises positioning the portion of the ultrasound probe on at least one of the group consisting of: a preauricular region, a frontal region, and a mandibular region of a face.

4. The method of claim 1, wherein positioning a portion of the ultrasound probe on the skin surface comprises positioning the portion of the ultrasound probe on a wrinkle.

5. The method of claim 1, wherein positioning a portion of the ultrasound probe on the skin surface comprises positioning the portion of the ultrasound probe on at least one of the group consisting of: a brow and a hair line of a face.

6. The method of claim 1, wherein the treating of the region of interest results in any one or more of the group consisting of: a brow lift, a blepharoplasty, and an otoplasty.

7. The method of claim 1, further comprising:
imaging the region of interest with an imaging element in the ultrasound probe,
wherein the imaging element is configured to image with an imaging frequency of between 2 kHz to 75 MHz and the at least one piezoelectric ultrasound therapy element is configured to treat with a treatment frequency of between 4 MHz and 15 MHz, and
displaying the region of interest on a display system in electric communication with the imaging element.

8. The method of claim 7, wherein the imaging element and the at least one piezoelectric ultrasound therapy element are combined in a dual-mode imaging/therapy transducer.

9. The method of claim 1, wherein the fixed depth of the focus is within a range of 3 mm to 9 mm from the skin surface, and wherein the temperature of the thermal focus is in the range of 60-90 degrees Celsius.

10. The method of claim 1, wherein the ultrasound probe is electronically coupled to at least one of the group consisting of: a battery, secure storage element, and a disposable tip.

11. A method of treating sagging skin, comprising:
providing a probe that emits ultrasound energy;
coupling the probe to a skin surface over a region comprising a subcutaneous tissue,
wherein the subcutaneous tissue comprises any one or more of the group consisting of: fat, muscle, muscular fascia, and connective tissue; and
delivering therapeutic ultrasound energy to at least the muscular fascia in the region of interest at a treatment frequency of between 4 MHz and 15 MHz,
wherein the therapeutic ultrasound energy thermally treats at least the muscular fascia at a specific depth under the skin surface to reduce skin sagging.

12. The method of claim 11, wherein coupling the probe to the skin surface comprises acoustically coupling the probe to at least one of the group consisting of: a forehead, an eyelid, a nose, a cheek, an ear, a mouth, and a chin.

13. The method of claim 11, wherein delivering therapeutic ultrasound energy comprises delivering ultrasound energy from a single one of the at least one piezoelectric ultrasound therapy element in the probe.

14. The method of claim 13, further comprising activating a motion mechanism to move the single one of the at least one piezoelectric ultrasound therapy element to form a plurality of thermal foci along a line in the region to reduce skin sagging.

15. The method of claim 11, further comprising imaging the tissue under the skin surface.

16. The method of claim 11, wherein the therapeutic ultrasound energy thermally treats the region of interest resulting in any one or more of the group consisting of: a brow lift, a blepharoplasty, and an otoplasty.

17. A method of lifting sagging skin, comprising:
identifying a region of sagging skin;
providing an ultrasonic probe that emits ultrasound energy;
coupling the ultrasonic probe to a skin surface in a region selected from the group consisting of one or more of the following: a forehead, an eyelid, a nose, a cheek, an ear, a mouth, and a chin;
delivering therapeutic ultrasound energy at a treatment frequency of between 4 MHz and 15 MHz,
wherein the therapeutic ultrasound energy treats at least one of the group consisting of subcutaneous fat, muscle, cartilage, and connective tissue at a specific depth under the skin surface to lift the sagging skin.

18. The method of claim 17, wherein delivering therapeutic ultrasound energy comprises delivering ultrasound energy at a fixed depth up to 9 mm from the skin surface at a temperature in the range of 60-90 degrees Celsius.

19. The method of claim 17,
wherein delivering therapeutic ultrasound energy comprises delivering ultrasound energy from a single one of the at least one piezoelectric ultrasound therapy element in the probe, and
further comprising activating a motion mechanism to move the single one of the at least one piezoelectric ultrasound therapy element to form a plurality of thermal foci along a line in the region to reduce skin sagging.

20. The method of claim 17, further comprising imaging the tissue under the skin surface.

* * * * *